US012545678B2

(12) United States Patent
Li et al.

(10) Patent No.: US 12,545,678 B2
(45) Date of Patent: Feb. 10, 2026

(54) BLUE THERMALLY ACTIVATED DELAYED FLUORESCENT EMITTERS AND HOSTS BASED ON FUNCTIONALIZED IMIDAZOLYL GROUPS

(71) Applicant: ARIZONA BOARD OF REGENTS ON BEHALF OF ARIZONA STATE UNIVERSITY, Scottsdale, AZ (US)

(72) Inventors: Jian Li, Tempe, AZ (US); Jiang Wu, Chandler, AZ (US)

(73) Assignee: ARIZONA BOARD OF REGENTS ON BEHALF OF ARIZON STATE UNIVERSITY, Scottsdale, AZ (US)

( * ) Notice: Subject to any disclaimer, the term of this patent is extended or adjusted under 35 U.S.C. 154(b) by 1019 days.

(21) Appl. No.: 17/470,092

(22) Filed: Sep. 9, 2021

(65) Prior Publication Data

US 2022/0073517 A1 Mar. 10, 2022

Related U.S. Application Data

(60) Provisional application No. 63/075,924, filed on Sep. 9, 2020.

(51) Int. Cl.

| | |
|---|---|
| ***C07D 471/14*** | (2006.01) |
| ***C07D 471/22*** | (2006.01) |
| ***C07D 491/147*** | (2006.01) |
| ***C07D 491/22*** | (2006.01) |
| ***C07D 493/14*** | (2006.01) |
| ***C07D 493/22*** | (2006.01) |
| ***C07D 495/04*** | (2006.01) |
| ***C07D 495/14*** | (2006.01) |
| ***C07D 495/22*** | (2006.01) |
| ***H10K 85/60*** | (2023.01) |

(52) U.S. Cl.

CPC ......... *C07D 471/14* (2013.01); *C07D 471/22* (2013.01); *C07D 491/147* (2013.01); *C07D 491/22* (2013.01); *C07D 495/14* (2013.01); *C07D 495/22* (2013.01); *H10K 85/6572* (2023.02); *C07D 493/14* (2013.01); *C07D 493/22* (2013.01); *C07D 495/04* (2013.01); *H05K 2201/10106* (2013.01)

(58) Field of Classification Search

CPC ........................... C07D 471/14; C07D 471/22; C07D 491/157; C07D 491/22; C07D 495/14; C07D 495/22; C07D 493/14; C07D 493/22; C07D 495/04; H10K 85/6572; H10K 2201/10106; H10K 50/11; H10K 2101/20

See application file for complete search history.

(56) References Cited

U.S. PATENT DOCUMENTS

| | | | |
|---|---|---|---|
| 4,769,292 | A | 9/1988 | Tang |
| 5,707,745 | A | 1/1998 | Forrest |
| 5,844,363 | A | 12/1998 | Gu |
| 6,303,238 | B1 | 10/2001 | Thompson |
| 7,279,704 | B2 | 10/2007 | Walters |
| 8,106,199 | B2 | 1/2012 | Jabbour |
| 8,389,725 | B2 | 3/2013 | Li |
| 8,669,364 | B2 | 3/2014 | Li |
| 8,816,080 | B2 | 8/2014 | Li |
| 8,846,940 | B2 | 9/2014 | Li |
| 8,927,713 | B2 | 1/2015 | Li |
| 8,946,417 | B2 | 2/2015 | Li |
| 9,012,599 | B2 | 4/2015 | Stoessel |
| 9,076,974 | B2 | 7/2015 | Li |
| 9,082,989 | B2 | 7/2015 | Li |
| 9,203,039 | B2 | 12/2015 | Li |
| 9,221,857 | B2 | 12/2015 | Li |
| 9,224,963 | B2 | 12/2015 | Li |
| 9,238,668 | B2 | 1/2016 | Li |
| 9,312,502 | B2 | 4/2016 | Li |
| 9,318,725 | B2 | 4/2016 | Li |

(Continued)

FOREIGN PATENT DOCUMENTS

| | | | |
|---|---|---|---|
| CN | 108148088 | A | 6/2018 |
| CN | 108794539 | A | 11/2018 |

(Continued)

OTHER PUBLICATIONS

Bunz "Large N-Heteroacenes: New Tricks for Very Old Dogs?" Angew. Chem. Int. Ed. 2013, 52, 3810-3821.

(Continued)

*Primary Examiner* — Amanda L. Aguirre
(74) *Attorney, Agent, or Firm* — Riverside Law LLP

(57) ABSTRACT

Compounds of General Formula I may act as thermally activated delayed fluorescent emitters in organic electroluminescent devices. Compounds of General Formula I have donor and acceptor groups part of the same conjugated system. Devices incorporating compounds of General Formula I may have higher EQE and longer material lifetimes.

General Formula I

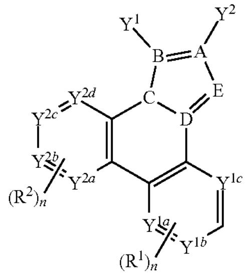

17 Claims, 2 Drawing Sheets

(56) References Cited

U.S. PATENT DOCUMENTS

| | | | | |
|---|---|---|---|---|
| 9,324,957 | B2 | 4/2016 | Li | |
| 9,382,273 | B2 | 7/2016 | Li | |
| 9,385,329 | B2 | 7/2016 | Li | |
| 9,425,415 | B2 | 8/2016 | Li | |
| 9,502,671 | B2 | 11/2016 | Li | |
| 9,550,801 | B2 | 1/2017 | Li | |
| 9,598,449 | B2 | 3/2017 | Li | |
| 9,617,291 | B2 | 4/2017 | Li | |
| 9,673,409 | B2 | 6/2017 | Li | |
| 9,698,359 | B2 | 7/2017 | Li | |
| 9,711,739 | B2 | 7/2017 | Li | |
| 9,711,741 | B2 | 7/2017 | Li | |
| 9,711,742 | B2 | 7/2017 | Li | |
| 9,755,163 | B2 | 9/2017 | Li | |
| 9,818,959 | B2 | 11/2017 | Li | |
| 9,865,825 | B2 | 1/2018 | Li | |
| 9,879,039 | B2 | 1/2018 | Li | |
| 9,882,150 | B2 | 1/2018 | Li | |
| 9,899,614 | B2 | 2/2018 | Li | |
| 9,920,242 | B2 | 3/2018 | Li | |
| 9,923,155 | B2 | 3/2018 | Li | |
| 9,941,479 | B2 | 4/2018 | Li | |
| 9,947,881 | B2 | 4/2018 | Li | |
| 9,985,224 | B2 | 5/2018 | Li | |
| 10,020,455 | B2 | 7/2018 | Li | |
| 10,033,003 | B2 | 7/2018 | Li | |
| 10,056,564 | B2 | 8/2018 | Li | |
| 10,056,567 | B2 | 8/2018 | Li | |
| 10,158,091 | B2 | 12/2018 | Li | |
| 10,177,323 | B2 | 1/2019 | Li | |
| 10,211,411 | B2 | 2/2019 | Li | |
| 10,211,414 | B2 | 2/2019 | Li | |
| 10,263,197 | B2 | 4/2019 | Li | |
| 10,294,417 | B2 | 5/2019 | Li | |
| 10,392,387 | B2 | 8/2019 | Li | |
| 10,411,202 | B2 | 9/2019 | Li | |
| 10,414,785 | B2 | 9/2019 | Li | |
| 10,516,117 | B2 | 12/2019 | Li | |
| 10,566,553 | B2 | 2/2020 | Li | |
| 10,566,554 | B2 | 2/2020 | Li | |
| 10,615,349 | B2 * | 4/2020 | Li | H10K 85/657 |
| 10,622,571 | B2 | 4/2020 | Li | |
| 10,727,422 | B2 | 7/2020 | Li | |
| 10,745,615 | B2 | 8/2020 | Li | |
| 10,790,457 | B2 | 9/2020 | Li | |
| 10,793,546 | B2 | 10/2020 | Li | |
| 10,804,476 | B2 | 10/2020 | Li | |
| 10,822,363 | B2 | 11/2020 | Li | |
| 10,836,785 | B2 | 11/2020 | Li | |
| 10,851,106 | B2 | 12/2020 | Li | |
| 10,886,478 | B2 | 1/2021 | Li | |
| 10,930,865 | B2 | 2/2021 | Li | |
| 10,937,976 | B2 | 3/2021 | Li | |
| 10,944,064 | B2 | 3/2021 | Li | |
| 10,964,897 | B2 | 3/2021 | Li | |
| 10,991,897 | B2 | 4/2021 | Li | |
| 10,995,108 | B2 | 5/2021 | Li | |
| 11,011,712 | B2 | 5/2021 | Li | |
| 11,063,228 | B2 | 7/2021 | Li | |
| 11,101,435 | B2 | 8/2021 | Li | |
| 11,114,626 | B2 | 9/2021 | Li | |
| 11,121,328 | B2 | 9/2021 | Li | |
| 11,145,830 | B2 | 10/2021 | Li | |
| 12,168,661 | B2 * | 12/2024 | Li | H10K 85/657 |
| 12,193,327 | B2 * | 1/2025 | Li | C07D 495/14 |
| 2005/0139810 | A1 | 6/2005 | Kuehl | |
| 2007/0160905 | A1 | 7/2007 | Morishita | |
| 2007/0252140 | A1 | 11/2007 | Limmert | |
| 2008/0269491 | A1 | 10/2008 | Jabbour | |
| 2009/0136779 | A1 | 5/2009 | Cheng | |
| 2009/0167167 | A1 | 7/2009 | Aoyama | |
| 2010/0288362 | A1 | 11/2010 | Hatwar | |
| 2011/0028723 | A1 | 2/2011 | Li | |
| 2011/0066763 | A1 | 3/2011 | Minot | |
| 2011/0301351 | A1 | 12/2011 | Li | |
| 2012/0095232 | A1 | 4/2012 | Li | |
| 2012/0108806 | A1 | 5/2012 | Li | |
| 2012/0146012 | A1 | 6/2012 | Limmert | |
| 2012/0202997 | A1 | 8/2012 | Parham | |
| 2012/0215001 | A1 | 8/2012 | Li | |
| 2012/0264938 | A1 | 10/2012 | Li | |
| 2012/0302753 | A1 | 11/2012 | Li | |
| 2013/0137870 | A1 | 5/2013 | Li | |
| 2013/0203996 | A1 | 8/2013 | Li | |
| 2013/0237706 | A1 | 9/2013 | Li | |
| 2014/0066628 | A1 | 3/2014 | Li | |
| 2014/0073798 | A1 | 3/2014 | Li | |
| 2014/0114072 | A1 | 4/2014 | Li | |
| 2014/0147996 | A1 | 5/2014 | Vogt | |
| 2014/0148594 | A1 | 5/2014 | Li | |
| 2014/0249310 | A1 | 9/2014 | Li | |
| 2014/0330019 | A1 | 11/2014 | Li | |
| 2014/0364605 | A1 | 12/2014 | Li | |
| 2015/0008419 | A1 | 1/2015 | Li | |
| 2015/0018558 | A1 | 1/2015 | Li | |
| 2015/0060804 | A1 | 3/2015 | Kanitz | |
| 2015/0105556 | A1 | 4/2015 | Li | |
| 2015/0123047 | A1 | 5/2015 | Maltenberger | |
| 2015/0162552 | A1 | 6/2015 | Li | |
| 2015/0194616 | A1 | 7/2015 | Li | |
| 2015/0207086 | A1 | 7/2015 | Li | |
| 2015/0228914 | A1 | 8/2015 | Li | |
| 2015/0274762 | A1 | 10/2015 | Li | |
| 2015/0287938 | A1 | 10/2015 | Li | |
| 2015/0311456 | A1 | 10/2015 | Li | |
| 2015/0318500 | A1 | 11/2015 | Li | |
| 2015/0349279 | A1 | 12/2015 | Li | |
| 2016/0028028 | A1 | 1/2016 | Li | |
| 2016/0028029 | A1 | 1/2016 | Li | |
| 2016/0043331 | A1 | 2/2016 | Li | |
| 2016/0133861 | A1 | 5/2016 | Li | |
| 2016/0133862 | A1 | 5/2016 | Li | |
| 2016/0190473 | A1 | 6/2016 | Kim | |
| 2016/0190474 | A1 | 6/2016 | Kim | |
| 2016/0194344 | A1 | 7/2016 | Li | |
| 2016/0197291 | A1 | 7/2016 | Li | |
| 2016/0285015 | A1 | 9/2016 | Li | |
| 2016/0359120 | A1 | 12/2016 | Li | |
| 2016/0359125 | A1 | 12/2016 | Li | |
| 2017/0005278 | A1 | 1/2017 | Li | |
| 2017/0012224 | A1 | 1/2017 | Li | |
| 2017/0040555 | A1 | 2/2017 | Li | |
| 2017/0047533 | A1 | 2/2017 | Li | |
| 2017/0066792 | A1 | 3/2017 | Li | |
| 2017/0069855 | A1 | 3/2017 | Li | |
| 2017/0077420 | A1 | 3/2017 | Li | |
| 2017/0125708 | A1 | 5/2017 | Li | |
| 2017/0267923 | A1 | 9/2017 | Li | |
| 2017/0271611 | A1 | 9/2017 | Li | |
| 2017/0301871 | A1 | 10/2017 | Li | |
| 2017/0305881 | A1 | 10/2017 | Li | |
| 2017/0331056 | A1 | 11/2017 | Li | |
| 2017/0342098 | A1 | 11/2017 | Li | |
| 2017/0373260 | A1 | 12/2017 | Li | |
| 2018/0006246 | A1 | 1/2018 | Li | |
| 2018/0053904 | A1 | 2/2018 | Li | |
| 2018/0130960 | A1 | 5/2018 | Li | |
| 2018/0138428 | A1 | 5/2018 | Li | |
| 2018/0148464 | A1 | 5/2018 | Li | |
| 2018/0159051 | A1 | 6/2018 | Li | |
| 2018/0166655 | A1 | 6/2018 | Li | |
| 2018/0175329 | A1 | 6/2018 | Li | |
| 2018/0194790 | A1 | 7/2018 | Li | |
| 2018/0219161 | A1 | 8/2018 | Li | |
| 2018/0226592 | A1 | 8/2018 | Li | |
| 2018/0226593 | A1 | 8/2018 | Li | |
| 2018/0277777 | A1 | 9/2018 | Li | |
| 2018/0301641 | A1 | 10/2018 | Li | |
| 2018/0312750 | A1 | 11/2018 | Li | |
| 2018/0331307 | A1 | 11/2018 | Li | |
| 2018/0334459 | A1 | 11/2018 | Li | |
| 2018/0337345 | A1 * | 11/2018 | Li | C09K 11/06 |
| 2018/0337349 | A1 | 11/2018 | Li | |
| 2018/0337350 | A1 | 11/2018 | Li | |

(56) References Cited

U.S. PATENT DOCUMENTS

| | | | | | |
|---|---|---|---|---|---|
| 2019/0013485 | A1 | 1/2019 | Li | | |
| 2019/0067602 | A1 | 2/2019 | Li | | |
| 2019/0109288 | A1 | 4/2019 | Li | | |
| 2019/0194536 | A1 | 6/2019 | Li | | |
| 2019/0259963 | A1 | 8/2019 | Li | | |
| 2019/0276485 | A1 | 9/2019 | Li | | |
| 2019/0312217 | A1 | 10/2019 | Li | | |
| 2019/0367546 | A1 | 12/2019 | Li | | |
| 2019/0389893 | A1 | 12/2019 | Li | | |
| 2020/0006678 | A1 | 1/2020 | Li | | |
| 2020/0071330 | A1 | 3/2020 | Li | | |
| 2020/0075868 | A1 | 3/2020 | Li | | |
| 2020/0119288 | A1 | 4/2020 | Li | | |
| 2020/0152891 | A1 | 5/2020 | Li | | |
| 2020/0227656 | A1 | 7/2020 | Li | | |
| 2020/0227660 | A1 | 7/2020 | Li | | |
| 2020/0239505 | A1 | 7/2020 | Li | | |
| 2020/0243776 | A1 | 7/2020 | Li | | |
| 2020/0287153 | A1 | 9/2020 | Li | | |
| 2020/0332185 | A1 | 10/2020 | Li | | |
| 2020/0373505 | A1 | 11/2020 | Li | | |
| 2020/0403167 | A1 | 12/2020 | Li | | |
| 2021/0024526 | A1 | 1/2021 | Li | | |
| 2021/0024559 | A1 | 1/2021 | Li | | |
| 2021/0047296 | A1 | 2/2021 | Li | | |
| 2021/0091316 | A1 | 3/2021 | Li | | |
| 2021/0104687 | A1 | 4/2021 | Li | | |
| 2021/0111355 | A1 | 4/2021 | Li | | |
| 2021/0126208 | A1 | 4/2021 | Li | | |
| 2021/0193936 | A1 | 6/2021 | Li | | |
| 2021/0193947 | A1 | 6/2021 | Li | | |
| 2021/0217973 | A1 | 7/2021 | Li | | |
| 2021/0230198 | A1 | 7/2021 | Li | | |
| 2021/0261589 | A1 | 8/2021 | Li | | |
| 2021/0273182 | A1 | 9/2021 | Li | | |
| 2021/0323963 | A1* | 10/2021 | Li | ...................... | H10K 85/6572 |
| 2025/0031574 | A1* | 1/2025 | Li | ........................ | C07D 495/14 |

FOREIGN PATENT DOCUMENTS

| | | | |
|---|---|---|---|
| CN | 108948044 | A | 12/2018 |
| CN | 110713482 | A | 1/2020 |
| EP | 1617493 | | 1/2006 |
| EP | 1968131 | | 9/2008 |
| EP | 2020694 | | 2/2009 |
| EP | 2684932 | | 1/2014 |
| KR | 20110066763 | | 6/2011 |
| KR | 20130043460 | A | 4/2013 |
| KR | 20140027030 | | 3/2014 |
| KR | 20140065357 | A | 5/2014 |
| KR | 20160067034 | A | 6/2016 |
| WO | 2000070655 | | 11/2000 |
| WO | 2006081780 | | 8/2006 |
| WO | 2009003455 | | 1/2009 |
| WO | 2009008277 | | 1/2009 |
| WO | 2009011327 | | 1/2009 |
| WO | 2009086209 | | 7/2009 |
| WO | 2009111299 | | 9/2009 |
| WO | 2010050778 | | 5/2010 |
| WO | 2010105141 | | 9/2010 |
| WO | 2010118026 | | 10/2010 |
| WO | 2010118026 | A2 | 10/2010 |
| WO | 2011137429 | | 11/2011 |
| WO | 2011137429 | A2 | 11/2011 |
| WO | 2011137431 | | 11/2011 |
| WO | 2011137431 | A2 | 11/2011 |
| WO | 2012074909 | | 6/2012 |
| WO | 2012112853 | | 8/2012 |
| WO | 2012112853 | A1 | 8/2012 |
| WO | 2012142387 | | 10/2012 |
| WO | 2012162488 | A1 | 11/2012 |
| WO | 2013130483 | A1 | 9/2013 |
| WO | 2014009310 | | 1/2014 |
| WO | 2014031977 | | 2/2014 |
| WO | 2014047616 | | 3/2014 |
| WO | 2014047616 | A1 | 3/2014 |
| WO | 2014109814 | | 7/2014 |
| WO | 2015027060 | | 2/2015 |
| WO | 2015027060 | A1 | 2/2015 |
| WO | 2015099507 | | 7/2015 |
| WO | 2015131158 | | 9/2015 |
| WO | 2016025921 | | 2/2016 |
| WO | 2016029137 | | 2/2016 |
| WO | 2016029186 | | 2/2016 |
| WO | 2016197019 | | 12/2016 |
| WO | 2018071697 | | 4/2018 |
| WO | 2018140765 | | 8/2018 |
| WO | 2019079505 | | 4/2019 |
| WO | 2019079508 | | 4/2019 |
| WO | 2019079509 | | 4/2019 |
| WO | 2019236541 | | 12/2019 |
| WO | 2020018476 | | 1/2020 |

OTHER PUBLICATIONS

Kader Azaindolo[3,2, 1-jk]carbazoles New Building Blocks for Functional Organic Materials Chem. Eur. J. 2019, 25, 4412-4425.

Kotwica "Azaacenes Based Electroactive Materials: Preparation, Structure, Electrochemistry, Spectroscopy and Applications—A Critical Review" Materials 2021, 14, 5155.

Miao "Ten Years of N-Heteropentacenes as Semiconductors for Organic Thin-Film Transistors" Adv. Mater. 2014, 26, 5541-5549.

Richards "Putting the 'N' in ACENE: Pyrazinacenes and their structural relatives" Org. Biomol. Chem., 2011, 9, 5005.

Baldo et al., "Highly Efficient Phosphorescent Emission from Organic Electroluminescent Devices," Nature, vol. 395, Sep. 10, 1998, pp. 151-154.

Baldo et al., "Very high-efficiency green organic light-emitting devices based on electrophosphorescence," Applied Physics Letters, vol. 75, No. 1, Jul. 5, 1999, pp. 4-6.

STN Abstract of KR 2013043460 A (Year: 2013).

Uoyama et al., "Highly efficient organic light-emitting diodes from delayed fluorescence" Nature, 492:234-238, (2012).

Yan, et al., "Palladium-catalyzed tandem N—H/C—H arylation: regioselective synthesis of N-heterocycle-fused phenanthridines as versatile blue-emitting luminophores," Organic & Biomolecular Chemistry, 11 (45), 2013, 7966-7977.

Su "Pyridine-Containing Bipolar Host Materials for Highly Efficient Blue Phosphorescent OLEDs" Chem. Mater. 2008, 20, 1691-1693 1691.

Bachowska, B. Monatshefte fuer Chemie, 126(2), 1995, 227-231.

Machine Translation of KR20160067034A (Year: 2016).

* cited by examiner

BLUE THERMALLY ACTIVATED DELAYED FLUORESCENT EMITTERS AND HOSTS BASED ON FUNCTIONALIZED IMIDAZOLYL GROUPS

CROSS-REFERENCE TO RELATED APPLICATIONS

The present application claims priority to U.S. Provisional Application No. 63/075,924, filed: Sep. 9, 2020, which is incorporated by reference herein in its entirety.

STATEMENT REGARDING FEDERALLY SPONSORED RESEARCH OR DEVELOPMENT

This invention was made with government support under DE-EE0008721 awarded by the Department of Energy. The government has certain rights in the invention.

BACKGROUND OF THE INVENTION

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

In recent years, organic light emitting diodes (OLEDs) have attracted great attention from both academic and industrial areas due to their outstanding merits, like high color quality, wide-viewing angle, low cost fabrication, low power consumption, fast respond speed and high electron to photon conversion efficiency. Most of the organic light emitting diodes (OLEDs) are phosphorescent OLEDs using Iridium (Ir), palladium (Pd) and platinum (Pt) complexes, as these metal complexes have strong Spin-Orbital Coupling, they can efficiently emit light from their triplet exited state and reach nearly 100% internal efficiency. The development of efficient and stable narrowband deep blue emitters is the most interesting research topic in recent years. Due to the high energy of blue emitters, blue phosphorescent OLEDs suffer from low lifetimes. The external quantum efficiency (EQE) of thermally activated delayed fluorescent (TADF) OLEDs is greater than that of traditional fluorescent materials.

There remains a need in the art for efficient and stable OLED components. This invention addresses this unmet need.

SUMMARY OF THE INVENTION

In one aspect, the present disclosure relates to a compound of General Formula I:

General Formula I

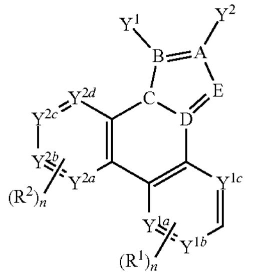

wherein:

$Y^{1a}$, $Y^{1b}$, $Y^{1c}$, $Y^{2a}$, $Y^{2b}$, $Y^{2c}$, $Y^{2d}$ each independently represents C or N;

each of A, B, C, D, and E independently represents C, N, O, or S;

each of $Y^1$ and $Y^2$ is independently absent or present, valency permitting;

$Y^1$ and $Y^2$ independently represent hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof; $Y^1$ and $Y^2$ may together form a ring;

$R^1$ and $R^2$ are independently absent or present, valency permitting, and each $R^1$ and $R^2$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof; any two adjacent $R^1$ and $R^2$ may together form a ring;

wherein at least two adjacent $R^2$ together represent a group of Formula A:

Formula A

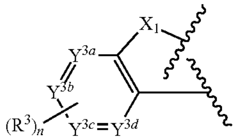

wherein:

waved lines indicate bonds to the respective $Y^{2a}$, $Y^{2b}$, $Y^{2c}$ or $Y^{2d}$;

$Y^{3a}$ $Y^{3b}$ $Y^{3c}$ and $Y^{3d}$ each independently represents C or N;

$X_1$ independently represents C, N, Si, O, S, Ge, P, As, Se, B, Al, or Bi, or if valency permits, $X_1$ independently represents $CR^4$, $SiR^4$, $GeR^4$, $NR^4$, P=O, As=O, B, $BR^4$, $AlR^4$, Bi═O, $CR^4R^5$, C═O, $SiR^4R^5$, $GeR^4R^5$, $PR^4$, $PR^4R^5$, $R^4$, P═O, $AsR^4$, $R^4As$═O, S═O, $SO_2$, Se═O, $SeO_2$, $BR^4$, $BR^4R^5$, $AlR^4$, $AlR^4R^5$, $R^4Bi$═O, or $BiR^4$;

$R^3$, $R^4$, and $R^5$ are independently absent or present, valency permitting, and each $R^3$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof; any two of $R^1$, $R^2$, $R^3$, $R^4$, and $R^5$ may together form a ring; and each n is an integer, valency permitting.

In one embodiment, an organic light emitting diode (OLED) including the compound is provided. According to another embodiment, a light emitting device comprising the light emitting diode is provided.

BRIEF DESCRIPTION OF THE DRAWINGS

The following detailed description of preferred embodiments of the disclosure will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Definitions

Figure 1:
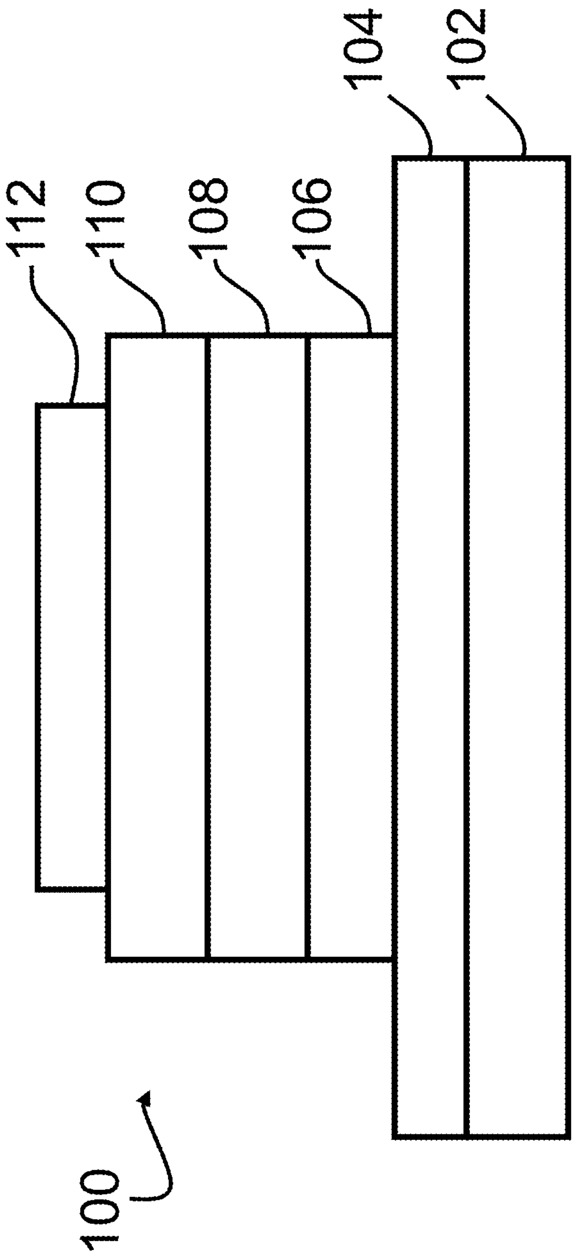
FIG. 1 is a schematic diagram of an organic light emitting device.

It is to be understood that the figures and descriptions in the present disclosure have been simplified to illustrate elements that are relevant for a clear understanding of the present invention, while eliminating, for the purpose of clarity, many other elements found in the art related to phosphorescent organic light emitting devices and the like. Those of ordinary skill in the art may recognize that other elements and/or steps are desirable and/or required in implementing the disclosed embodiments. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this disclosure belongs. Although any methods, materials and components similar or equivalent to those described herein can be used in the practice or testing of the disclosed embodiments, the preferred methods, and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B—F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As referred to herein, a linking atom or a linking group can connect two groups such as, for example, an N and C group. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include, but are not limited to, hydrogen, hydroxyl, alkyl, alkoxy, =O, halogen, nitro, amine, amide, thiol, aryl, heteroaryl, cycloalkyl, and heterocyclyl.

The term "cyclic structure" or the like terms used herein refer to any cyclic chemical structure which includes, but is not limited to, aryl, heteroaryl, cycloalkyl, cycloalkenyl, and heterocyclyl.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bond, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula $—NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula $—N(\text{-alkyl})_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula $—OC(O)A^1$ or $—C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula $-(A^1O(O)C\text{-}A^2\text{-}C(O)O)$, or $-(A^1O(O)C\text{-}A^2\text{-}OC(O))_a—$, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula $-(A^1O\text{-}A^2O)_a—$, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocyclyl," as used herein refers to single and multi-cyclic non-aromatic ring systems and "heteroaryl" as used herein refers to single and multi-cyclic aromatic ring systems: in which at least one of the ring members is other than carbon. The term "heterocyclyl" includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula $—N_3$.

The term "nitro" as used herein is represented by the formula $—NO_2$.

The term "nitrile" as used herein is represented by the formula —CN.

The term "ureido" as used herein refers to a urea group of the formula $—NHC(O)NH_2$ or —NHC(O)NH—.

The term "phosphoramide" as used herein refers to a group of the formula $—P(O)(NA^1A^2)_2$, where $A^1$ and $A^2$ can be, independently, hydrogen or an alkyl, cycloalkyl, alkoxy, alkenyl, cycloalkenyl, alkynyl, cycloalkynyl, aryl, or heteroaryl group as described herein.

The term "carbamoyl" as used herein refers to an amide group of the formula —$CONA^1A^2$, where $A^1$ and $A^2$ can be, independently, hydrogen or an alkyl, cycloalkyl, alkoxy, alkenyl, cycloalkenyl, alkynyl, cycloalkynyl, aryl, or heteroaryl group as described herein.

The term "sulfamoyl" as used herein refers to a group of the formula —$S(O)_2NA^1A^2$, where $A^1$ and $A^2$ can be, independently, hydrogen or an alkyl, cycloalkyl, alkoxy, alkenyl, cycloalkenyl, alkynyl, cycloalkynyl, aryl, or heteroaryl group as described herein.

The term "silyl" as used herein is represented by the formula —$SiA\ 1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ is hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula —$S(O)_2A^1$, where $A^1$ is hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

The term "polymeric" includes polyalkylene, polyether, polyester, and other groups with repeating units, such as, but not limited to —$(CH_2O)_n$—$CH_3$, —$(CH_2CH_2O)_n$—$CH_3$, —$[CH_2CH(CH_3)]_n$—$CH_3$, —$[CH_2CH(COOCH_3)]_n$—$CH_3$, —$[CH_2CH(COOCH_2CH_3)]_n$—$CH_3$, and —$[CH_2CH(COO^tBu)]_n$—$CH_3$, where n is an integer (e.g., n>1 or n>2).

"R," "$R^1$," "$R^2$," "$R^3$," "$R^n$," where n is an integer, as used herein can, independently, include hydrogen or one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within a second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. It is also contemplated that, in certain aspects, unless expressly indicated to the contrary, individual substituents can be further optionally substituted (i.e., further substituted or unsubstituted).

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2,2' positions in a biphenyl, or 1,8 position in a naphthalene, as long as they can form a stable fused ring system.

In some aspects, a structure of a compound can be represented by a formula:

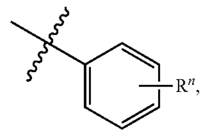

which is understood to be equivalent to a formula:

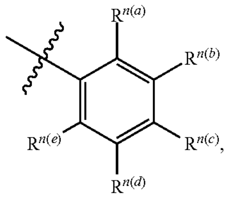

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Several references to R, $R^1$, $R^2$, $R^3$, $R^4$, $R^5$, $R^6$, etc. are made in chemical structures and moieties disclosed and described herein. Any description of R, $R^1$, $R^2$, $R^3$, $R^4$, $R^5$, $R^6$, etc. in the specification is applicable to any structure or moiety reciting R, $R^1$, $R^2$, $R^3$, $R^4$, $R^5$, $R^6$, etc. respectively.

Compounds

The compounds disclosed herein are suited for use in a wide variety of optical and electro-optical devices, including, but not limited to, photo-absorbing devices such as solar- and photo-sensitive devices, organic light emitting devices (OLEDs), photo-emitting devices, or devices capable of both photo-absorption and emission and as markers for bio-applications.

The compounds disclosed herein are useful in a variety of applications. As light emitting materials, the compounds can be useful in organic light emitting devices (OLEDs), luminescent devices and displays, and other light emitting devices.

In another aspect, the compounds can provide improved efficiency, improved operational lifetimes, or both in lighting devices, such as, for example, organic light emitting devices, as compared to conventional materials.

The compounds of the disclosure can be made using a variety of methods, including, but not limited to those recited in the examples provided herein.

In one aspect, the present invention relates to a compound of General Formula I:

General Formula I

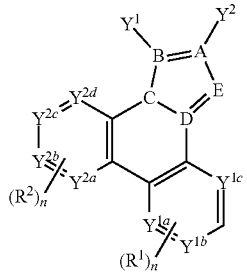

wherein:

- $Y^{1a}$, $Y^{1b}$, $Y^{1c}$, $Y^{2a}$, $Y^{2b}$, $Y^{2c}$, $Y^{2d}$ each independently represents C or N;
- each of A, B, C, D, and E independently represents C, N, O, or S;
- each of $Y^1$ and $Y^2$ is independently absent or present, valency permitting;
- $Y^1$ and $Y^2$ independently represent hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof; $Y^1$ and $Y^2$ may together form a ring;
- $R^1$ and $R^2$ are independently absent or present, valency permitting, and each $R^1$ and $R^2$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof; any two adjacent $R^1$ and $R^2$ may together form a ring;
- provided that at least two adjacent $R^2$ together represent a group of Formula A:

Formula A

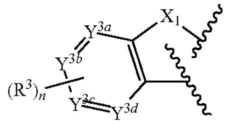

wherein:

- waved lines indicate bonds to the respective $Y^{2a}$, $Y^{2b}$, $Y^{2c}$, or $Y^{2d}$;
- $Y^{3a}$ $Y^{3b}$ $Y^{3c}$ and $Y^{3d}$ each independently represents C or N;
- $X_1$ independently represents C, N, Si, O, S, Ge, P, As, Se, B, Al, or Bi, or if valency permits, $X_1$ independently represents $CR^4$, $SiR^4$, $GeR^4$, $NR^4$, P=O, As=O, B, $BR^4$, $AlR^4$, Bi=O, $CR^4R^5$, C=O, $SiR^4R^5$, $GeR^4R^5$, $PR^4$, $PR^4R^5$, $R^4$, P=O, $AsR^4$, $R^4As$=O, S=O, $SO_2$, Se=O, $SeO_2$, $BR^4$, $BR^4R^5$, $AlR^4$, $AlR^4R^5$, $R^4Bi$=O, or $BiR^4$;
- $R^3$, $R^4$, and $R^5$ are independently absent or present, valency permitting, and each $R^3$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof; any two of $R^1$, $R^2$, $R^3$, $R^4$, and $R^5$ may together form a ring; and
- each n is an integer, valency permitting.

In one embodiment, the compound is represented by one of the following General Formulae:

General Formula 1

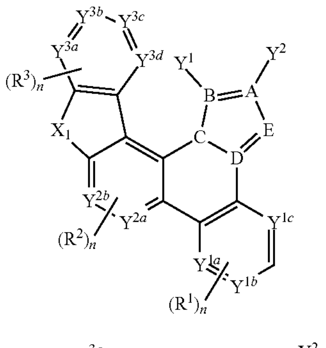

General Formula 2

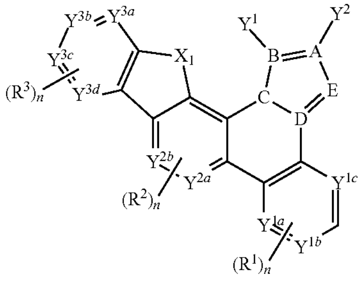

-continued

General Formula 3

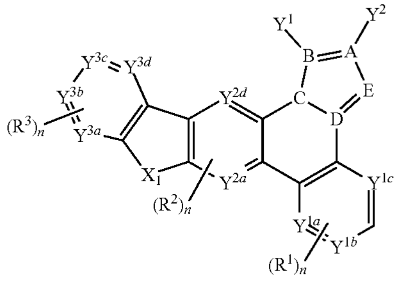

General Formula 4

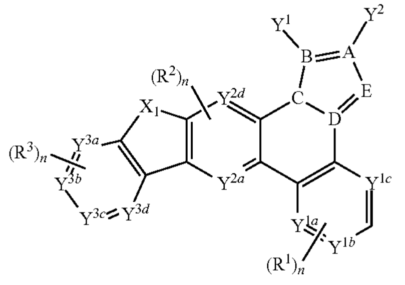

General Formula 5

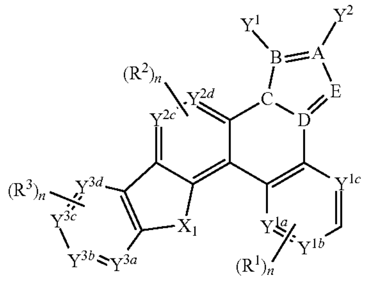

General Formula 6

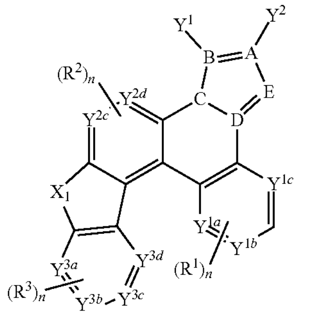

wherein, in General Formula 1 to General Formula 6:

$Y^{1a}$, $Y^{1b}$, $Y^{1c}$, $Y^{2a}$, $Y^{2b}$, $Y^{2c}$, $Y^{2d}$, $Y^{3a}$, $Y^{3b}$, $Y^{3c}$ and $Y^{3d}$ each independently represents C or N;

each of A, B, C, D, and E independently represents C, N, O, or S;

$X_1$ independently represents C, N, Si, O, S, Ge, P, As, Se, B, Al, or Bi, or if valency permits, $X_1$ independently represents $CR^4$, $SiR^4$, $GeR^4$, $NR^4$, P═O, As═O, B, $BR^4$, $AlR^4$, Bi═O, $CR^4R^5$, C═O, $SiR^4R^5$, $GeR^4R^5$, $PR^4$, $PR^4R^5$, $R^4$, P═O, $AsR^4$, $R^4$As═O, S═O, $SO_2$, Se═O, $SeO_2$, $BR^4$, $BR^4R^5$, $AlR^4$, $AlR^4R^5$, $R^4$Bi═O, or $BiR^4$;

each of $Y^1$ and $Y^2$ is independently absent or present, valency permitting; $Y^1$ and $Y^2$ independently represent hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof; $Y^1$ and $Y^2$ may together form a ring;

each of $R^1$, $R^2$, $R^3$, $R^4$, and $R^5$ is independently absent or present, valency permitting, and each of $R^1$, $R^2$, $R^3$, $R^4$, and $R^5$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof; any two of $R^1$, $R^2$, $R^3$, $R^4$, and $R^5$ may together form a ring; and n is an integer, valency permitting.

In one embodiment, at least two adjacent $R^3$ together represent a group of

Formula B

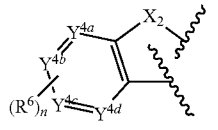

wherein waved lines indicate bonds to the respective $Y^{3a}$, $Y^{3b}$, $Y^{3c}$, and $Y^{3d}$;

$Y^{4a}$, $Y^{4b}$, $Y^{4c}$ and $Y^{4d}$ each independently represents C or N;

$X_2$ independently represents C, N, Si, O, S, Ge, P, As, Se, B, Al, or Bi, or if valency permits, $X_2$ independently represents $CR^7$, $SiR^7$, $GeR^7$, $NR^7$, P═O, As═O, B, $BR^7$, $AlR^7$, Bi═O, $CR^7R^8$, C═O, $SiR^7R^8$, $GeR^7R^8$, $PR^7$, $PR^7R^8$, $R^7$P═O, $AsR^7$, $R^7$As═O, S═O, $SO_2$, Se═O, $SeO_2$, $BR^7$, $BR^7R^8$, $AlR^7$, $AlR^7R^8$, $R^7$Bi═O, or $BiR^7$;

each of $R^6$, $R^7$, and $R^8$ is independently absent or present as a single substituent or multiple substituents, valency permitting, and each of $R^6$, $R^7$, and $R^8$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof; any two of $R^6$, $R^7$, and $R^8$ may together form a ring; and n is an integer, valency permitting.

In one embodiment, the compound is represented by one of the following General Formulae:

General Formula 7
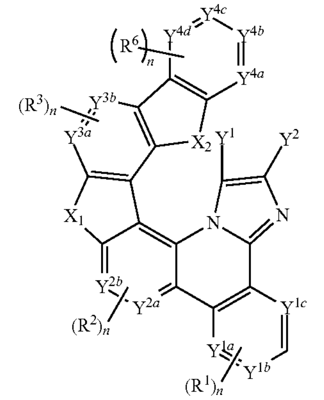
General Formula 8
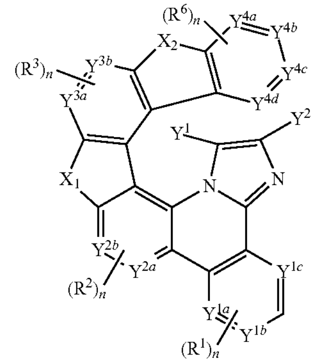
General Formula 9
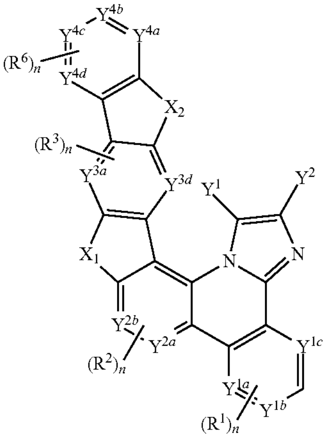
General Formula 10
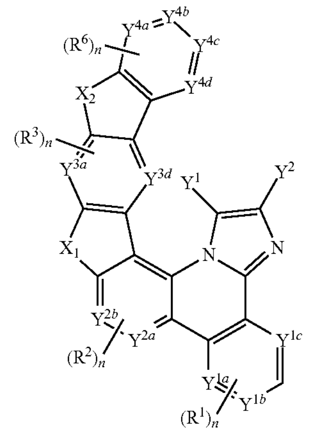
-continued
General Formula 11
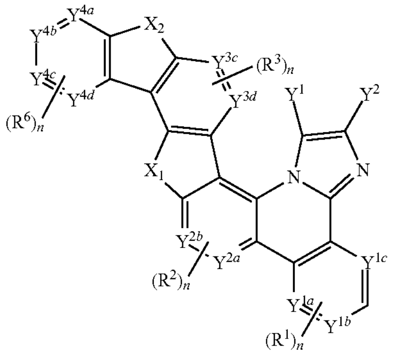
General Formula 12
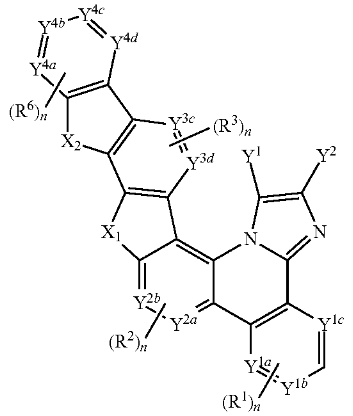
General Formula 13
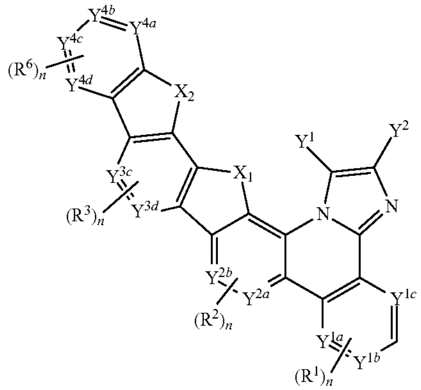
General Formula 14
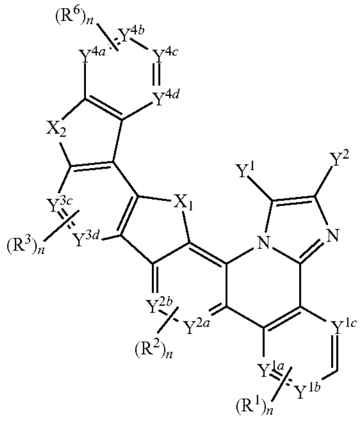

-continued
General Formula 15
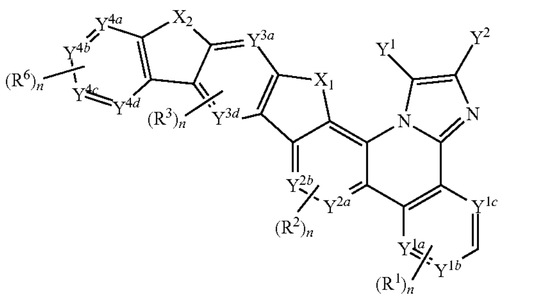
General Formula 16
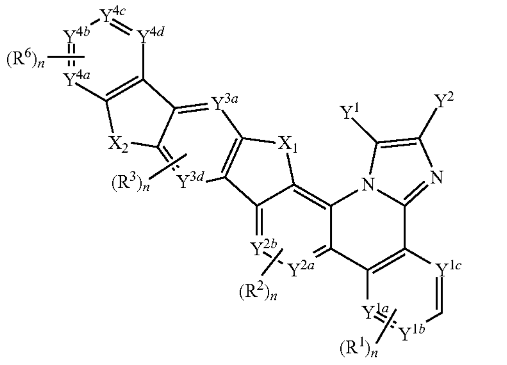
General Formula 17
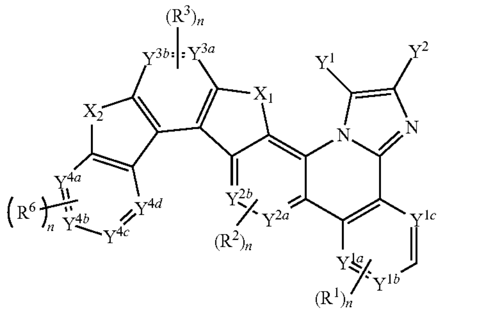
General Formula 18
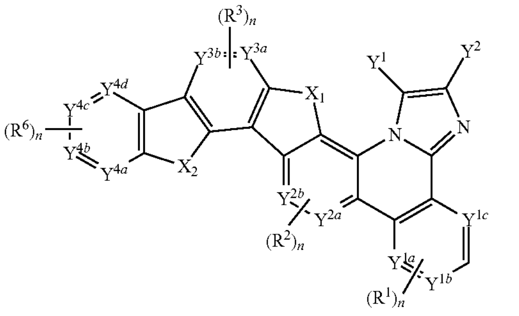
-continued
General Formula 19
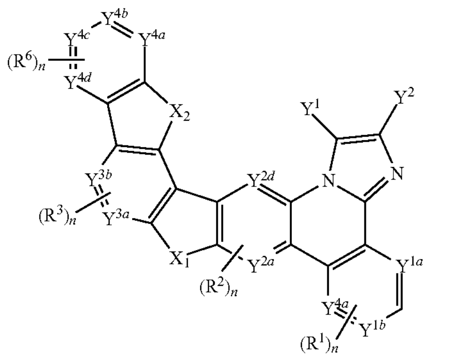
General Formula 20
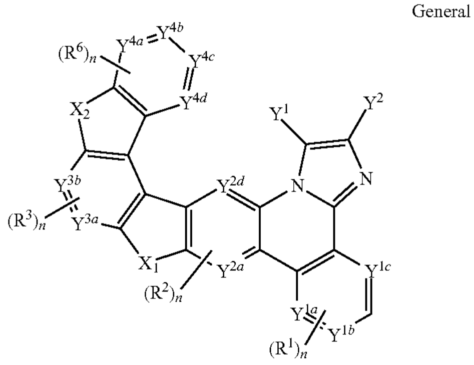
General Formula 21
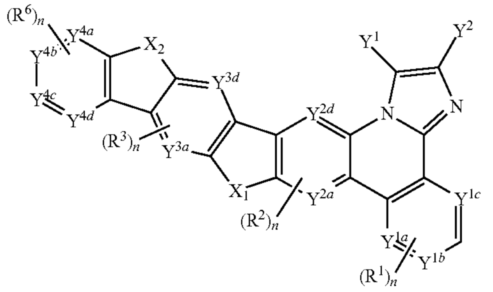
General Formula 22
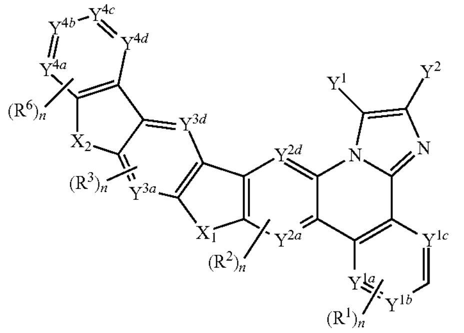

-continued
General Formula 23
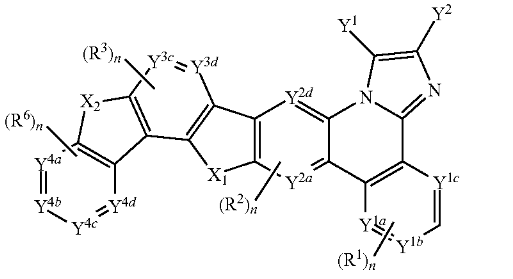
General Formula 24
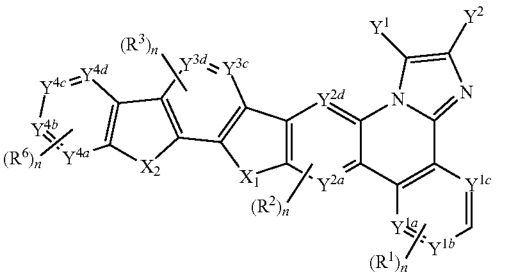
General Formula 25
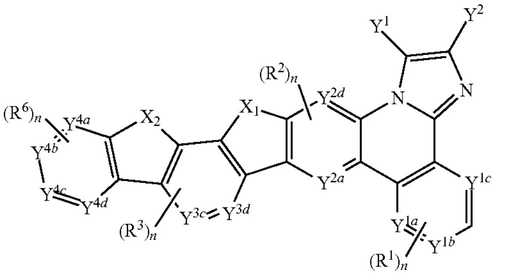
General Formula 26
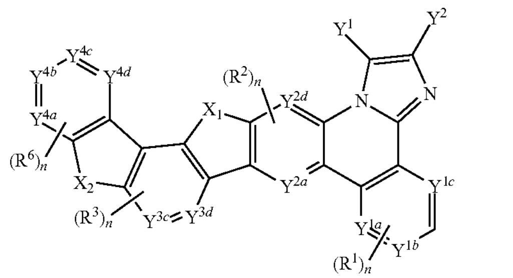
General Formula 27
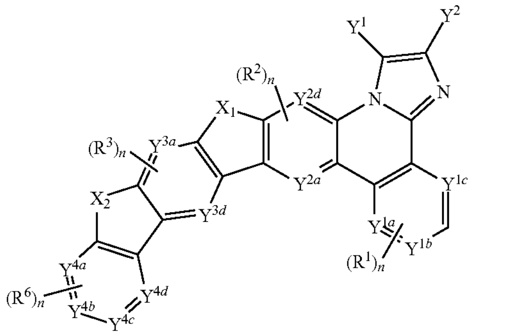
-continued
General Formula 28
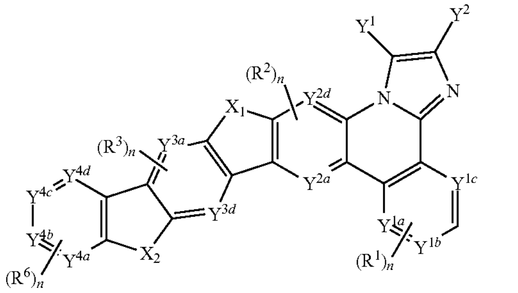
General Formula 29
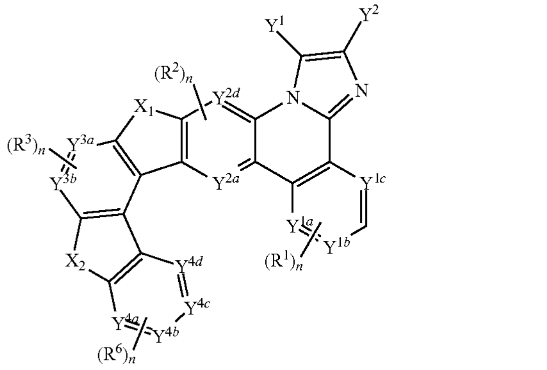
General Formula 30
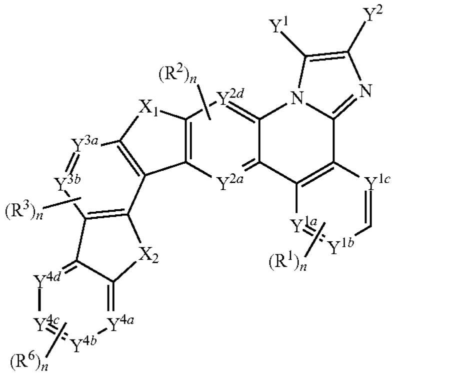
General Formula 31
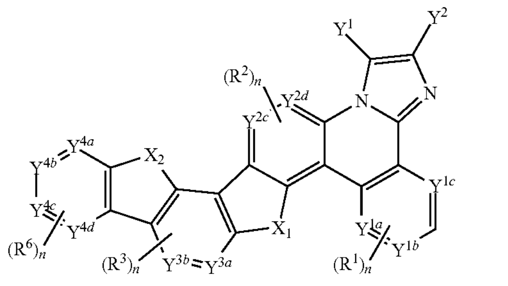

-continued
General Formula 32
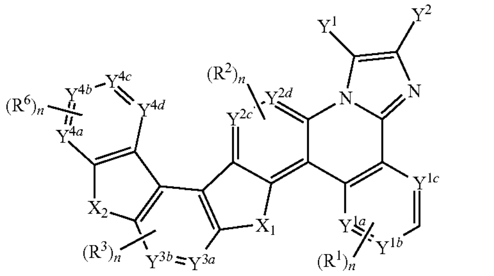
General Formula 33
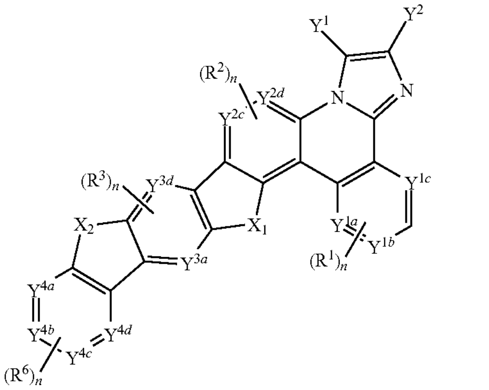
General Formula 34
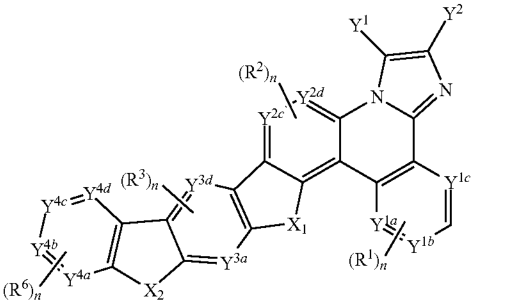
General Formula 35
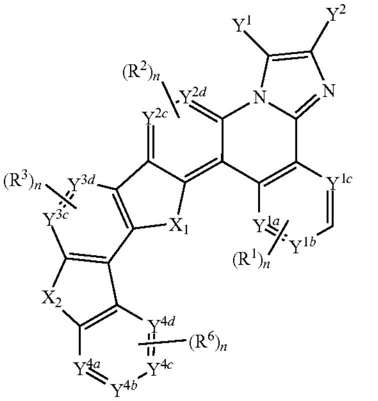
-continued
General Formula 36
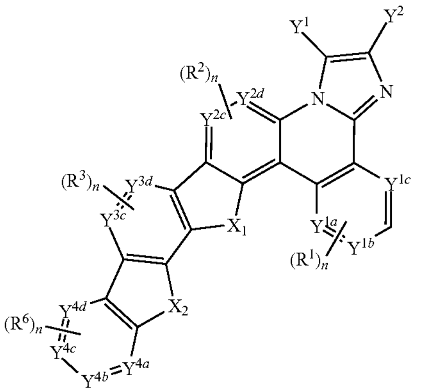
General Formula 37
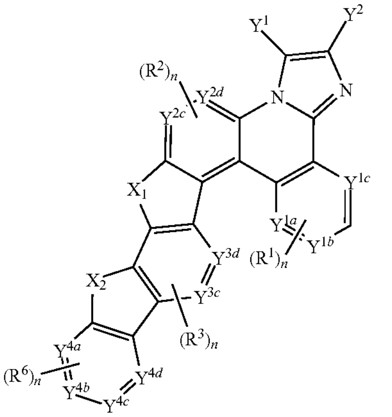
General Formula 38
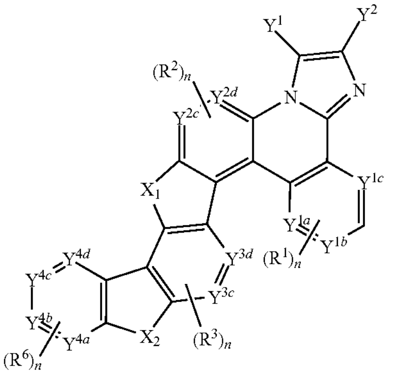
General Formula 39
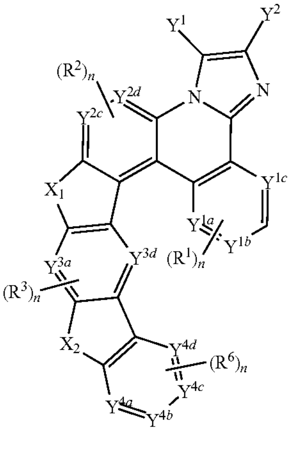

-continued

General Formula 40

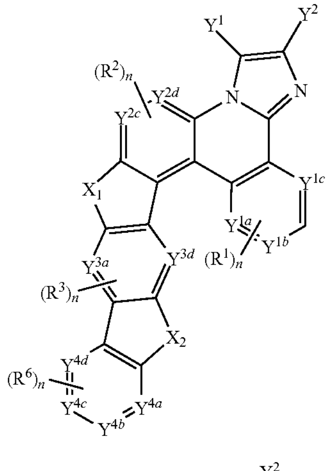

General Formula 41

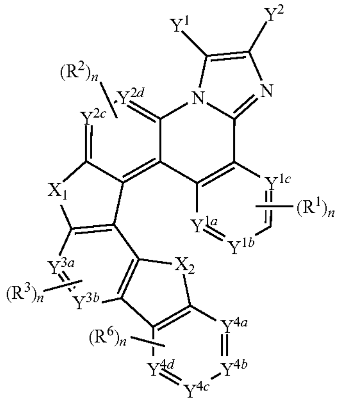

General Formula 42

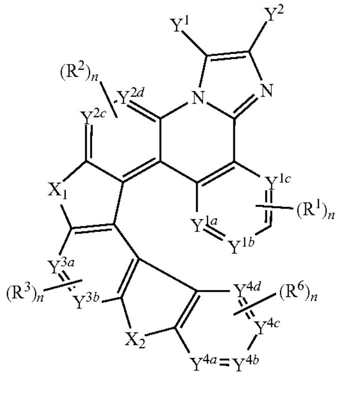

In one embodiment, two adjacent $R^2$ together represent a group of Formula A and two adjacent $R^2$ together represent a group of Formula B:

Formula B

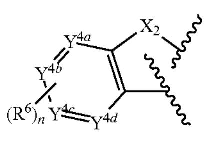

wherein waved lines indicate bonds to the respective $Y^{2a}$ and $Y^{2b}$, or $Y^{2c}$ and $Y^{2d}$;

$Y^{4a}$, $Y^{4b}$, $Y^{4c}$ and $Y^{4d}$ each independently represents C or N;

$X_2$ independently represents C, N, Si, O, S, Ge, P, As, Se, B, Al, or Bi, or if valency permits, $X_2$ independently represents $CR^7$, $SiR^7$, $GeR^7$, $NR^7$, P=O, As=O, B, $BR^7$, $AlR^7$, Bi=O, $CR^7R^8$, C=O, $SiR^7R^8$, $GeR^7R^8$, $PR^7$, $PR^7R^8$, $R^7P$=O, $AsR^7$, $R^7As$=O, S=O, $SO_2$, Se=O, $SeO_2$, $BR^7$, $BR^7R^8$, $AlR^7$, $AlR^7R^8$, $R^7Bi$=O, or $BiR^7$;

each of $R^6$, $R^7$, and $R^8$ is independently absent or present as a single substituent or multiple substituents, valency permitting, and each of $R^6$, $R^7$, and $R^8$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof; any two of $R^6$, $R^7$, and $R^8$ may together form a ring; and n is an integer, valency permitting.

In one embodiment, the compound is represented by one of the following General Formulae:

General formula 43

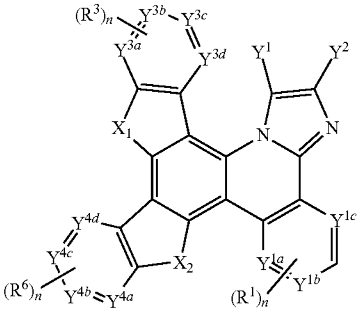

General formula 44

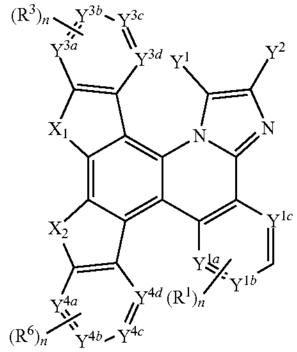

General formula 45

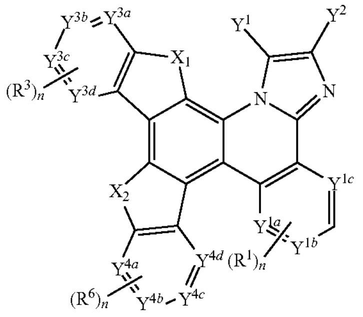

-continued
General formula 46
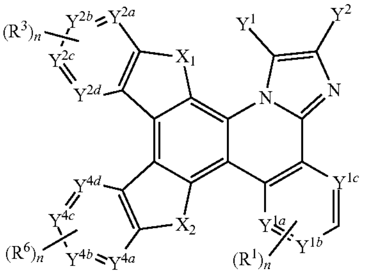
General formula 47
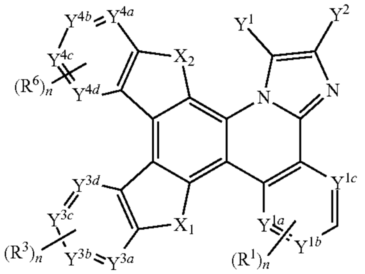
General formula 48
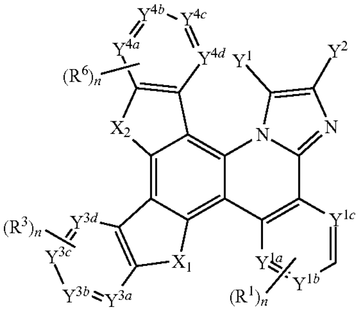
General formula 49
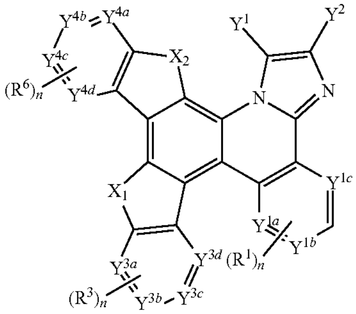
General formula 50
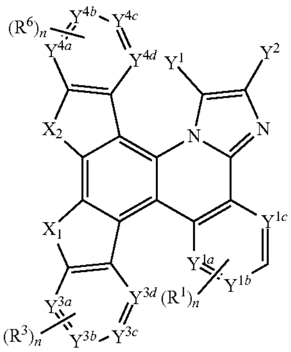
In one embodiment, the compound is represented by one of the following structures:
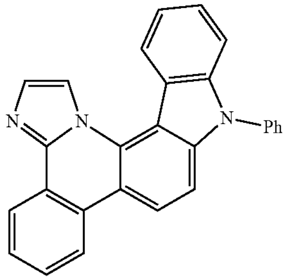
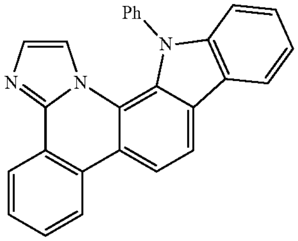
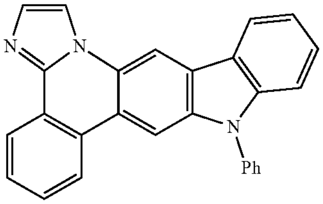
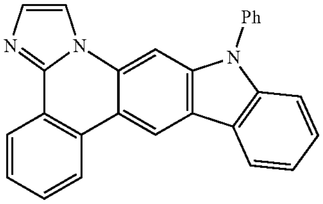
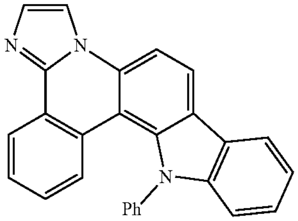
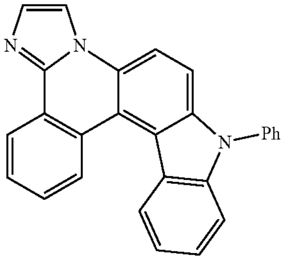
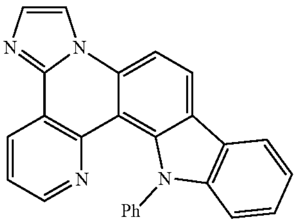

-continued
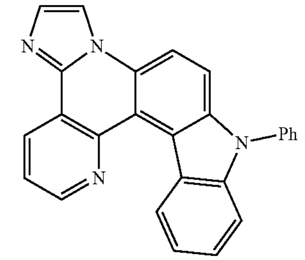
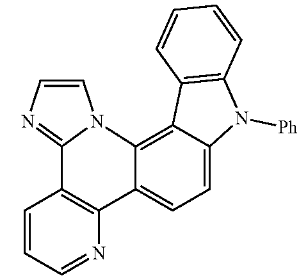
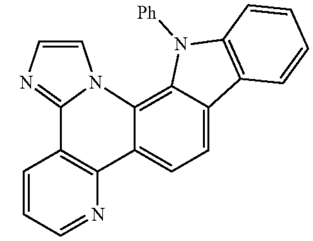
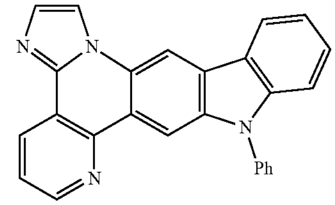
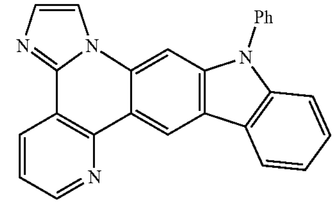
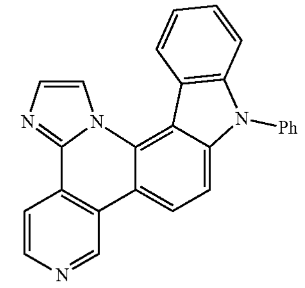
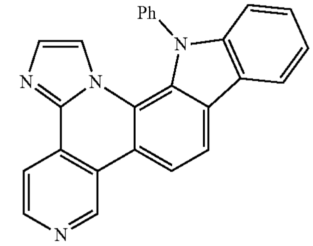
-continued
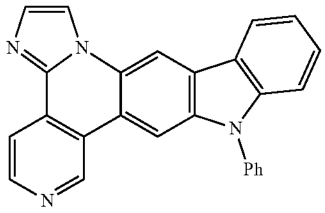
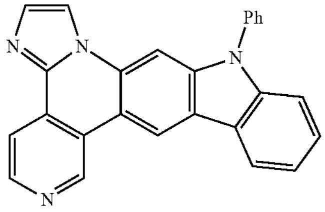
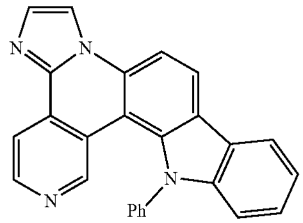
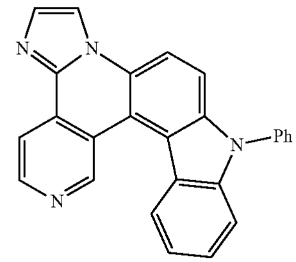
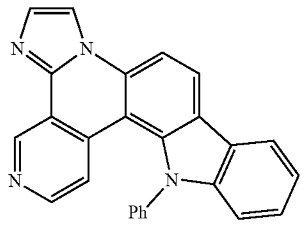
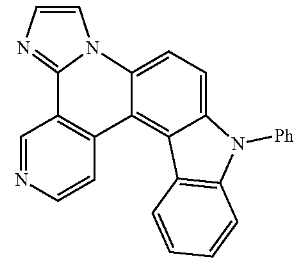
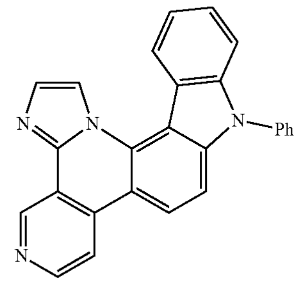

-continued
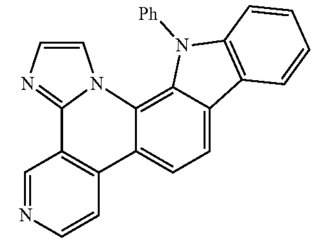
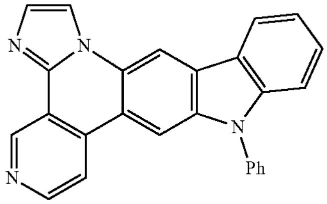
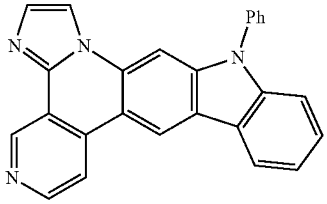
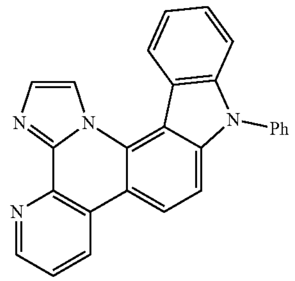
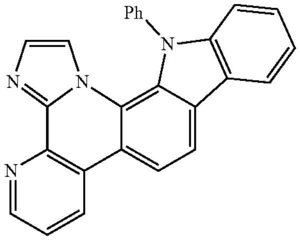
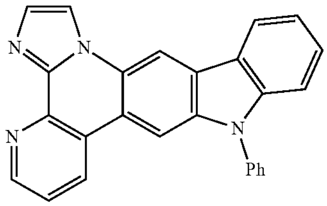
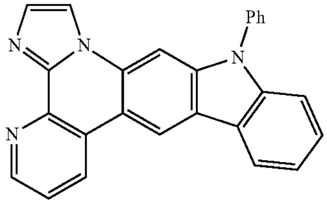
-continued
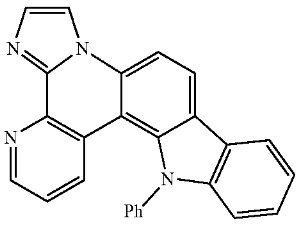
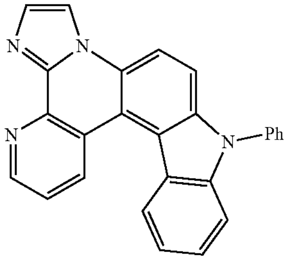
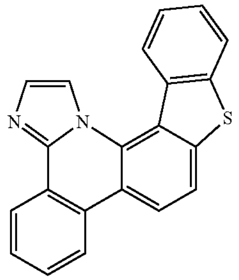
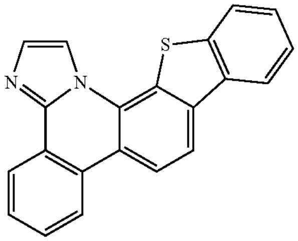
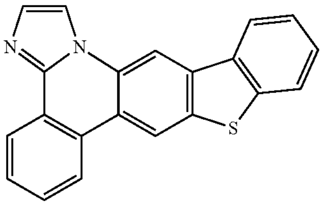
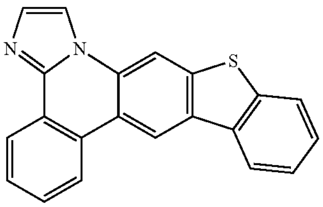
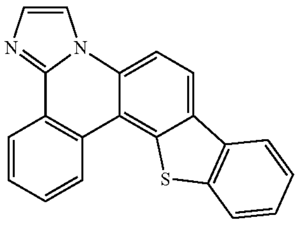

-continued
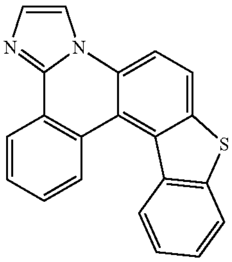
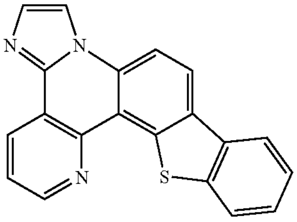
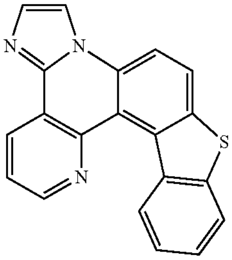
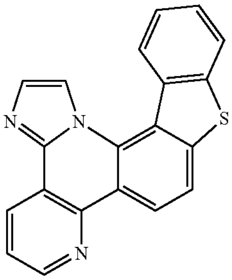
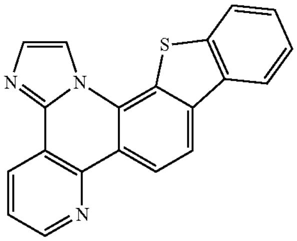
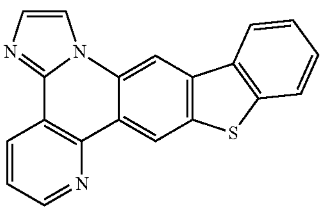
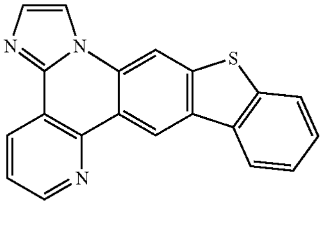
-continued
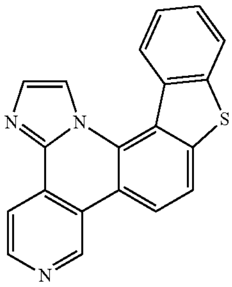
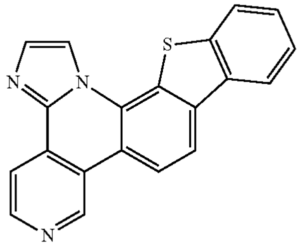
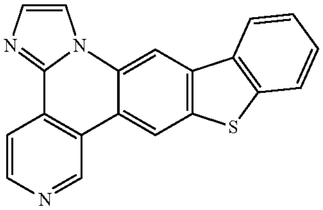
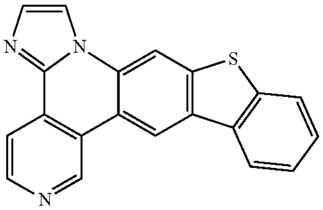
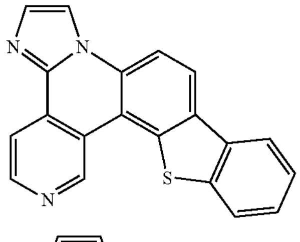
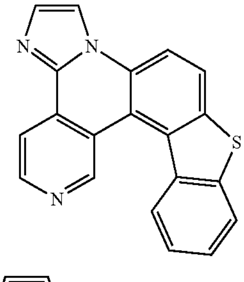
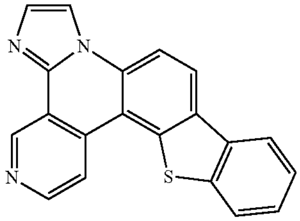

-continued
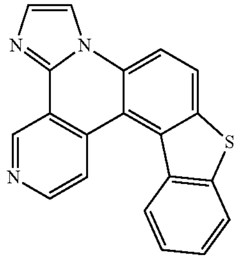
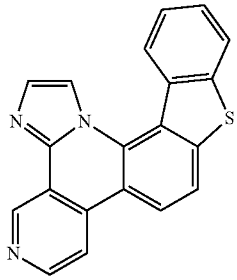
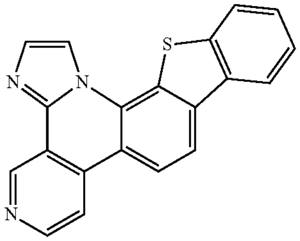
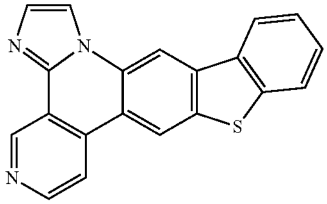
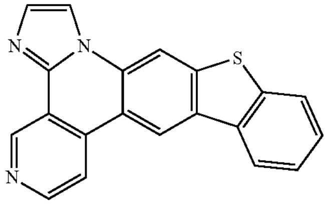
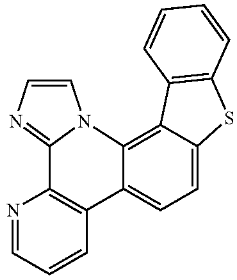
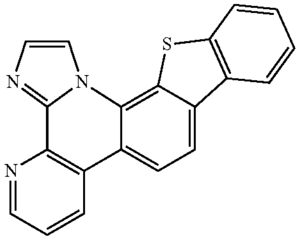
-continued
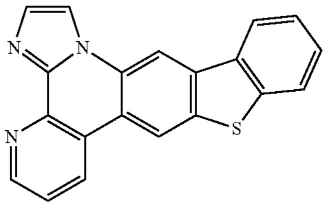
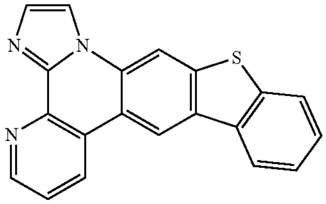
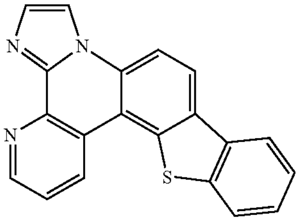
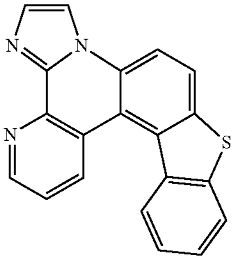
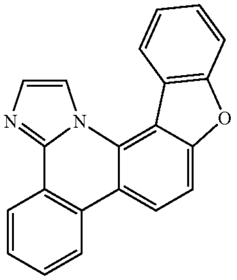
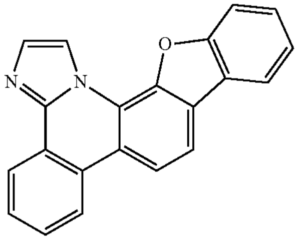
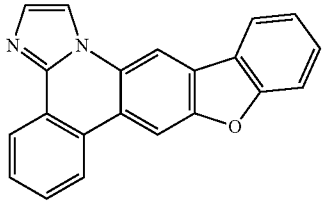

-continued
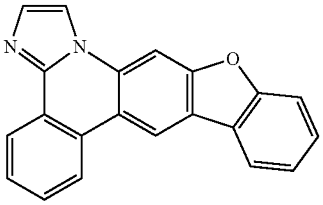
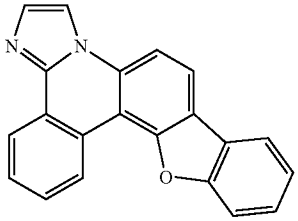
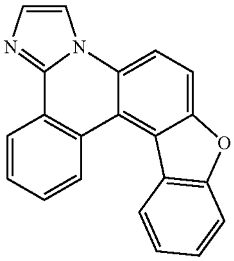
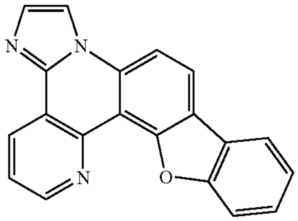
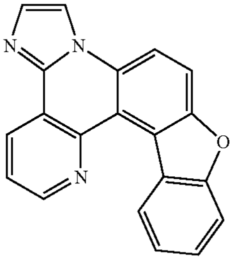
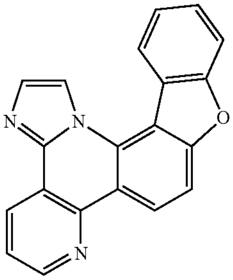
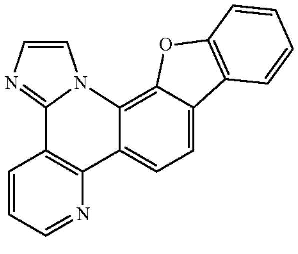
-continued
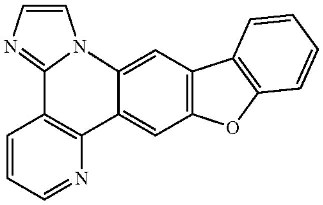
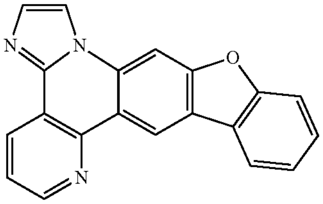
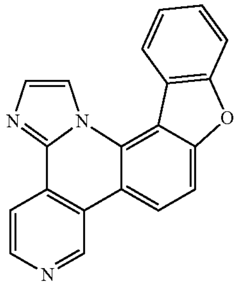
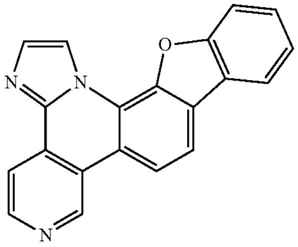
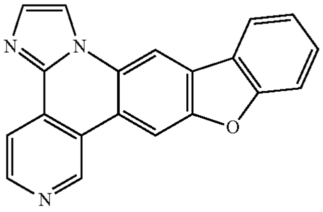
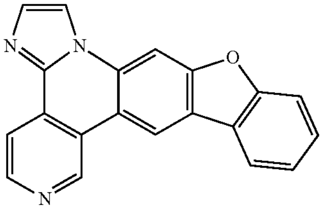
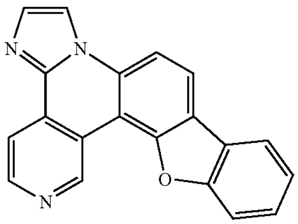

-continued
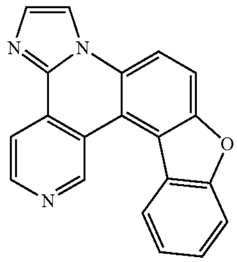
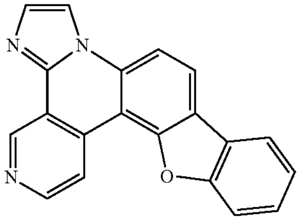
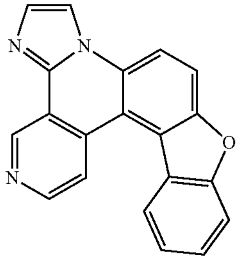
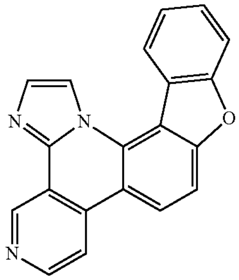
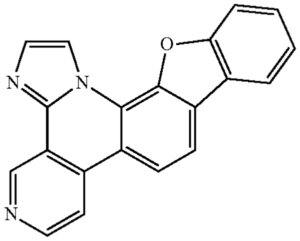
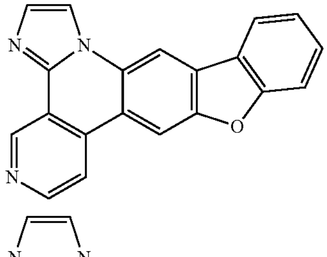
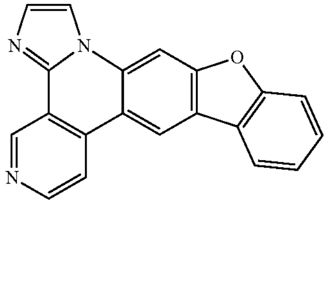
-continued
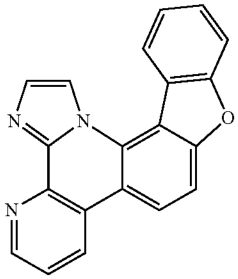
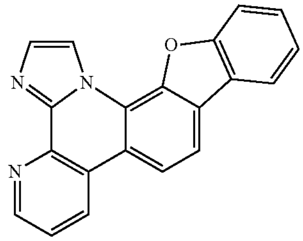
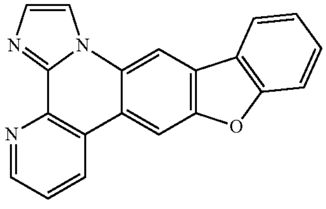
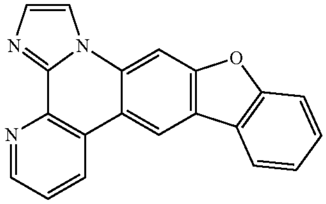
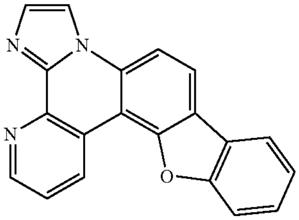
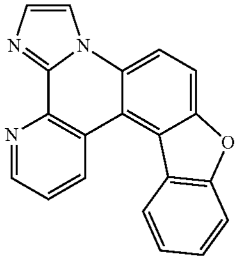
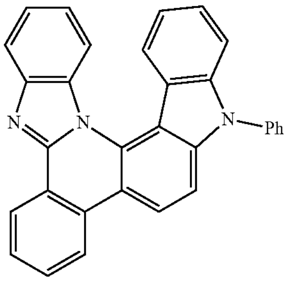

-continued
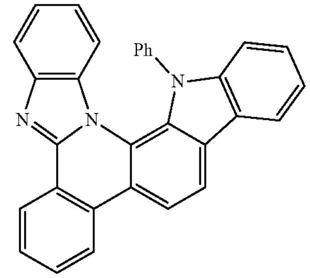
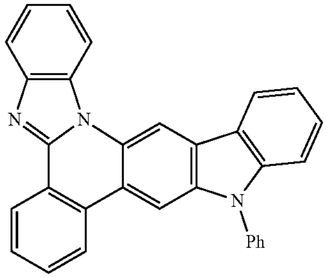
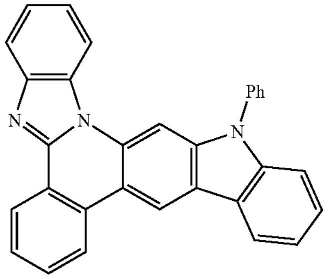
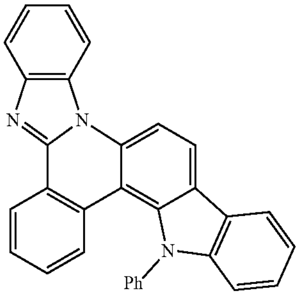
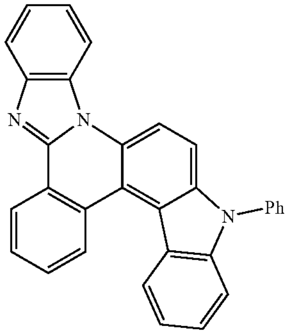
-continued
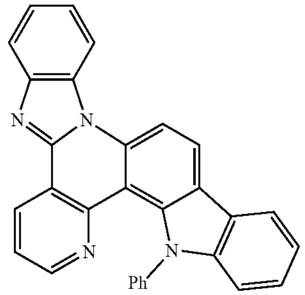
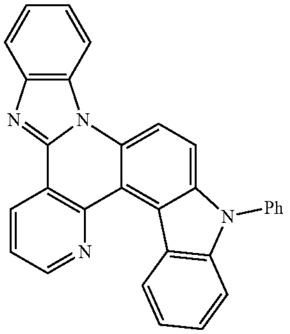
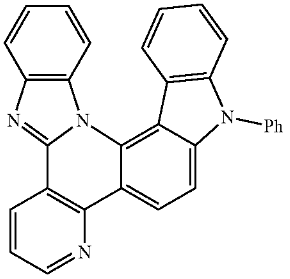
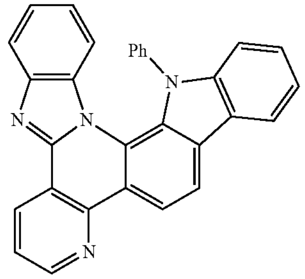
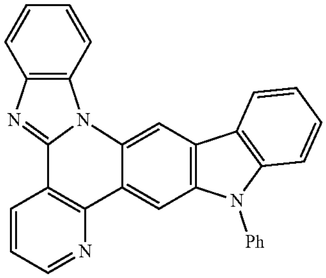

-continued
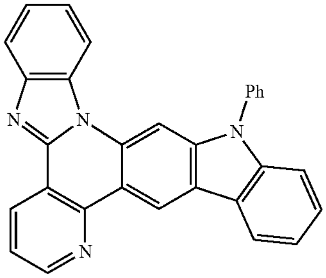
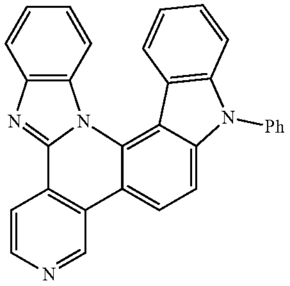
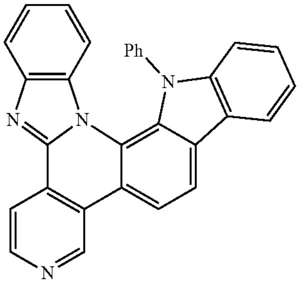
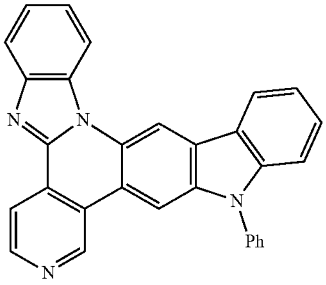
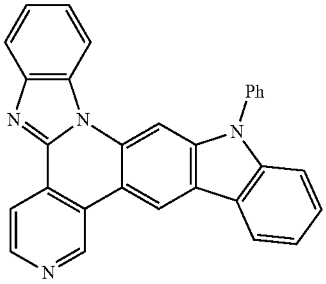
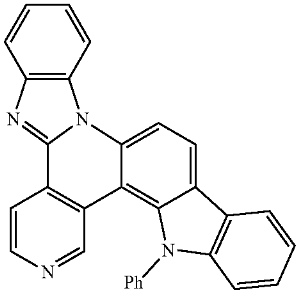
-continued
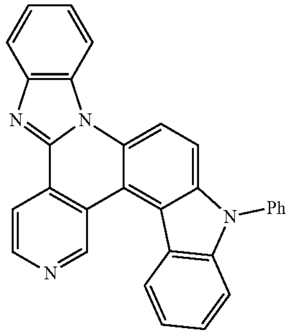
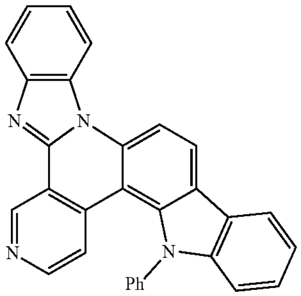
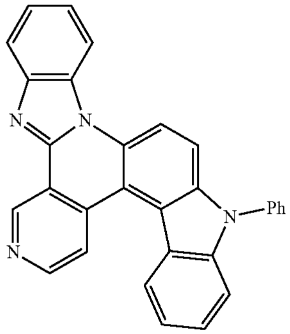
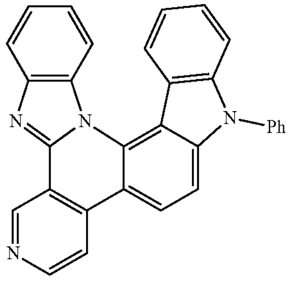
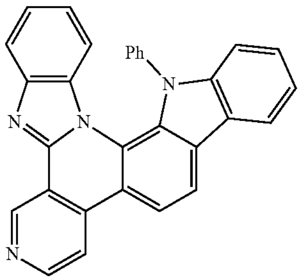

-continued
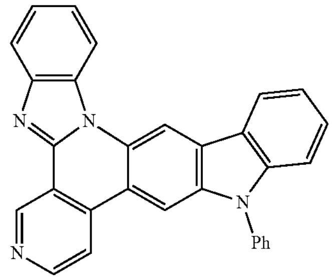
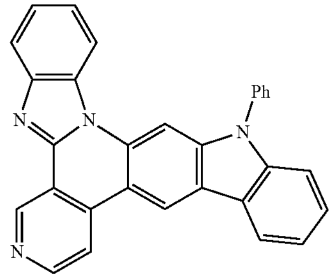
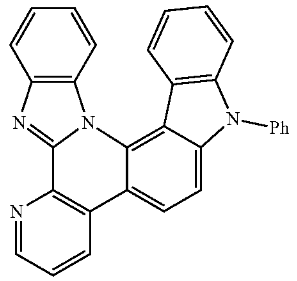
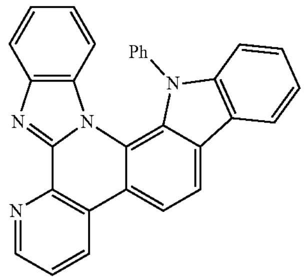
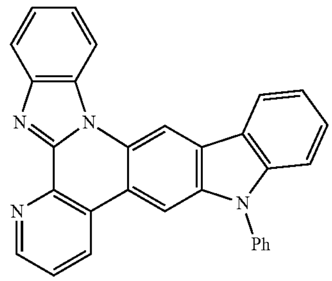
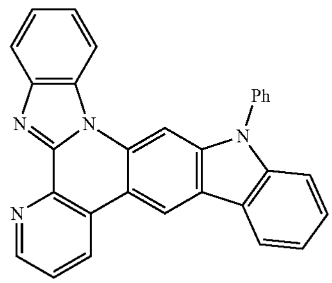
-continued
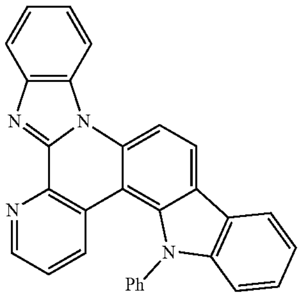
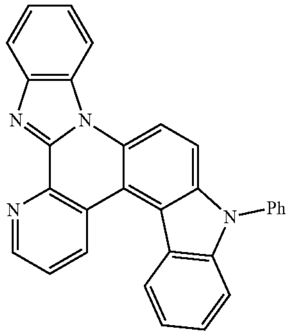
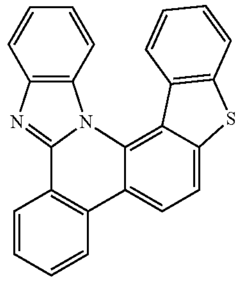
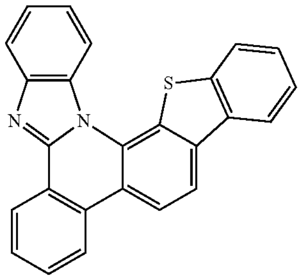
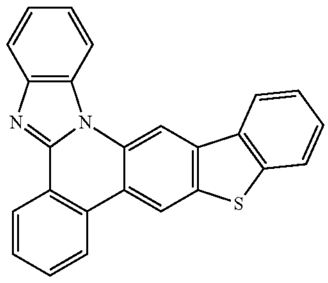

-continued
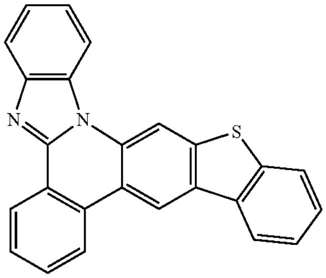
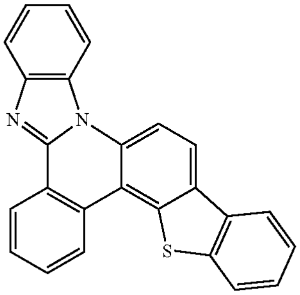
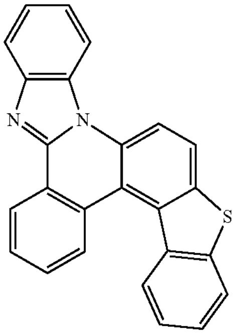
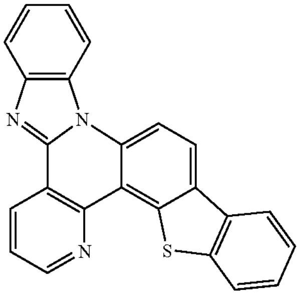
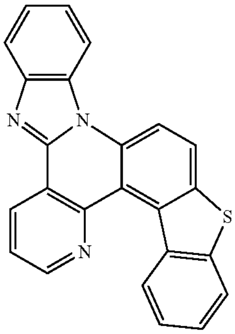
-continued
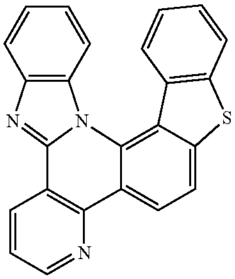
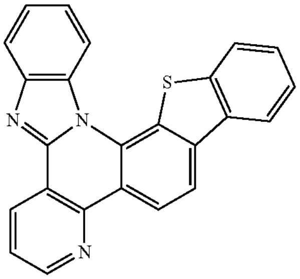
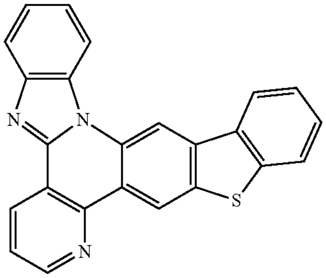
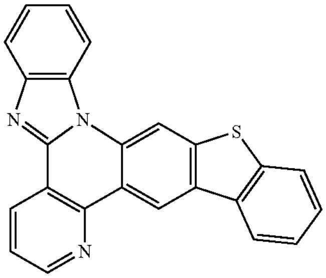
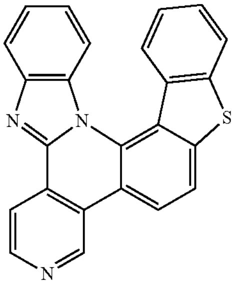
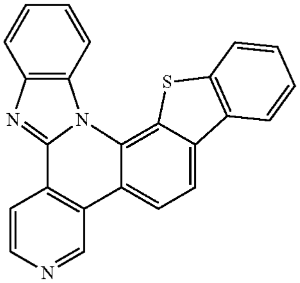

-continued
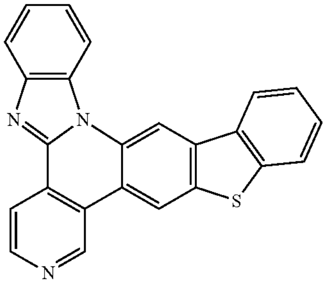
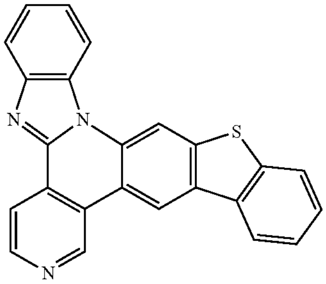
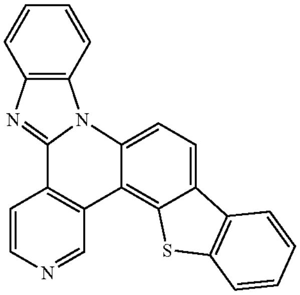
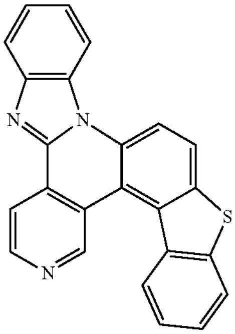
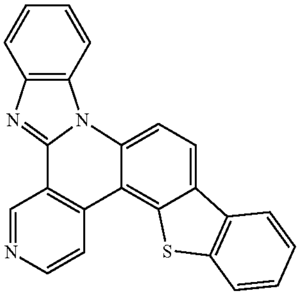
-continued
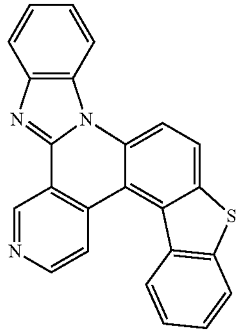
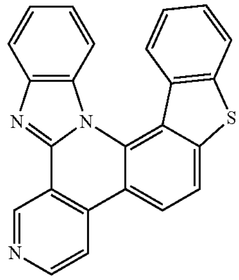
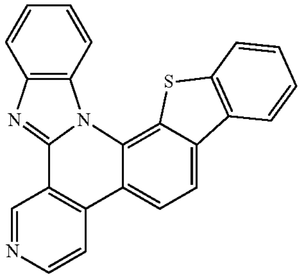
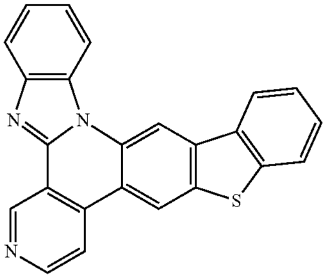
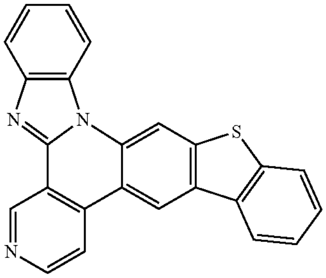
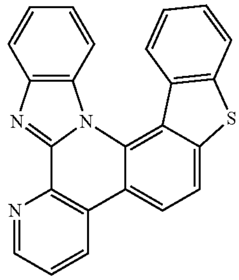

-continued
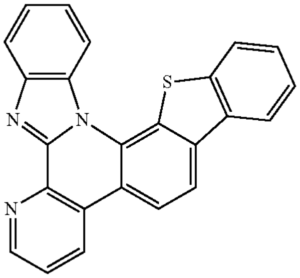
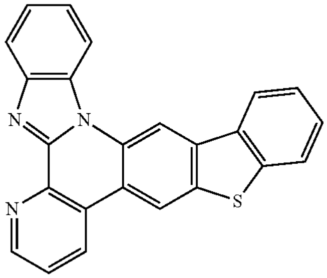
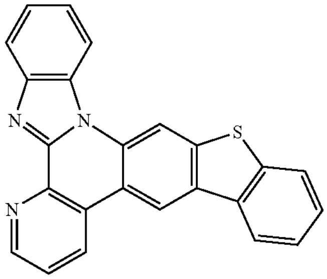
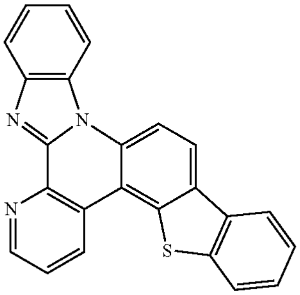
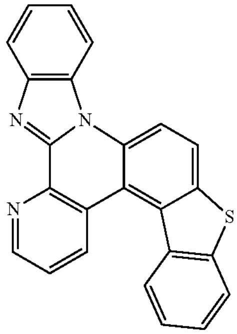
-continued
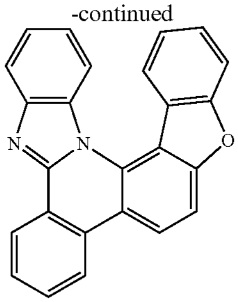
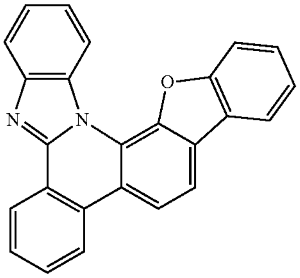
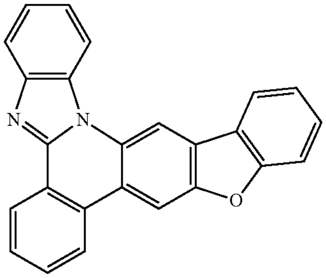
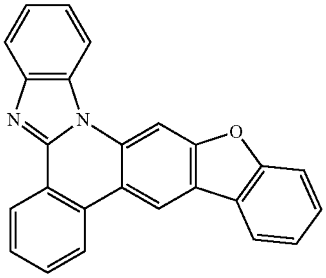
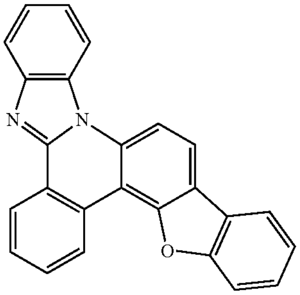
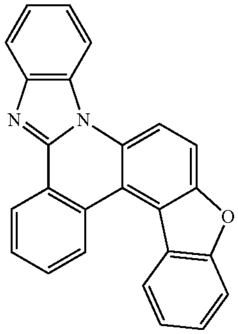

-continued
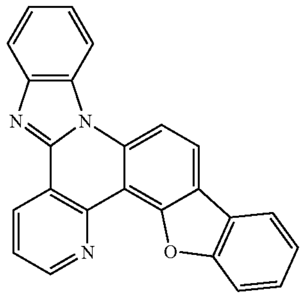
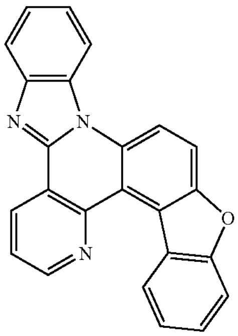
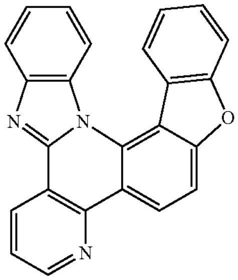
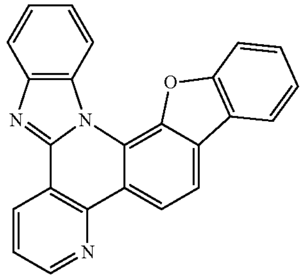
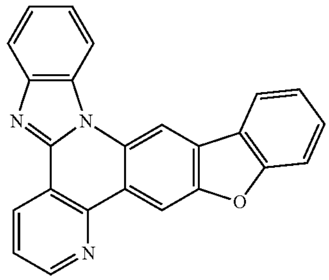
-continued
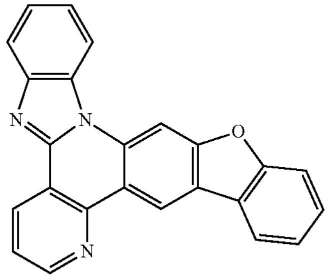
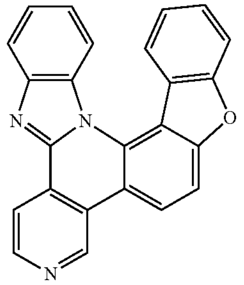
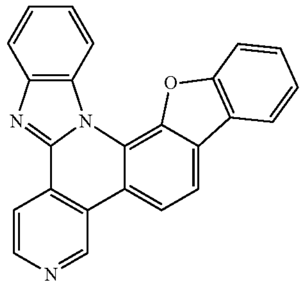
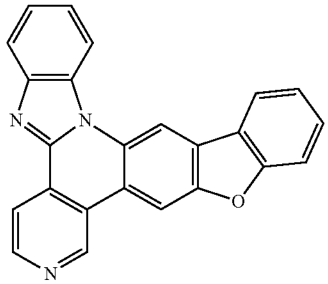
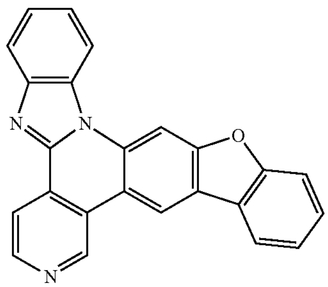
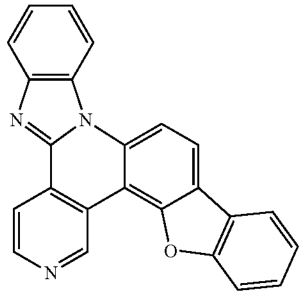

-continued
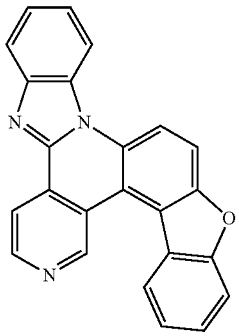
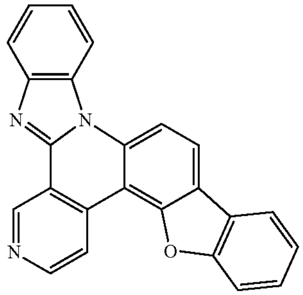
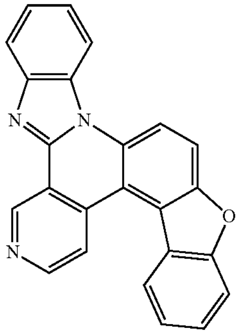
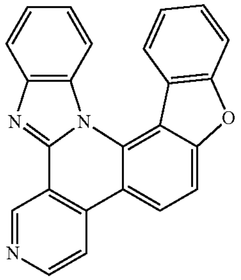
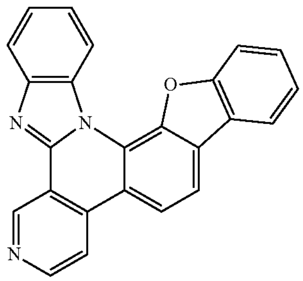
-continued
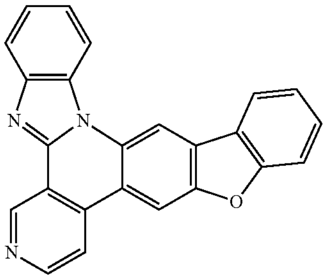
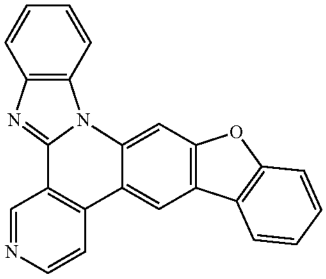
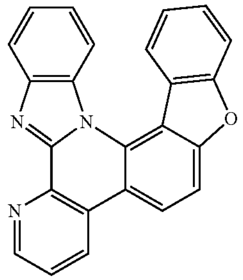
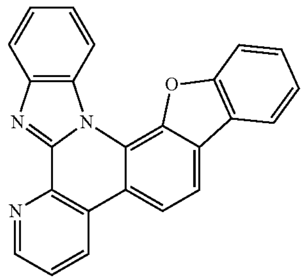
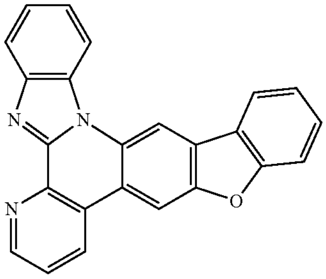
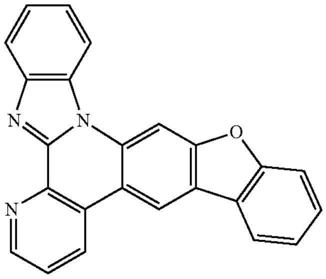

-continued
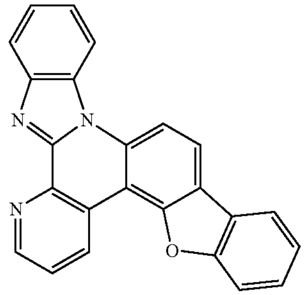
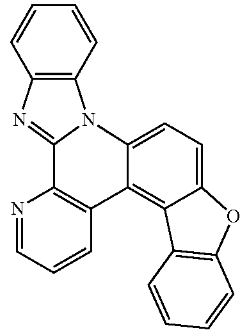
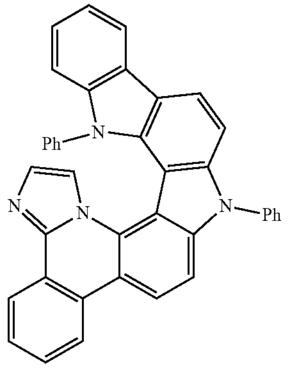
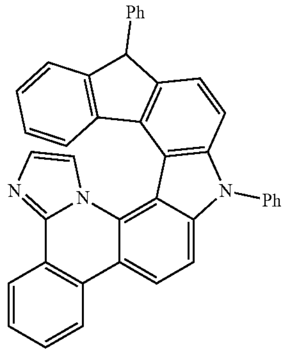
-continued
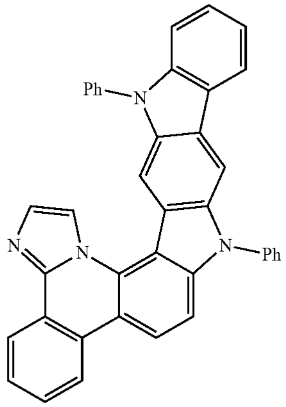
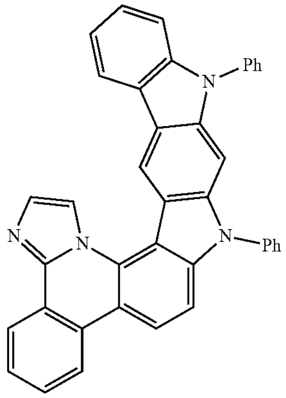
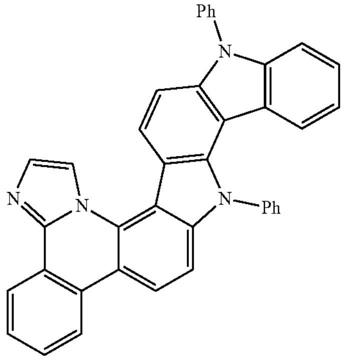
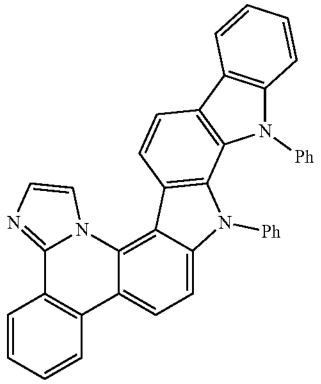

-continued
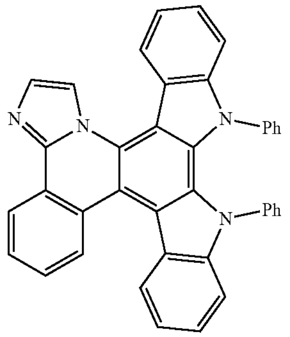
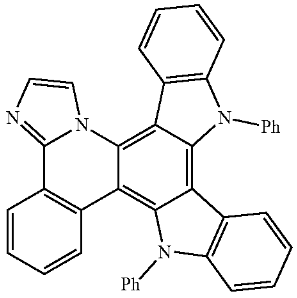
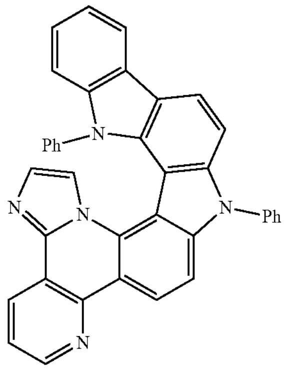
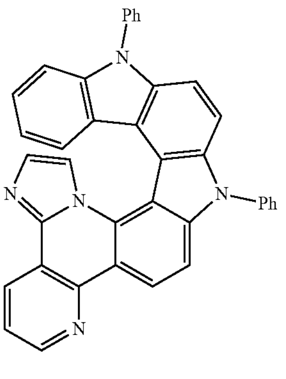
-continued
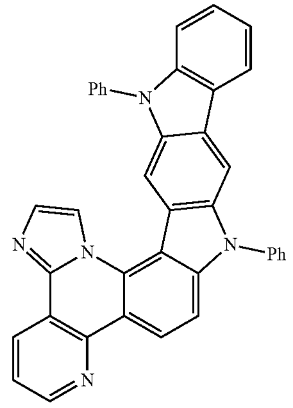
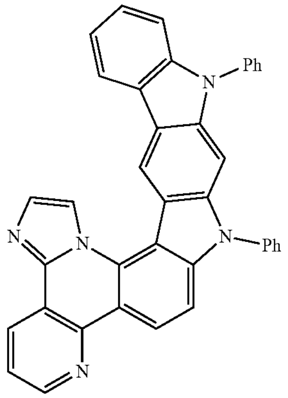
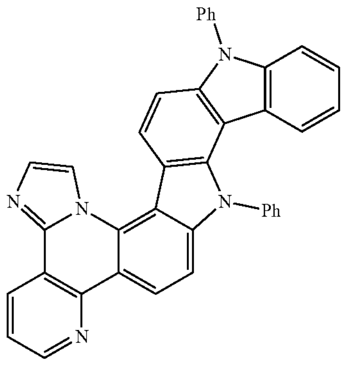
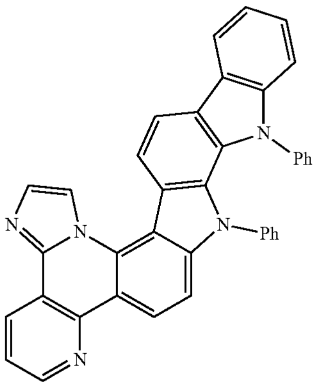

-continued
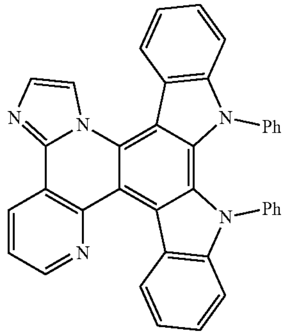
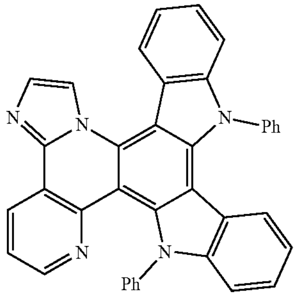
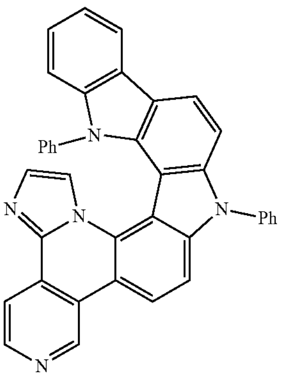
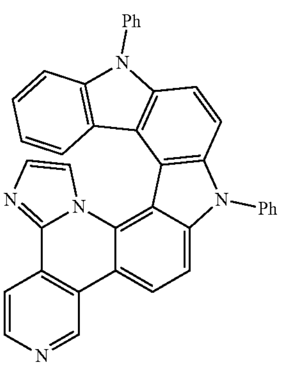
-continued
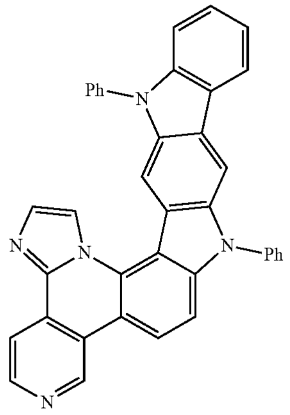
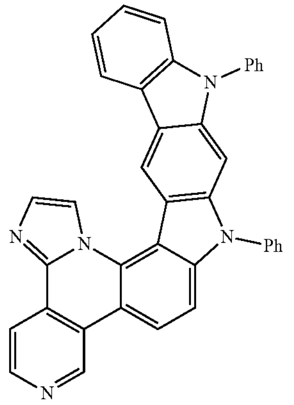
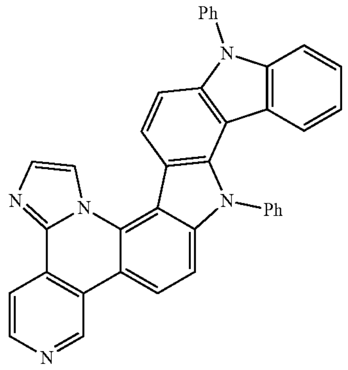
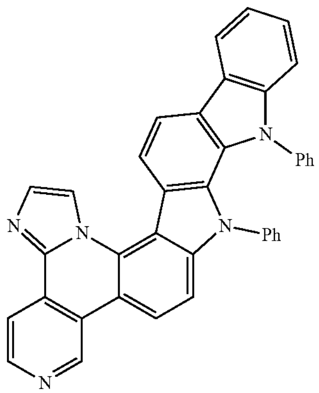

-continued
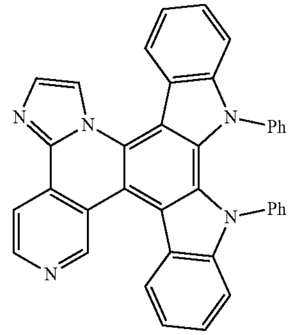
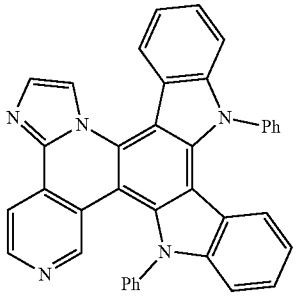
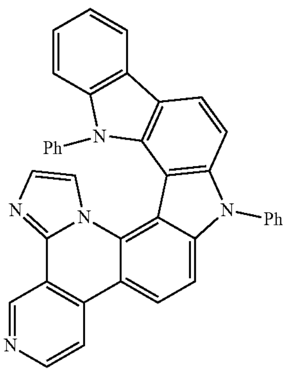
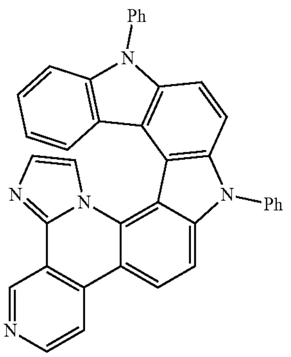
-continued
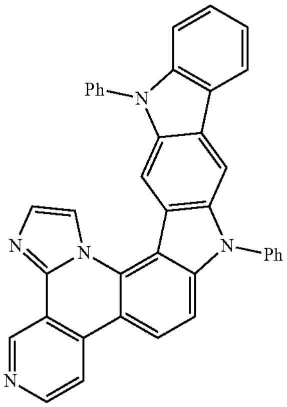
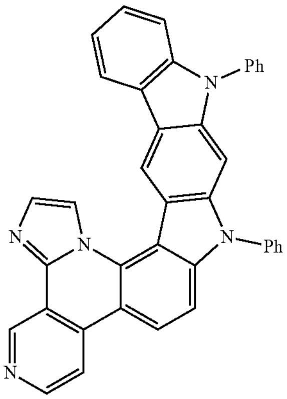
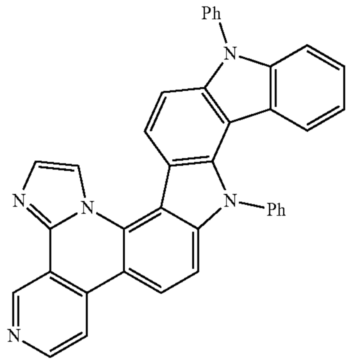
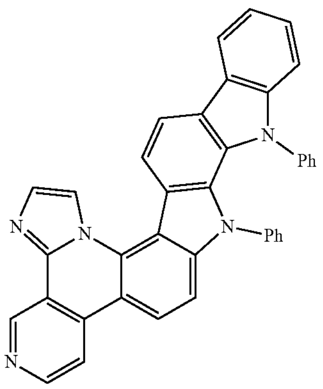

-continued
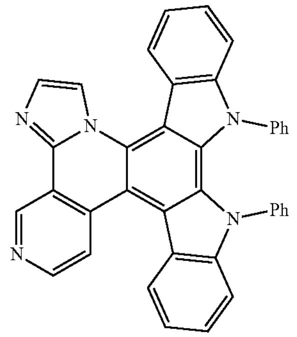
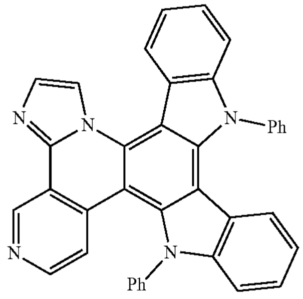
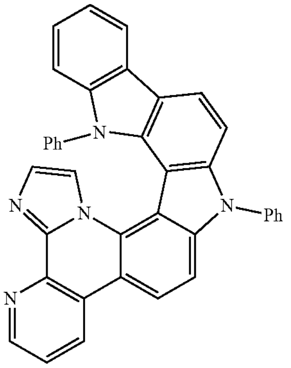
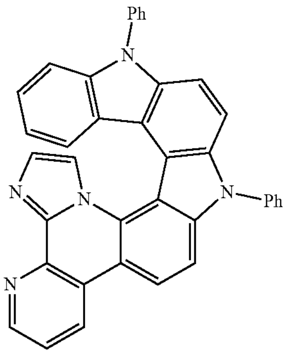
-continued
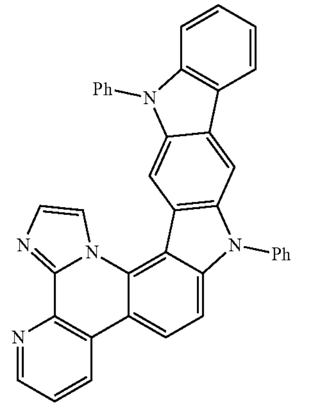
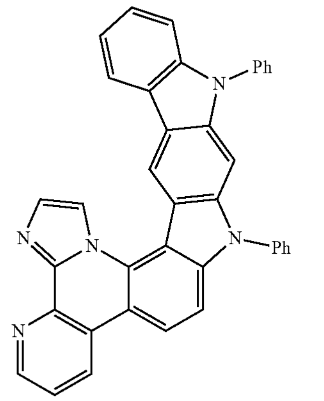
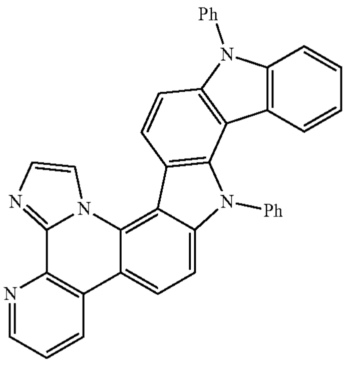
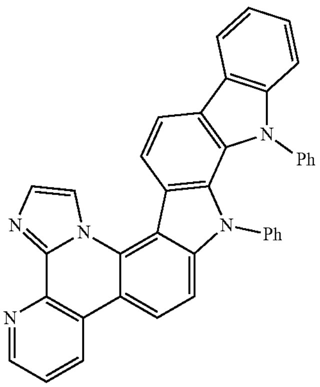

-continued
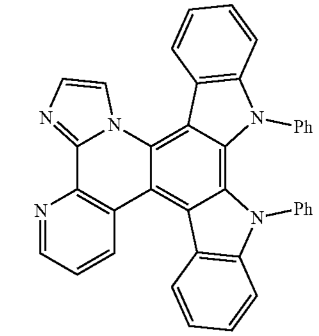
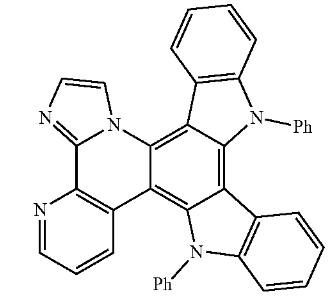
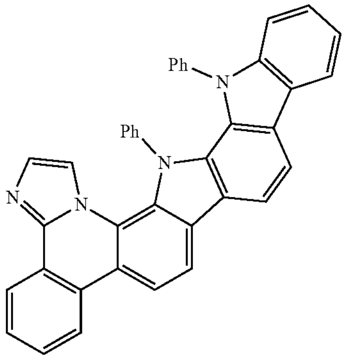
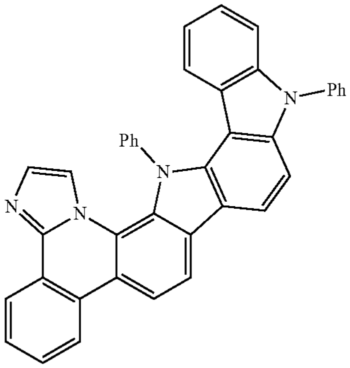
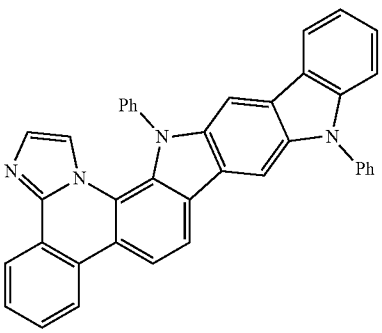
-continued
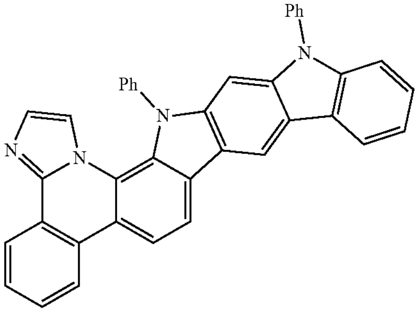
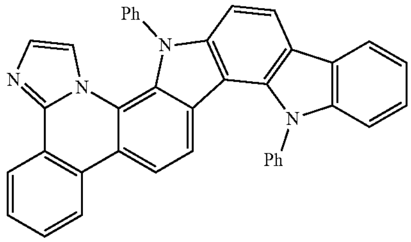
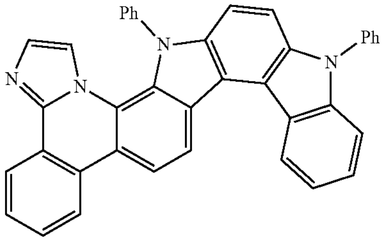
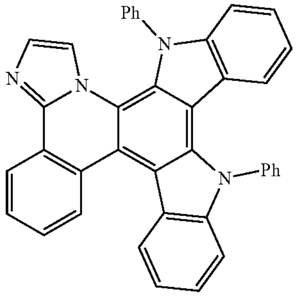
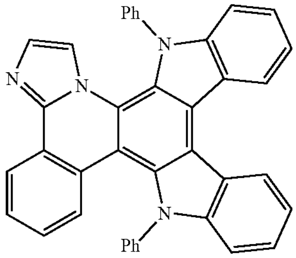
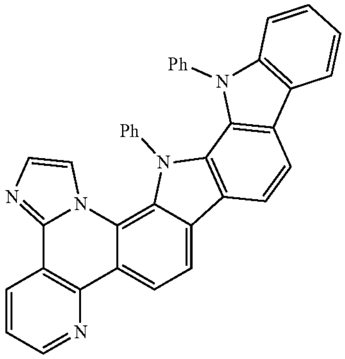

-continued
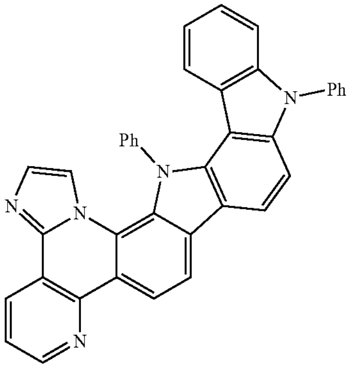
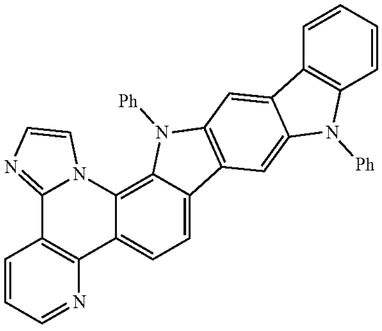
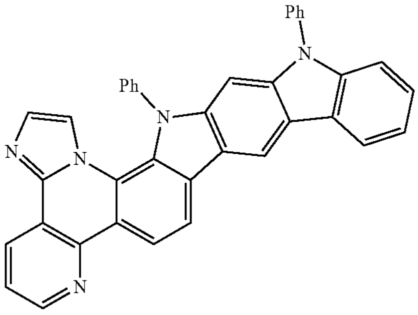
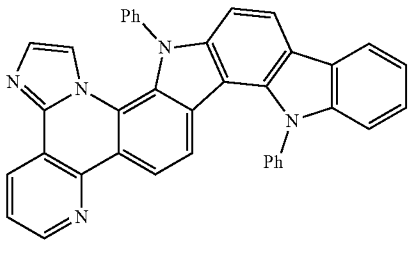
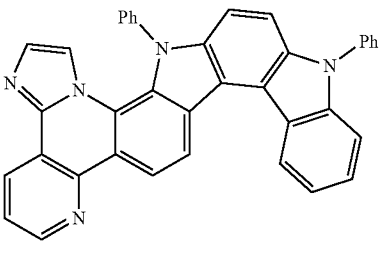
-continued
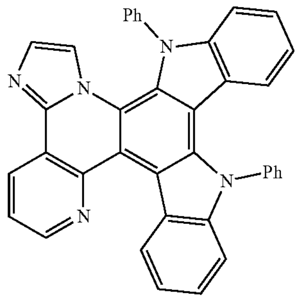
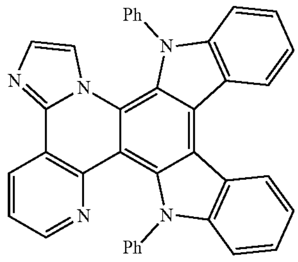
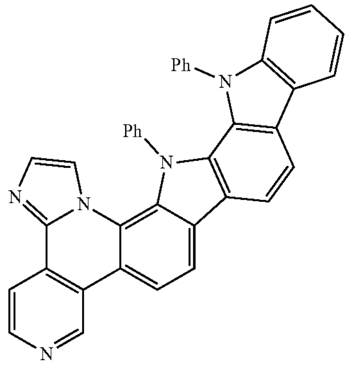
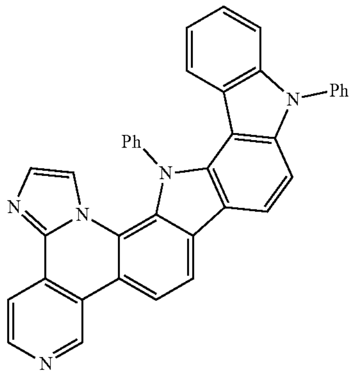
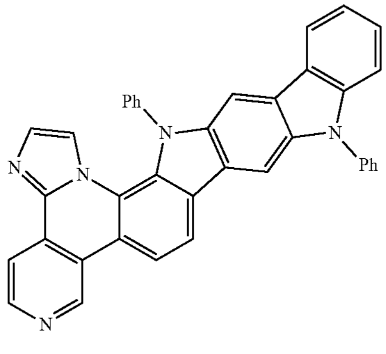

-continued
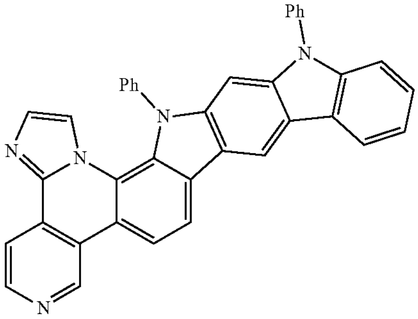
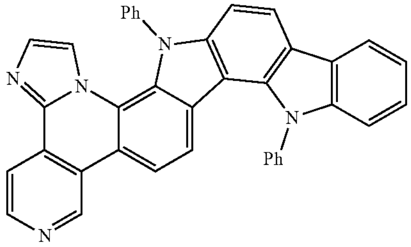
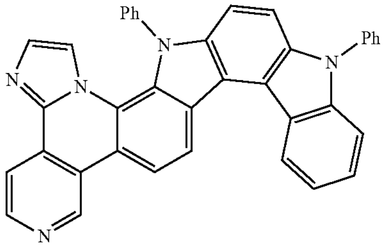
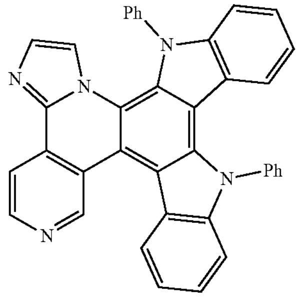
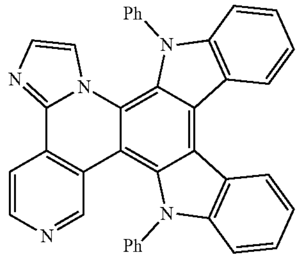
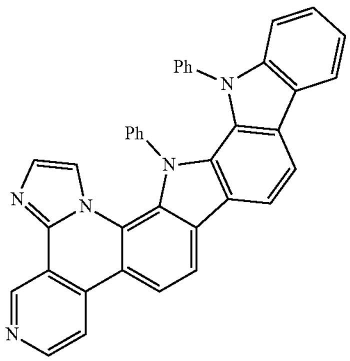
-continued
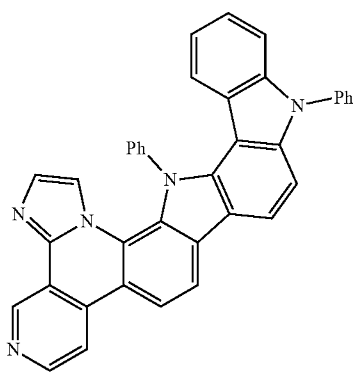
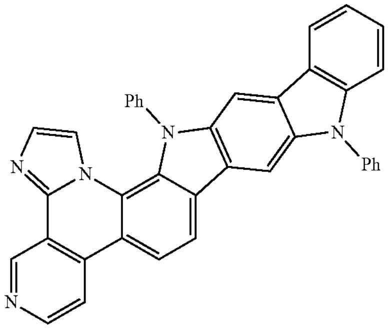
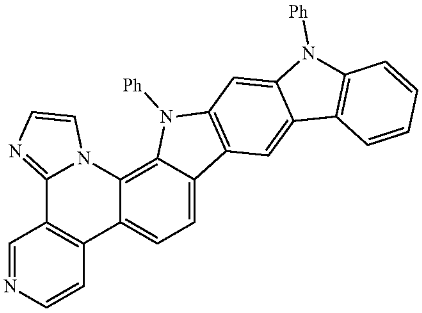
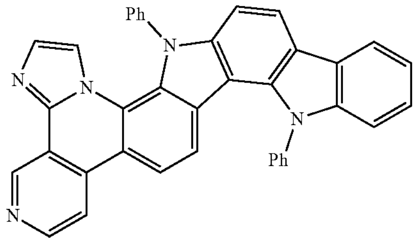
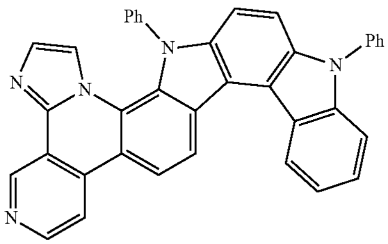

-continued
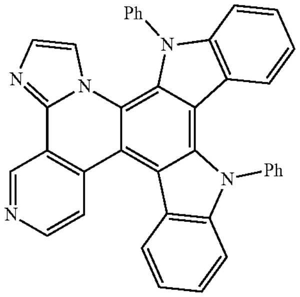
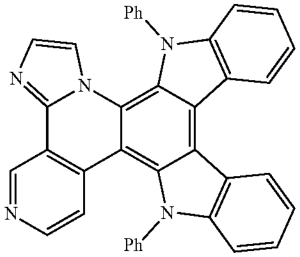
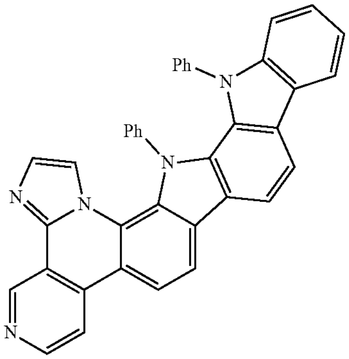
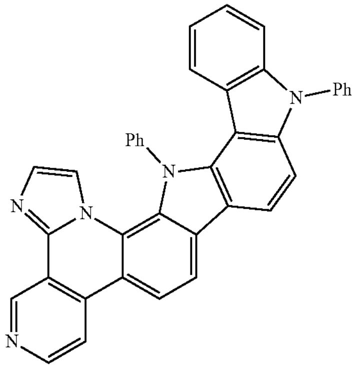
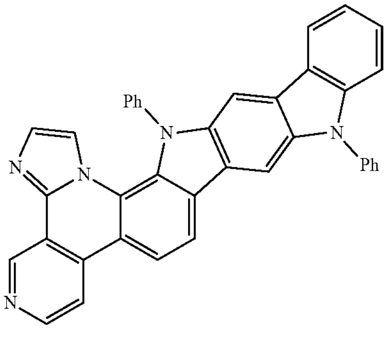
-continued
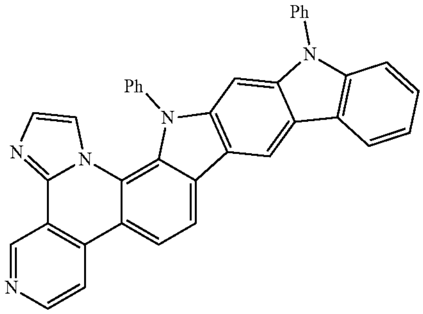
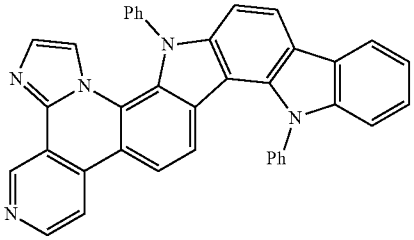
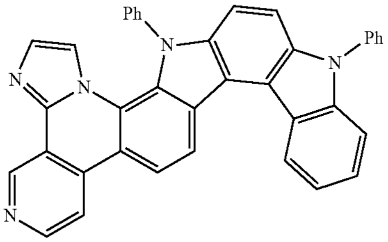
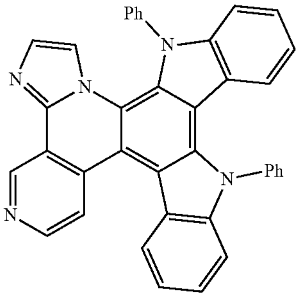
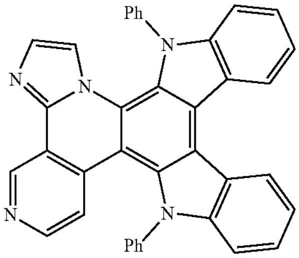
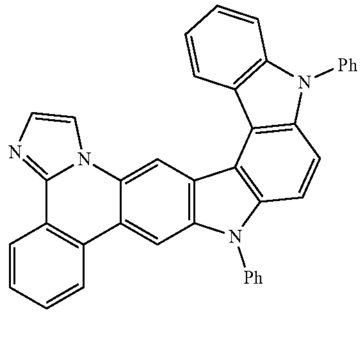

-continued
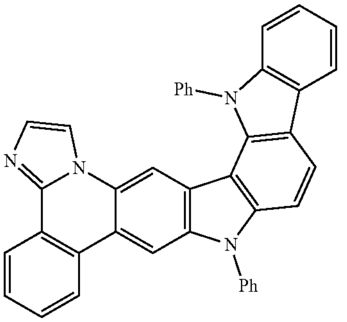
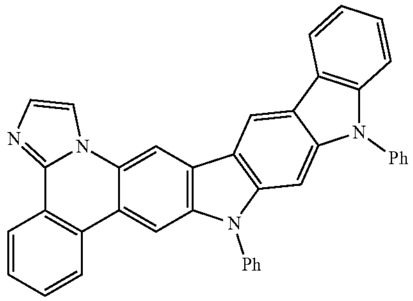
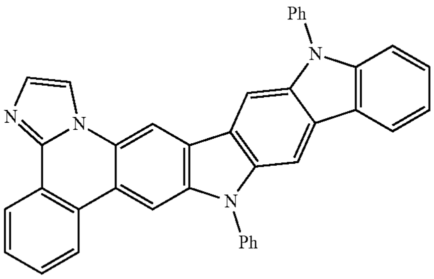
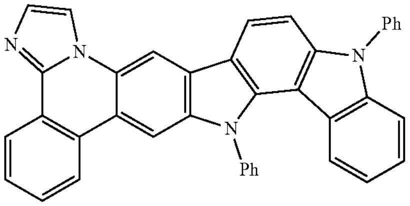
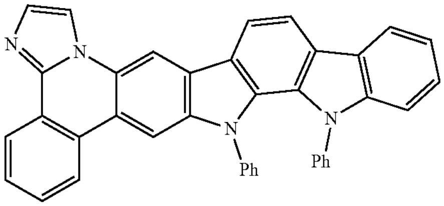
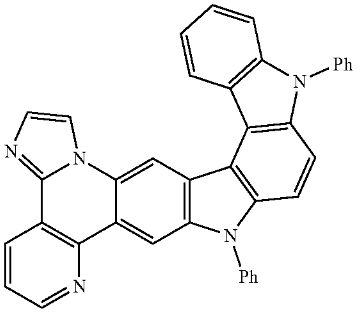
-continued
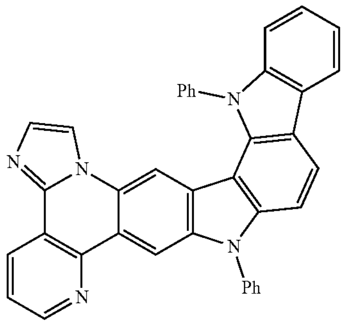
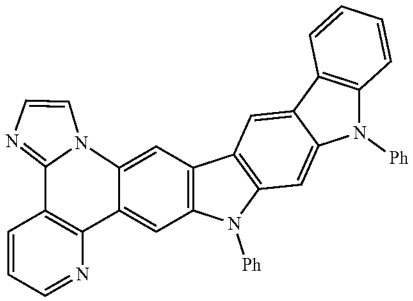
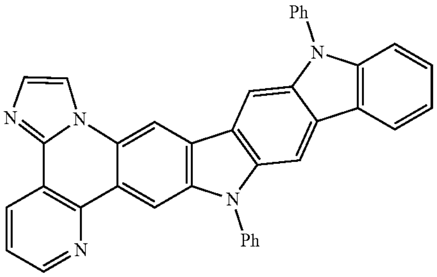
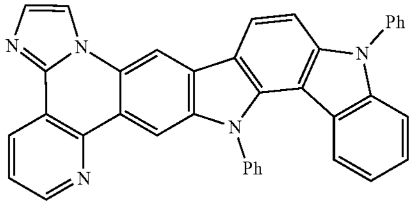
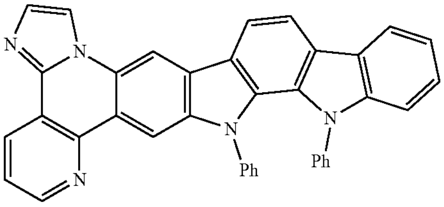
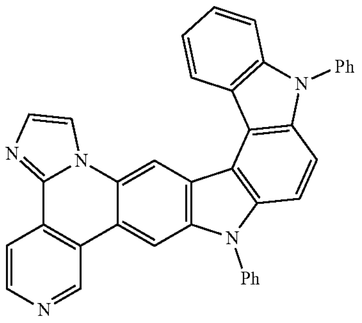

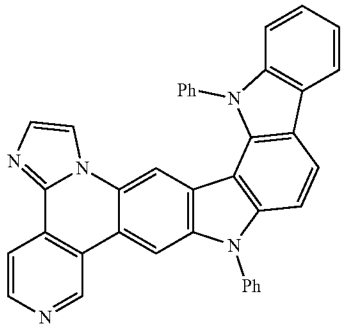
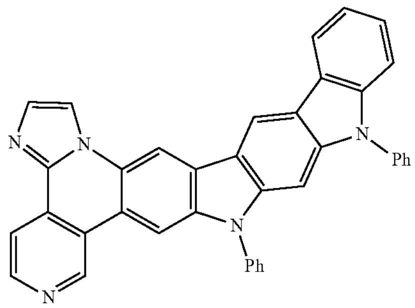
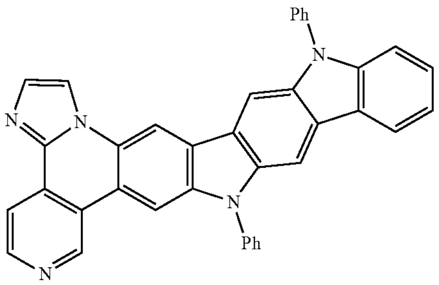
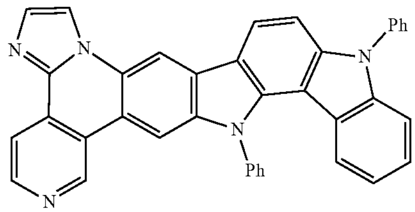
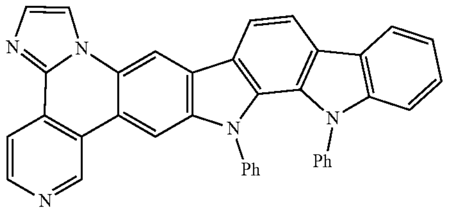
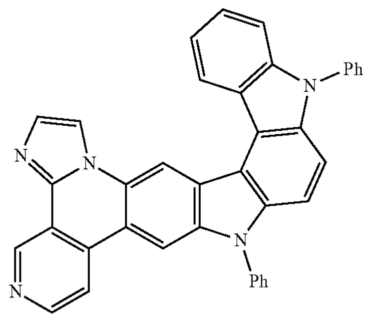
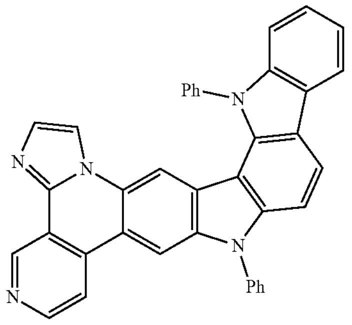
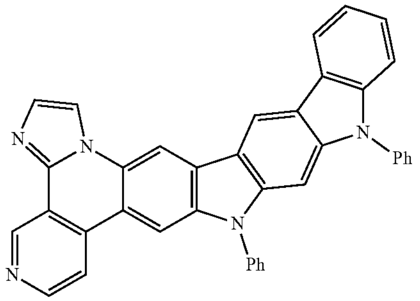
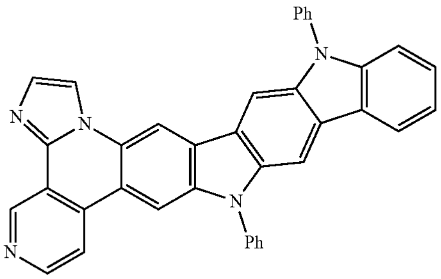
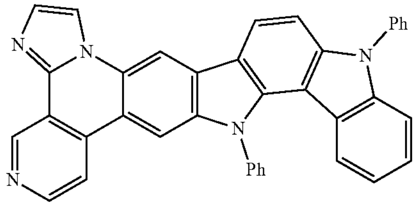
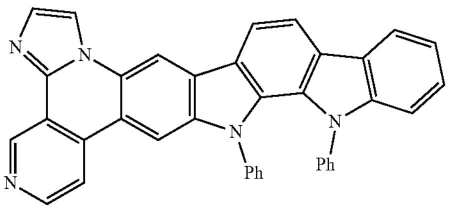
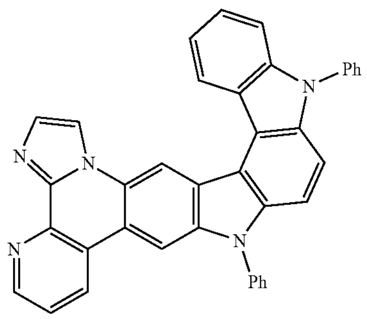

-continued
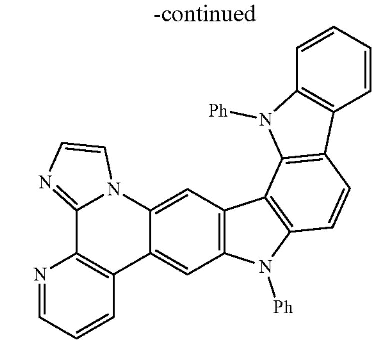
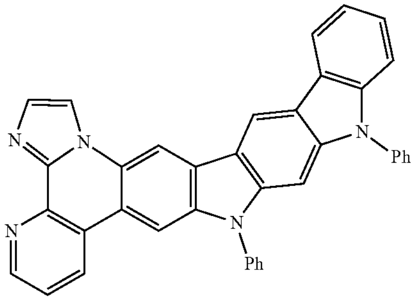
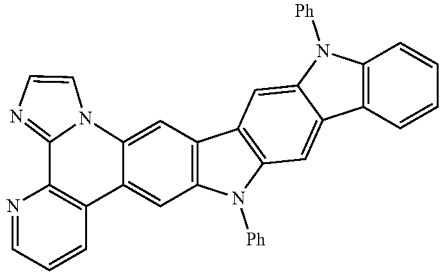
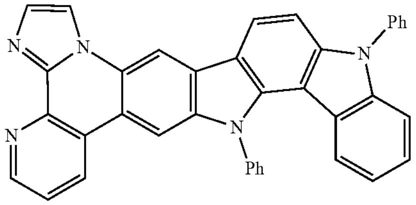
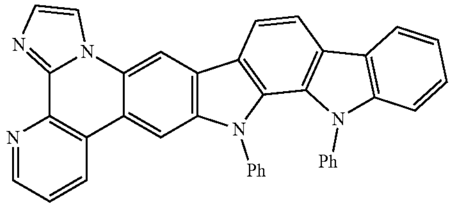
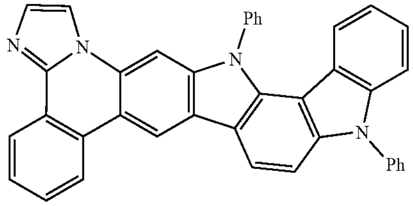
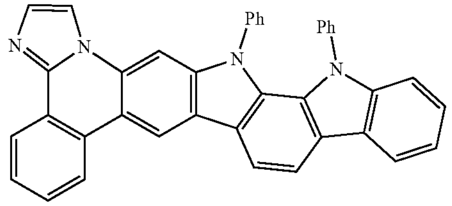
-continued
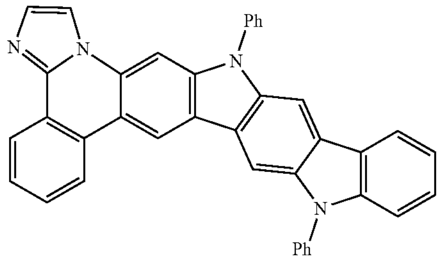
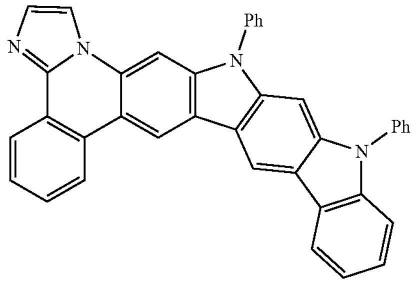
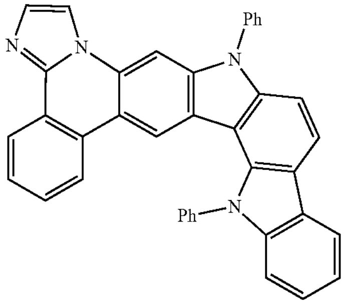
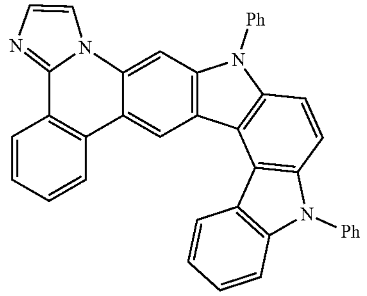
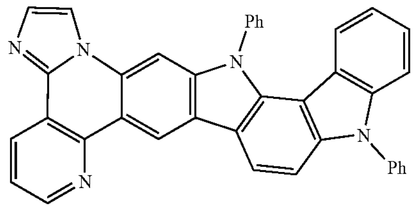
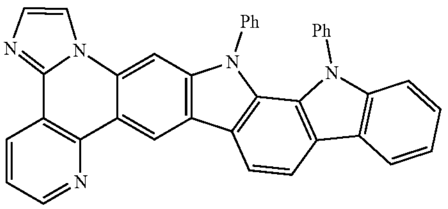

-continued
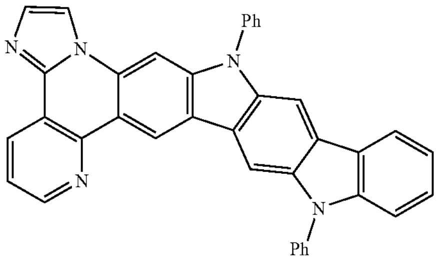
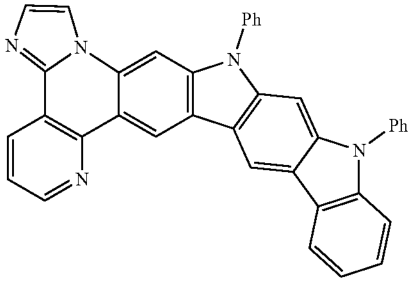
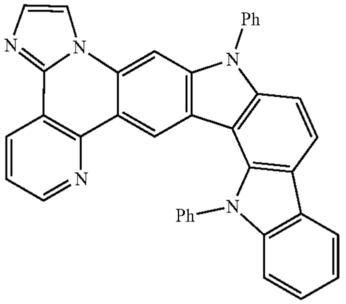
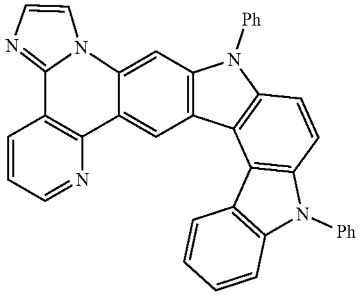
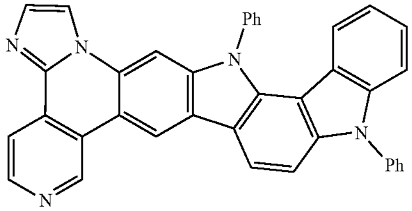
lp;2p
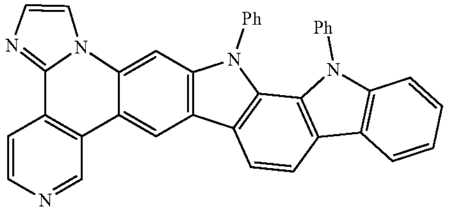
-continued
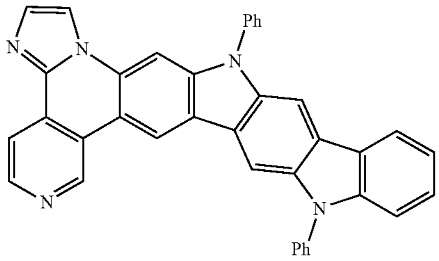
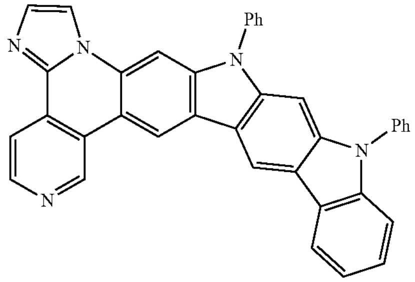
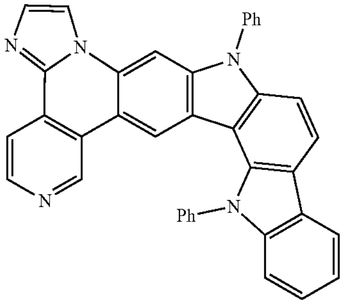
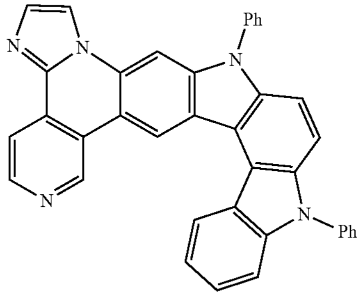
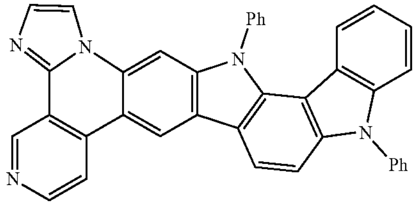
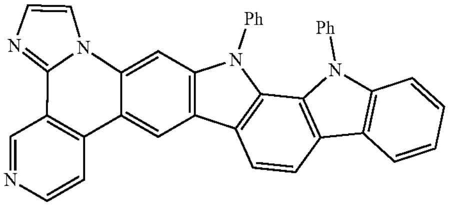

-continued
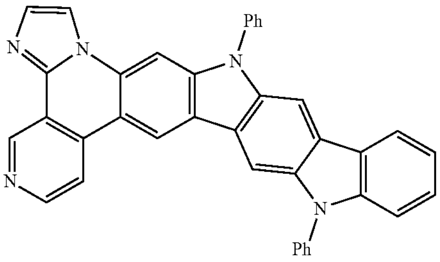
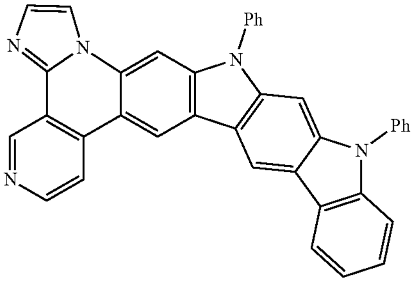
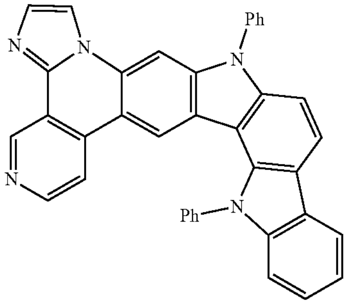
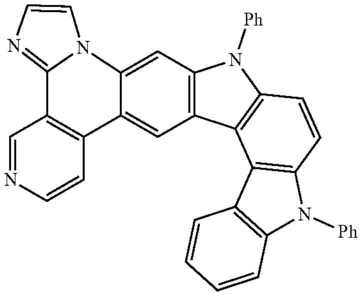
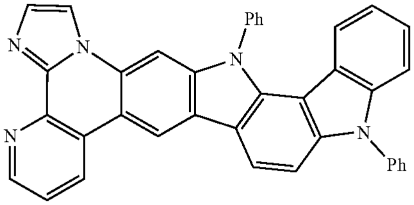
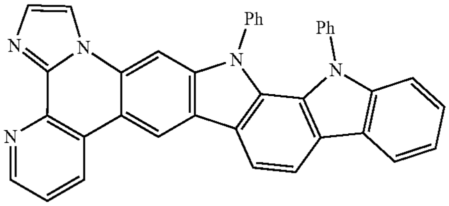
-continued
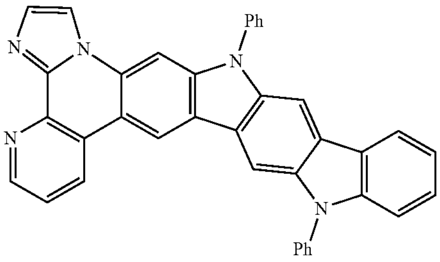
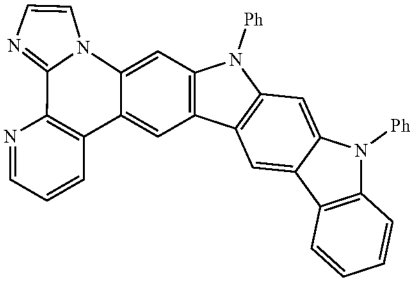
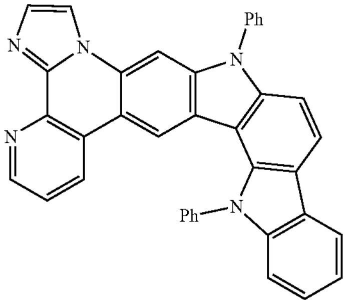
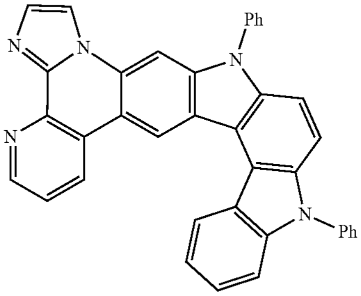
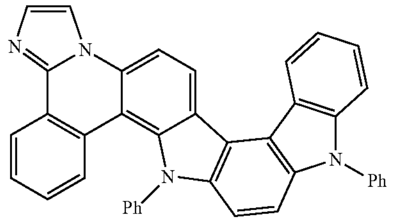
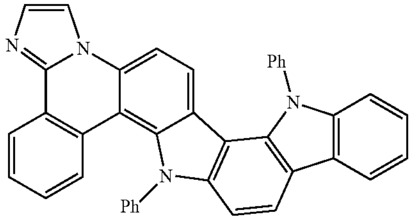

-continued
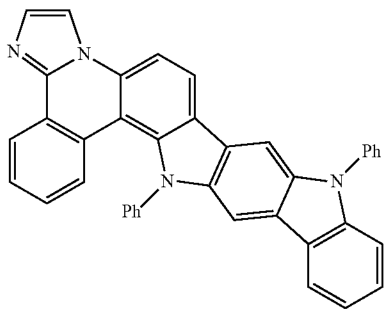
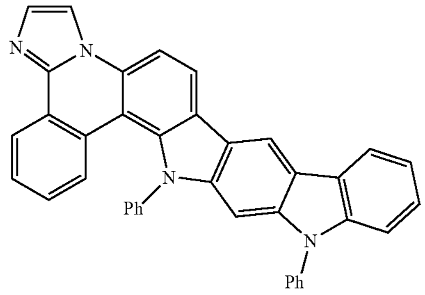
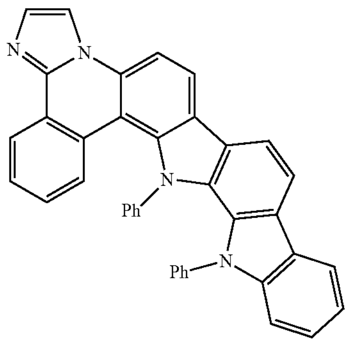
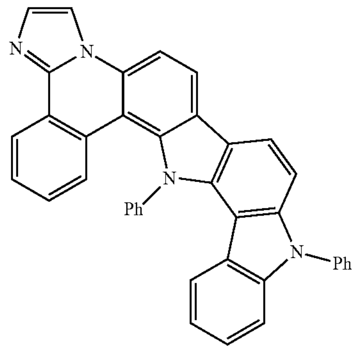
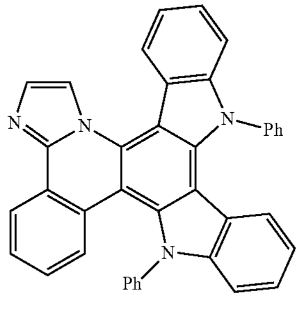
-continued
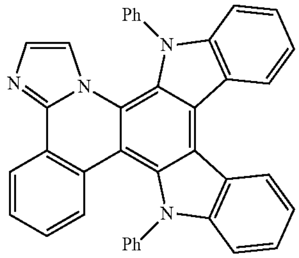
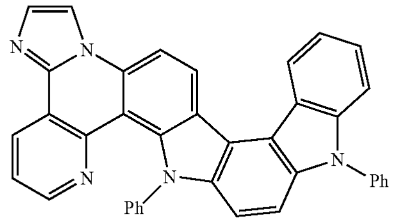
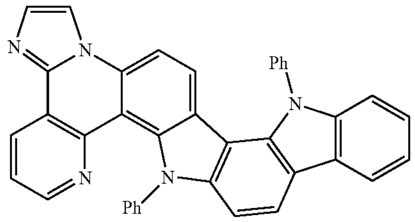
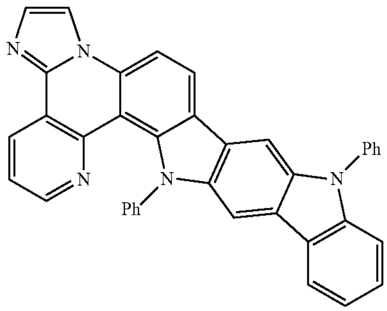
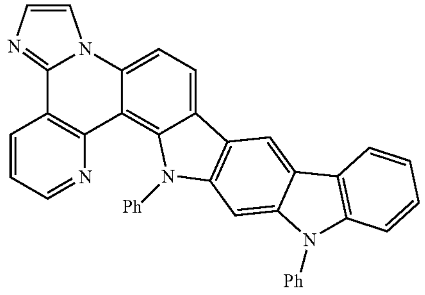
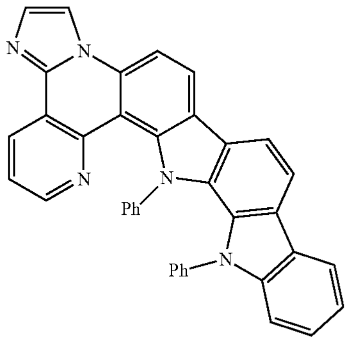

-continued
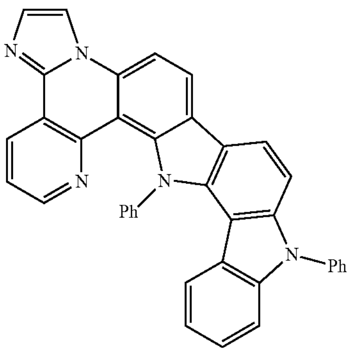
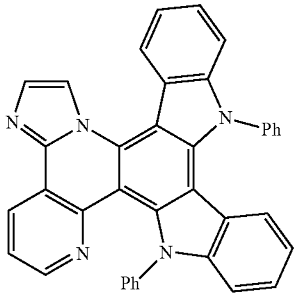
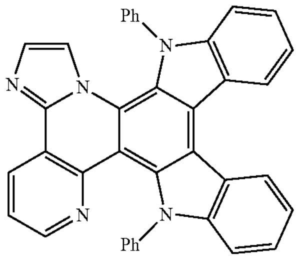
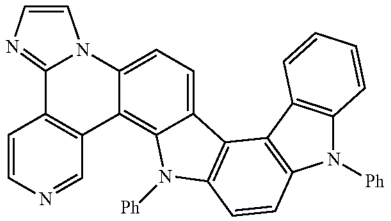
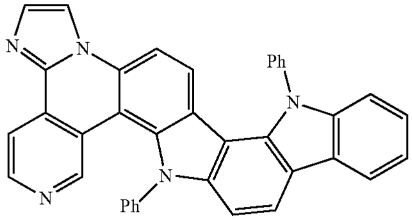
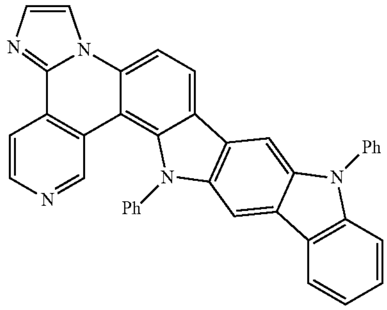
-continued
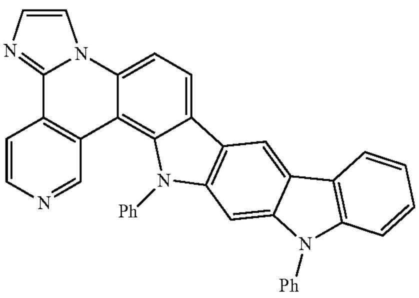
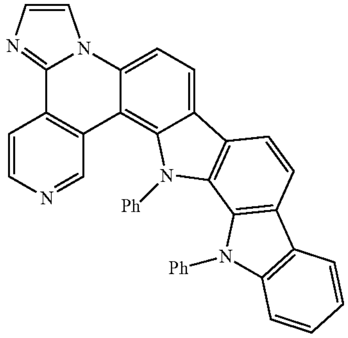
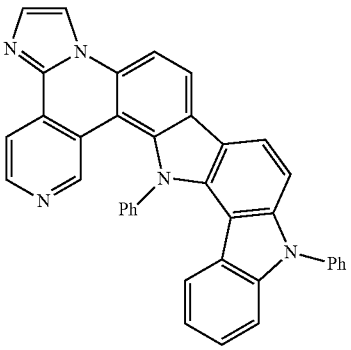
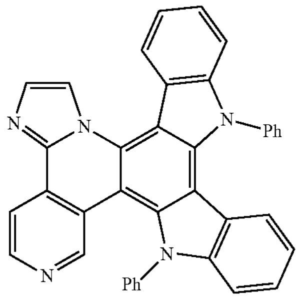
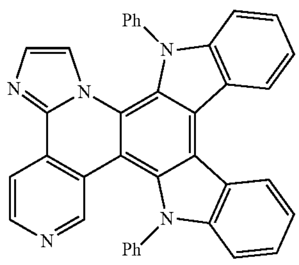

-continued
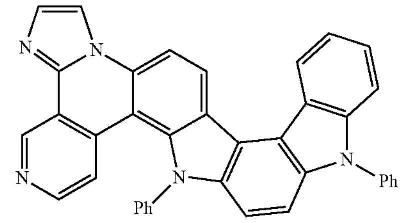
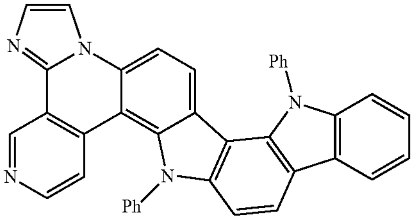
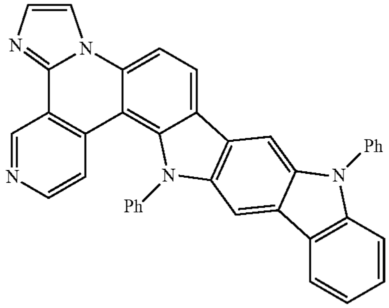
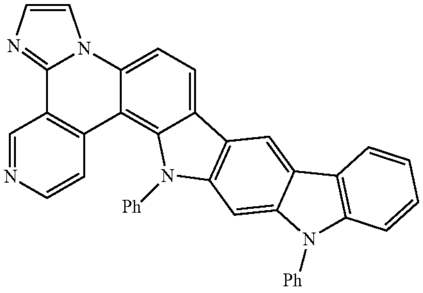
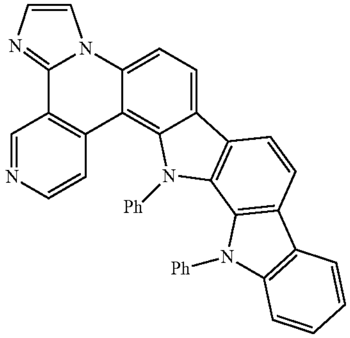
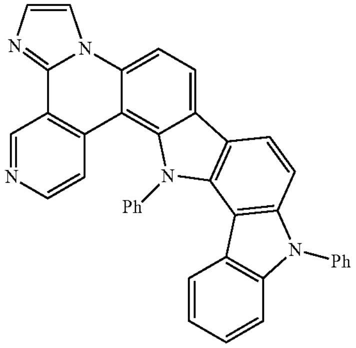
-continued
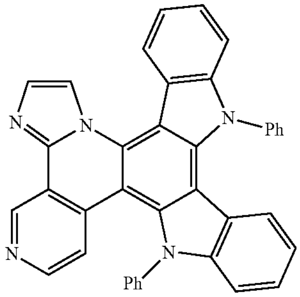
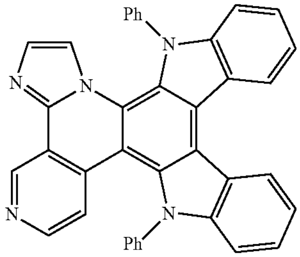
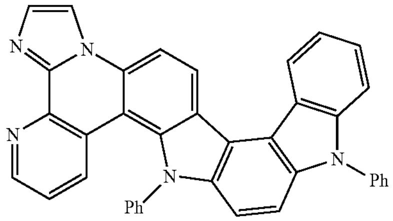
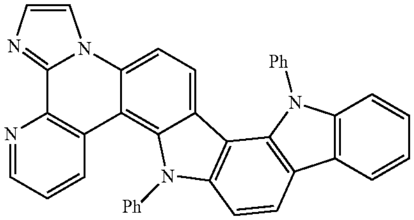
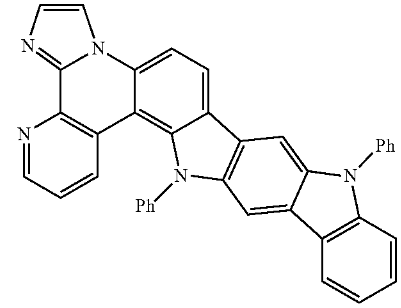
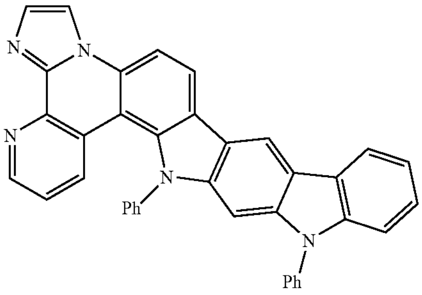

-continued
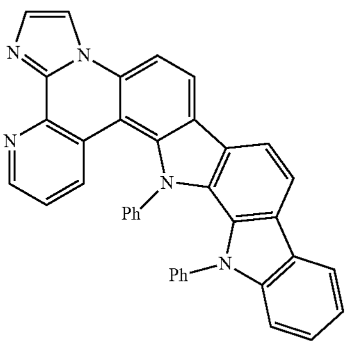
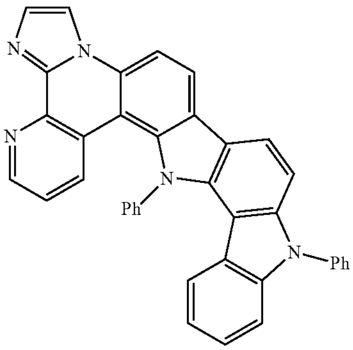
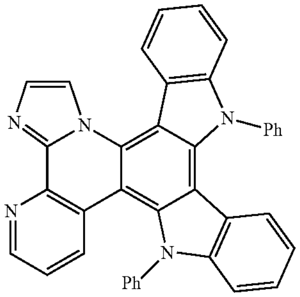
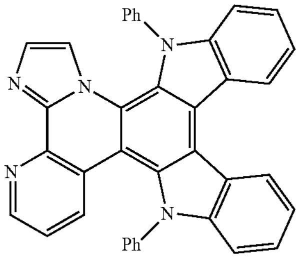
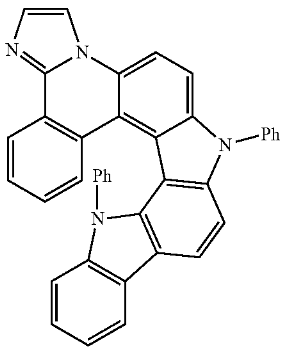
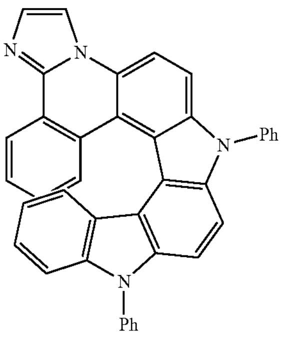
-continued
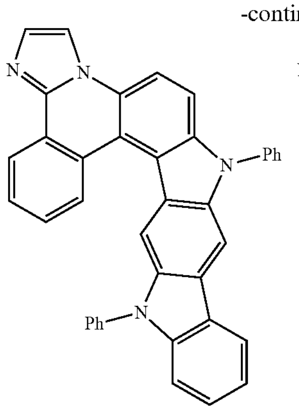
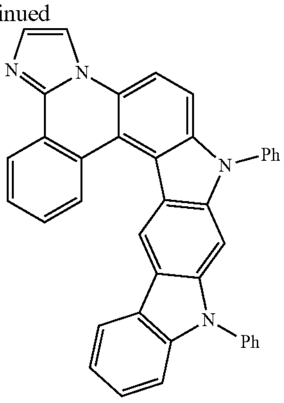
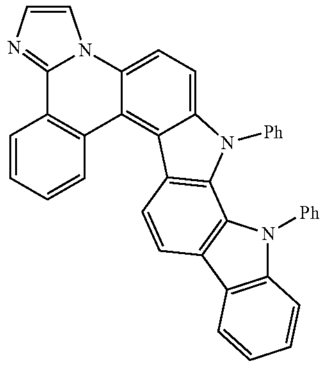
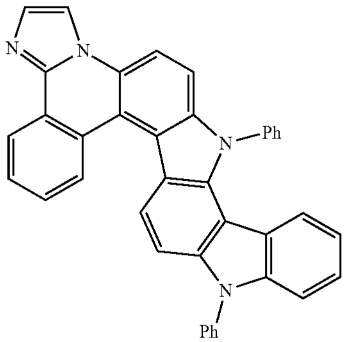
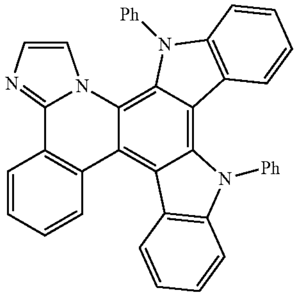
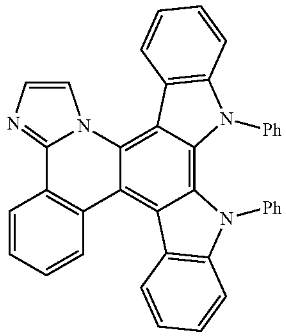

-continued
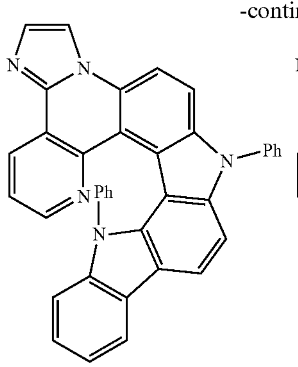
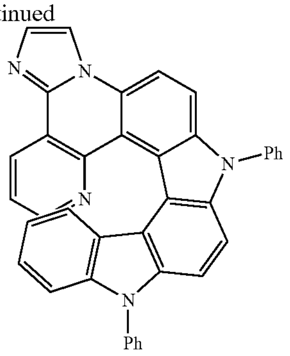
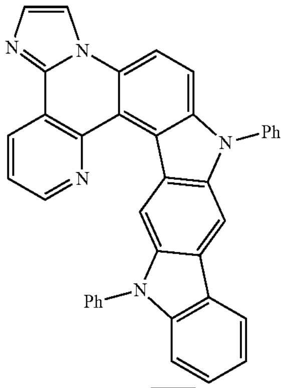
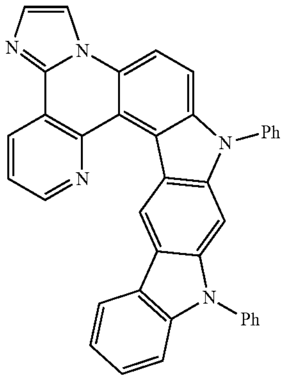
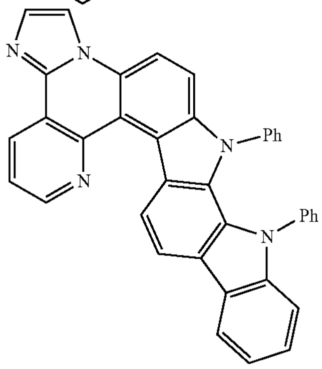
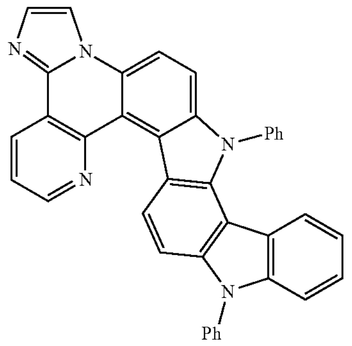
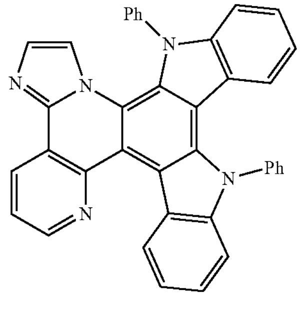
-continued
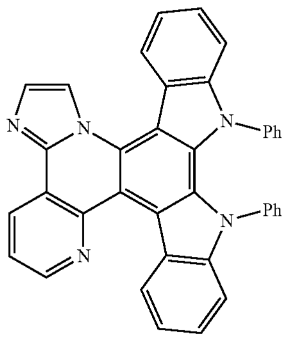
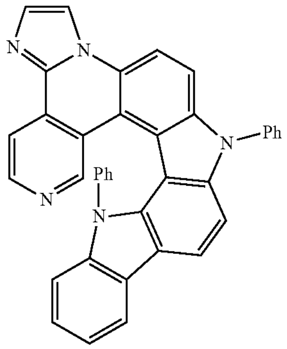
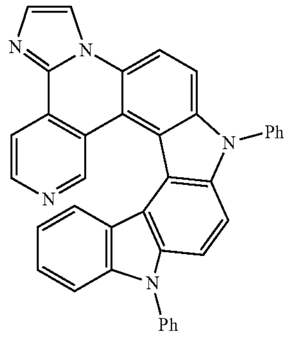
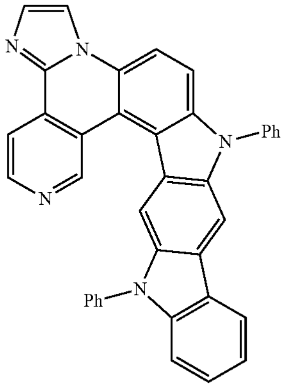
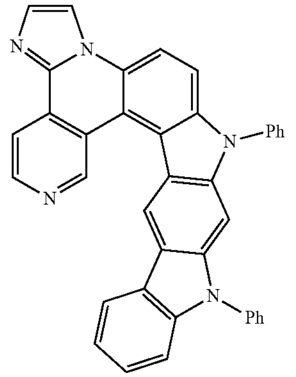
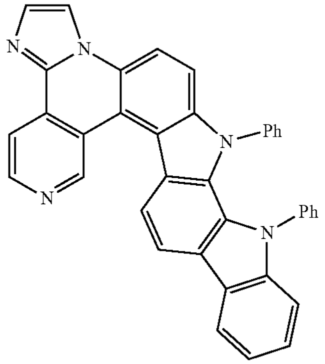

-continued
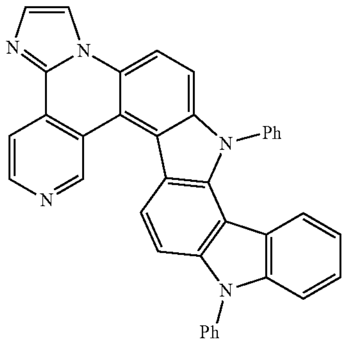
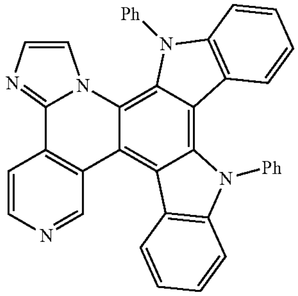
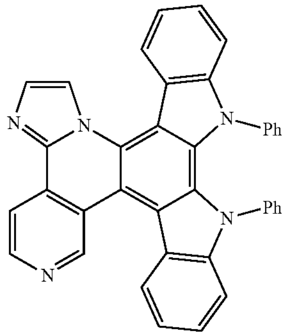
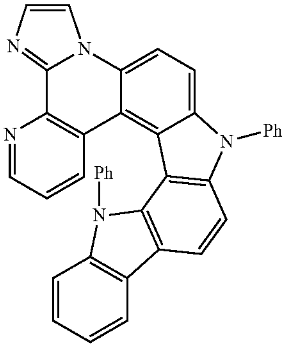
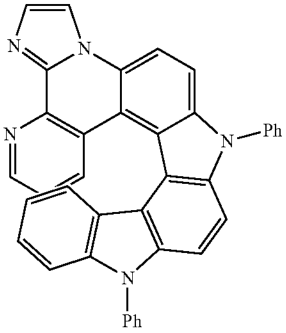
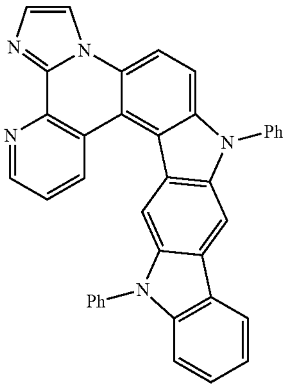
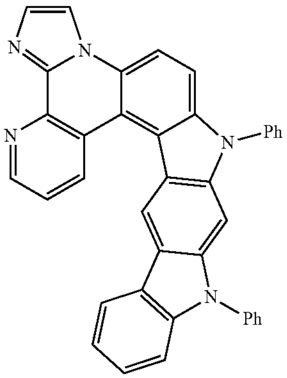
-continued
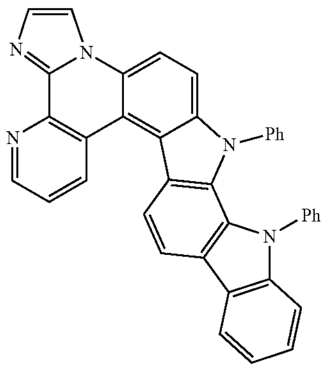
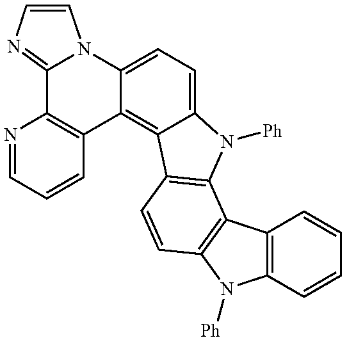
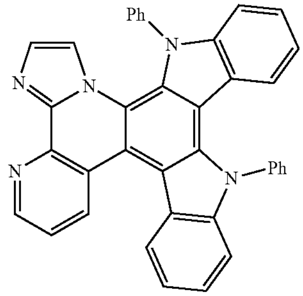
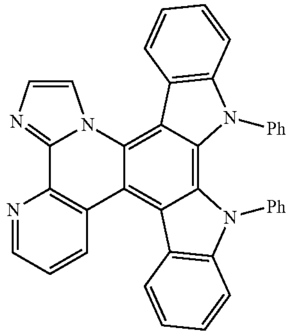
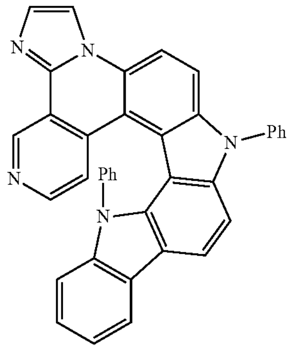
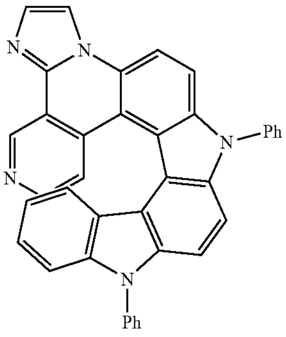

-continued
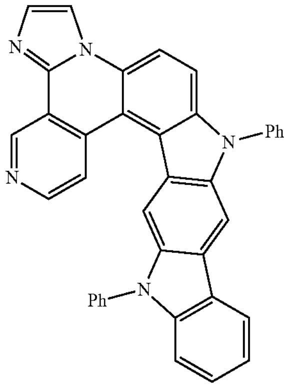
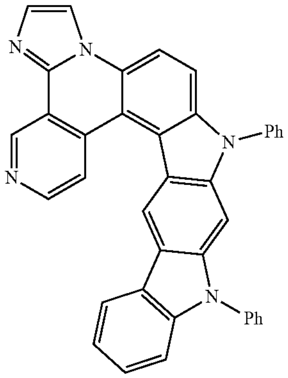
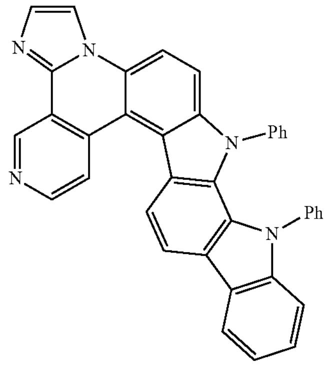
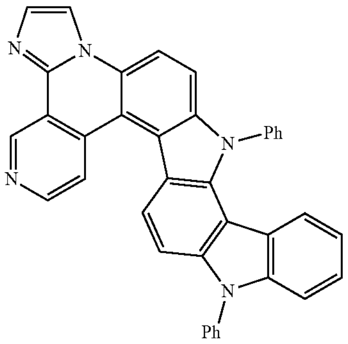
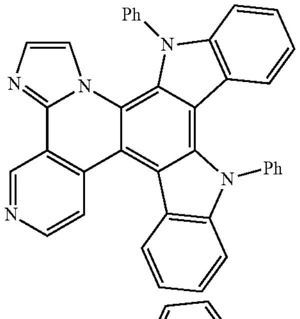
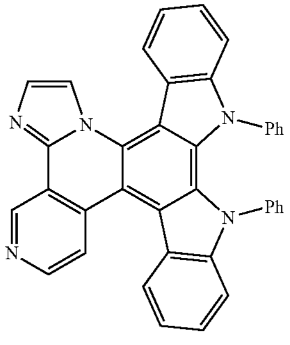
-continued
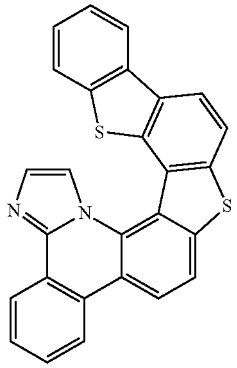
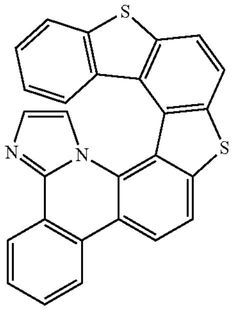
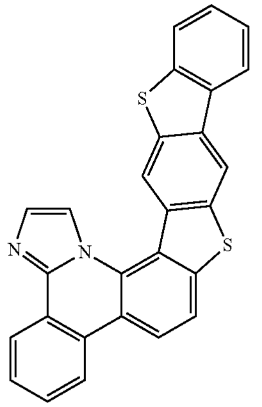
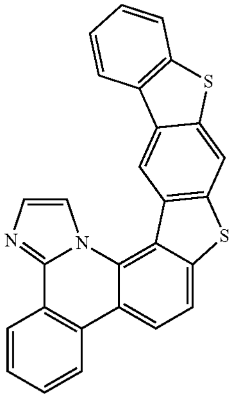
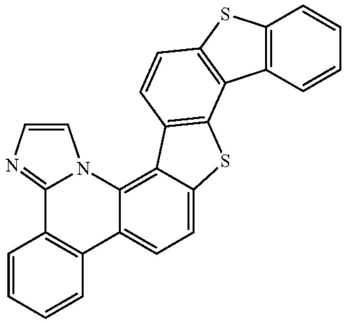
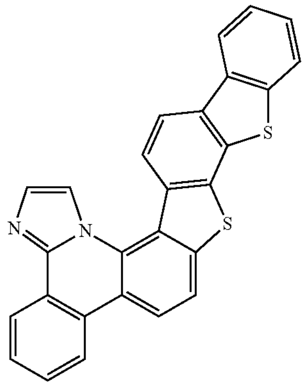

-continued
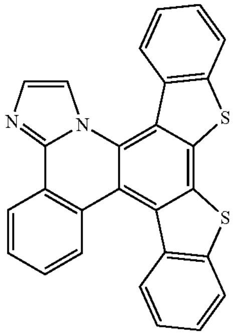
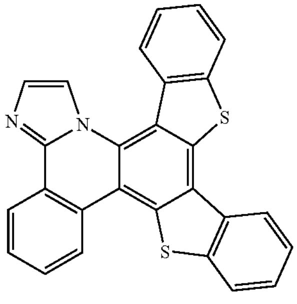
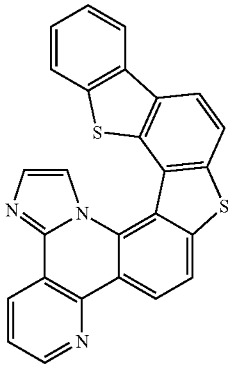
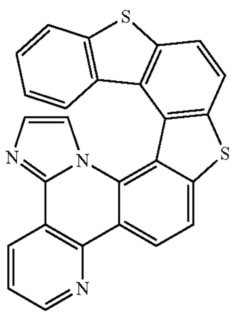
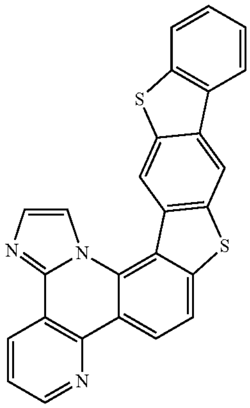
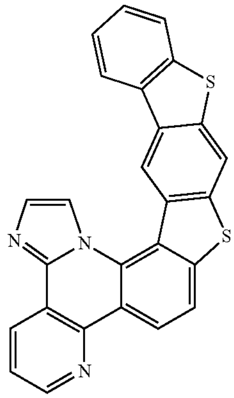
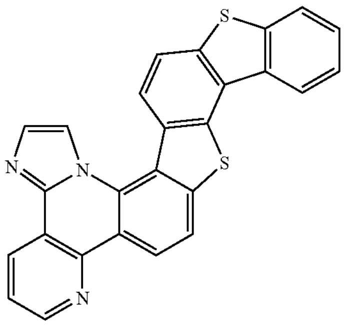
-continued
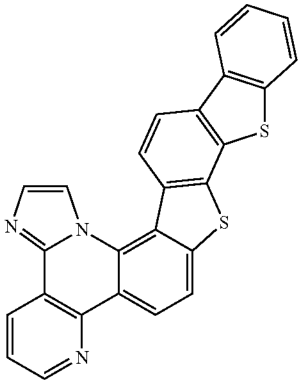
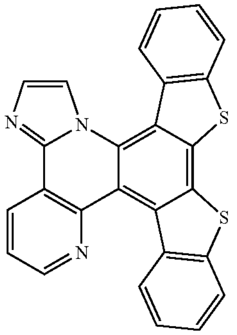
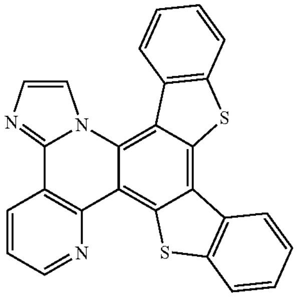
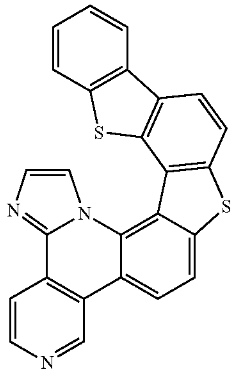
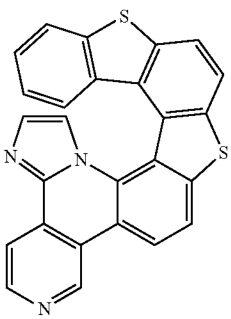
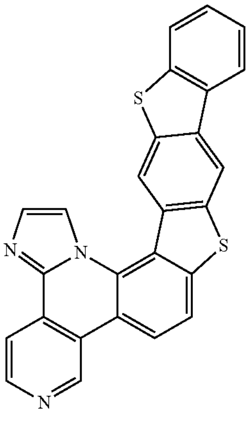
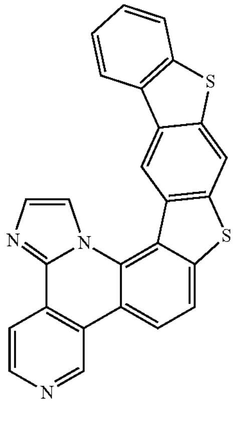

-continued
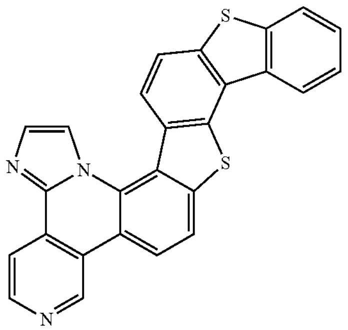
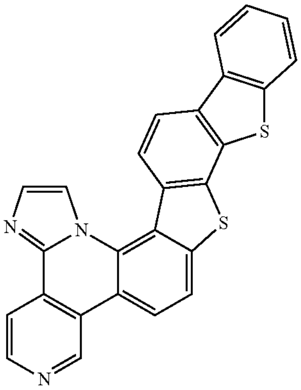
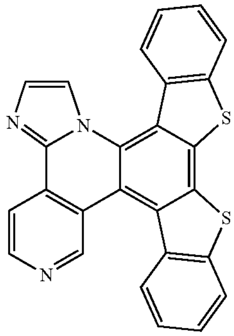
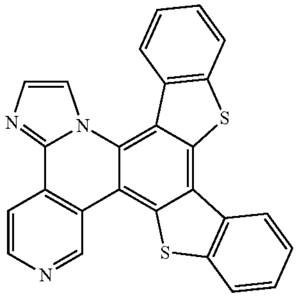
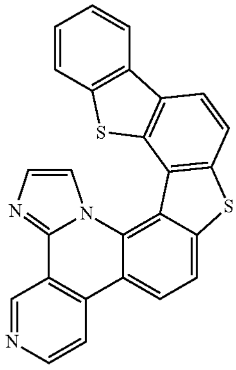
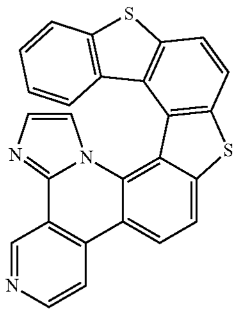
-continued
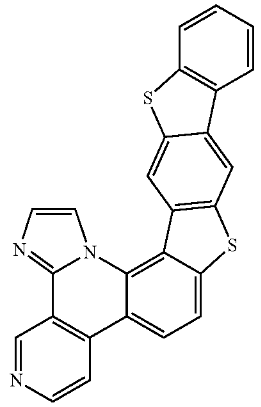
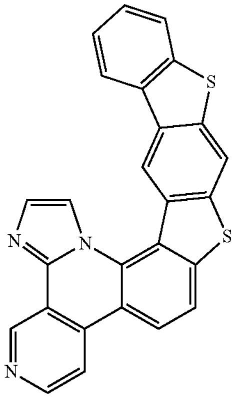
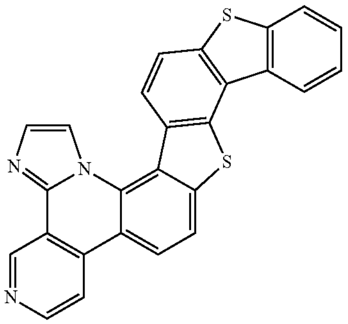
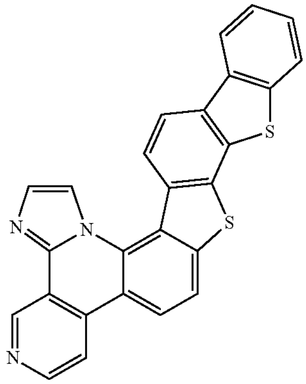
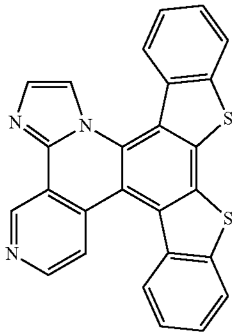
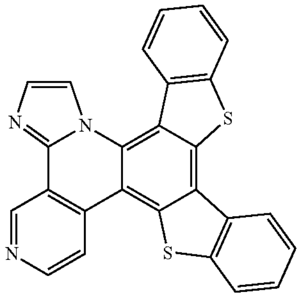

-continued
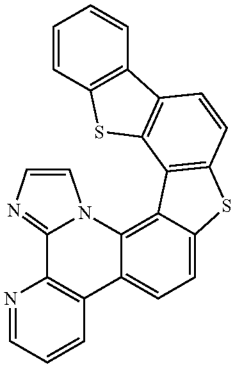
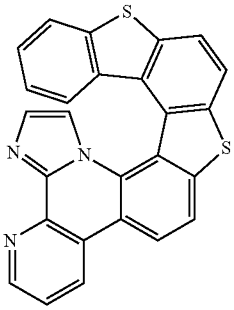
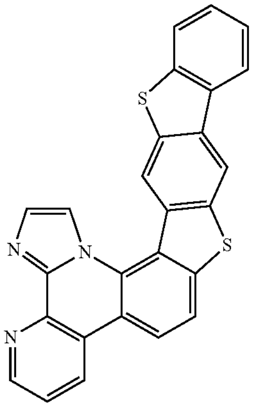
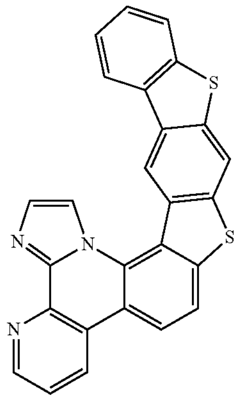
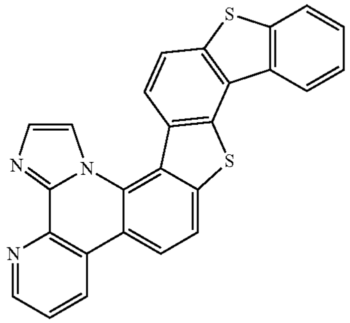
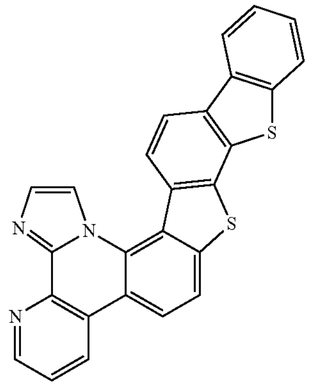
-continued
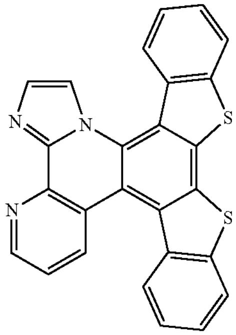
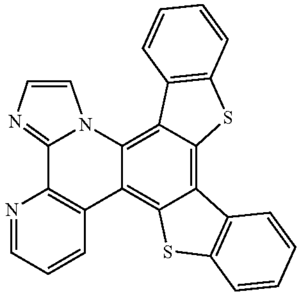
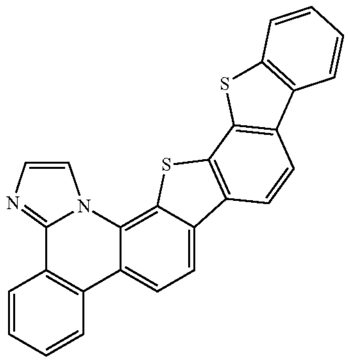
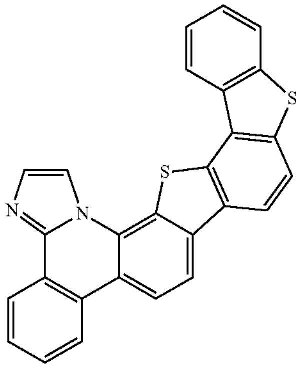
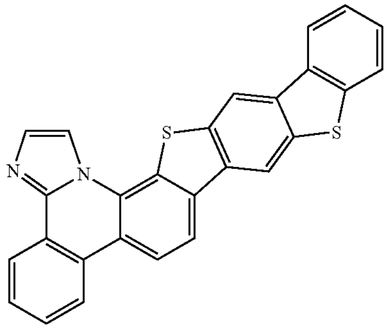
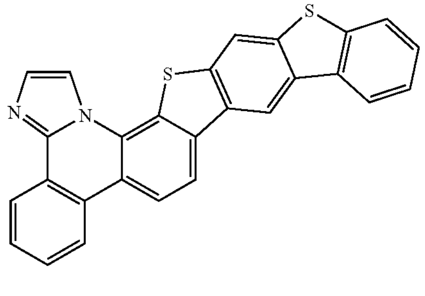

-continued
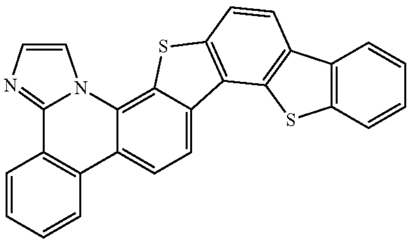
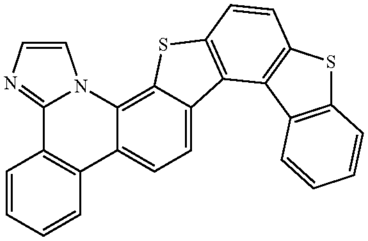
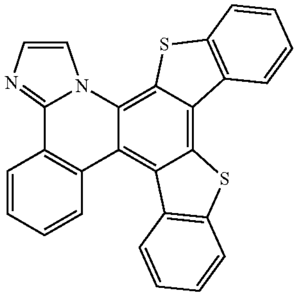
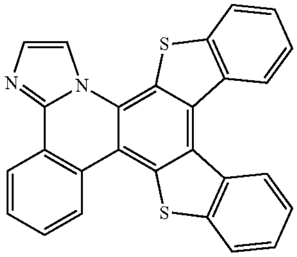
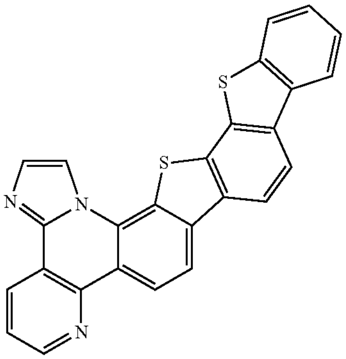
-continued
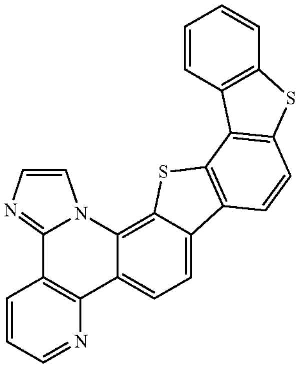
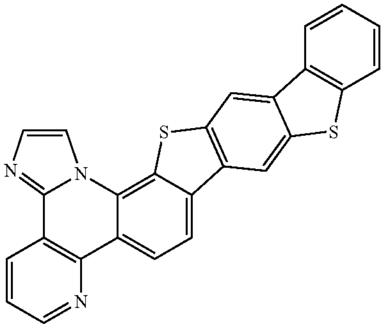
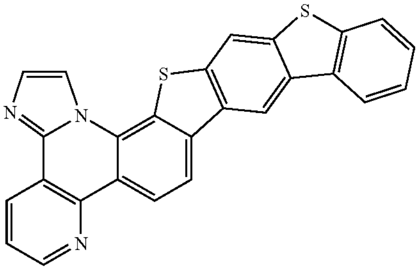
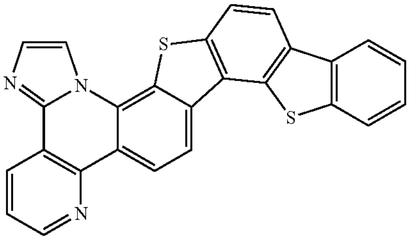
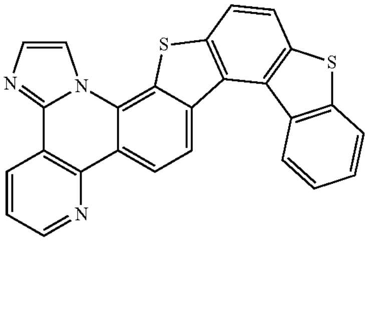

-continued
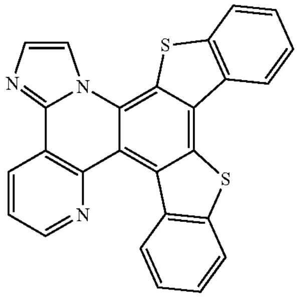
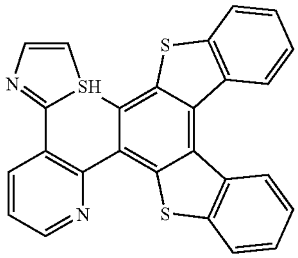
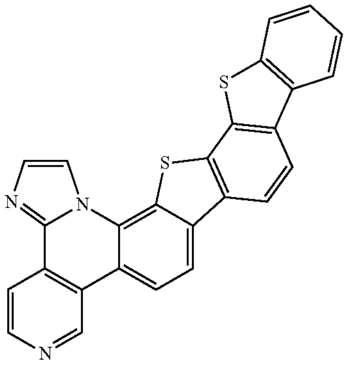
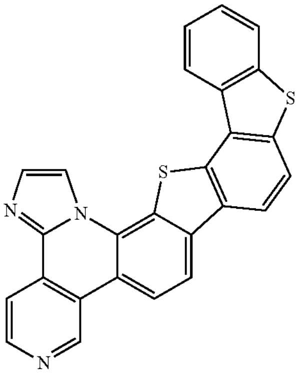
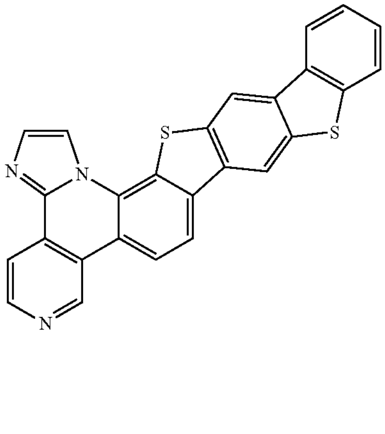
-continued
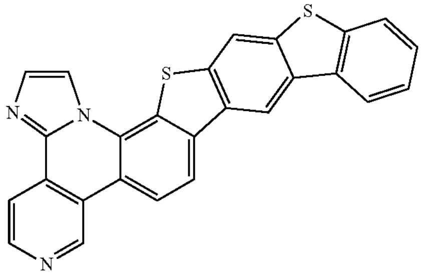
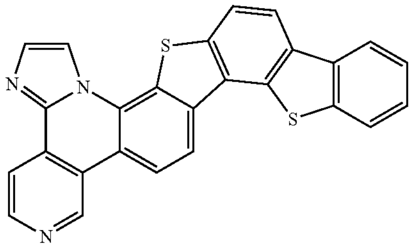
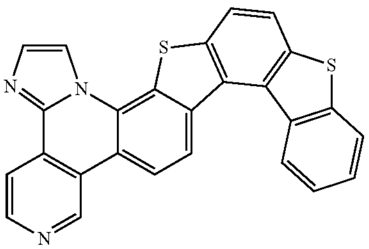
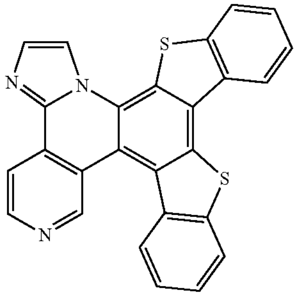
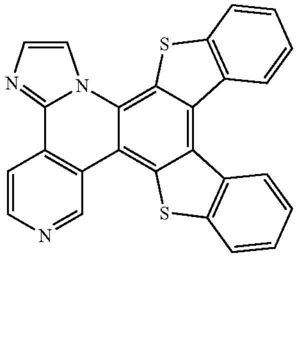

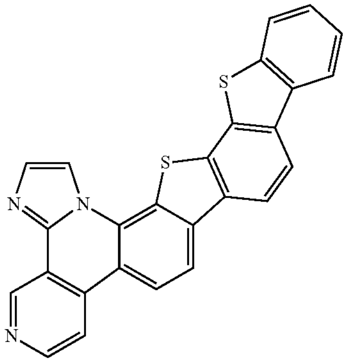
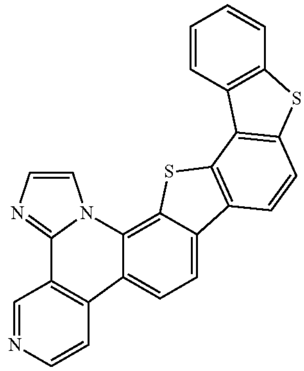
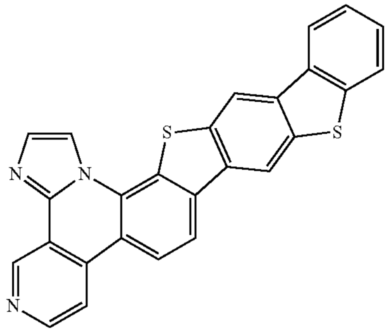
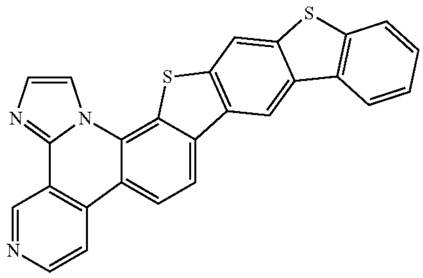
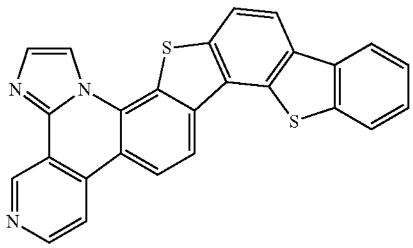
-continued
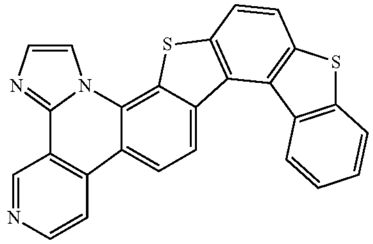
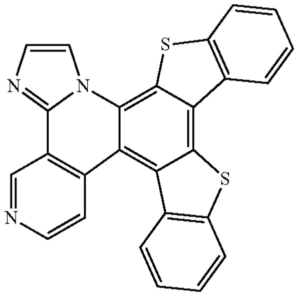
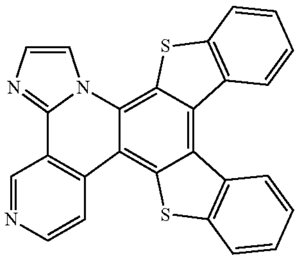
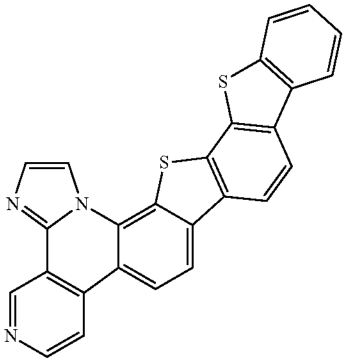
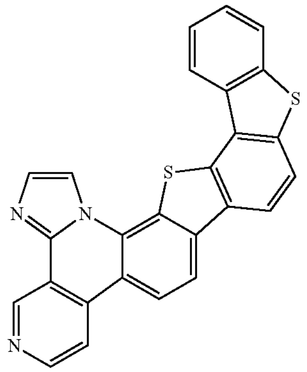

-continued
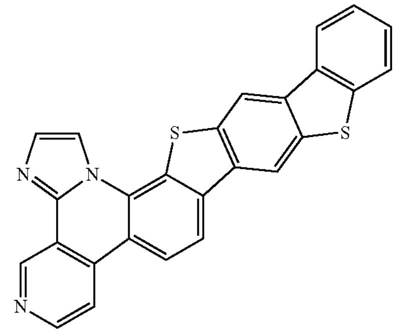
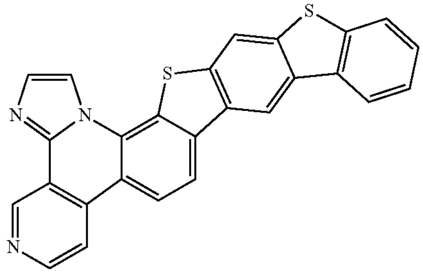
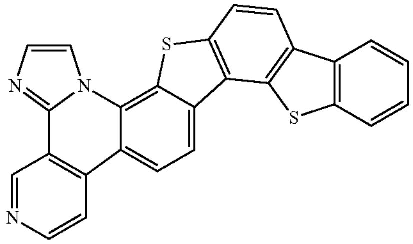
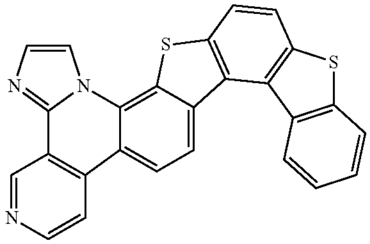
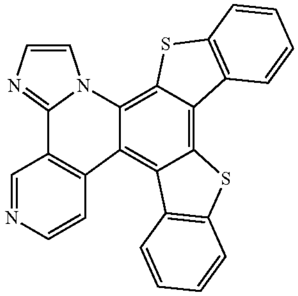
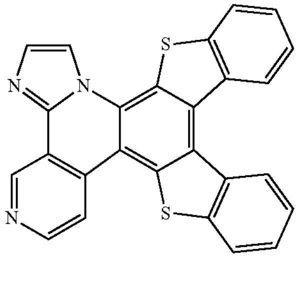
-continued
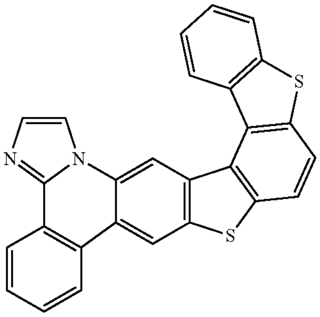
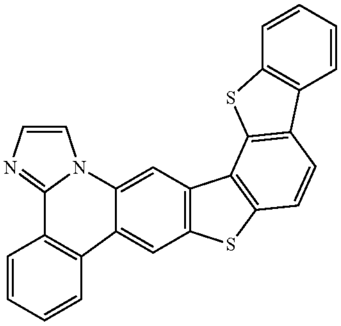
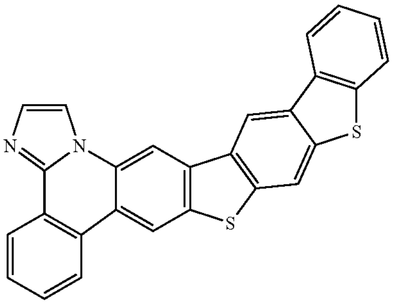
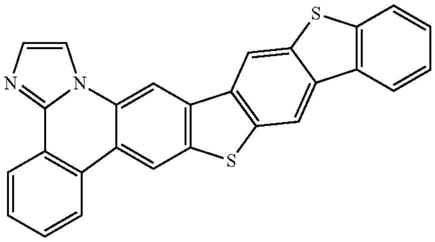
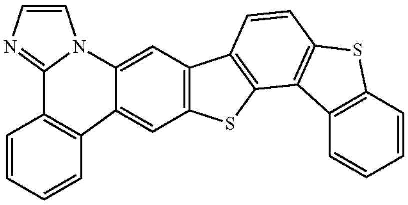
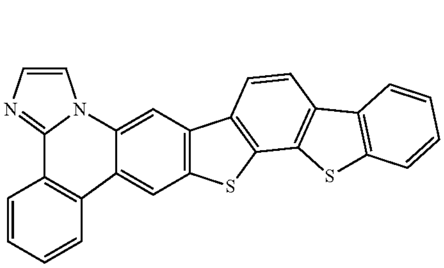

-continued
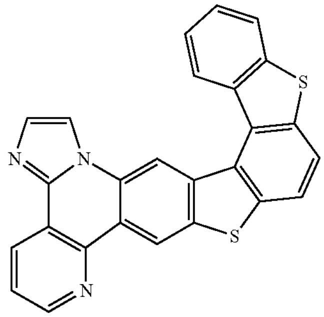
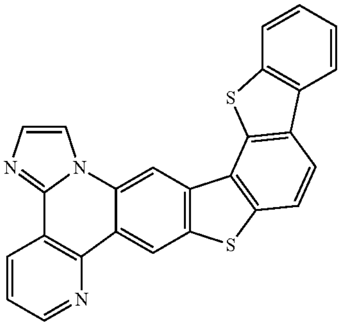
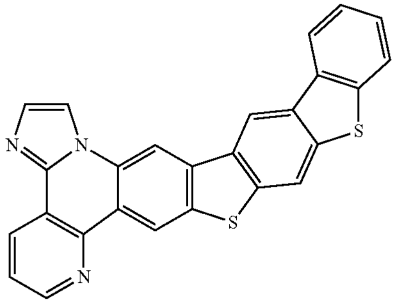
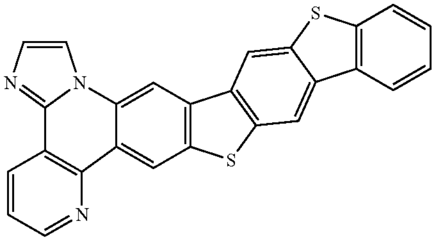
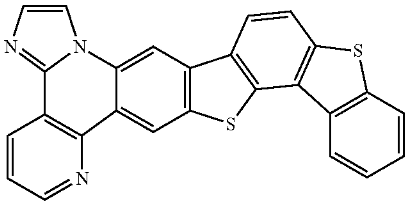
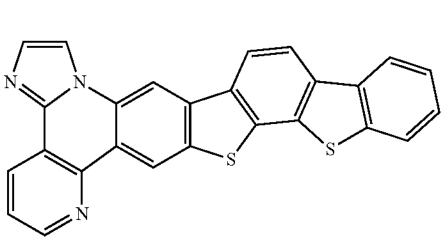
-continued
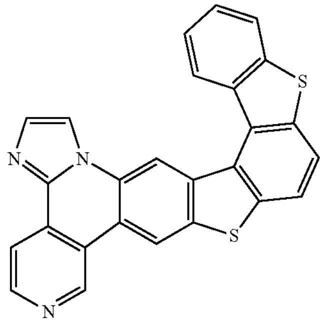
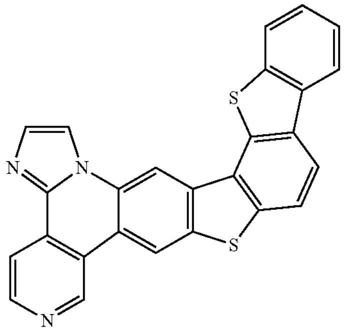
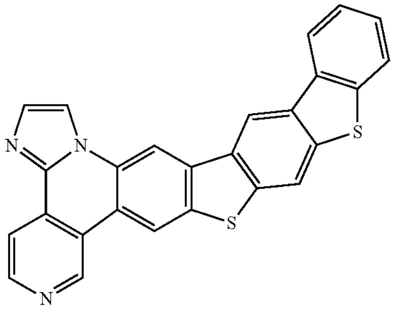
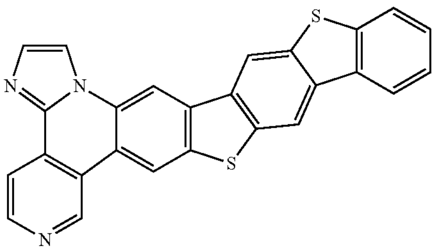
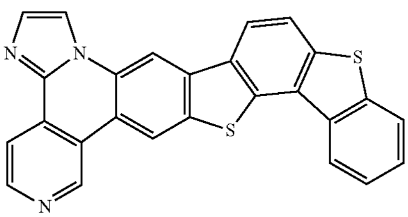
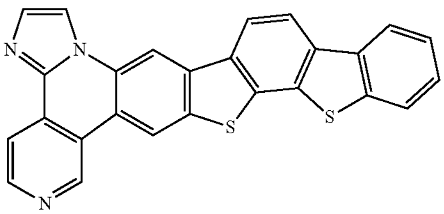

-continued
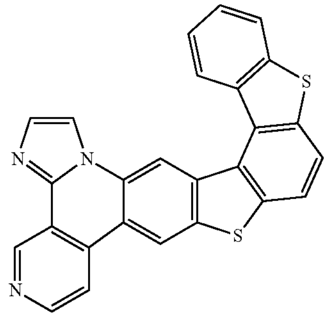
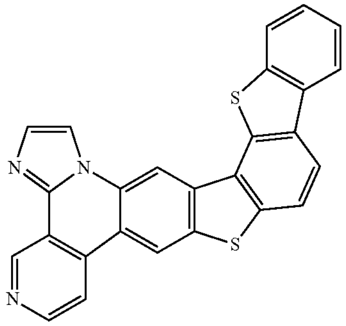
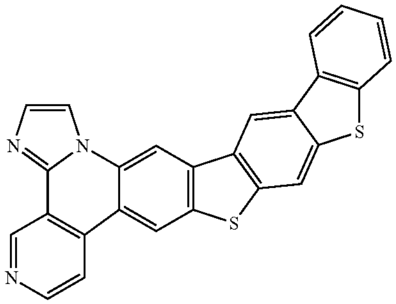
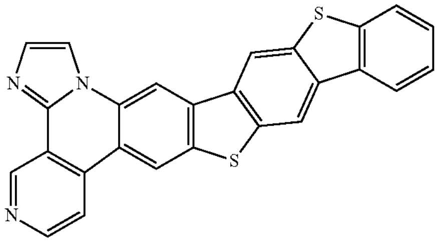
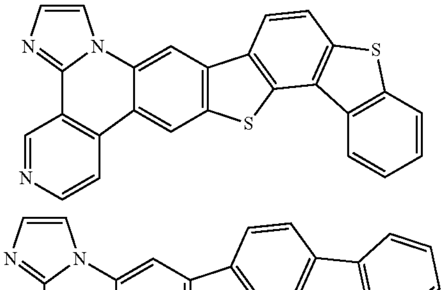
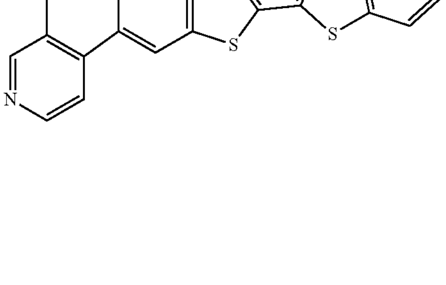
-continued
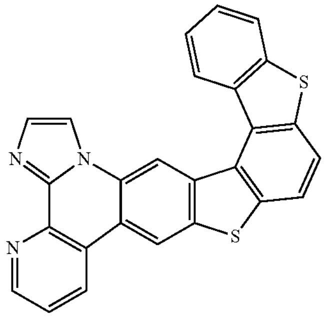
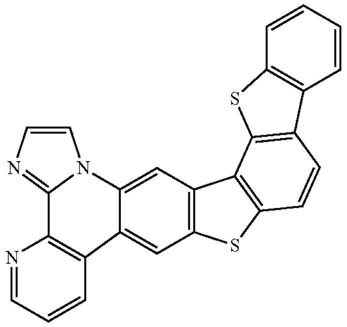
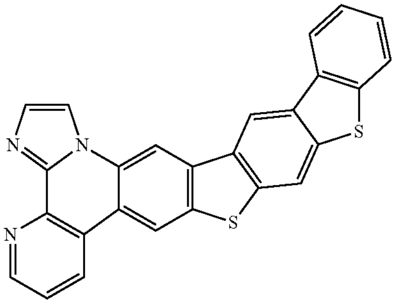
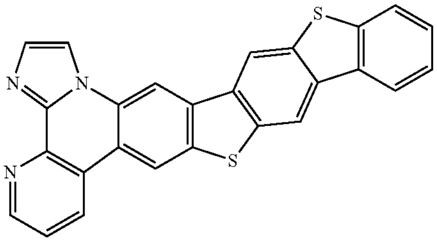
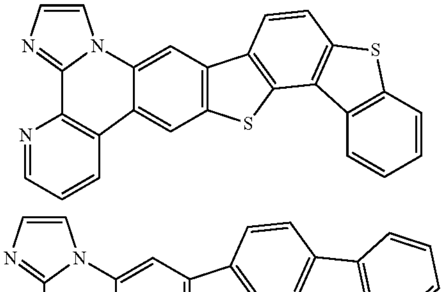
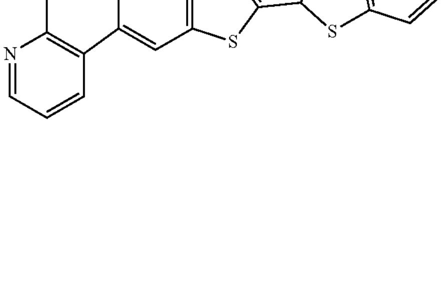

-continued
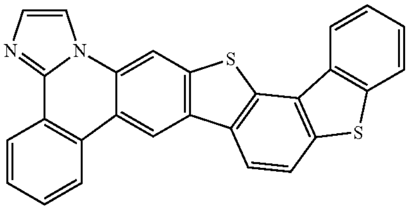
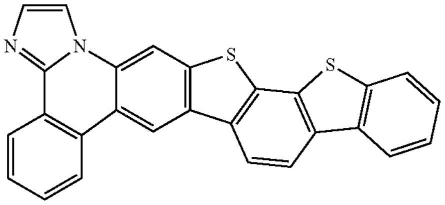
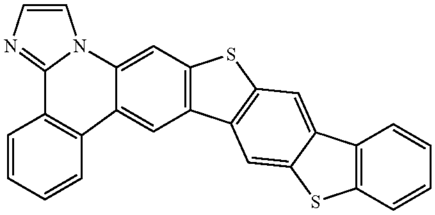
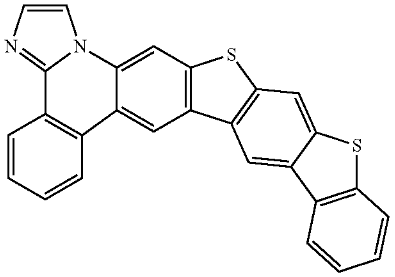
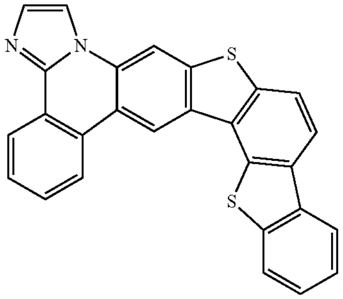
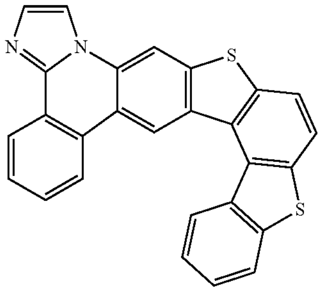
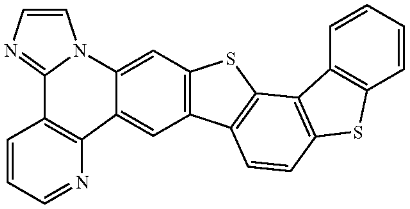
-continued
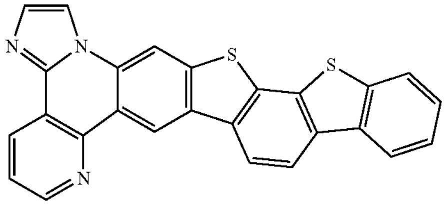
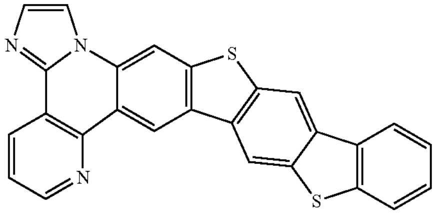
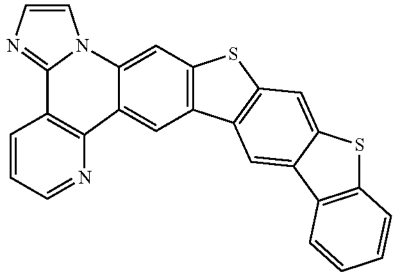
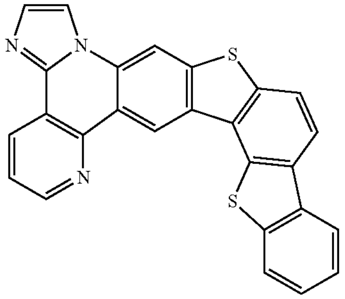
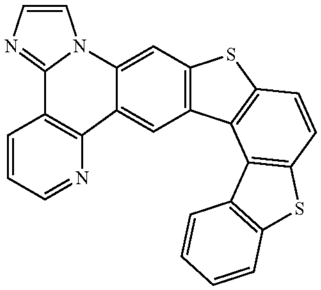
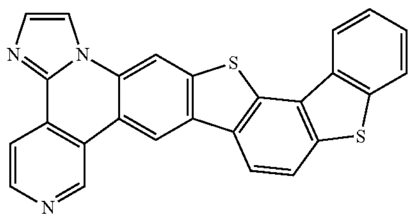
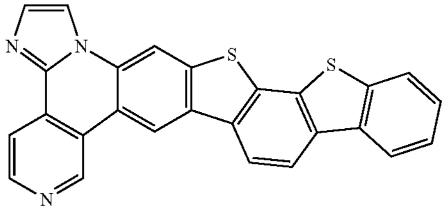

-continued
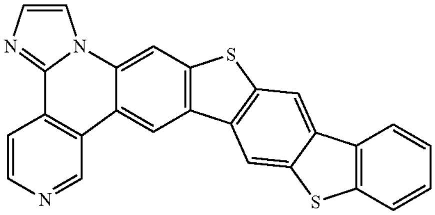
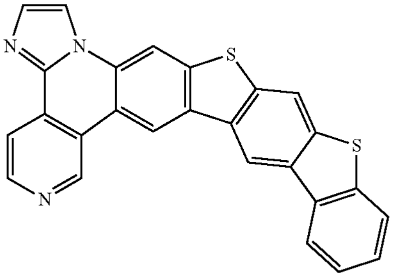
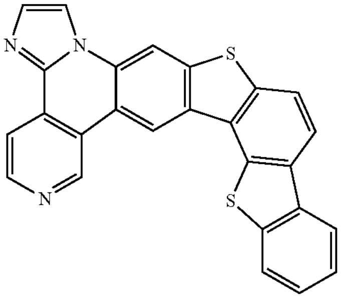
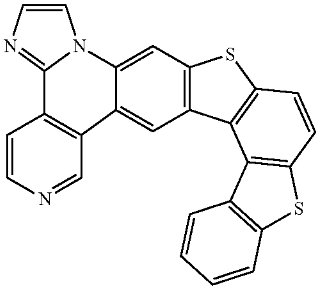
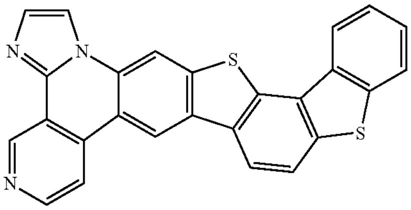
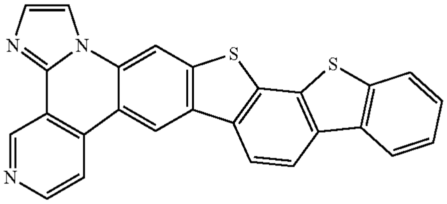
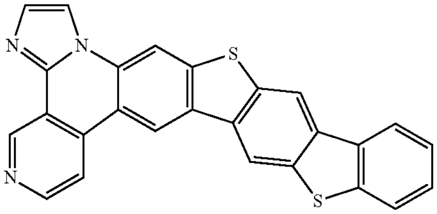
-continued
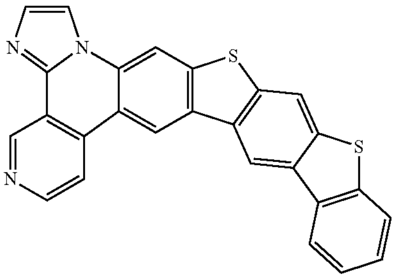
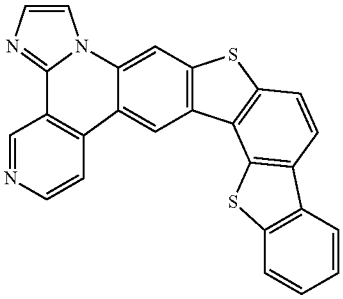
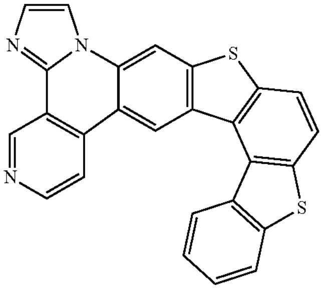
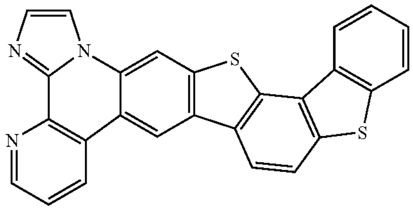
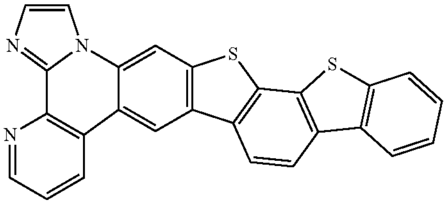
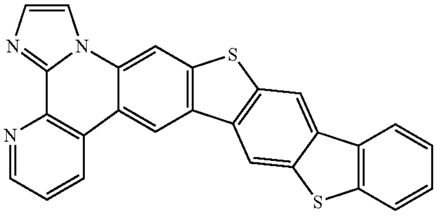

-continued
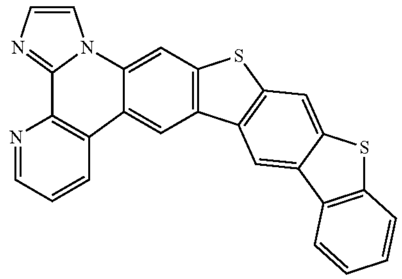
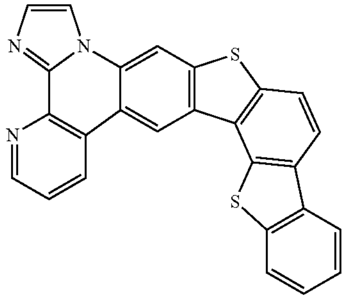
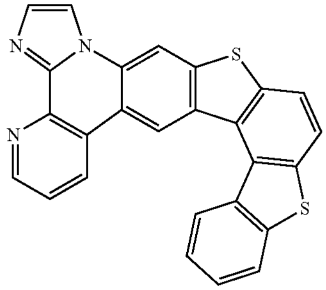
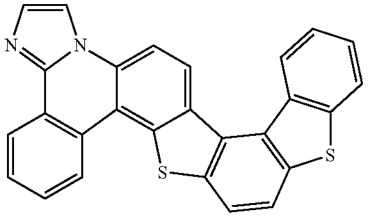
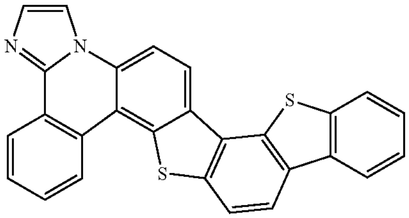
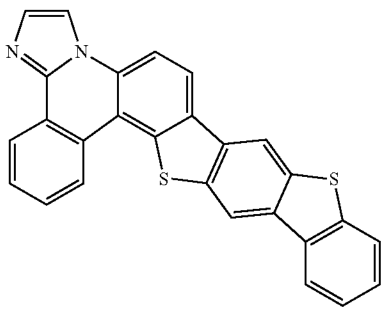
-continued
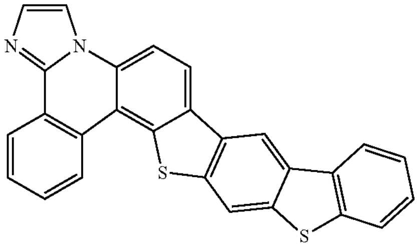
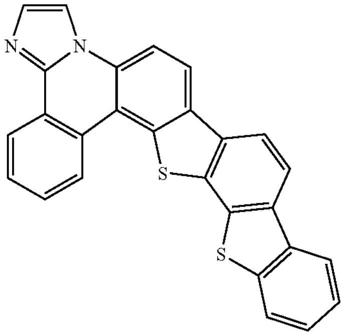
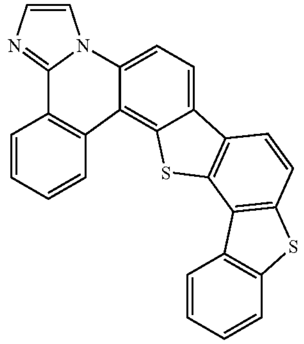
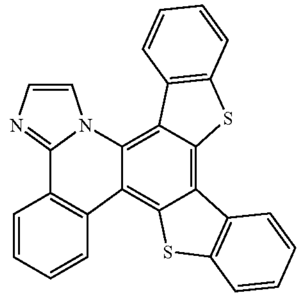
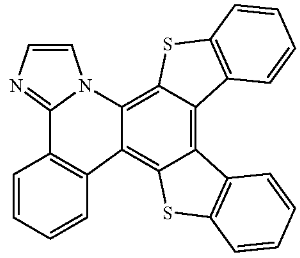
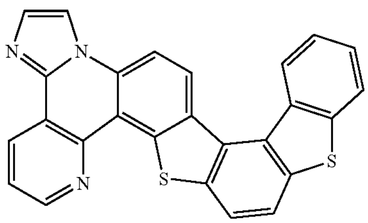

-continued
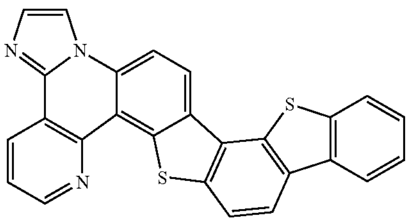
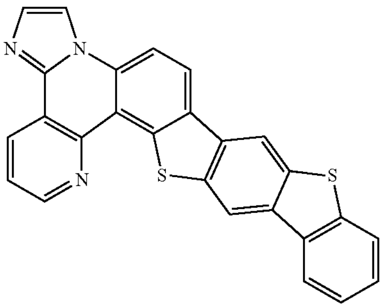
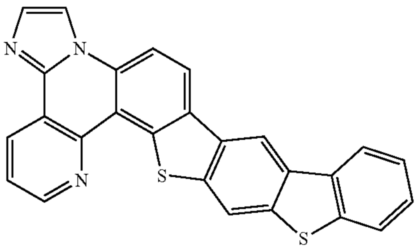
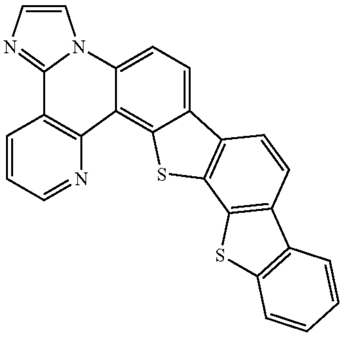
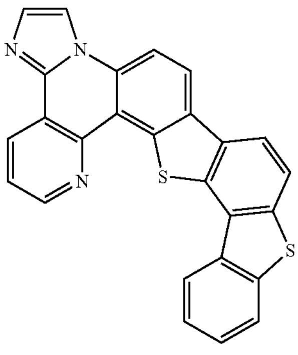
-continued
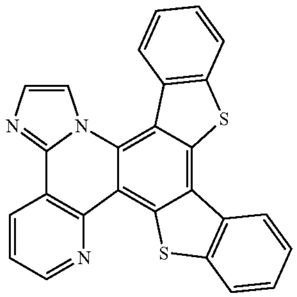
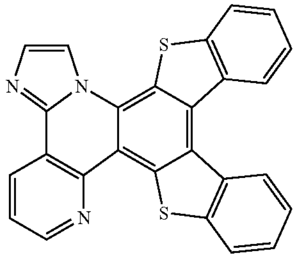
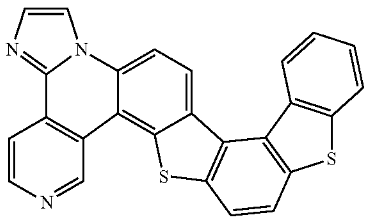
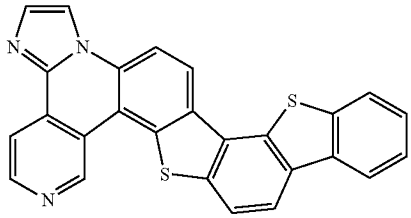
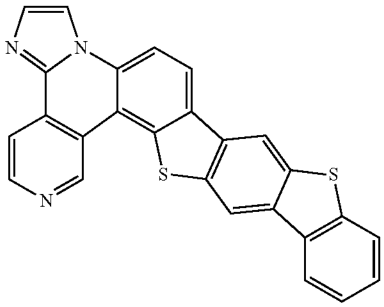
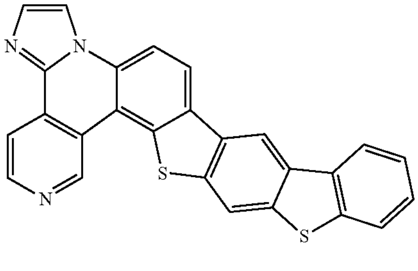

-continued
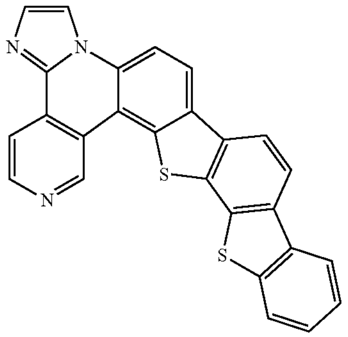
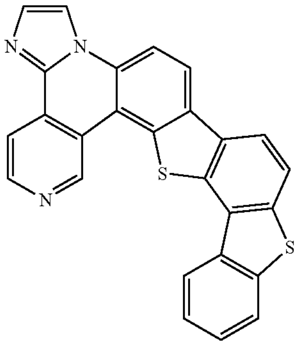
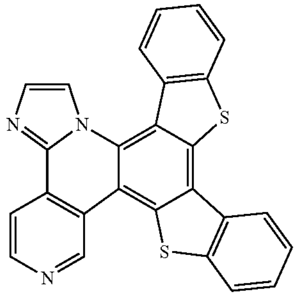
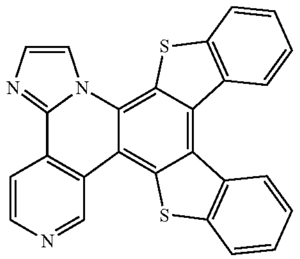
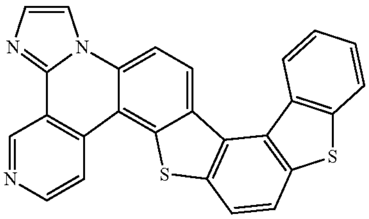
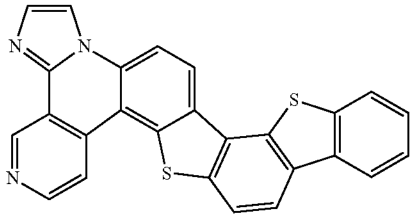
-continued
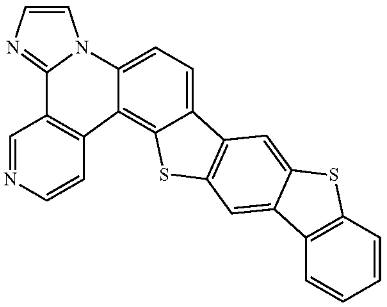
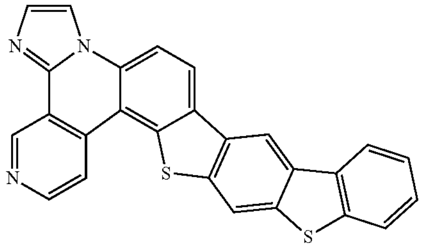
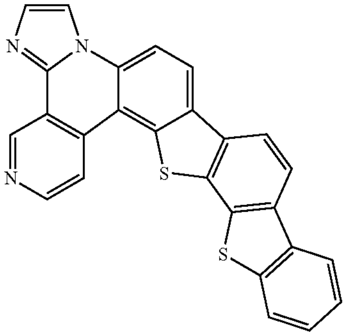
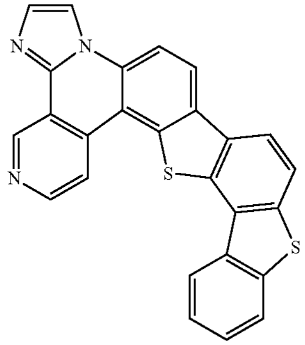
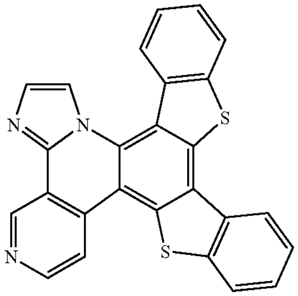

-continued
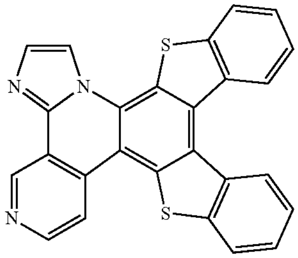
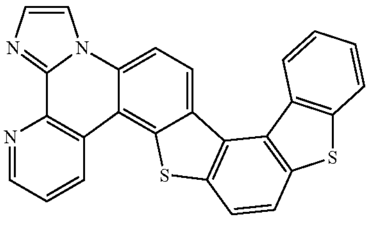
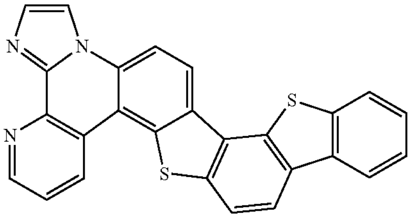
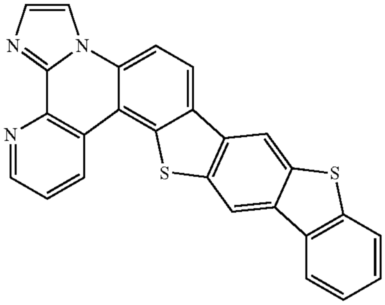
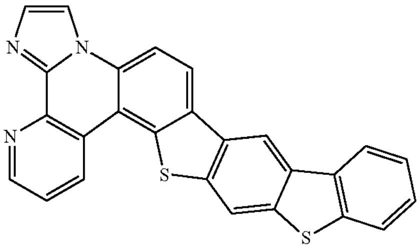
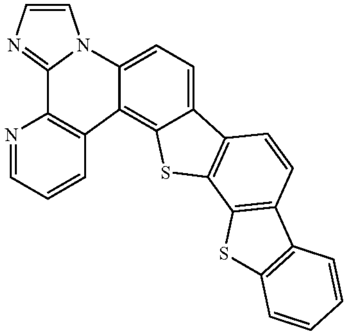
-continued
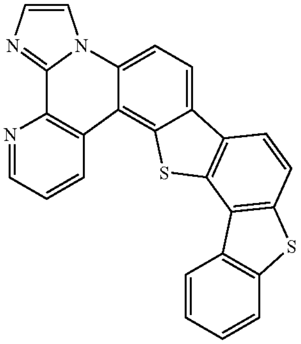
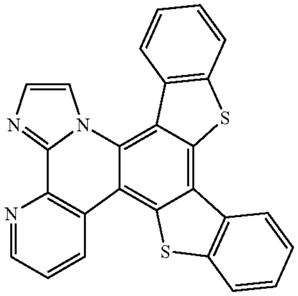
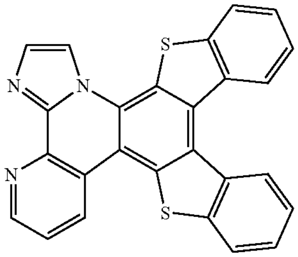
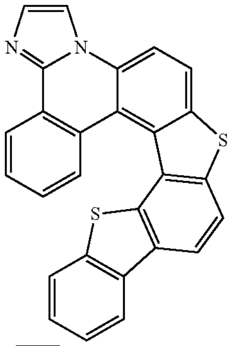
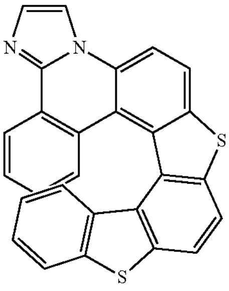
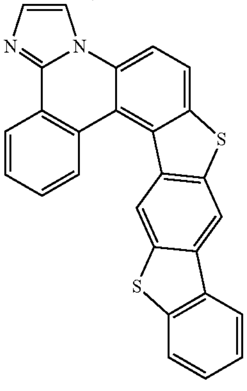
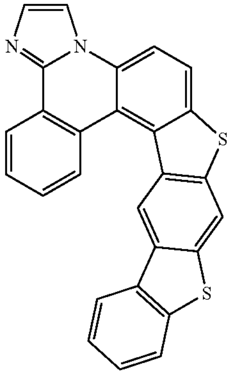

-continued
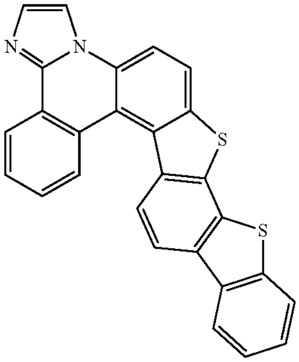
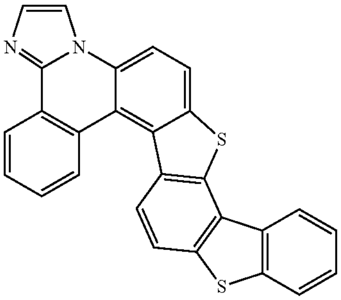
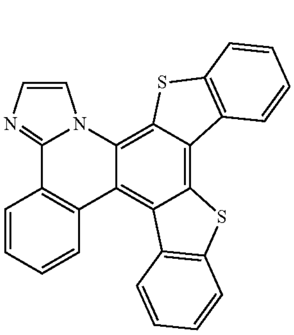
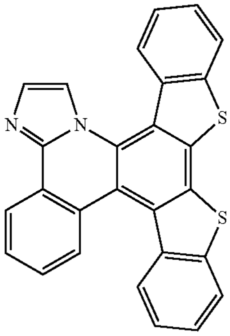
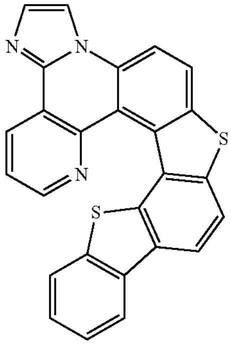
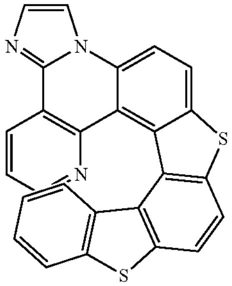
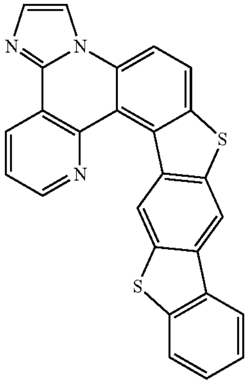
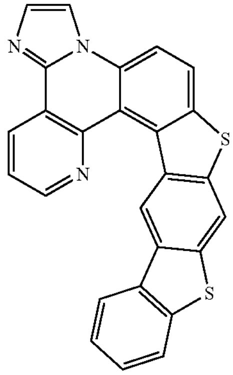
-continued
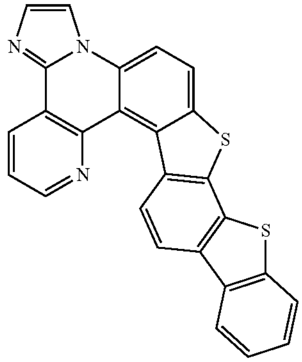
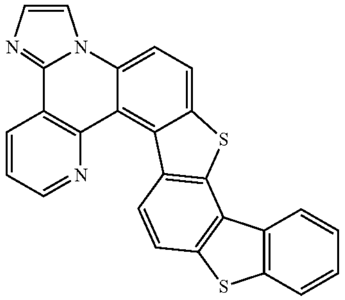
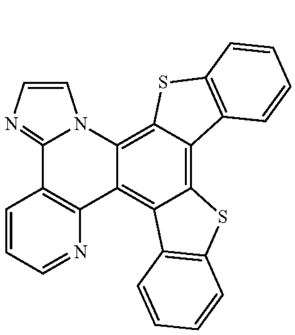
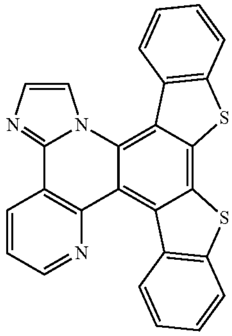
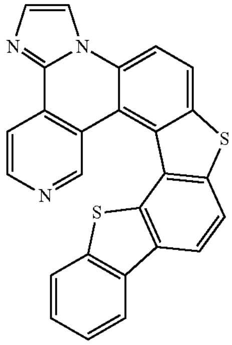
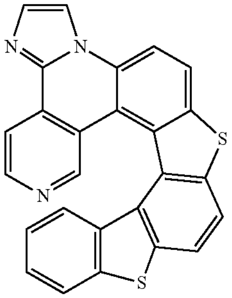
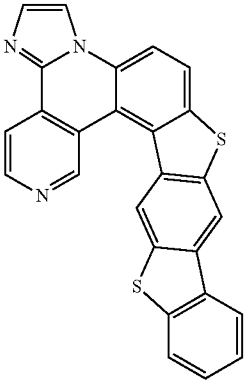
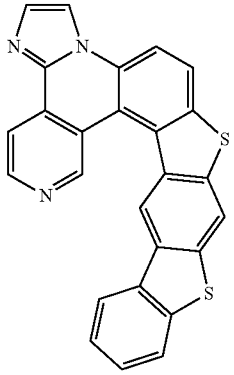

-continued
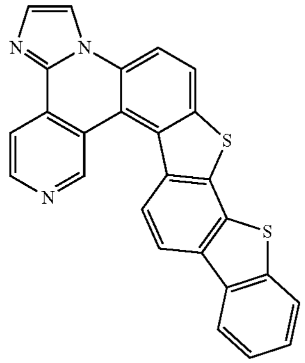
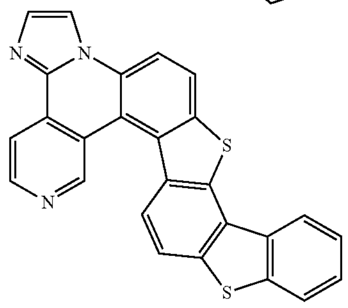
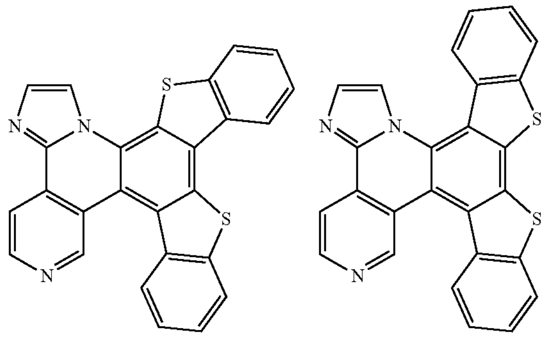
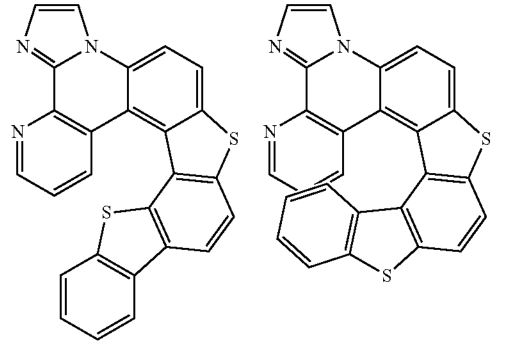
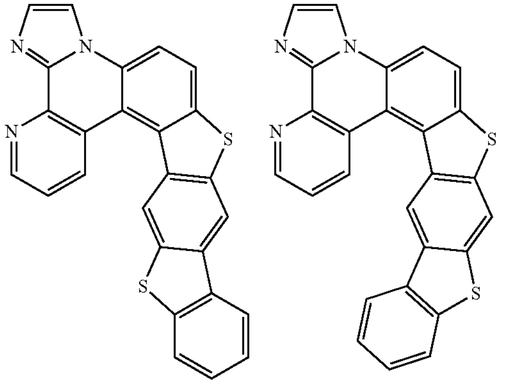
-continued
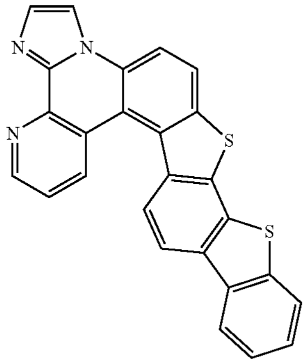
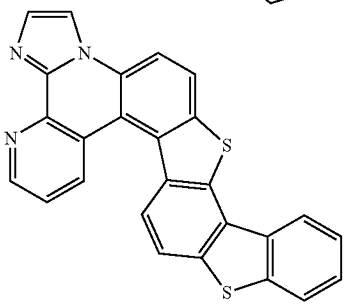
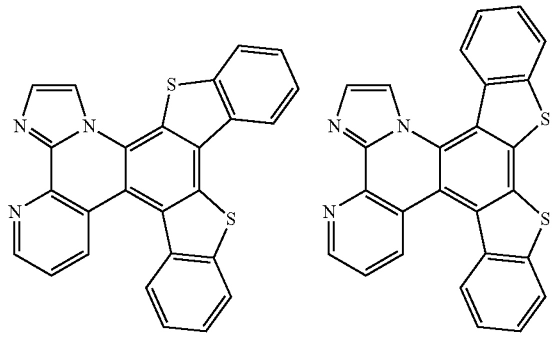
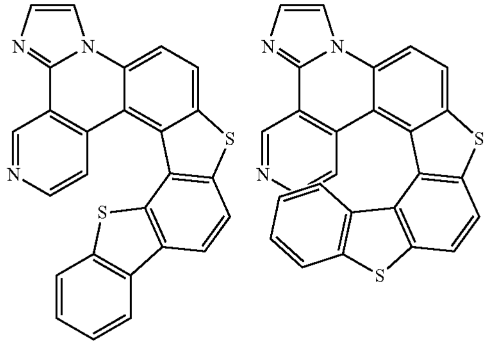
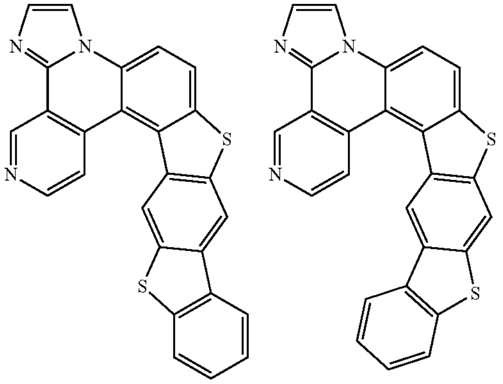

-continued
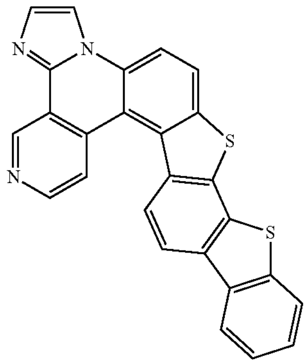
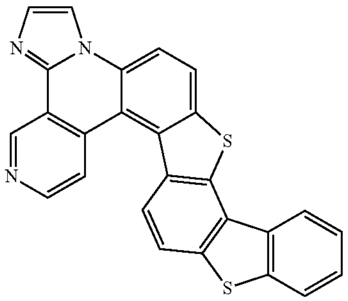
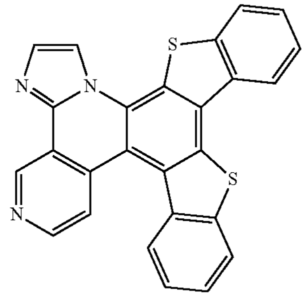
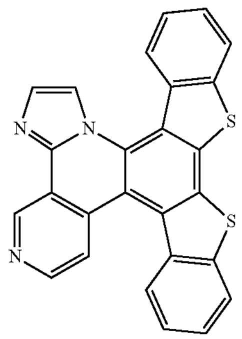
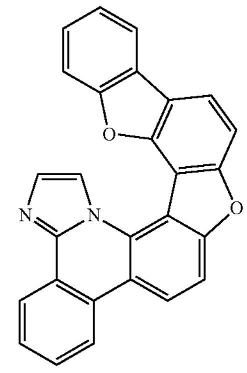
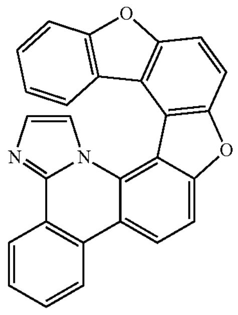
-continued
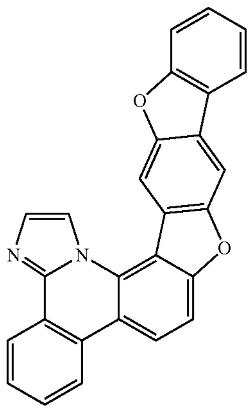
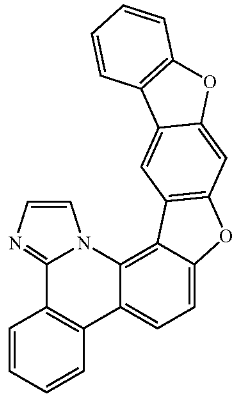
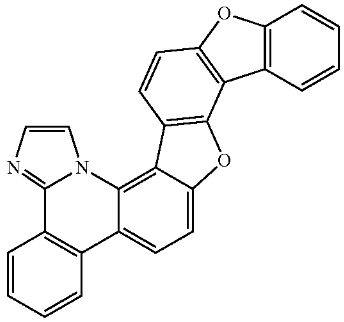
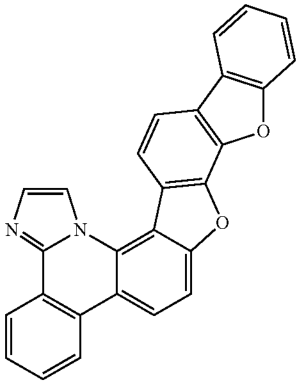
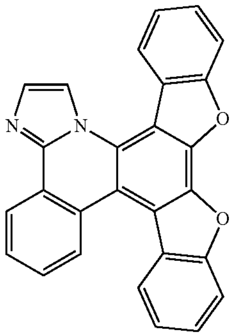
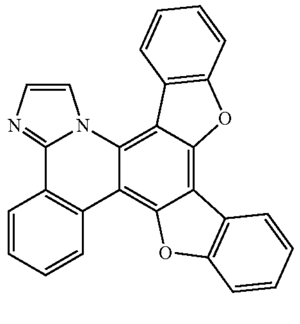
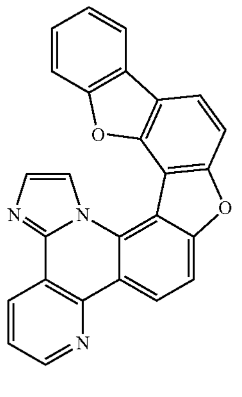

-continued
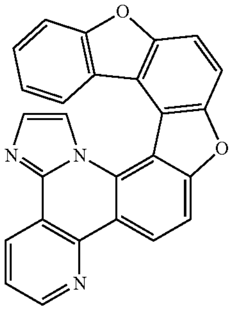
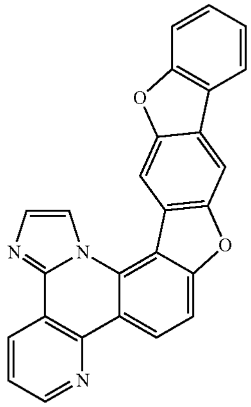
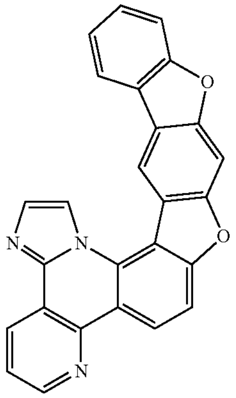
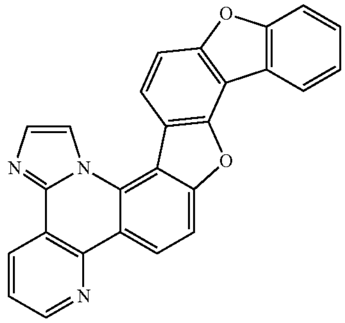
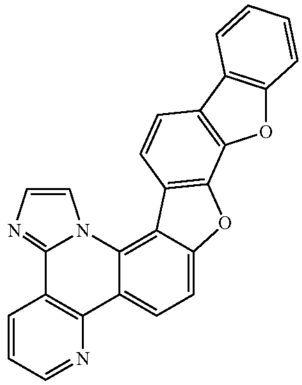
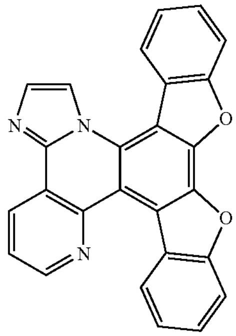
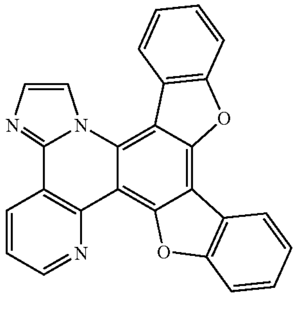
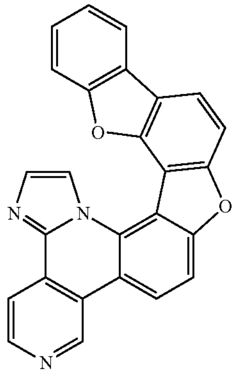
-continued
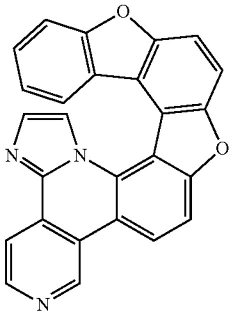
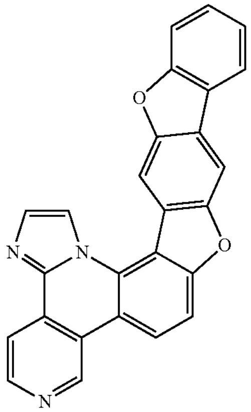
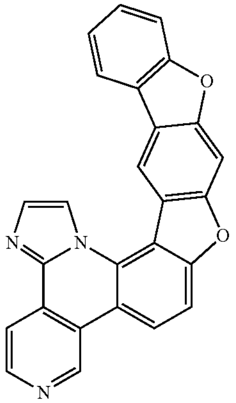
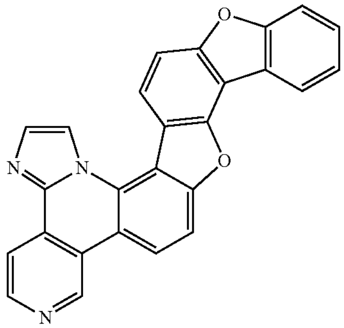
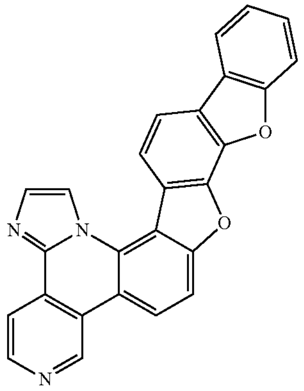
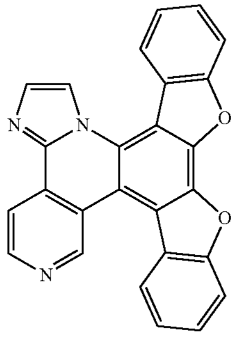
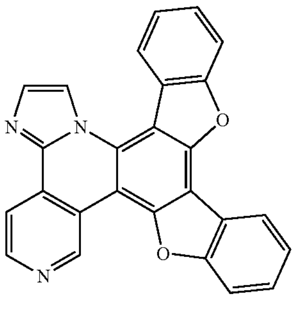
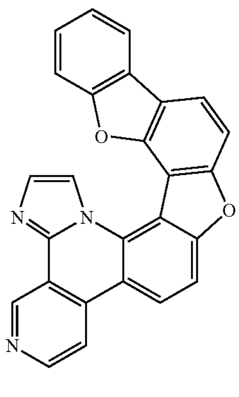

-continued
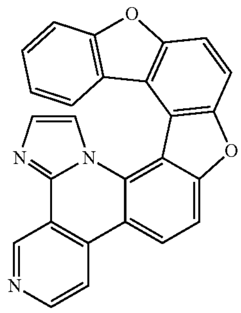
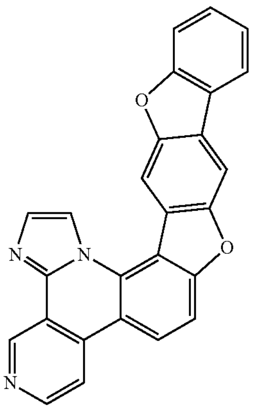
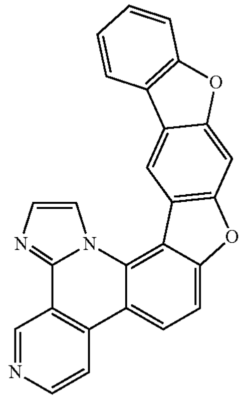
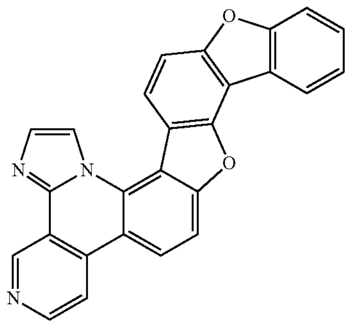
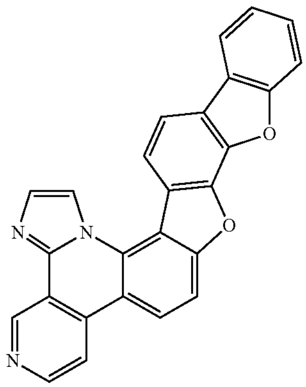
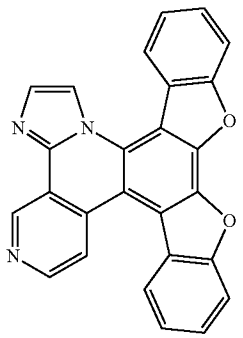
-continued
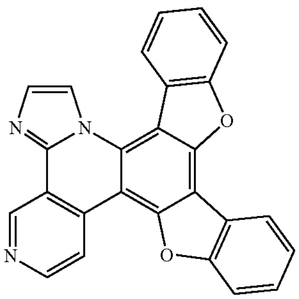
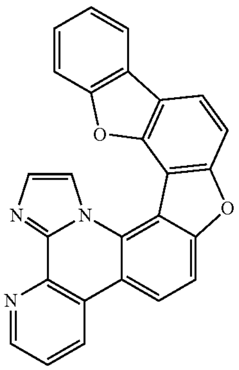
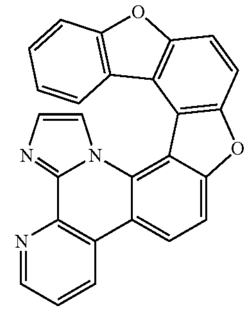
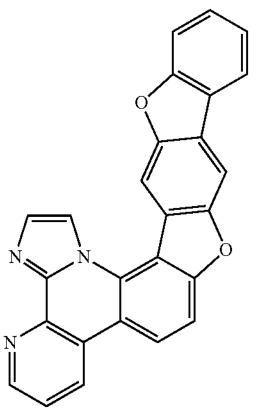
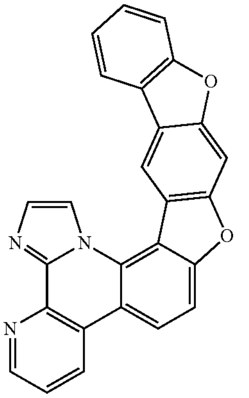
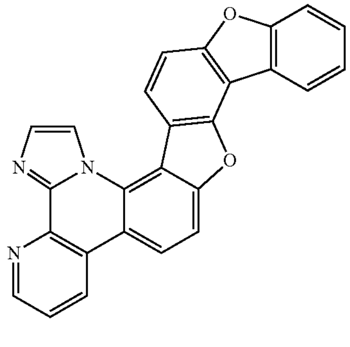

-continued
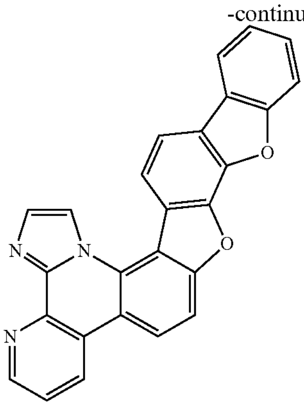
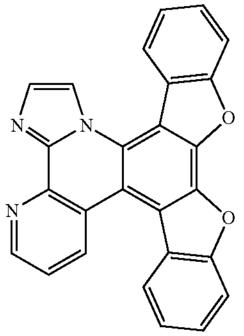
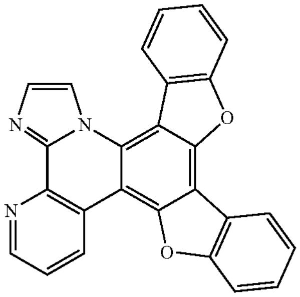
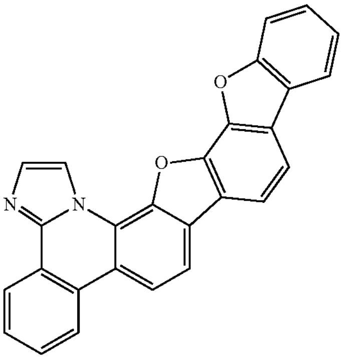
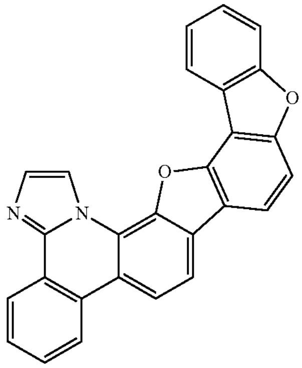
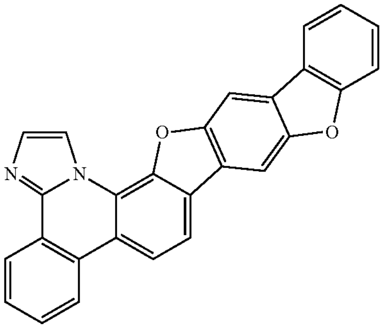
-continued
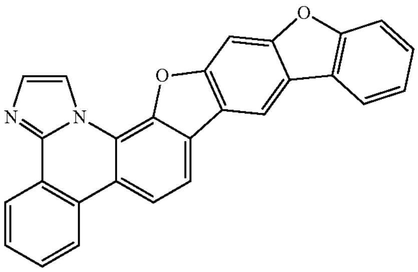
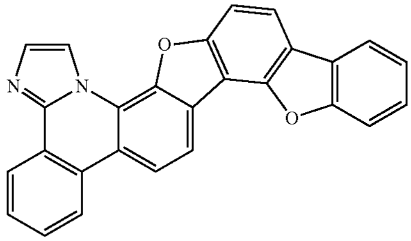
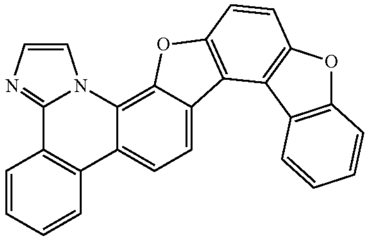
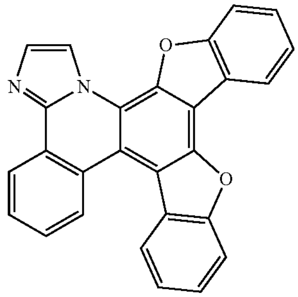
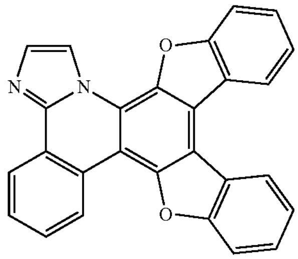
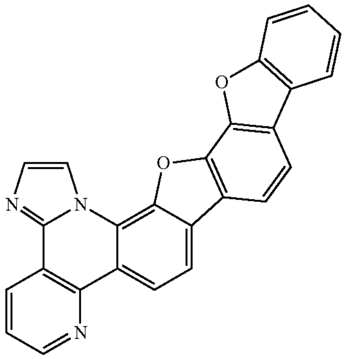

-continued
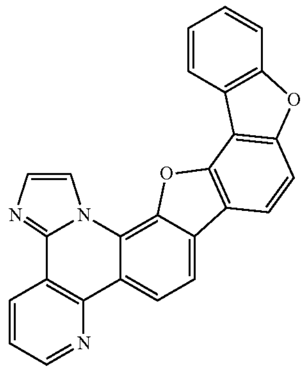
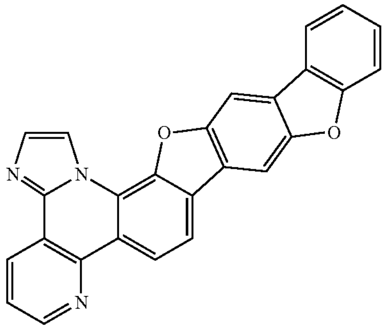
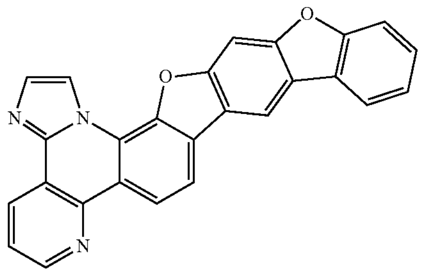
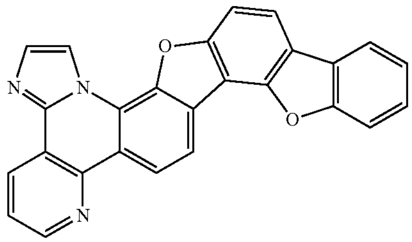
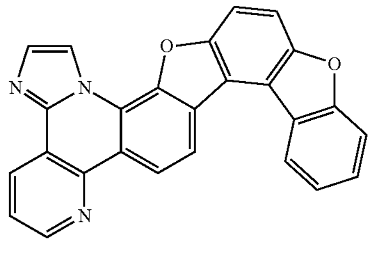
-continued
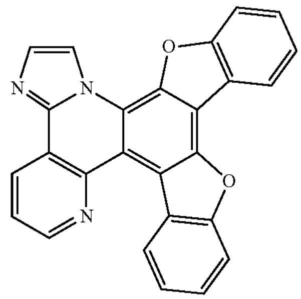
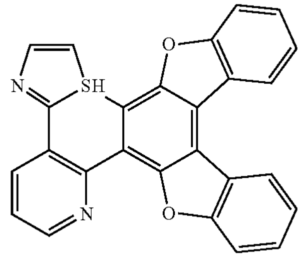
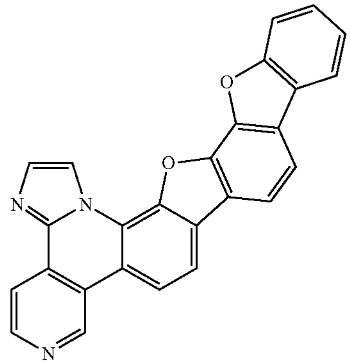
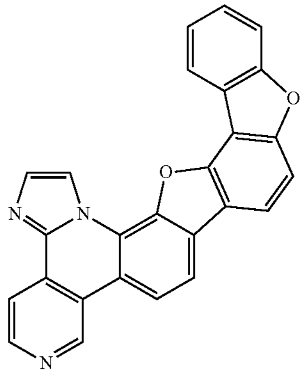
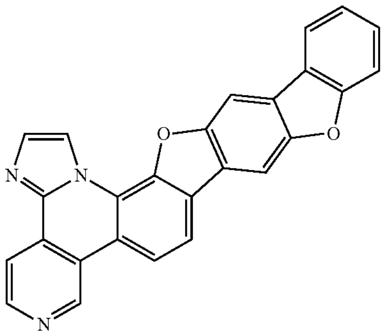

-continued
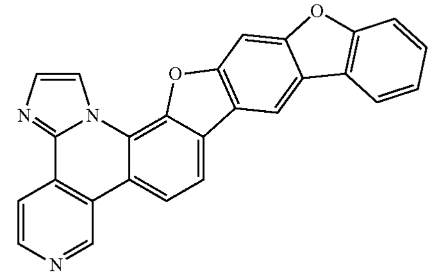
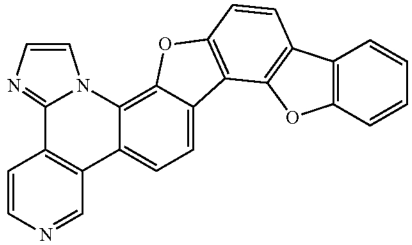
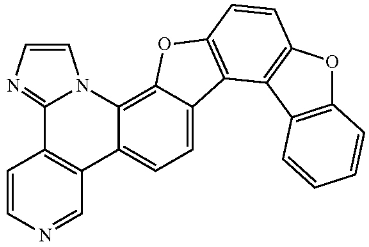
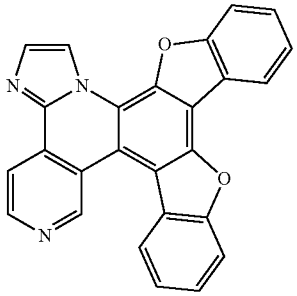
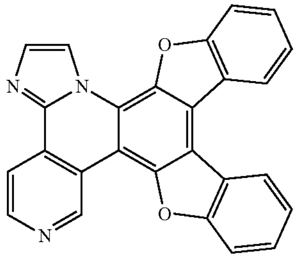
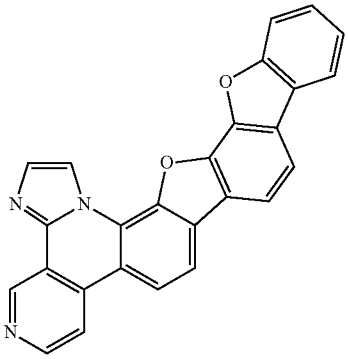
-continued
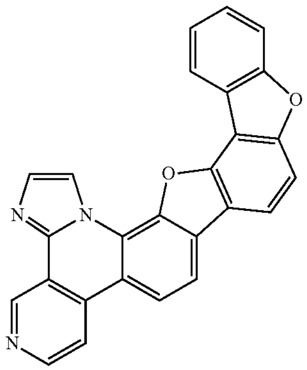
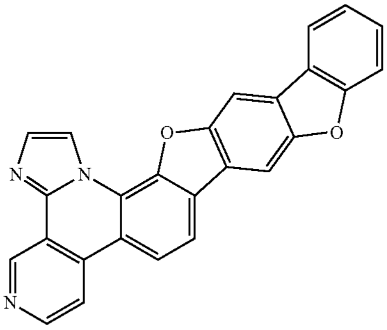
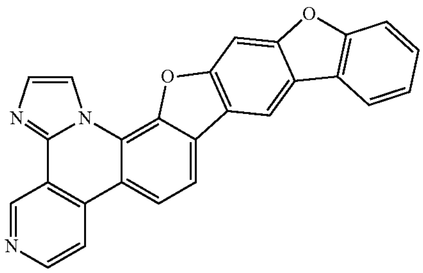
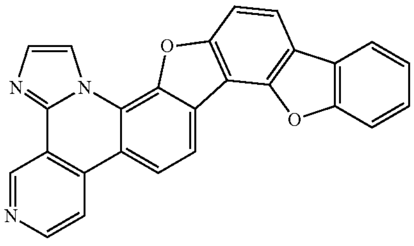
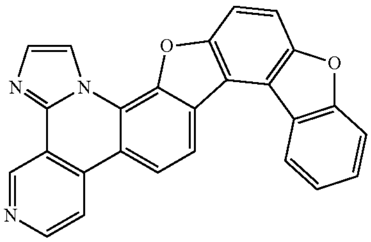

-continued
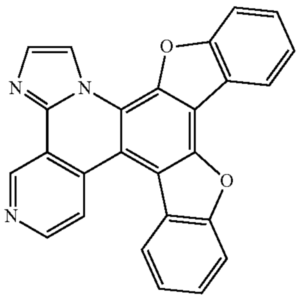
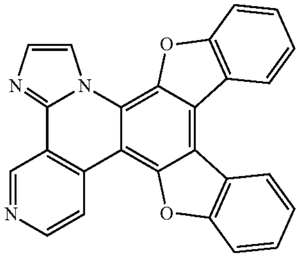
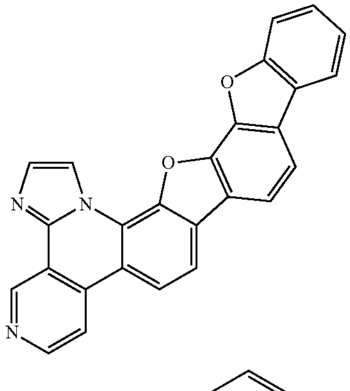
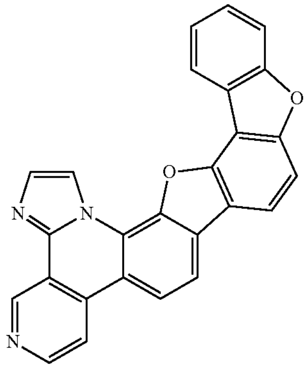
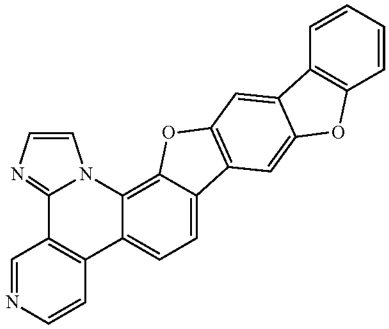
-continued
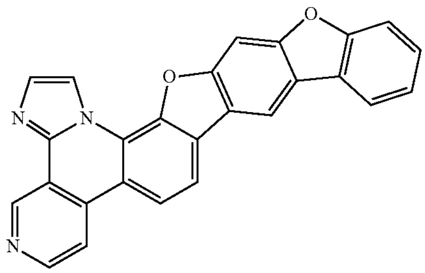
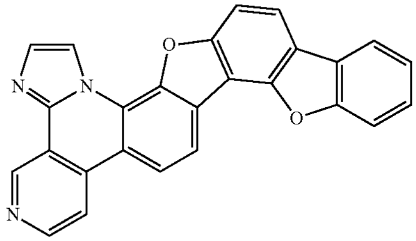
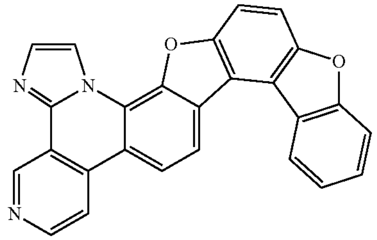
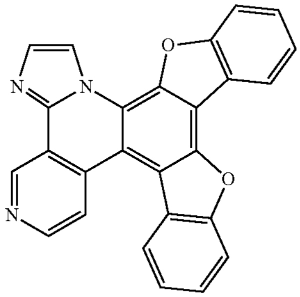
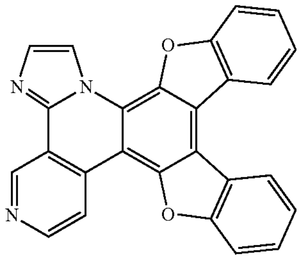
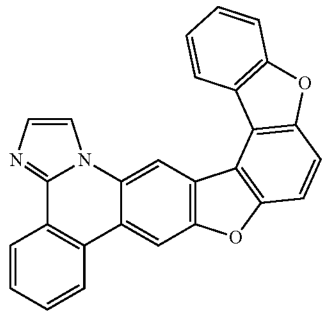

-continued
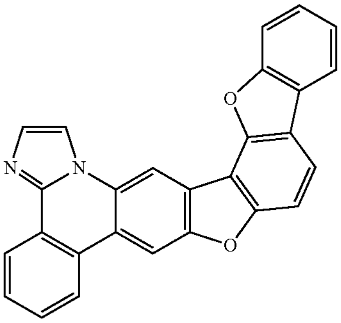
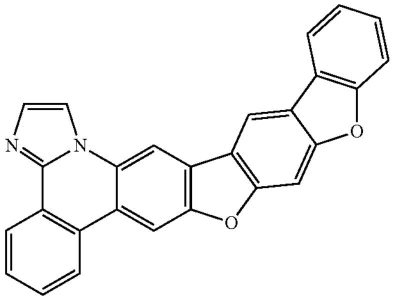
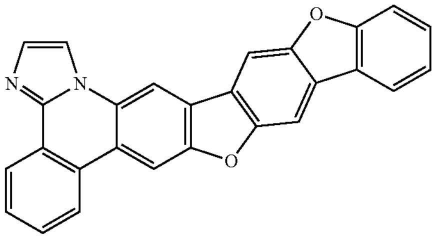
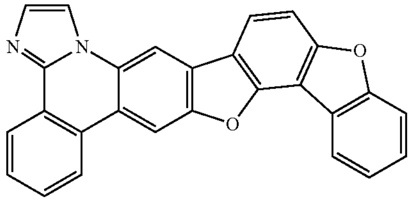
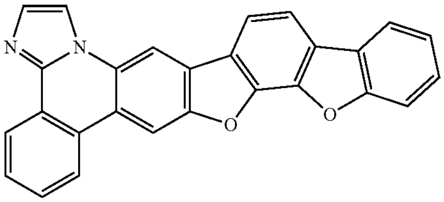
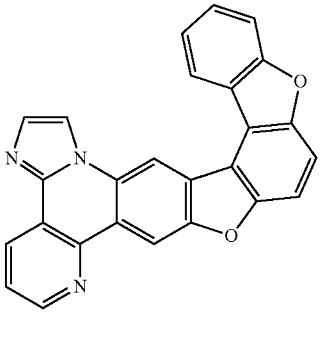
-continued
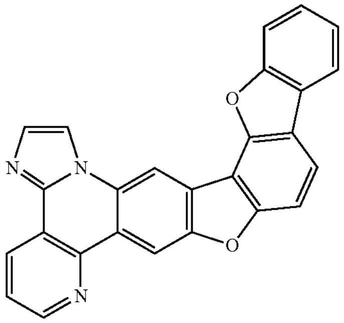
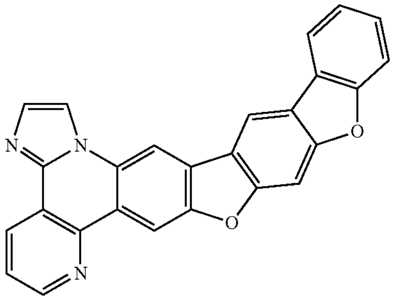
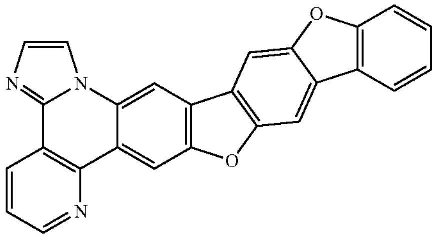
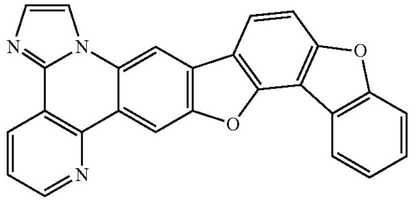
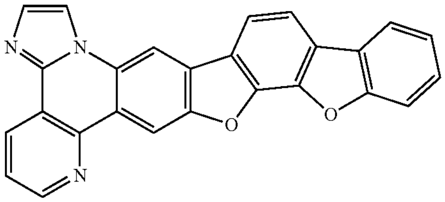
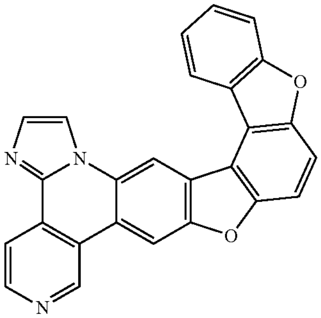

-continued
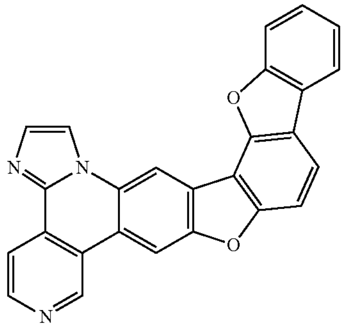
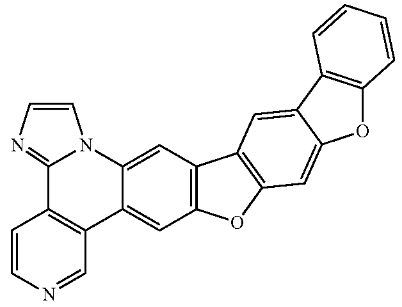
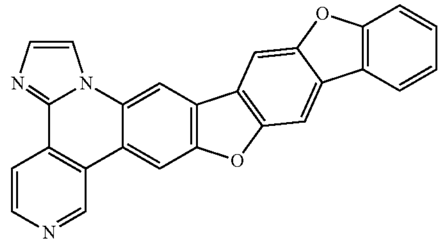
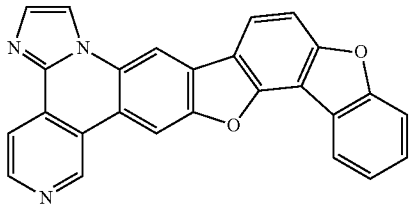
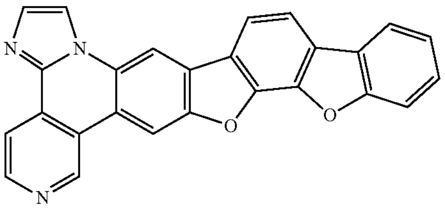
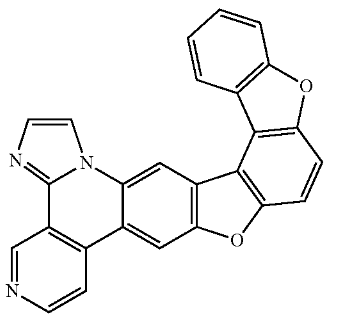
-continued
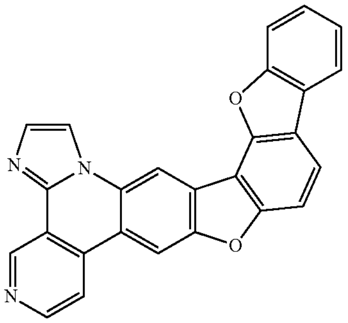
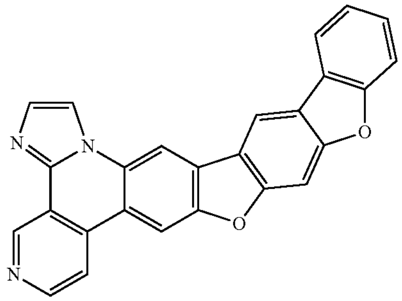
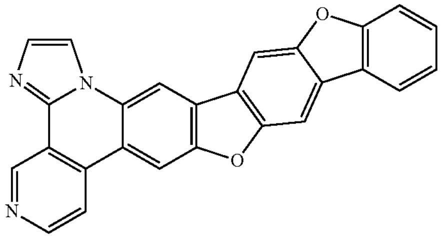
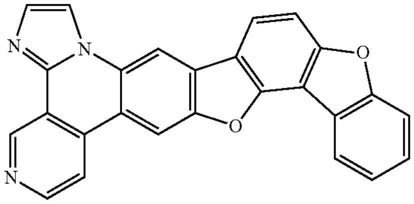
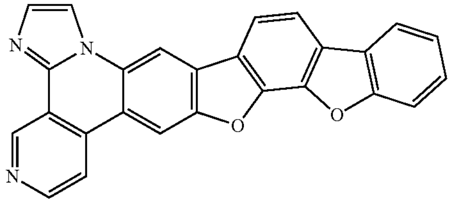
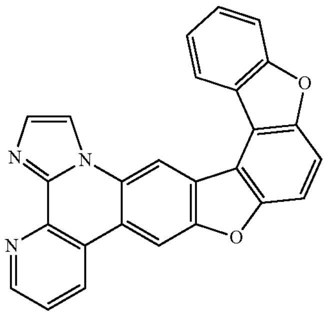

-continued
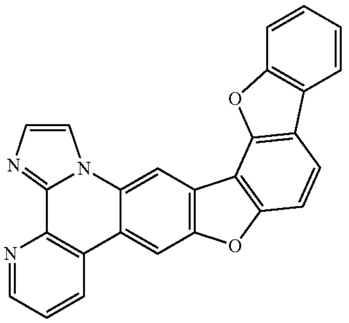
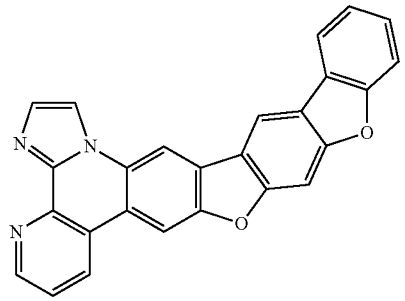
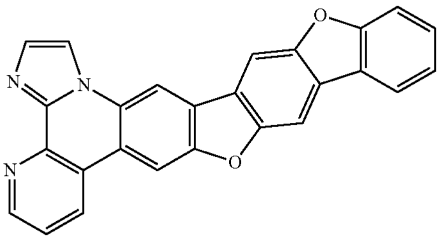
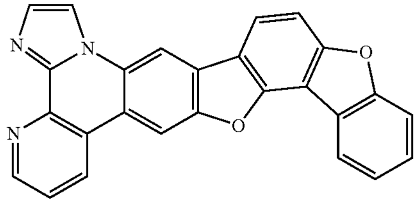
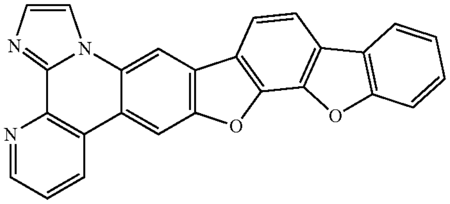
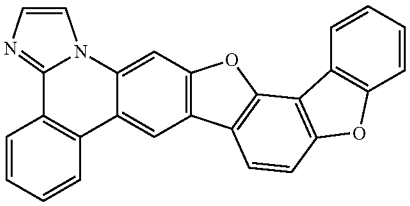
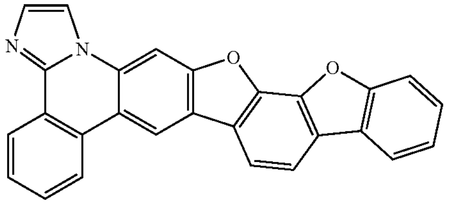
-continued
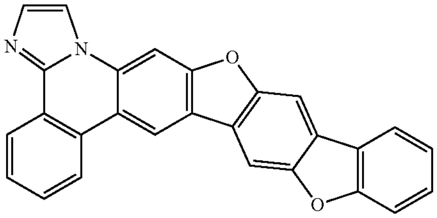
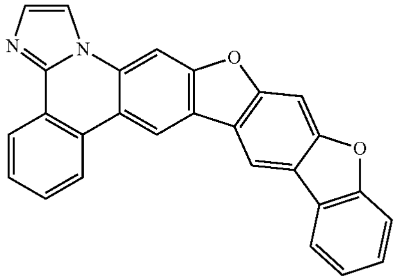
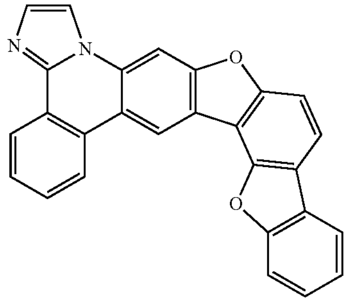
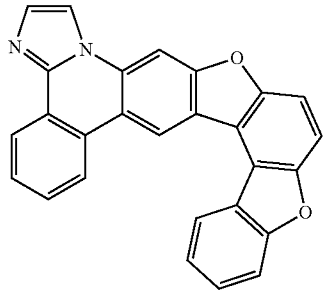
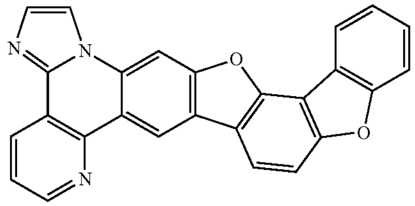
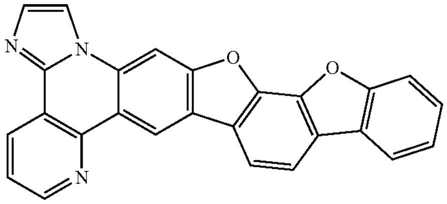
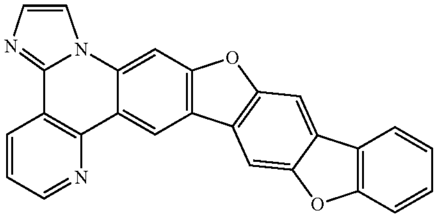

-continued
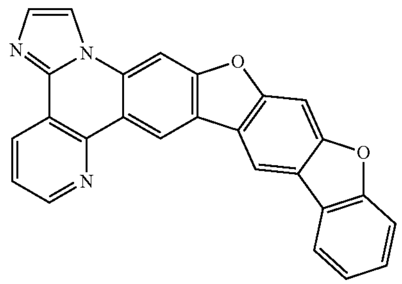
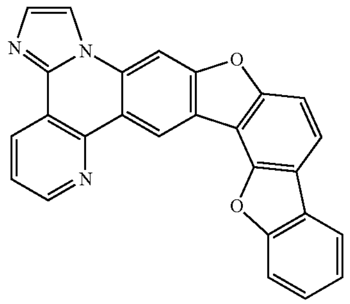
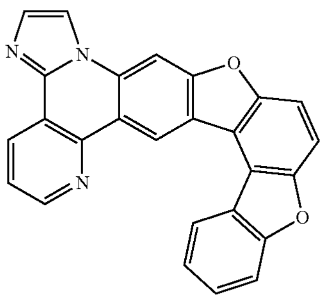
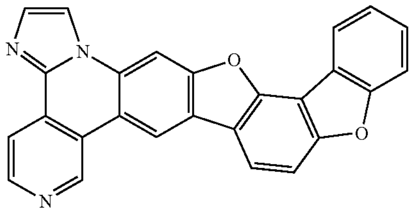
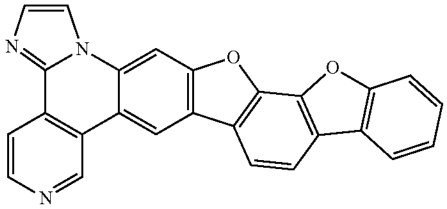
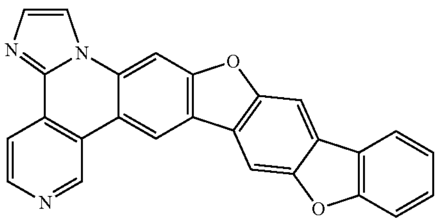
-continued
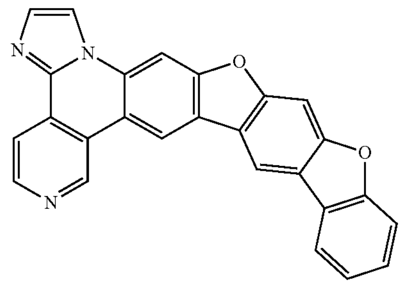
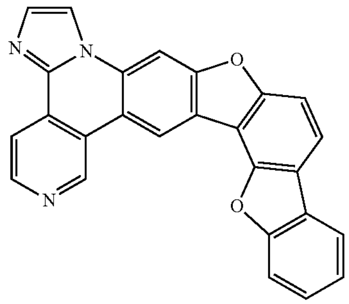
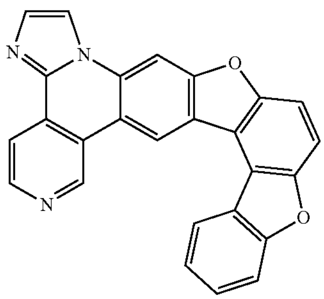
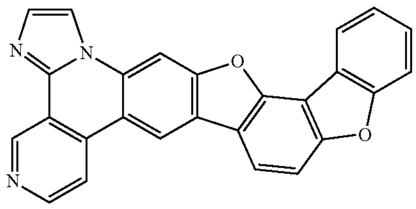
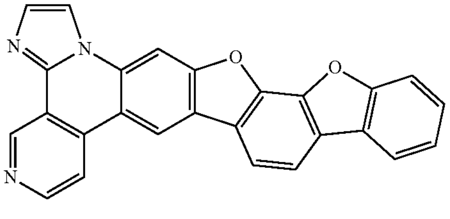
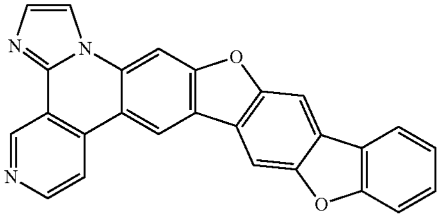

-continued
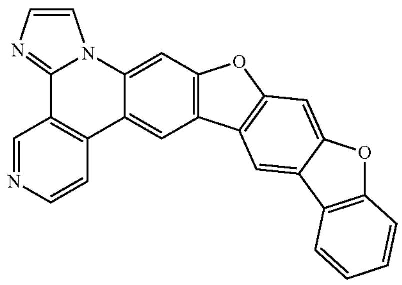
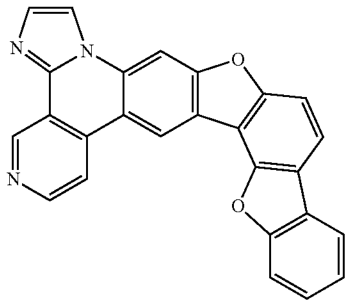
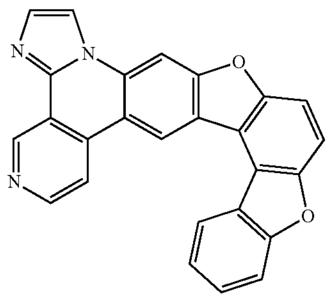
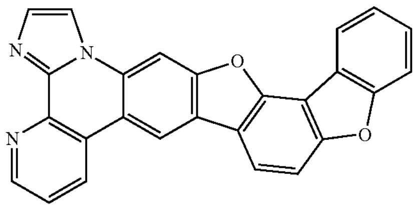
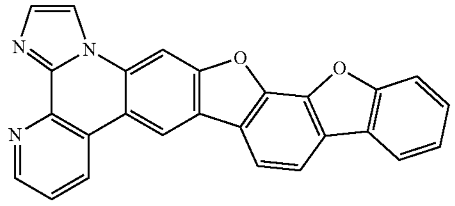
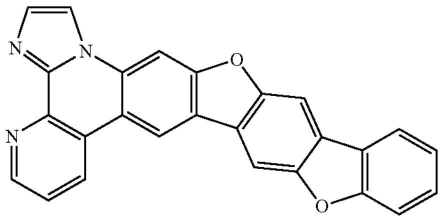
-continued
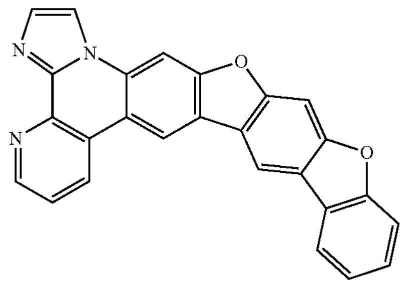
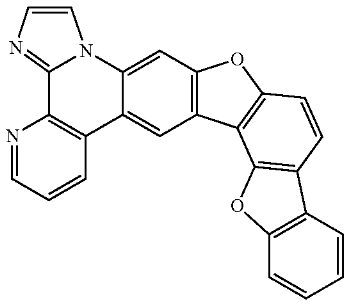
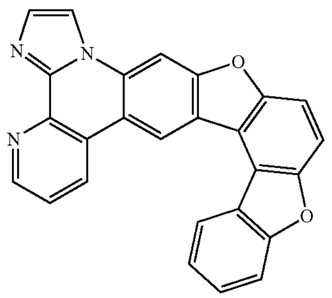
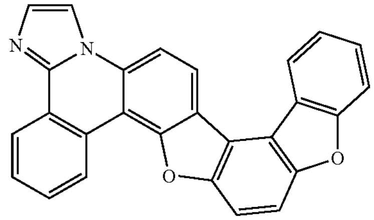
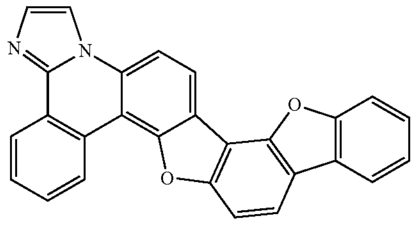
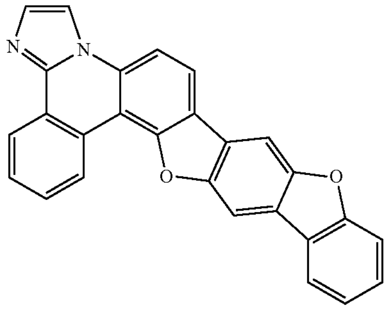

-continued
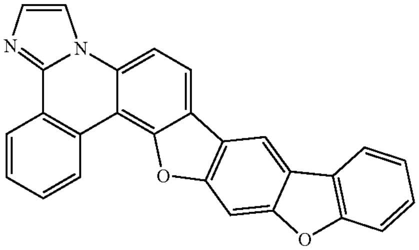
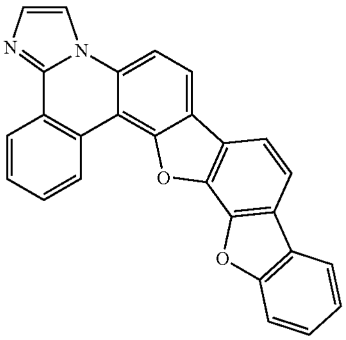
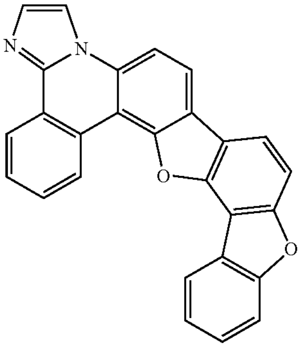
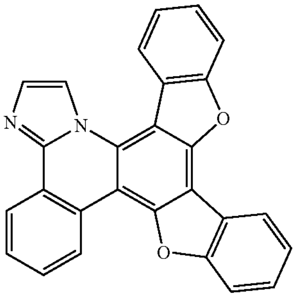
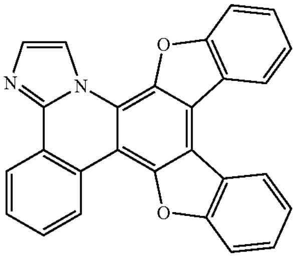
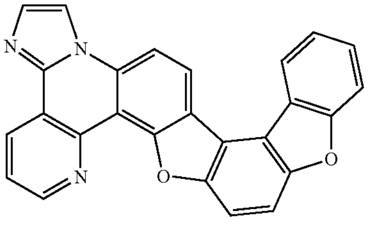
-continued
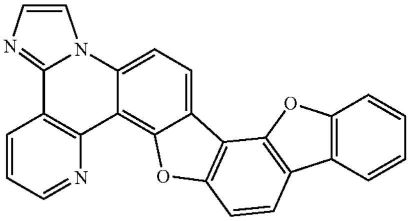
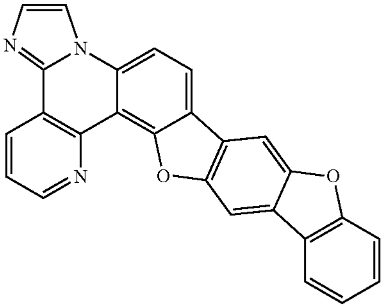
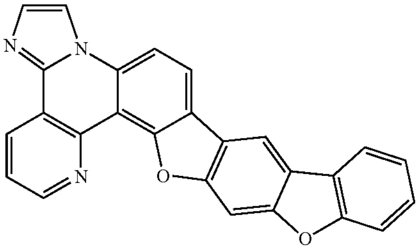
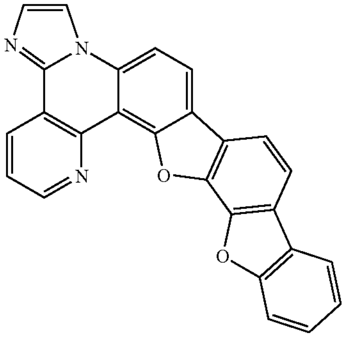
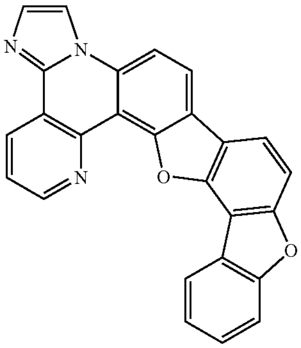

-continued
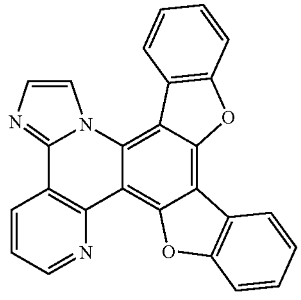
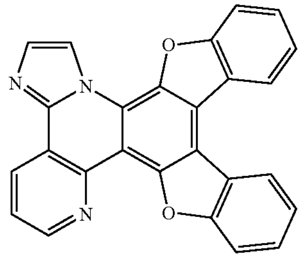
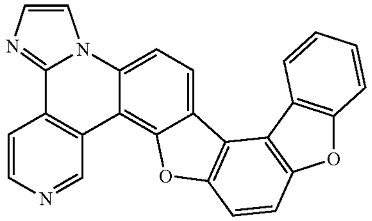
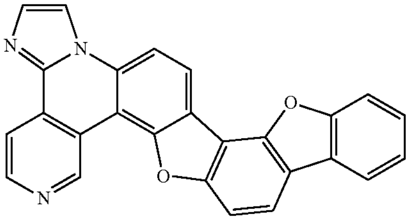
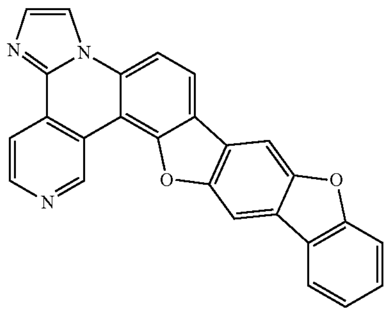
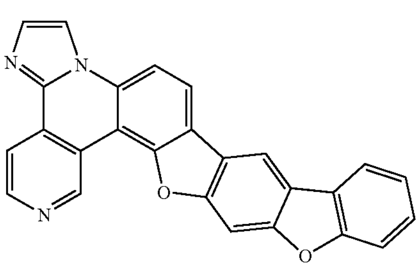
-continued
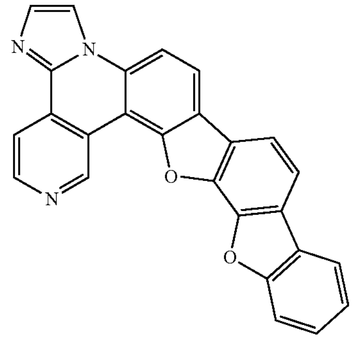
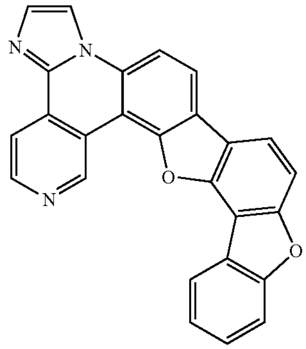
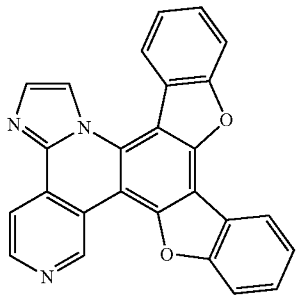
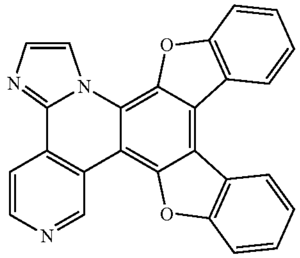
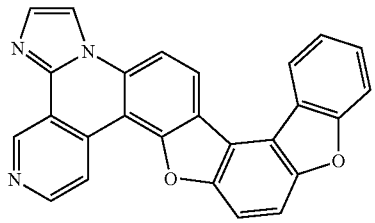
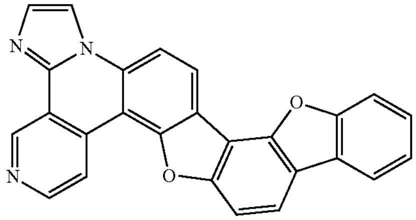

-continued
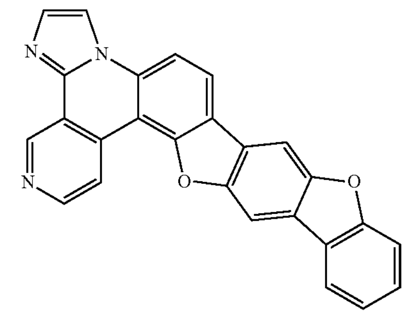
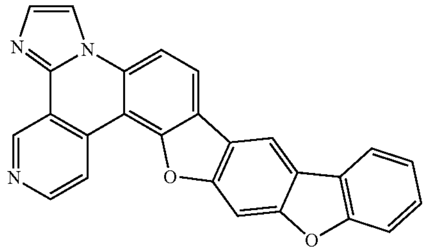
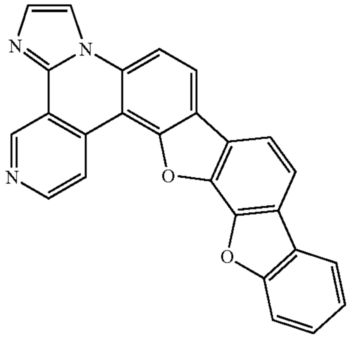
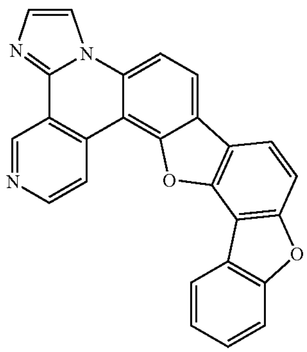
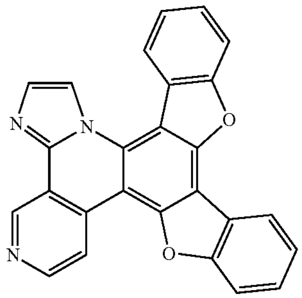
-continued
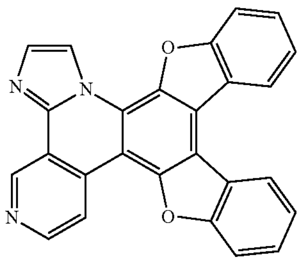
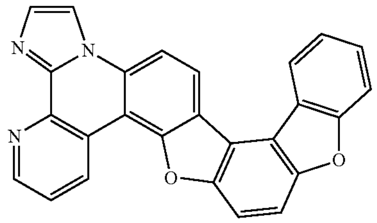
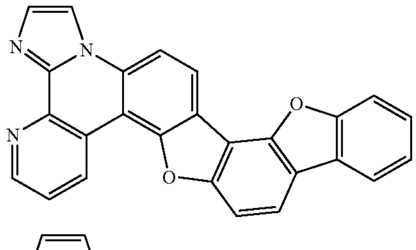
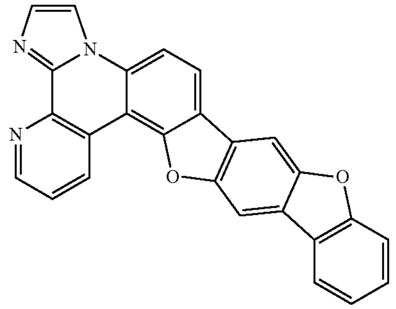
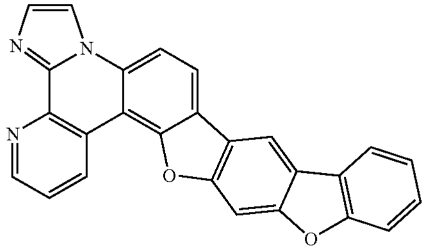
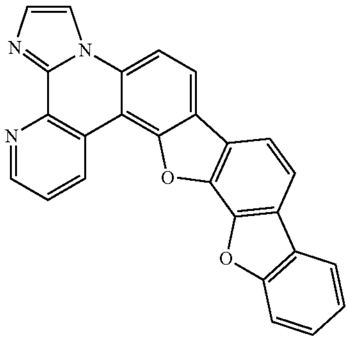

-continued
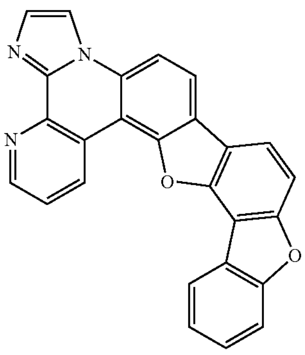
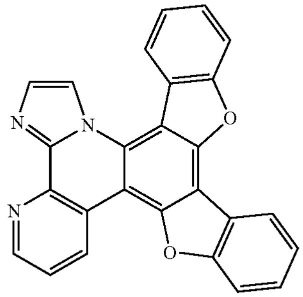
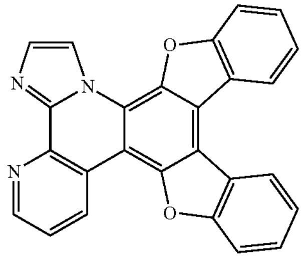
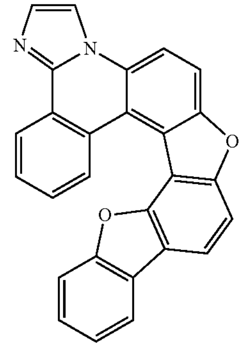
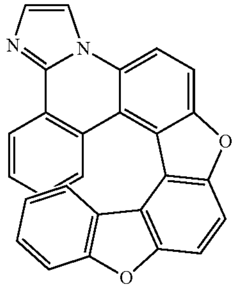
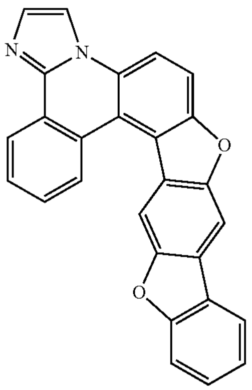
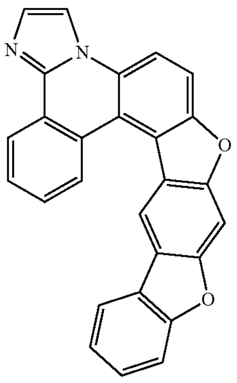
-continued
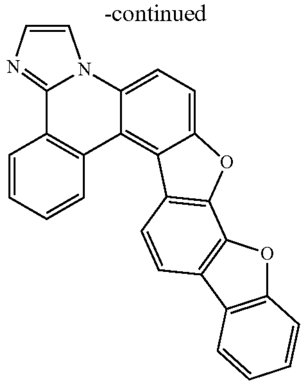
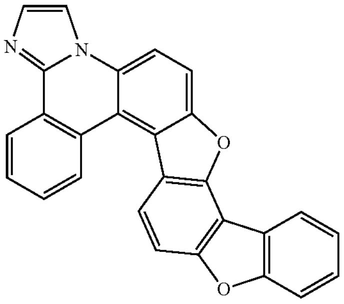
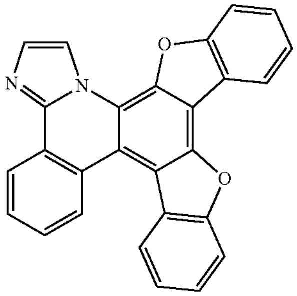
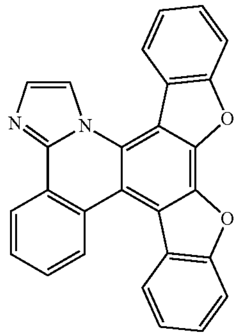
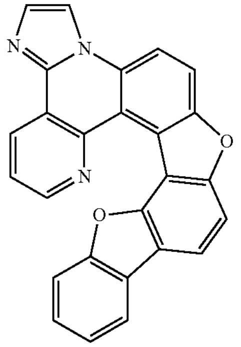
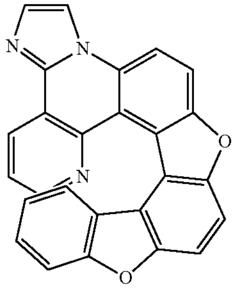
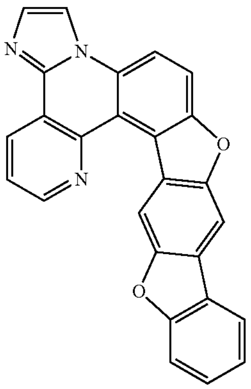
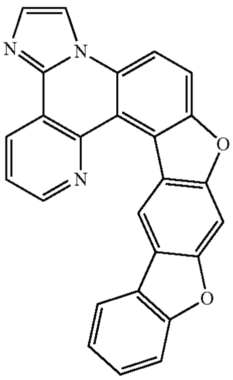

-continued
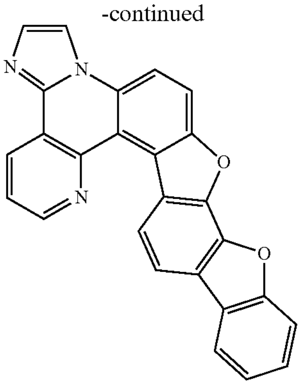
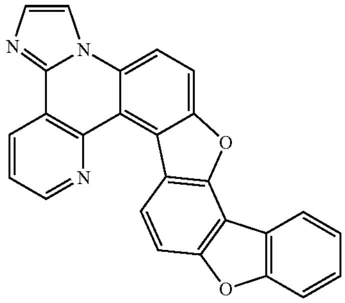
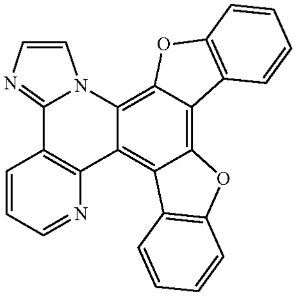
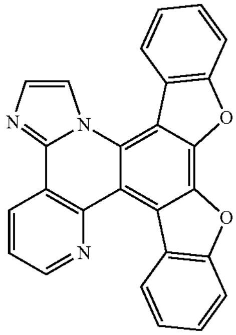
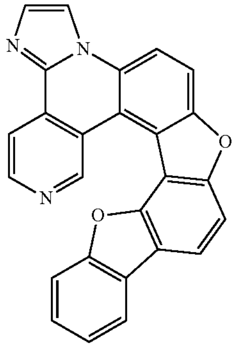
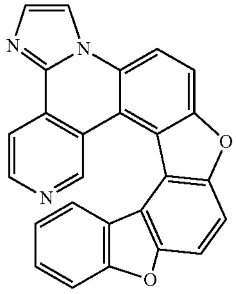
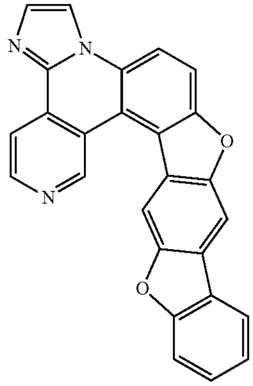
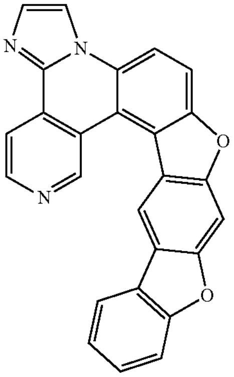
-continued
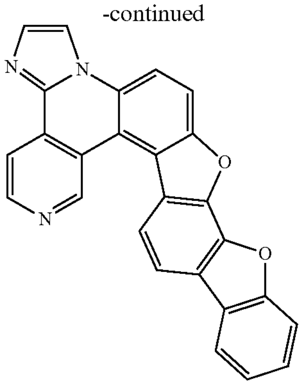
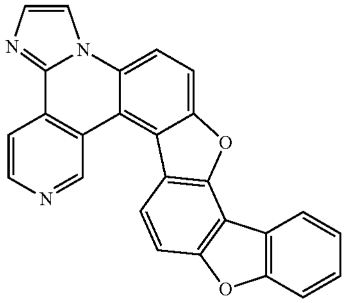
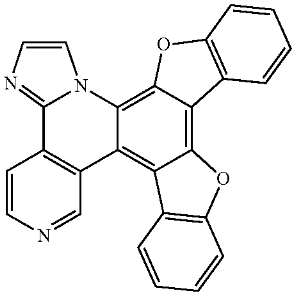
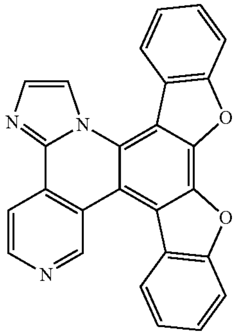
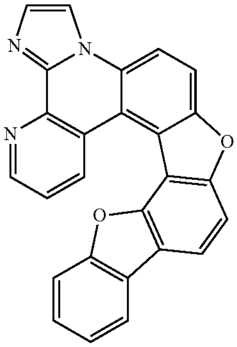
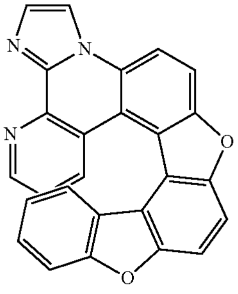
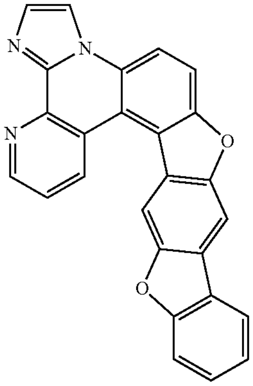
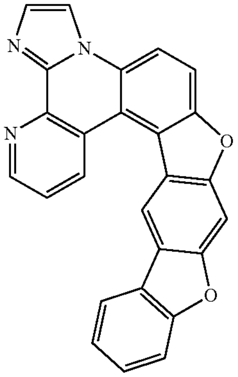

-continued

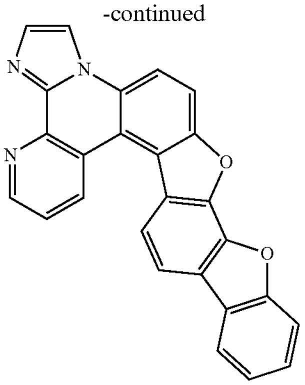

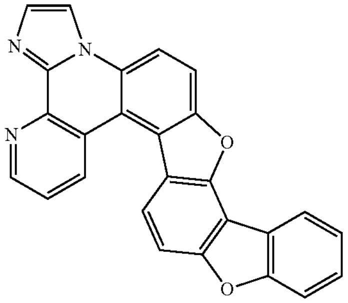

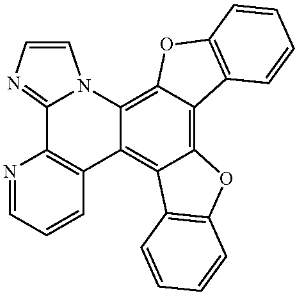

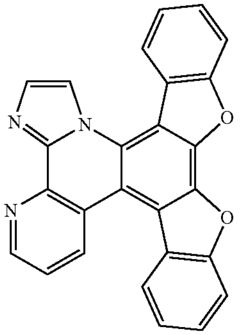

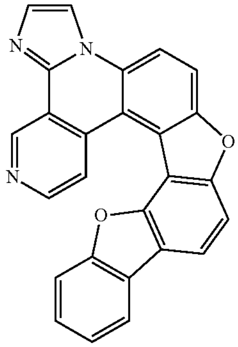

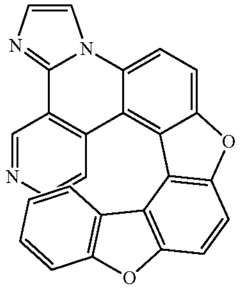

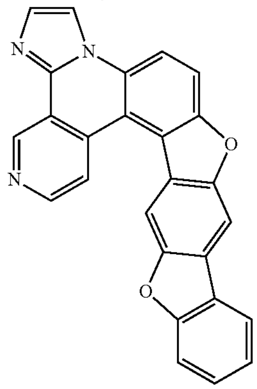

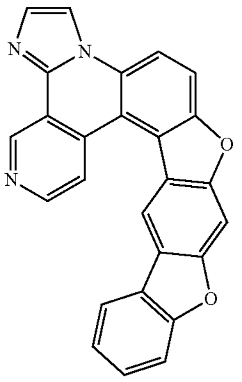

-continued

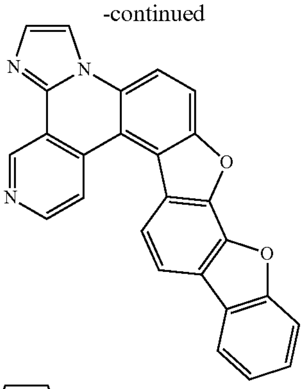

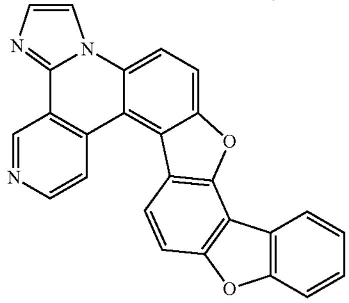

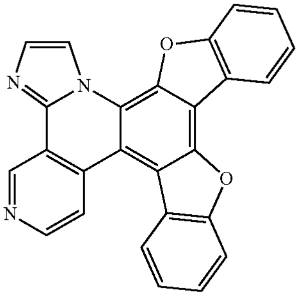

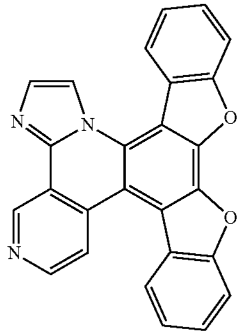

Compositions and Devices of the Invention

Also disclosed herein are organic emitting diodes or light emitting devices comprising one or more compound and/or compositions disclosed herein.

In one aspect, the device is an electro-optical device. Electro-optical devices include, but are not limited to, photo-absorbing devices such as solar- and photo-sensitive devices, organic light emitting devices, photo-emitting devices, or devices capable of both photo-absorption and emission and as markers for bio-applications. For example, the device can be an OLED.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art. Such devices are disclosed herein which comprise one or more of the compounds or compositions disclosed herein.

OLEDs can be produced by methods known to those skilled in the art. In general, the OLED is produced by successive vapor deposition of the individual layers onto a suitable substrate. Suitable substrates include, for example, glass, inorganic materials such as ITO or IZO or polymer films. For the vapor deposition, customary techniques may be used, such as thermal evaporation, chemical vapor deposition (CVD), physical vapor deposition (PVD) and others.

In an alternative process, the organic layers may be coated from solutions or dispersions in suitable solvents, in which case coating techniques known to those skilled in the art are employed. Suitable coating techniques are, for example, spin-coating, the casting method, the Langmuir-Blodgett ("LB") method, the inkjet printing method, dip-coating, letterpress printing, screen printing, doctor blade printing, slit-coating, roller printing, reverse roller printing, offset lithography printing, flexographic printing, web printing, spray coating, coating by a brush or pad printing, and the like. Among the processes mentioned, in addition to the aforementioned vapor deposition, preference is given to spin-coating, the inkjet printing method and the casting method since they are particularly simple and inexpensive to perform. In the case that layers of the OLED are obtained by the spin-coating method, the casting method or the inkjet printing method, the coating can be obtained using a solution prepared by dissolving the composition in a concentration of 0.0001 to 90% by weight in a suitable organic solvent such as benzene, toluene, xylene, tetrahydrofuran, methyltetrahydrofuran, N,N-dimethylformamide, acetone, acetonitrile, anisole, dichloromethane, dimethyl sulfoxide, water and mixtures thereof.

Compounds described herein can be used in a light emitting device such as an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4' diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

As contemplated herein, an OLED of the present invention may include an anode, a cathode, and an organic layer disposed between the anode and the cathode. The organic layer may include a host and a phosphorescent dopant. The organic layer can include a compound of the invention and its variations as described herein.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In one embodiment, the consumer product is selected from the group consisting of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, and a sign.

In some embodiments of the emissive region, the emissive region further comprises a host, wherein the host comprises at least one selected from the group consisting of metal complex, triphenylene, carbazole, dibenzothiophene, dibenzofuran, dibenzoselenophene, aza-triphenylene, aza-carbazole, aza-dibenzothiophene, aza-dibenzofuran, and aza-dibenzoselenophene.

The organic layer can also include a host. In some embodiments, two or more hosts are preferred. In some embodiments, the hosts used may be a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr^1$, $N(C_nH_{2n+1})_2$, $N(Ar^1)(Ar^2)$, $CH{=}CH{-}C_nH_{2n+1}$, $C{\equiv}C{-}C_nH_{2n+1}$, $Ar^1$, $Ar^1{-}Ar^2$, and $C_nH_{2n}{-}Ar^1$, or the host has no substitutions. In the preceding substituents n can range from 1 to 10; and $Ar^1$ and $Ar^2$ can be independently selected from the group consisting of benzene, biphenyl, naphthalene, triphenylene, carbazole, and heteroaromatic analogs thereof. The host can be an inorganic compound. For example, a Zn containing inorganic material e.g. ZnS.

Suitable hosts may include, but are not limited to, mCP (1,3-bis(carbazol-9-yl)benzene), mCPy (2,6-bis(N-carbazolyl)pyridine), TCP (1,3,5-tris(carbazol-9-yl)benzene), TCTA (4,4',4''-tris(carbazol-9-yl)triphenylamine), TPBi (1,3,5-tris(1-phenyl-1-H-benzimidazol-2-yl)benzene), mCBP (3,3-di(9H-carbazol-9-yl)biphenyl), pCBP (4,4'-bis(carbazol-9-yl)biphenyl), CDBP (4,4'-bis(9-carbazolyl)-2,2'-dimethylbiphenyl), DMFL-CBP (4,4'-bis(carbazol-9-yl)-9,9-dimethylfluorene), FL-4CBP (4,4'-bis(carbazol-9-yl)-9,9-bis(9-phenyl-9H-carbazole)fluorene), FL-2CBP (9,9-bis(4-carbazol-9-yl)phenyl)fluorene, also abbreviated as CPF), DPFL-CBP (4,4'-bis(carbazol-9-yl)-9,9-ditolylfluorene), FL-2CBP (9,9-bis(9-phenyl-9H-carbazole)fluorene), Spiro-CBP (2,2',7,7'-tetrakis(carbazol-9-yl)-9,9'-spirobifluorene), ADN (9,10-di(naphth-2-yl)anthracene), TBADN (3-tert-butyl-9,10-di(naphth-2-yl)anthracene), DPVBi (4,4'-bis(2,2-diphenylethen-1-yl)-4,4'-dimethylphenyl), p-DMDPVBi (4,4'-bis(2,2-diphenylethen-1-yl)-4,4'-dimethylphenyl), TDAF (tert(9,9-diarylfluorene)), BSBF (2-(9,9'-spirobifluoren-2-yl)-9,9'-spirobifluorene), TSBF (2,7-bis(9,9'-spirobifluoren-2-yl)-9,9'-spirobifluorene), BDAF (bis(9,9-diarylfluorene)), p-TDPVBi (4,4'-bis(2,2-diphenylethen-1-yl)-4,4'-di-(tert-butyl)phenyl), TPB3 (1,3,5-tri(pyren-1-yl) benzene, PBD (2-(4-biphenylyl)-5-(4-tert-butylphenyl)-1,3,4-oxadiazole), BCP (2,9-dimethyl-4,7-diphenyl-1,10-phenanthroline), BP-OXD-Bpy (6,6'-bis[5-(biphenyl-4-yl)-1,3,4-oxadiazo-2-yl]-2,2'-bipyridyl), NTAZ (4-(naphth-1-yl)-3,5-diphenyl-4H-1,2,4-triazole), Bpy-OXD (1,3-bis[2-(2,2'-bipyrid-6-yl)-1,3,4oxadiazo-5-yl]benzene), BPhen (4,7-diphenyl-1,10-phenanthroline), TAZ (3-(4-biphenylyl)-4-phenyl-5-tert-butylphenyl-1,2,4-triazole), PADN (2-phenyl-9,10-di(naphth-2-yl)anthracene), Bpy-FOXD (2,7-bis[2-(2,2'-bipyrid-6-yl)-1,3,4-oxadiazol-5-yl]-9,9-dimethylfluorene), OXD-7 (1,3-bis[2-(4-tert-butylphenyl)-1,3,4-oxadiazol-5-yl]benzene), HNBphen (2-(naphth-2-yl)-4,7-diphenyl-1,10-phenanthroline), NBphen (2,9-bis(naphth-2-yl)-4,7-diphenyl-1,10-phenanthroline), 3TPYMB (tris(2,4,6-trimethyl-3-(pyrid-3-yl)phenyl)borane), 2-NPIP (1-methyl-2-(4-(naphth-2-yl)phenyl)-1H-imidazo[4,5-f]-[1,10]phenanthroline), Liq (8-hydroxyquinolinolatolithium), and Alq (bis(2-methyl-8-quinolinolate)-4-(phenylphenolato) aluminum), and also of mixtures of the aforesaid substances.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a "monovalent variant of a compound" refers to a moiety that is identical to the compound except that one hydrogen has been removed and replaced with a bond to the rest of the chemical structure. As used herein, a "polyvalent variant of a compound" refers to a moiety that is identical to the compound except that more than one hydrogen has been removed and replaced with a bond or bonds to the rest of the chemical structure. In the instance of a supramolecule, the inventive compound can also be incorporated into the supramolecule complex without covalent bonds.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified in references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

In yet another aspect of the present disclosure, a formulation that comprises the novel compound disclosed herein is described. The formulation can include one or more components selected from the group consisting of a solvent, a host, a hole injection material, hole transport material, and an electron transport layer material, disclosed herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the composite materials of the present invention and practice the claimed methods. The following working examples therefore, specifically point out the preferred embodiments of the present invention, and are not to be construed as limiting in any way the remainder of the disclosure.

Example 1: TADF Materials

Figure 2:
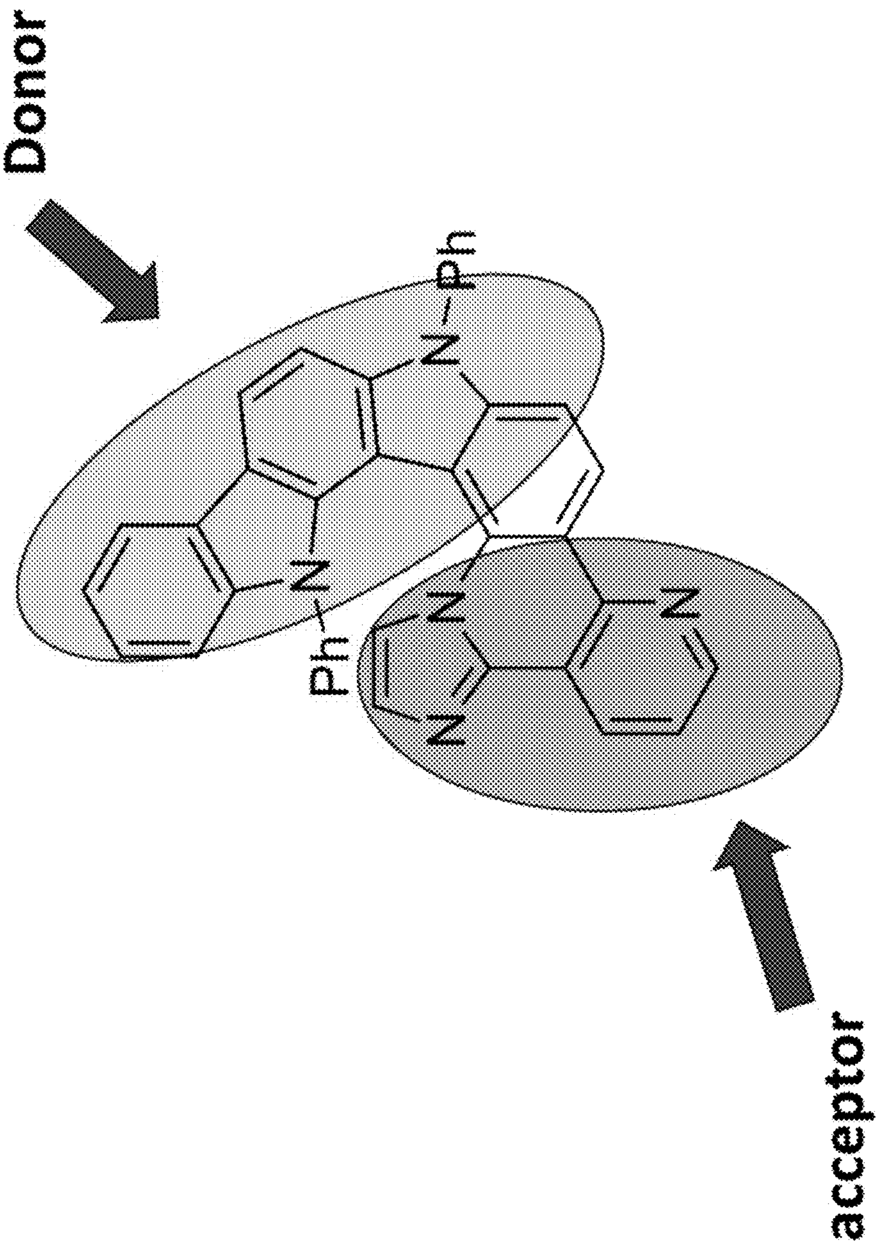
FIG. 2 is a diagram of the electronic properties of the various moieties of the inventive compounds

The design of traditional Thermally Activated Delayed Fluorescence (TADF) OLED materials is based on a strongly electron donating and a strongly electron accepting group in the compound. The strong donor and acceptor lead to the lower stability. A new structure of TADF OLED materials is described herein, in which weak donor and acceptor groups are part of the same conjugated system (FIG. 2). The resulting structures may impart higher EQE and better material lifetimes.

In one embodiment, an exemplary compound may be prepared according to the following scheme.

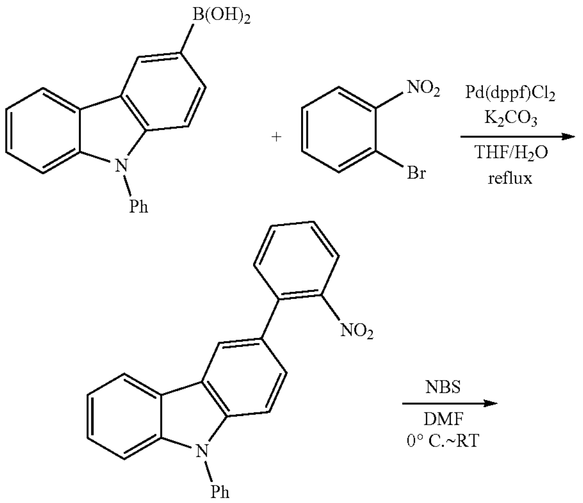

-continued
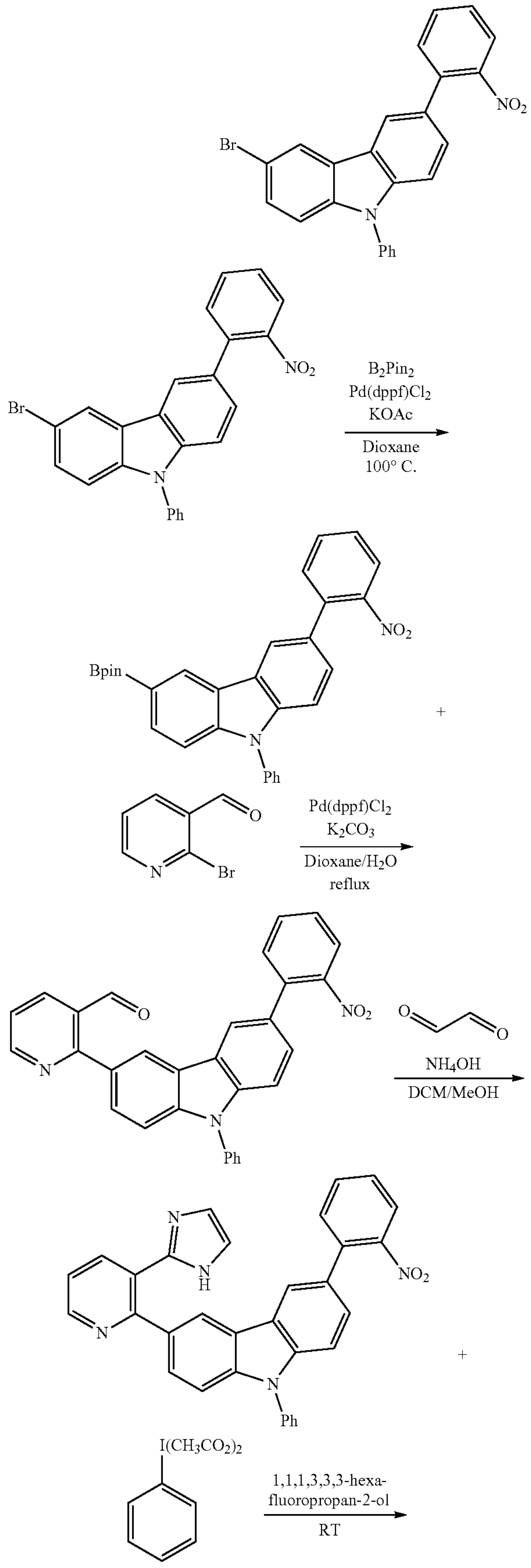
-continued
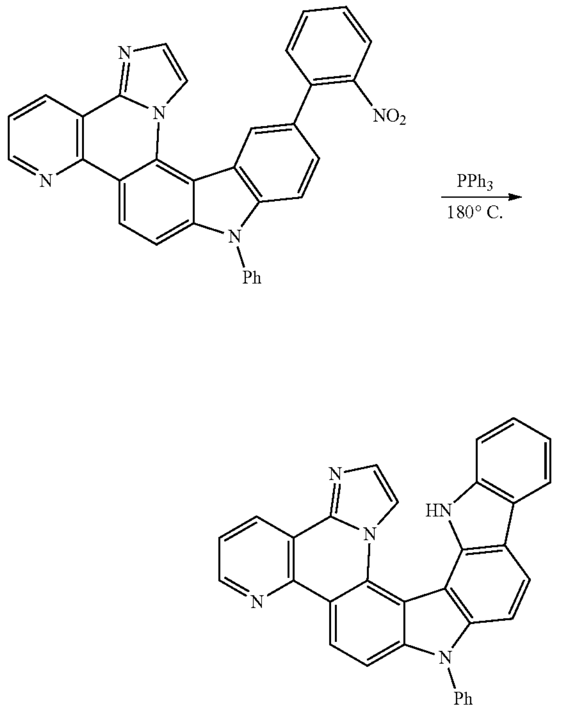
In one embodiment, an exemplary compound may be prepared according to the following scheme:
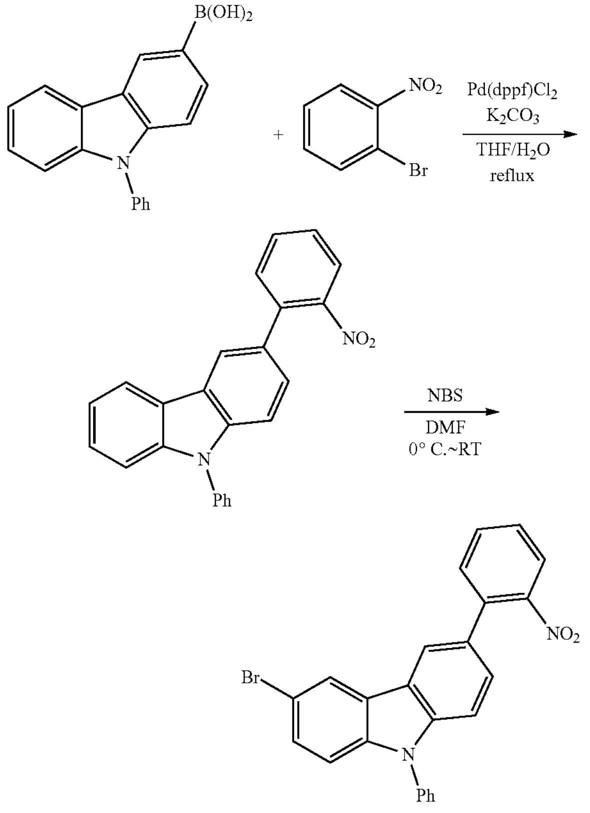

-continued
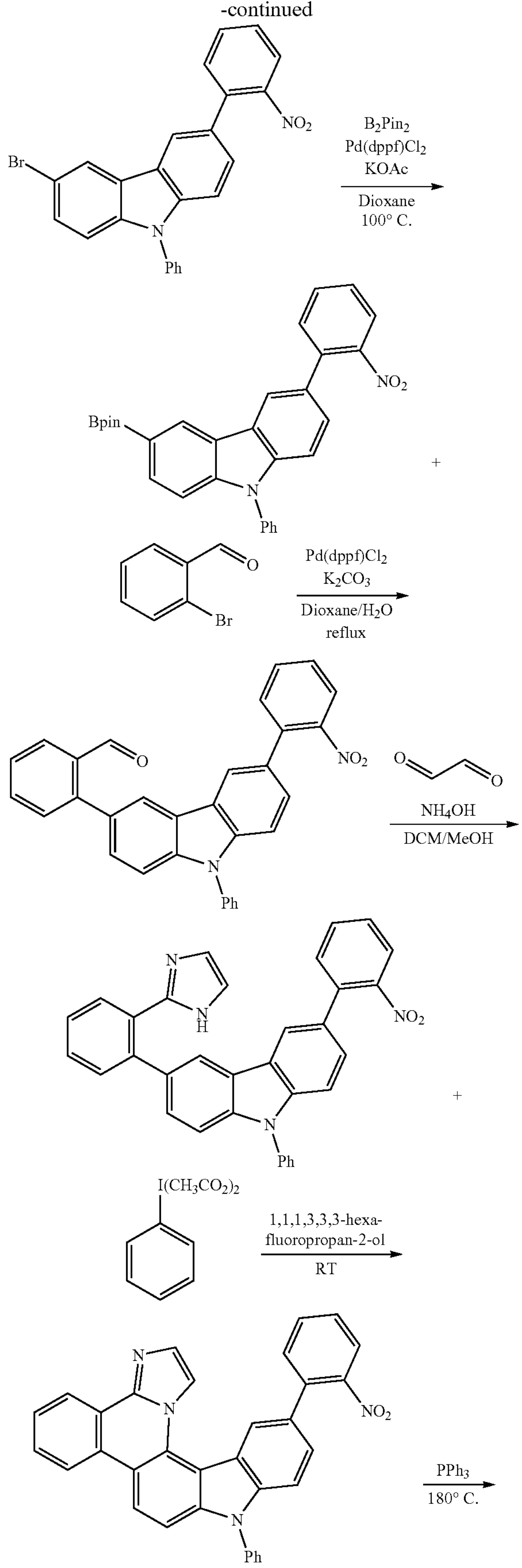
-continued
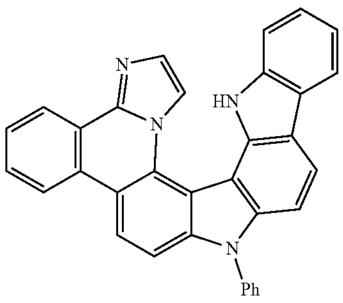 [SMILES: c1ccc(-n2c3ccc4c5ccccc5n(-c5ccccc5)c4c3c3c2ccc2c4ncccc4c4nccn4c23)cc1]
In one embodiment, an exemplary compound may be prepared according to the following scheme:
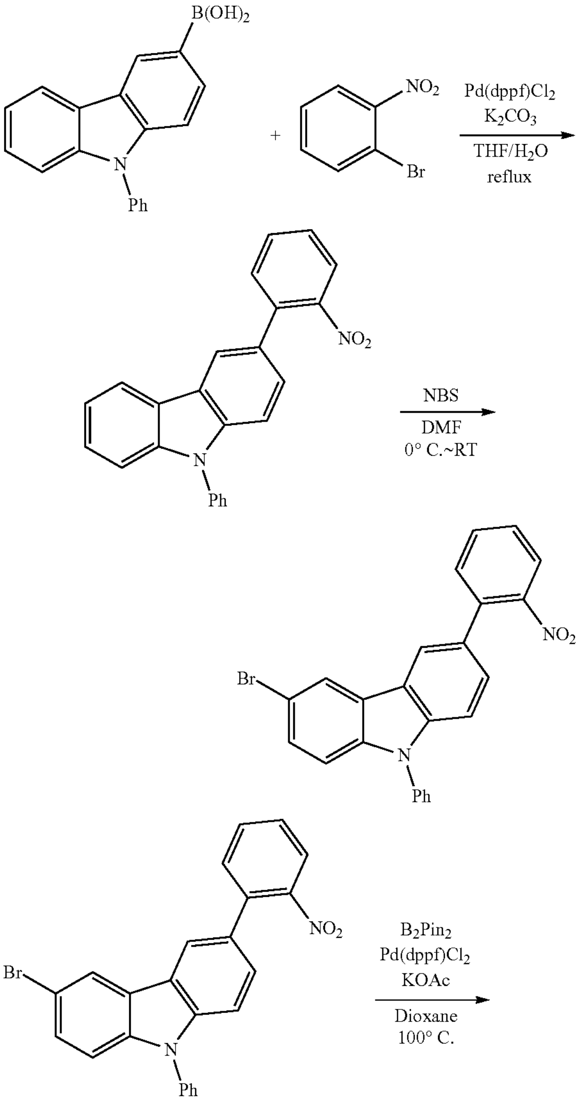

-continued

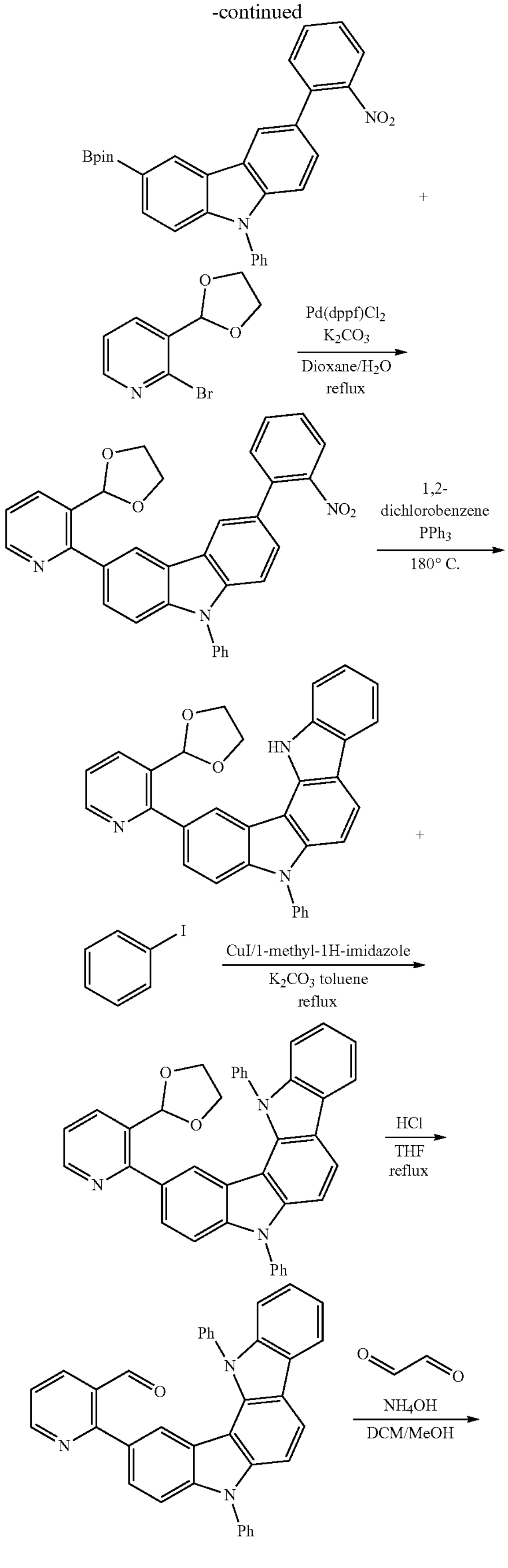

-continued

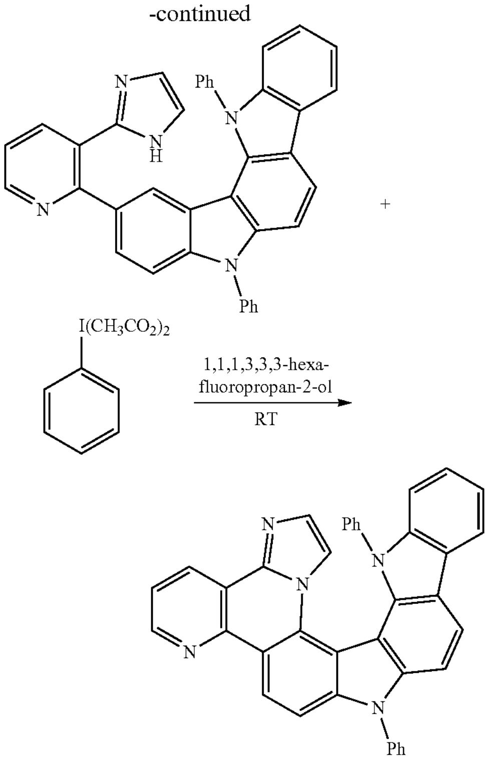

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A compound of General Formula I:

General Formula I

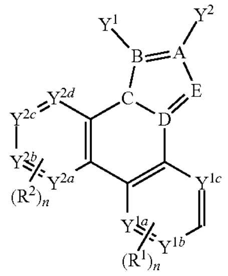

wherein:

$Y^{1a}$, $Y^{1b}$, $Y^{1c}$, $Y^{2a}$ $Y^{2b}$, $Y^{2c}$, and $Y^{2d}$ each independently represents C or N;

C and E each represent N;

each A, B, and D independently represent C or N;

each of $Y^1$ and $Y^2$ is independently absent or present, valency permitting;

$Y^1$ and $Y^2$ independently represent hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; or $Y^1$ and $Y^2$ may together form a ring;

$R^1$ and $R^2$ are independently absent or present, valency permitting, and each $R^1$ and $R^2$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; any two adjacent $R^1$ and $R^2$ may together form a ring;

provided that at least two adjacent $R^2$ together represent a group of Formula A:

Formula A

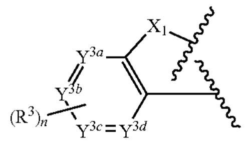

wherein:

waved lines indicate bonds to the respective $Y^{2a}$, $Y^{2b}$, $Y^{2c}$, or $Y^{2d}$;

$Y^{3a}$ $Y^{3b}$, $Y^{3c}$, and $Y^{3d}$ each independently represents C or N;

$X_1$ independently represents C, N, Si, O, S, Ge, P, As, Se, B, Al, or Bi, or if valency permits, $X_1$ independently represents $CR^4$, $SiR^4$, $GeR^4$, $NR^4$, P═O, As═O, B, $BR^4$, $AlR^4$, Bi═O, $CR^4R^5$, C═O, $SiR^4R^5$, $GeR^4R^5$, $PR^4$, $PR^4R^5$, $R^4$P═O, $AsR^4$, $R^4$As═O, S═O, $SO_2$, Se═O, $SeO_2$, $BR^4$, $BR^4R^5$, $AlR^4$, $AlR^4R^5$, $R^4$Bi═O, or $BiR^4$;

$R^3$, $R^4$, and $R^5$ are independently absent or present, valency permitting, and each $R^3$, $R^4$ and $R^5$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; any two of $R^1$, $R^2$, $R^3$, $R^4$, and $R^5$ may together form a ring;

each n is an integer, valency permitting; and wherein at least two adjacent $R^3$ together represent a group of Formula B:

Formula B

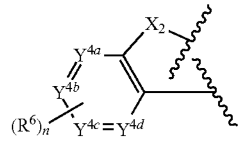

wherein waved lines indicate bonds to the respective $Y^{3a}$, $Y^{3b}$, $Y^{3c}$, and $Y^{3d}$;

$Y^{4a}$, $Y^{4b}$, $Y^{4c}$, and $Y^{4d}$ each independently represents C or N;

$X_2$ independently represents C, N, Si, O, S, Ge, P, As, Se, B, Al, or Bi, or if valency permits, $X_2$ independently represents $CR^7$, $SiR^7$, $GeR^7$, $NR^7$, P═O, As═O, B, $BR^7$, $AlR^7$, Bi═O, $CR^7R^8$, C═O, $SiR^7R^8$, $GeR^7R^8$, $PR^7$, $PR^7R^8$, $R^7$P═O, $AsR^7$, $R^7$As═O, S═O, $SO_2$, Se═O, $SeO_2$, $BR^7$, $BR^7R^8$, $AlR^7$, $AlR^7R^8$, $R^7$Bi═O, or $BiR^7$;

each of $R^6$, $R^7$, and $R^8$ is independently absent or present as a single substituent or multiple substituents, valency permitting, and each of $R^6$, $R^7$, and $R^8$ independently represents hydrogen, deuterium, halogen, hydroxyl, thiol, nitro, cyano, nitrile, isonitrile, sulfinyl, mercapto, sulfo, carboxyl, hydrazino: substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; any two of $R^6$, $R^7$, and $R^8$ may together form a ring; and n is an integer, valency permitting.

2. The compound of claim 1, wherein the compound is represented by General Formula 1:

General Formula 1

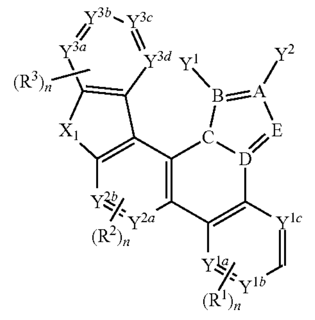

wherein, in General Formula 1:

$Y^{1a}$, $Y^{1b}$, $Y^{1c}$, $Y^{2a}$, $Y^{2b}$, $Y^{3a}$ $Y^{3b}$ $Y^{3c}$, and $Y^{3d}$ each independently represents C or N;

C and E each represent N;

each A, B, and D independently represent C or N;

$X_1$ independently represents C, N, Si, O, S, Ge, P, As, Se, B, Al, or Bi, or if valency permits, $X_1$ independently represents $CR^4$, $SiR^4$, $GeR^4$, $NR^4$, P═O, As═O, B, $BR^4$, $AlR^4$, Bi═O, $CR^4R^5$, C═O, $SiR^4R^5$, $GeR^4R^5$, $PR^4$, $PR^4R^5$, $R^4$, P═O, $AsR^4$, $R^4$As═O, S═O, $SO_2$, Se═O, $SeO_2$, $BR^4$, $BR^4R^5$, $AlR^4$, $AlR^4R^5$, $R^4$Bi═O, or $BiR^4$;

each of $Y^1$ and $Y^2$ is independently absent or present, valency permitting; $Y^1$ and $Y^2$ independently represent hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; or $Y^1$ and $Y^2$ may together form a ring;

each of $R^1$, $R^2$, $R^3$, $R^4$, and $R^5$ is independently absent or present, valency permitting, and each of $R^1$, $R^2$, $R^3$, $R^4$, and $R^5$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, A sulfonylamino, sulfamoyl, carbamoyl, alkylthio, ureido, phosphoramide, silyl, or polymeric; or any combination thereof; any two of $R^1$, $R^2$, $R^3$, $R^4$, and $R^5$ may together form a ring; and n is an integer, valency permitting.

3. The compound of claim 1, wherein the compound is represented by General Formula 2:

General Formula 2

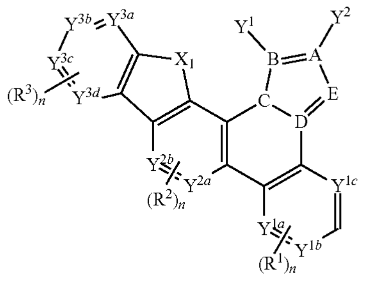

wherein, in General Formula 2:

$Y^{1a}$, $Y^{1b}$, $Y^{1c}$, $Y^{2a}$ $Y^{2b}$ $Y^{3a}$ $Y^{3b}$ $Y^{3c}$, and $Y^{3d}$ each independently represents C or N;

C and E each represent N;

each A, B, and D independently represent C or N;

$X_1$ independently represents C, N, Si, O, S, Ge, P, As, Se, B, Al, or Bi, or if valency permits, $X_1$ independently represents $CR^4$, $SiR^4$, $GeR^4$, $NR^4$, P═O, As═O, B, $BR^4$, $AlR^4$, Bi═O, $CR^4R^5$, C═O, $SiR^4R^5$, $GeR^4R^5$, $PR^4$, $PR^4R^5$, $R^4$, P═O, $AsR^4$, $R^4As$═O, S═O, $SO_2$, Se═O, $SeO_2$, $BR^4$, $BR^4R^5$, $AlR^4$, $AlR^4R^5$, $R^4Bi$═O, or $BiR^4$;

each of $Y^1$ and $Y^2$ is independently absent or present, valency permitting; $Y^1$ and $Y^2$ independently represent hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; or $Y^1$ and $Y^2$ may together form a ring;

each of $R^1$, $R^2$, $R^3$, $R^4$, and $R^5$ is independently absent or present, valency permitting, and each of $R^1$, $R^2$, $R^3$, $R^4$, and $R^5$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; any two of $R^1$, $R^2$, $R^3$, $R^4$, and $R^5$ may together form a ring; and n is an integer, valency permitting.

4. The compound of claim 1, wherein the compound is represented by General Formula 3:

General Formula 3

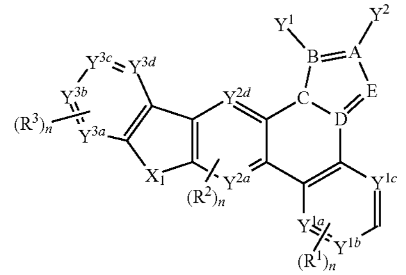

wherein, in General Formula 3:

$Y^{1a}$, $Y^{1b}$, $Y^{1c}$, $Y^{2a}$, $Y^{2d}$, $Y^{3a}$, $Y^{3b}$, $Y^{3c}$ and $Y^{3d}$ each independently represents C or N;

C and E each represent N;

each A, B, and D independently represent C or N;

$X_1$ independently represents C, N, Si, O, S, Ge, P, As, Se, B, Al, or Bi, or if valency permits, $X_1$ independently represents $CR^4$, $SiR^4$, $GeR^4$, $NR^4$, P═O, As═O, B, $BR^4$, $AlR^4$, Bi═O, $CR^4R^5$, C═O, $SiR^4R^5$, $GeR^4R^5$, $PR^4$, $PR^4R^5$, $R^4$, P═O, $AsR^4$, $R^4As$═O, S═O, $SO_2$, Se═O, $SeO_2$, $BR^4$, $BR^4R^5$, $AlR^4$, $AlR^4R^5$, $R^4Bi$═O, or $BiR^4$;

each of $Y^1$ and $Y^2$ is independently absent or present, valency permitting; $Y^1$ and $Y^2$ independently represent hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; or $Y^1$ and $Y^2$ may together form a ring;

each of $R^1$, $R^2$, $R^3$, $R^4$, and $R^5$ is independently absent or present, valency permitting, and each of $R^1$, $R^2$, $R^3$, $R^4$, and $R^5$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; any two of $R^1$, $R^2$, $R^3$, $R^4$, and $R^5$ may together form a ring; and n is an integer, valency permitting.

5. The compound of claim 1, wherein the compound is represented by General Formula 4:

General Formula 4

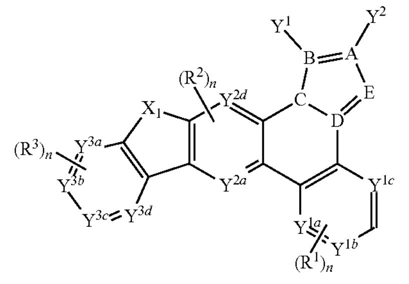

wherein, in General Formula 4:

$Y^{1a}$, $Y^{1b}$, $Y^{1c}$, $Y^{2a}$, $Y^{2d}$, $Y^{3a}$, $Y^{3b}$, $Y^{3c}$ and $Y^{3d}$ each independently represents C or N;

C and E each represent N;

each A, B, and D independently represent C or N;

$X_1$ independently represents C, N, Si, O, S, Ge, P, As, Se, B, Al, or Bi, or if valency permits, $X_1$ independently represents $CR^4$, $SiR^4$, $GeR^4$, $NR^4$, P=O, As=O, B, $BR^4$, $AlR^4$, Bi=O, $CR^4R^5$, C=O, $SiR^4R^5$, $GeR^4R^5$, $PR^4$, $PR^4R^5$, $R^4$, P=O, $AsR^4$, $R^4As$=O, S=O, $SO_2$, Se=O, $SeO_2$, $BR^4$, $BR^4R^5$, $AlR^4$, $AlR^4R^5$, $R^4Bi$=O, or $BiR^4$;

each of $Y^1$ and $Y^2$ is independently absent or present, valency permitting; $Y^1$ and $Y^2$ independently represent hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; or $Y^1$ and $Y^2$ may together form a ring;

each of $R^1$, $R^2$, $R^3$, $R^4$, and $R^5$ is independently absent or present, valency permitting, and each of $R^1$, $R^2$, $R^3$, $R^4$, and $R^5$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; any two of $R^1$, $R^2$, $R^3$, $R^4$, and $R^5$ may together form a ring; and n is an integer, valency permitting.

6. The compound of claim 1, wherein the compound is represented by General Formula 5:

General Formula 5

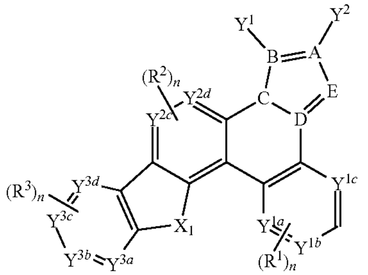

wherein, in General Formula 5:

$Y^{1a}$, $Y^{1b}$, $Y^{1c}$, $Y^{2c}$, $Y^{2d}$, $Y^{3a}$, $Y^{3b}$, $Y^{3c}$ and $Y^{3d}$ each independently represents C or N;

C and E each represent N;

each A, B, and D independently represent C or N;

$X_1$ independently represents C, N, Si, O, S, Ge, P, As, Se, B, Al, or Bi, or if valency permits, $X_1$ independently represents $CR^4$, $SiR^4$, $GeR^4$, $NR^4$, P=O, As=O, B, $BR^4$, $AlR^4$, Bi=O, $CR^4R^5$, C=O, $SiR^4R^5$, $GeR^4R^5$, $PR^4$, $PR^4R^5$, $R^4$, P=O, $AsR^4$, $R^4As$=O, S=O, $SO_2$, Se=O, $SeO_2$, $BR^4$, $BR^4R^5$, $AlR^4$, $AlR^4R^5$, $R^4Bi$=O, or $BiR^4$;

each of $Y^1$ and $Y^2$ is independently absent or present, valency permitting; $Y^1$ and $Y^2$ independently represent hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; or $Y^1$ and $Y^2$ may together form a ring;

each of $R^1$, $R^2$, $R^3$, $R^4$, and $R^5$ is independently absent or present, valency permitting, and each of $R^1$, $R^2$, $R^3$, $R^4$, and $R^5$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; any two of $R^1$, $R^2$, $R^3$, $R^4$, and $R^5$ may together form a ring; and n is an integer, valency permitting.

7. The compound of claim 1, wherein the compound is represented by General Formula 6:

General Formula 6

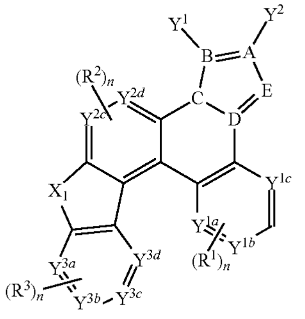

wherein, in General Formula 6:

$Y^{1a}$, $Y^{1b}$, $Y^{1c}$, $Y^{2c}$, $Y^{2d}$, $Y^{3a}$, $Y^{3b}$, $Y^{3c}$ and $Y^{3d}$ each independently represents C or N;

C and E each represent N;

each A, B, and D independently represent C or N;

$X_1$ independently represents C, N, Si, O, S, Ge, P, As, Se, B, Al, or Bi, or if valency permits, $X_1$ independently represents $CR^4$, $SiR^4$, $GeR^4$, $NR^4$, P=O, As=O, B, $BR^4$, $AlR^4$, Bi=O, $CR^4R^5$, C=O, $SiR^4R^5$, $GeR^4R^5$, $PR^4$, $PR^4R^5$, $R^4$, P=O, $AsR^4$, $R^4As$=O, S=O, $SO_2$, Se=O, $SeO_2$, $BR^4$, $BR^4R^5$, $AlR^4$, $AlR^4R^5$, $R^4Bi$=O, or $BiR^4$;

each of $Y^1$ and $Y^2$ is independently absent or present, valency permitting; $Y^1$ and $Y^2$ independently represent hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; or $Y^1$ and $Y^2$ may together form a ring;

each of $R^1$, $R^2$, $R^3$, $R^4$, and $R^5$ is independently absent or present, valency permitting, and each of $R^1$, $R^2$, $R^3$, $R^4$, and $R^5$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; any two of $R^1$, $R^2$, $R^3$, $R^4$, and $R^5$ may together form a ring; and n is an integer, valency permitting.

8. The compound of claim 1, wherein the compound is represented by one of the following General Formulae:

General Formula 7

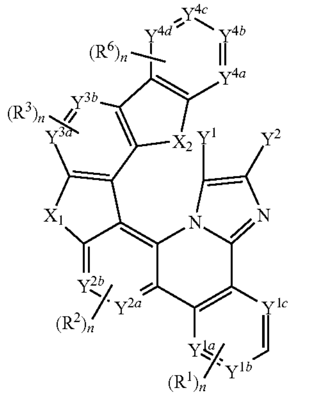

General Formula 8

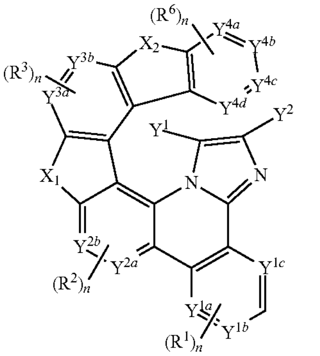

General Formula 9

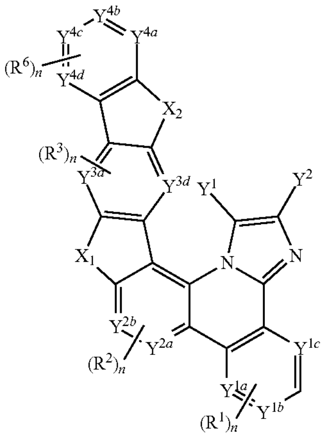

General Formula 10

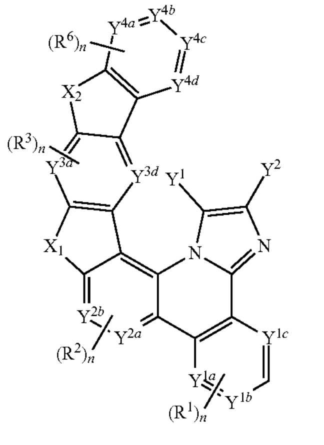

-continued
General Formula 11
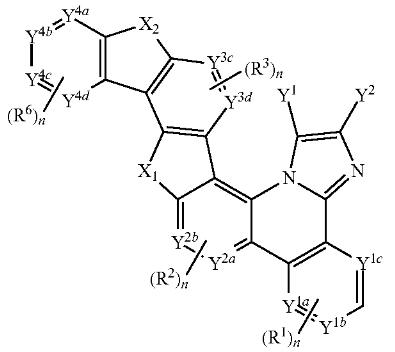
General Formula 12
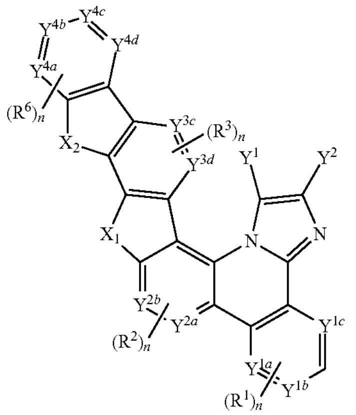
General Formula 13
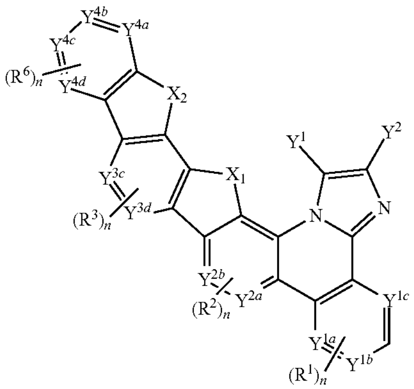
General Formula 14
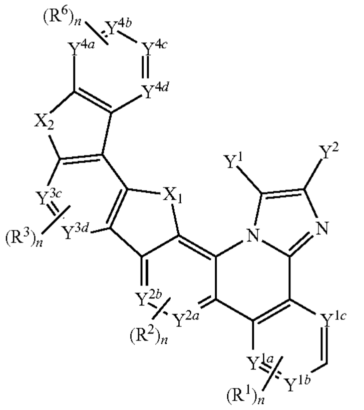
-continued
General Formula 15
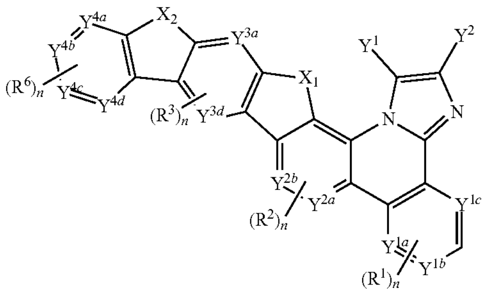
General Formula 16
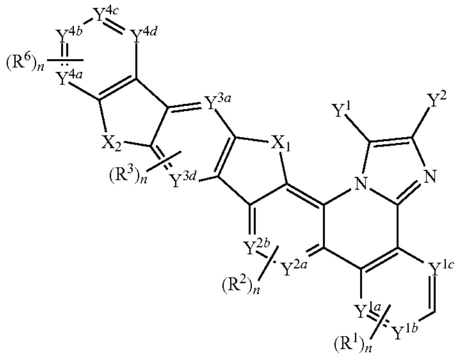
General Formula 17
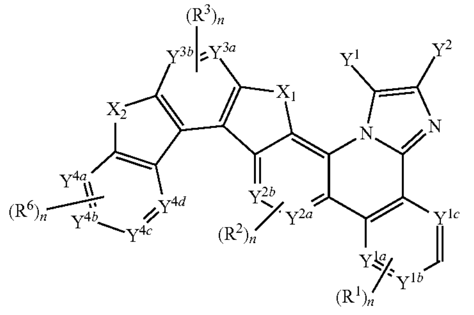
General Formula 18
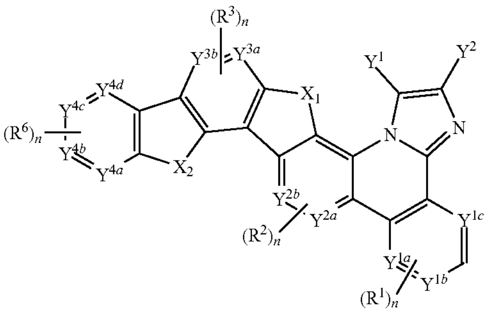

-continued
General Formula 19
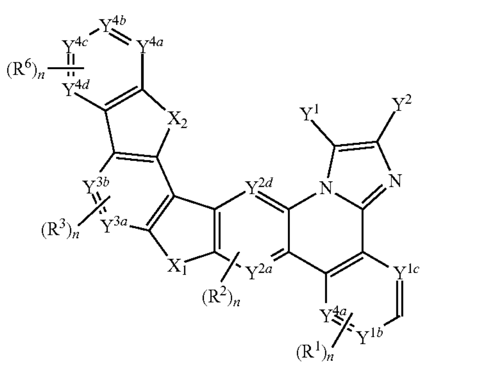
General Formula 20
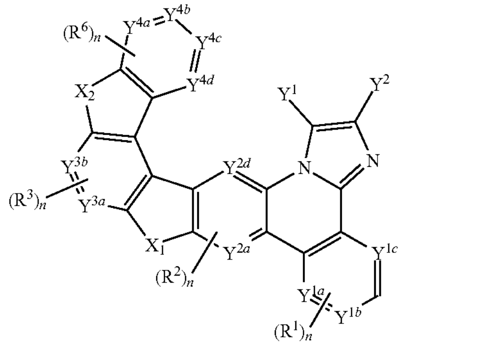
General Formula 21
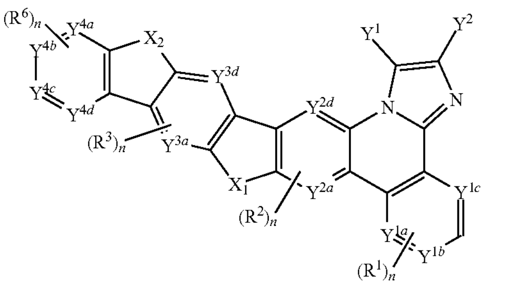
General Formula 22
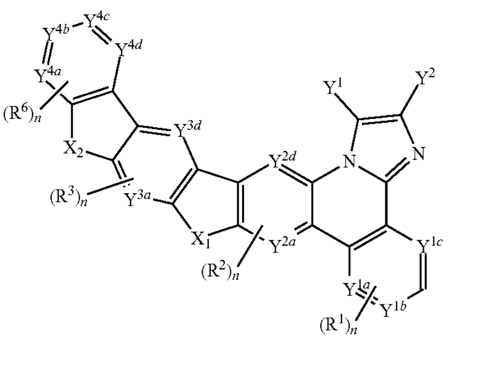
-continued
General Formula 23
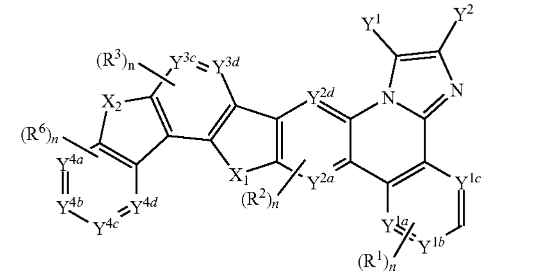
General Formula 24
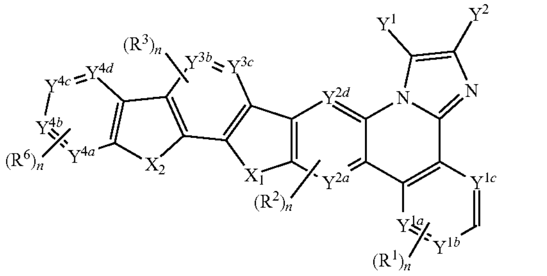
General Formula 25
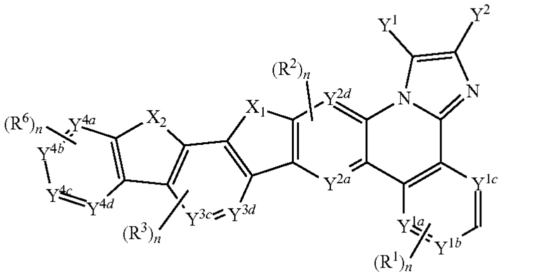
General Formula 26
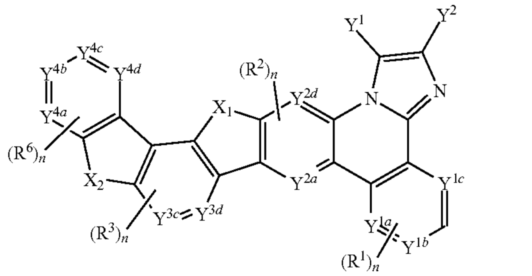
General Formula 29
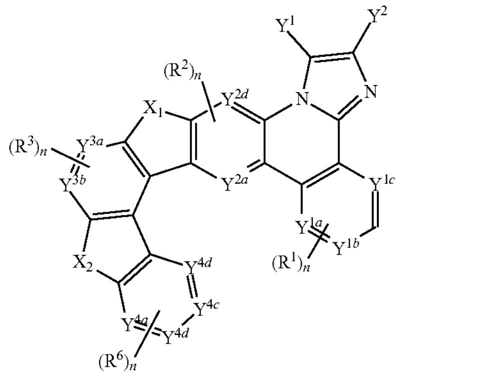

General Formula 30
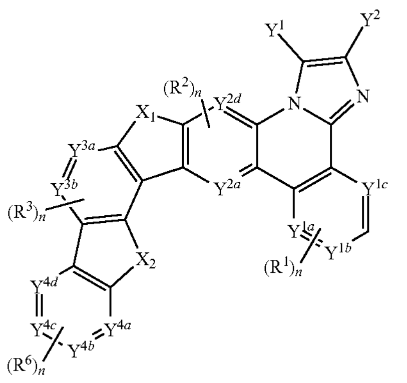
General Formula 31
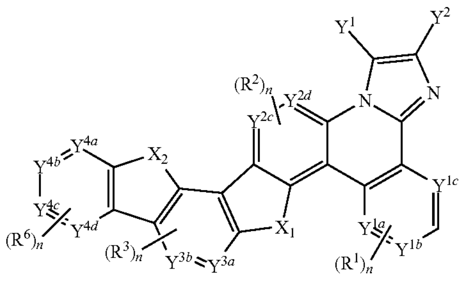
General Formula 32
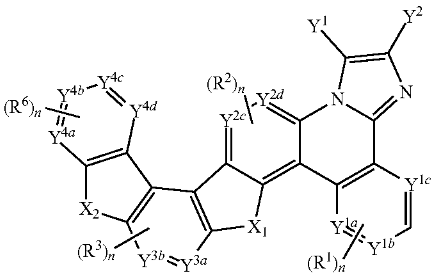
General Formula 33
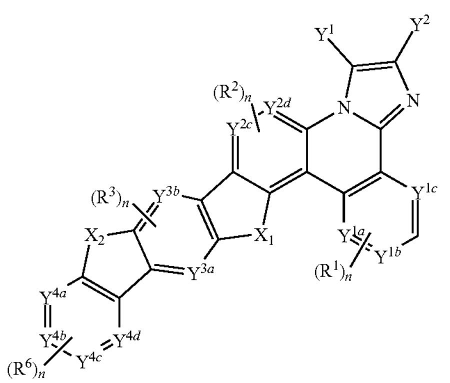
-continued
General Formula 34
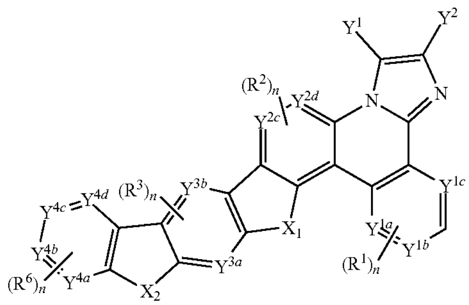
General Formula 35
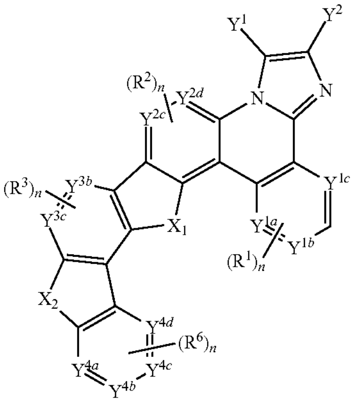
General Formula 36
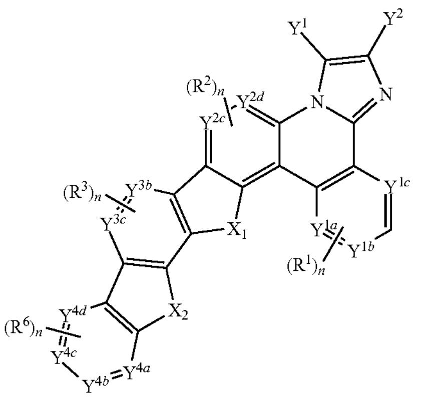
General Formula 37
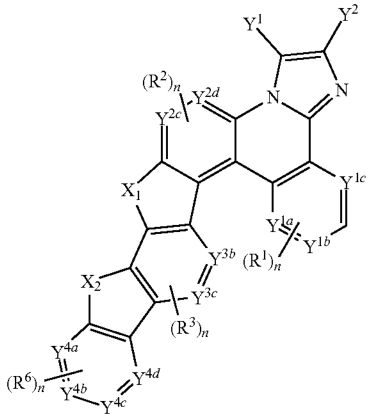

-continued

General Formula 38

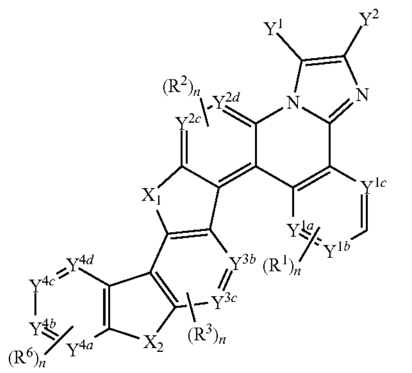

General Formula 39

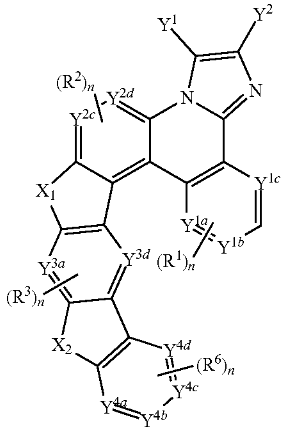

General Formula 40

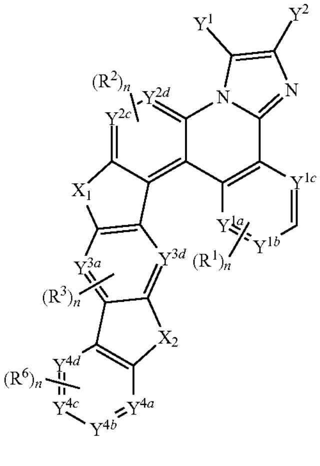

-continued

General Formula 41

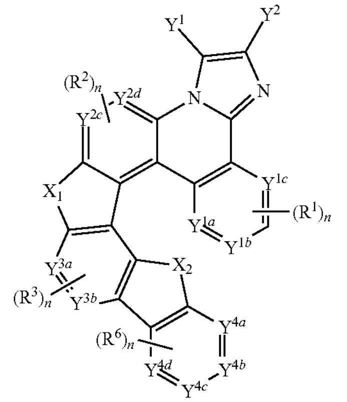

General Formula 42

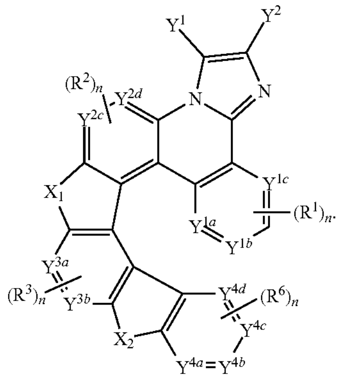

9. The compound of claim 1, wherein two adjacent $R^2$ together represent a group of Formula A and two adjacent $R^2$ together represent a group of Formula B:

Formula B

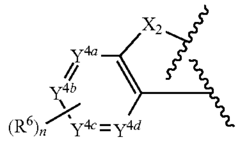

wherein waved lines indicate bonds to the respective $Y^{2a}$ and $Y^{2b}$, or $Y^{2c}$ and $Y^{2d}$;

$Y^{4a}$, $Y^{4b}$, $Y^{4c}$, and $Y^{4d}$ each independently represents C or N;

$X_2$ independently represents C, N, Si, O, S, Ge, P, As, Se, B, Al, or Bi, or if valency permits, $X_2$ independently represents $CR^7$, $SiR^7$, $GeR^7$, $NR^7$, P═O, As═O, B, $BR^7$, $AlR^7$, Bi═O, $CR^7R^8$, C═O, $SiR^7R^8$, $GeR^7R^8$, $PR^7$, $PR^7R^8$, $R^7P$═O, $AsR^7$, $R^7As$═O, S═O, $SO_2$, Se═O, $SeO_2$, $BR^7$, $BR^7R^8$, $AlR^7$, $AlR^7R^8$, $R^7Bi$═O, or $BiR^7$;

each of $R^6$, $R^7$, and $R^8$ is independently absent or present as a single substituent or multiple substituents, valency permitting, and each of $R^6$, $R^7$, and $R^8$ independently represents hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric; or any combination thereof; any two of $R^6$, $R^7$, and $R^8$ may together form a ring; and n is an integer, valency permitting.

10. The compound of claim 9, wherein the compound is represented by one of the following General Formulae:

General formula 43

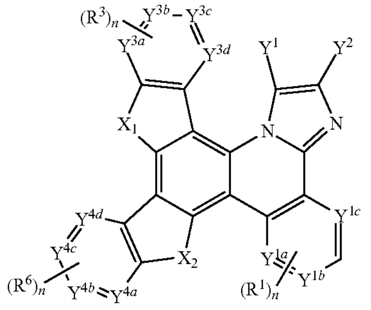

General formula 44

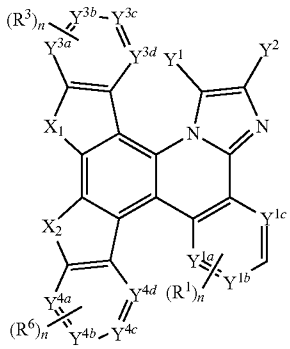

General formula 45

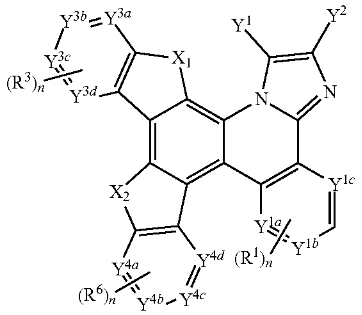

General formula 46

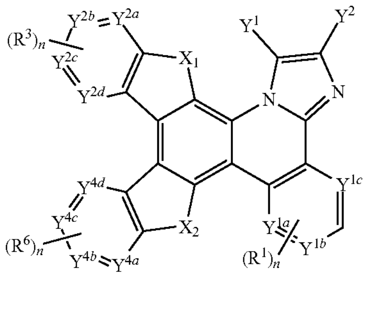

-continued

General formula 47

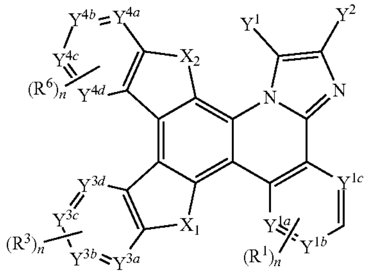

General formula 48

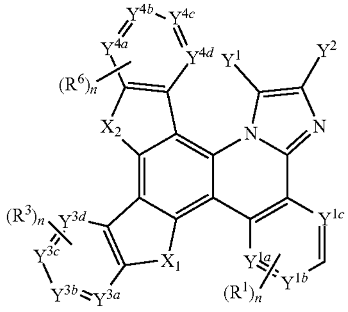

General formula 49

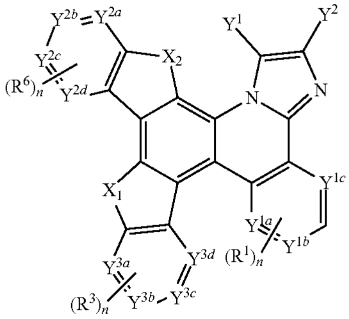

General formula 50

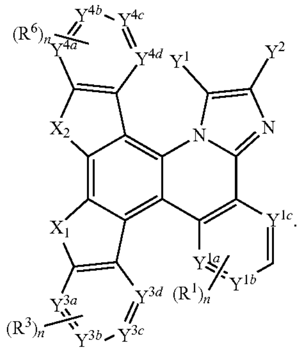

11. An organic light emitting diode comprising the compound of claim 9.

12. A light emitting device comprising the light emitting diode of claim 11.

13. An organic light emitting diode comprising the compound of claim 1.

14. A light emitting device comprising the light emitting diode of claim 13.

15. A compound represented by one of the following structures:

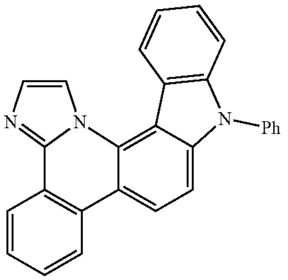
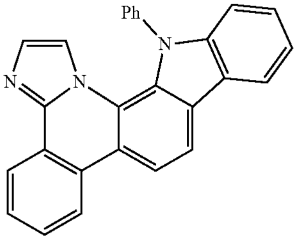
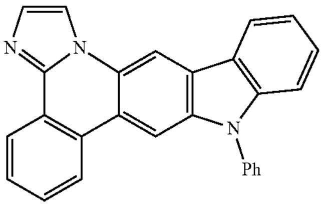
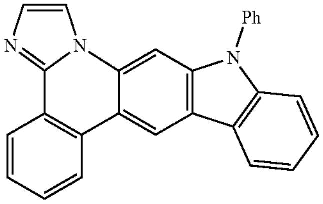
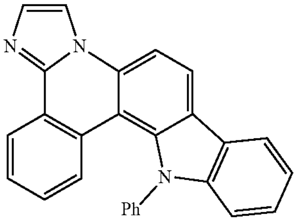
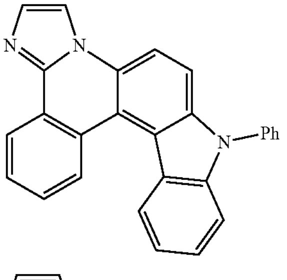
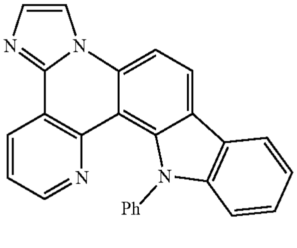
-continued
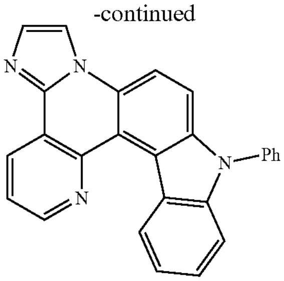
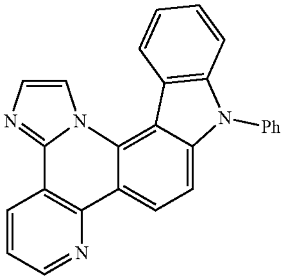
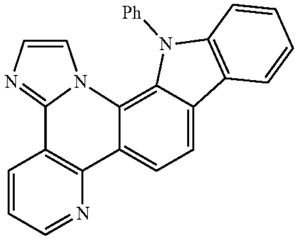
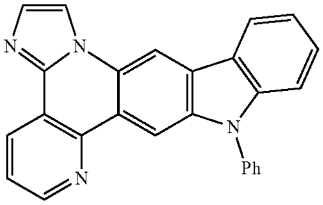
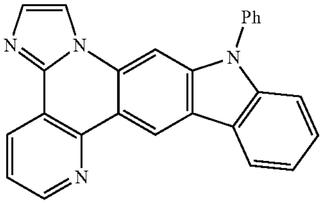
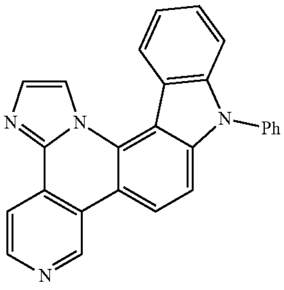
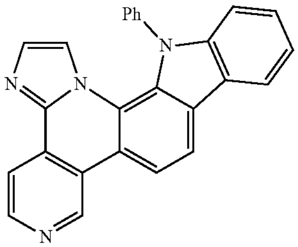

-continued
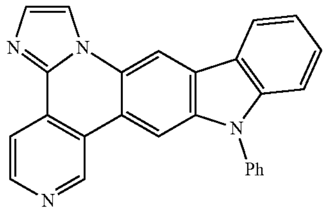
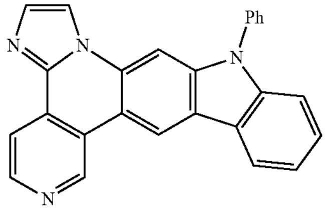
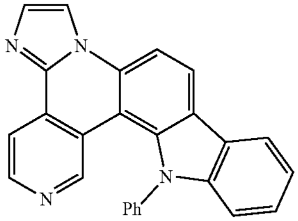
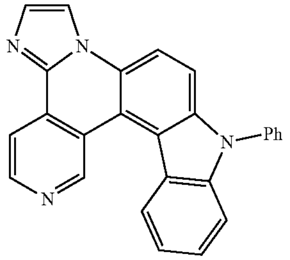
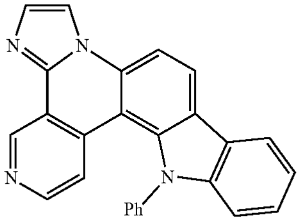
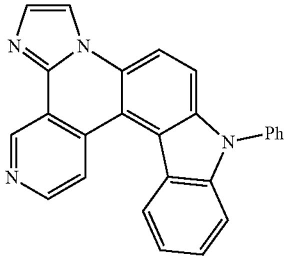
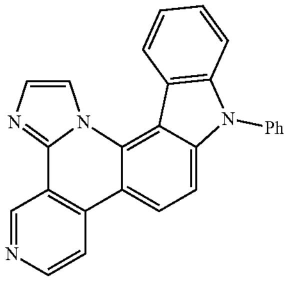
-continued
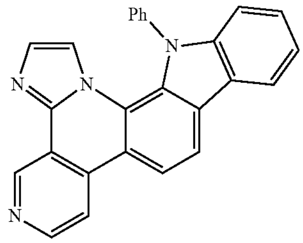
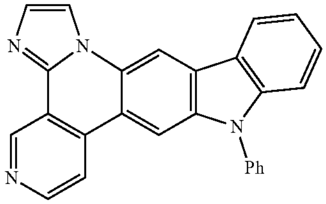
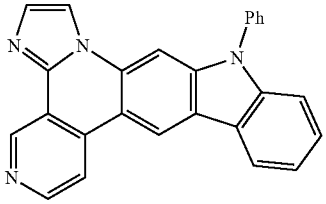
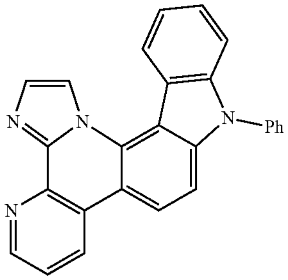
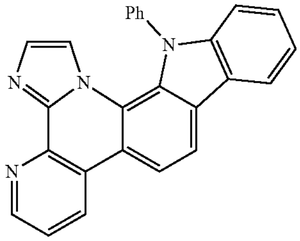
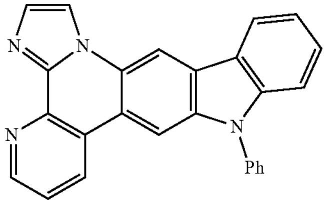
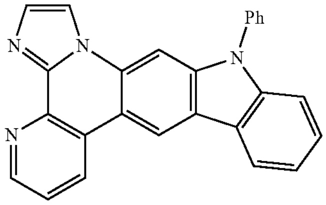

-continued
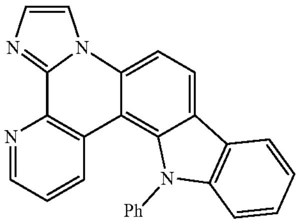
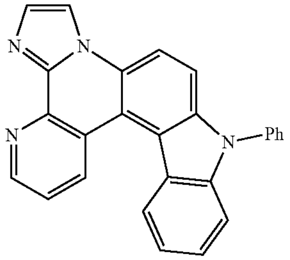
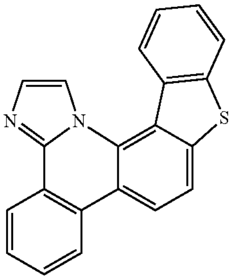
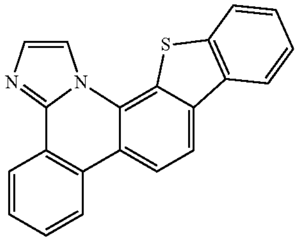
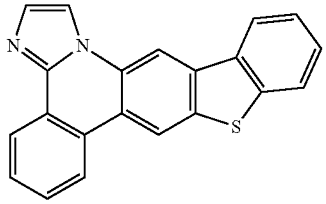
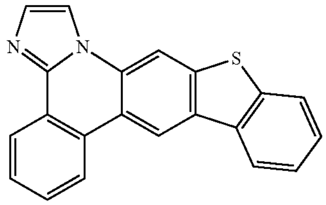
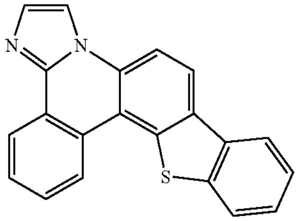
-continued
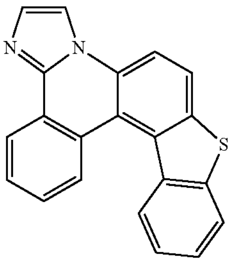
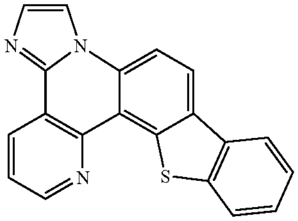
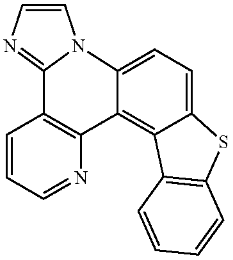
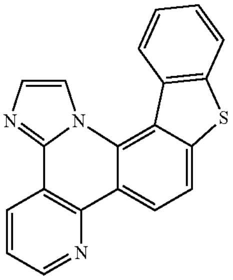
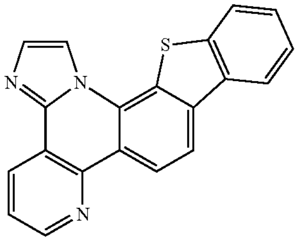
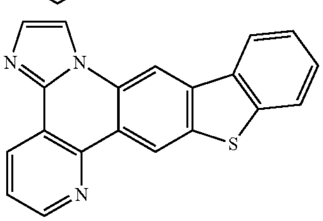
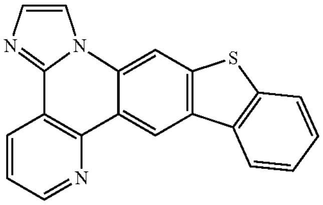

-continued
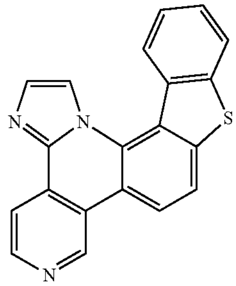
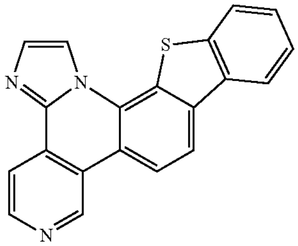
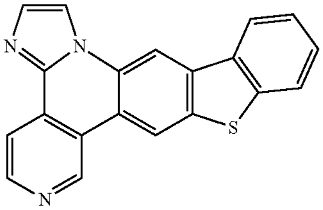
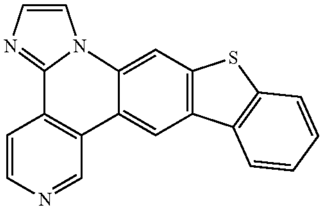
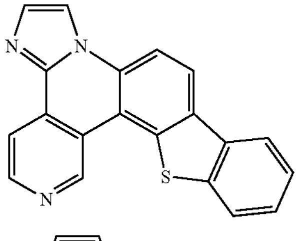
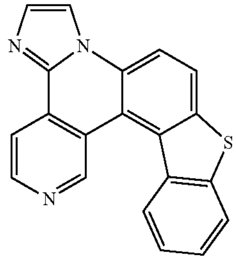
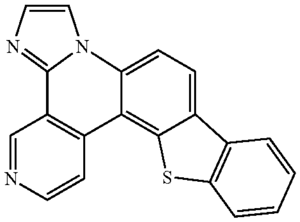
-continued
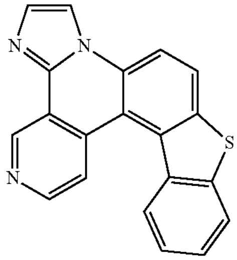
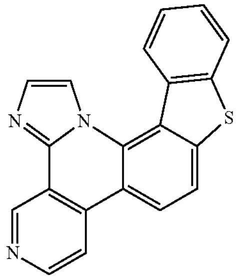
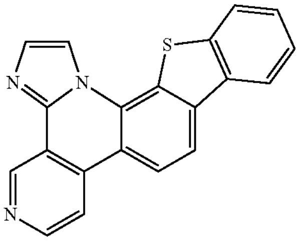
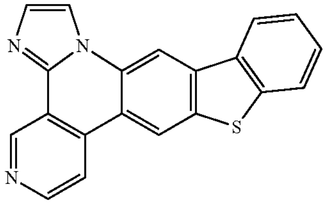
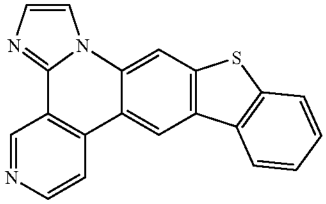
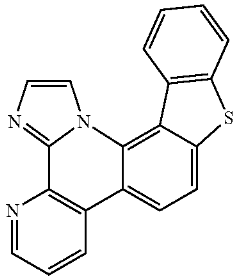

-continued
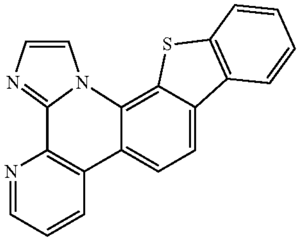
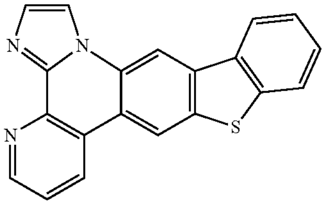
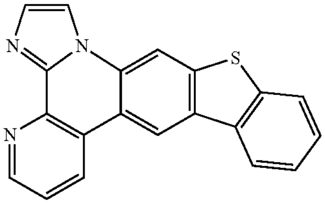
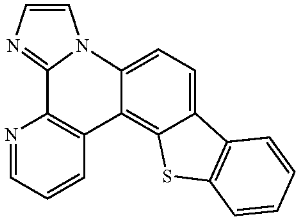
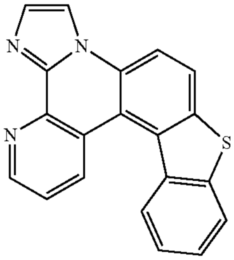
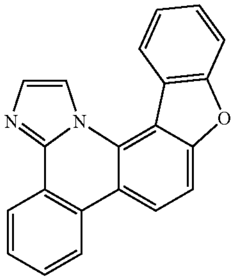
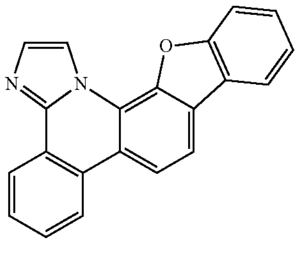
-continued
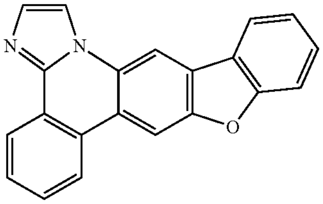
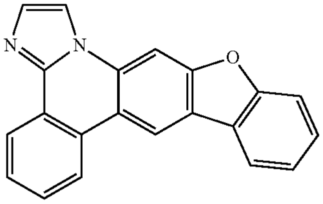
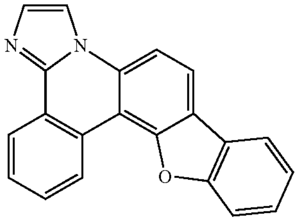
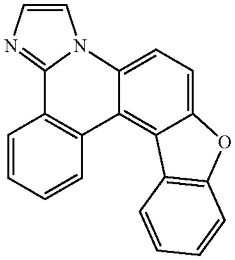
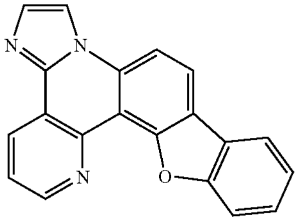
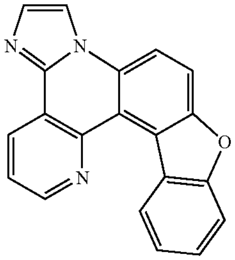
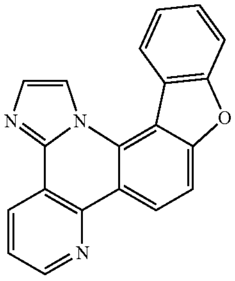

-continued
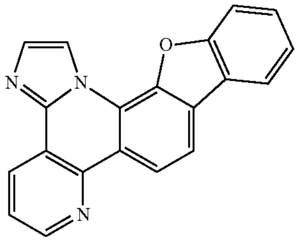
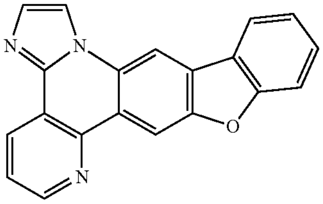
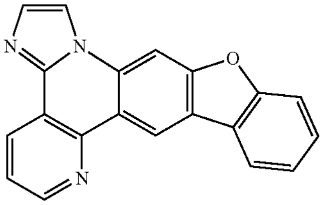
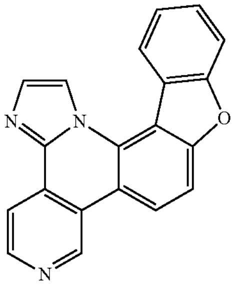
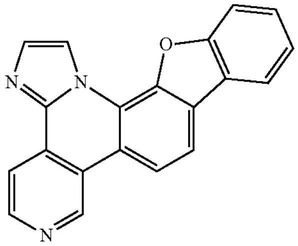
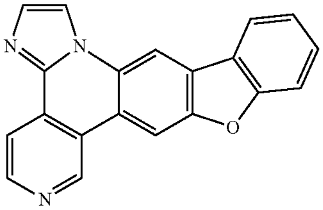
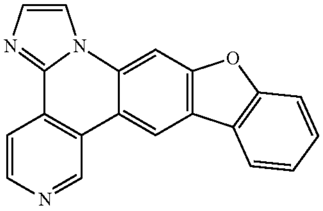
-continued
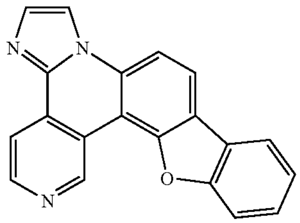
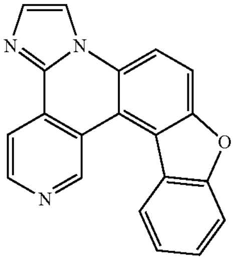
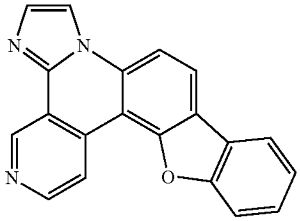
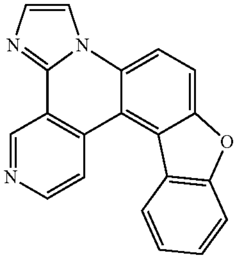
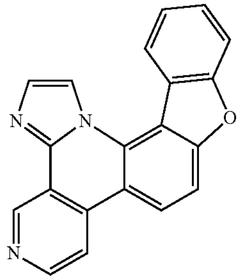
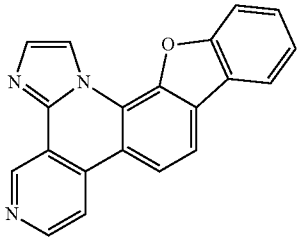
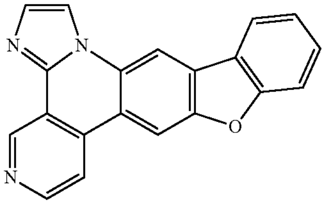

-continued
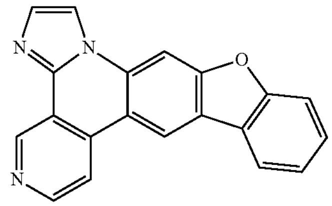
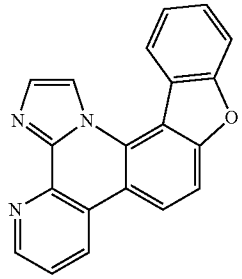
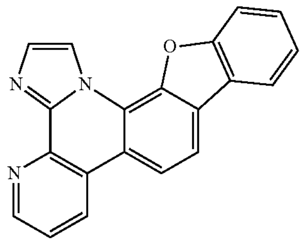
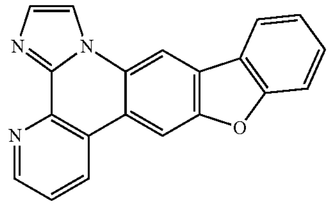
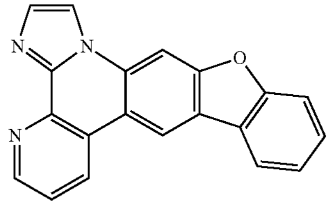
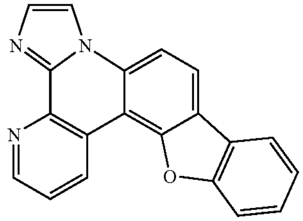
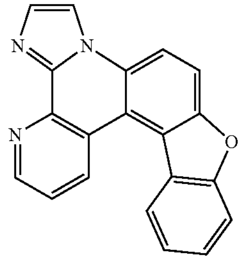
-continued
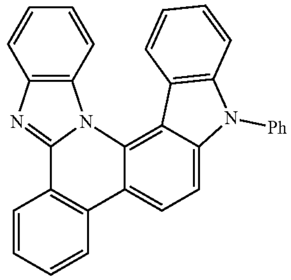
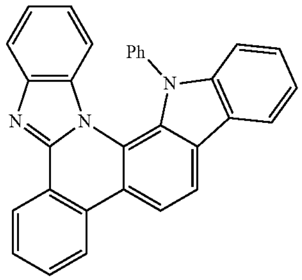
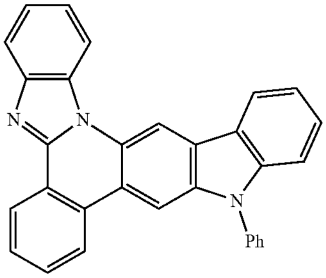
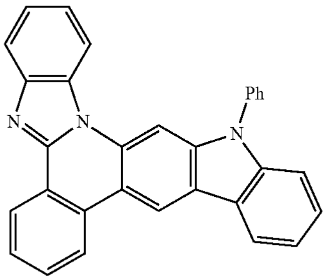
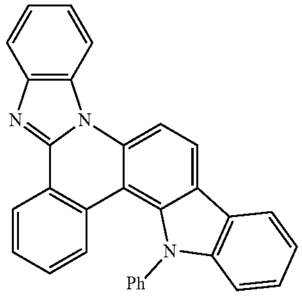

-continued
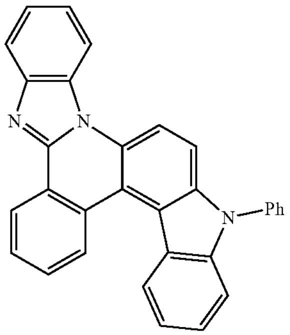
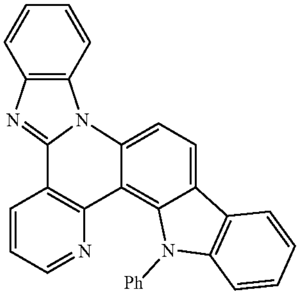
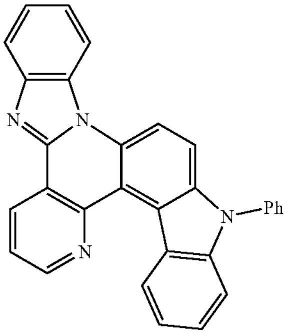
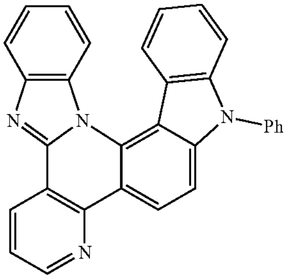
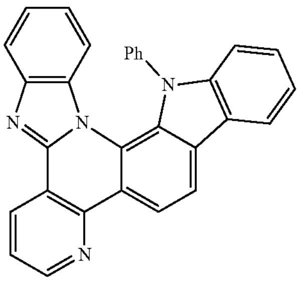
-continued
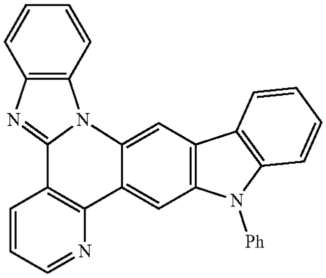
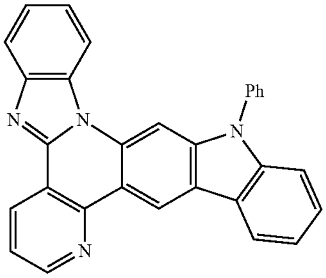
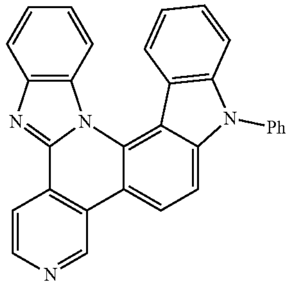
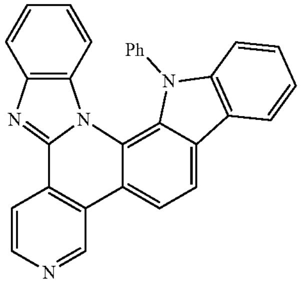
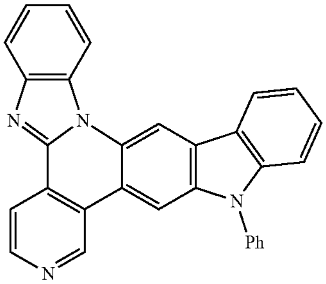
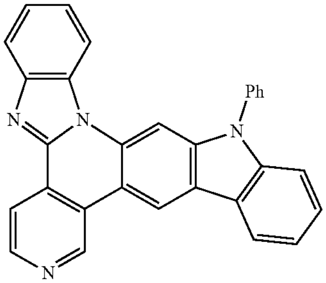

-continued
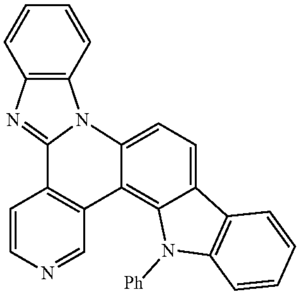
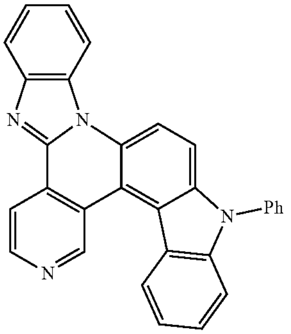
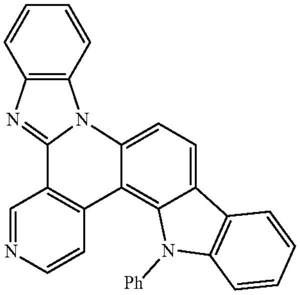
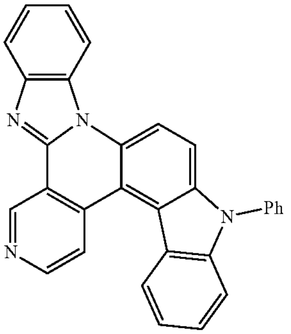
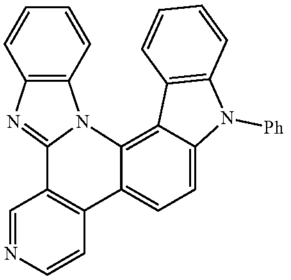
-continued
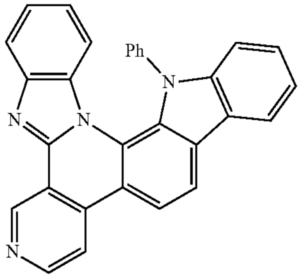
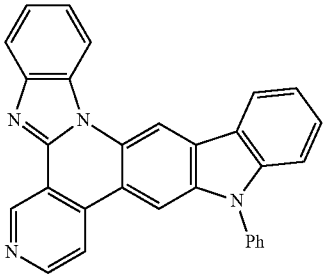
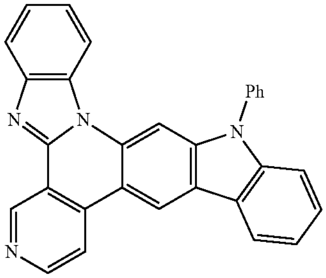
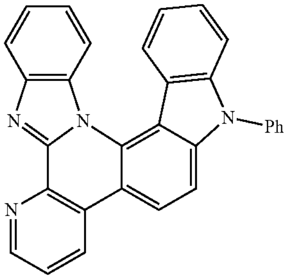
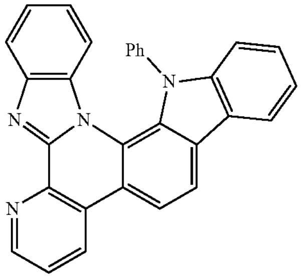
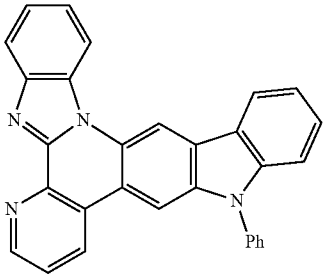

-continued
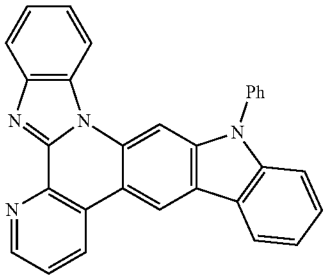
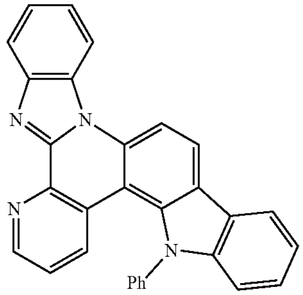
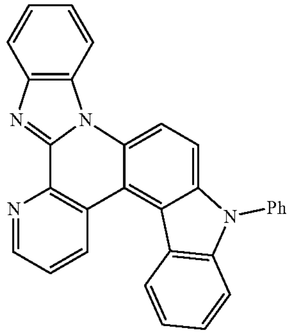
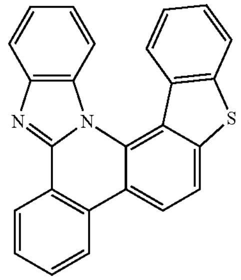
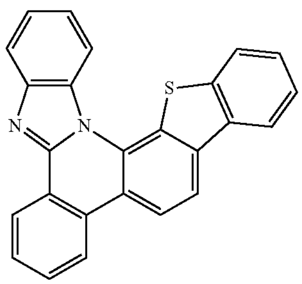
-continued
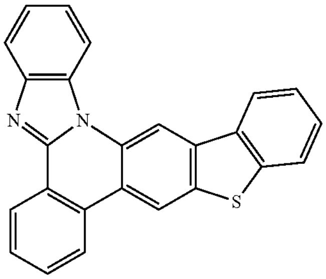
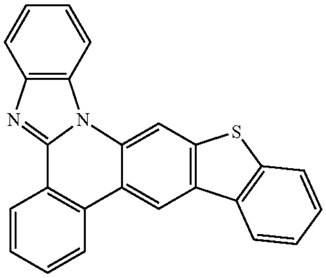
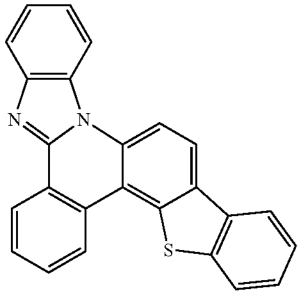
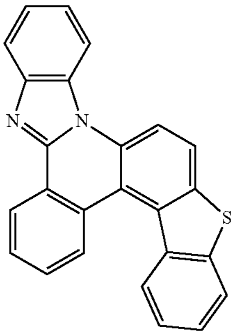
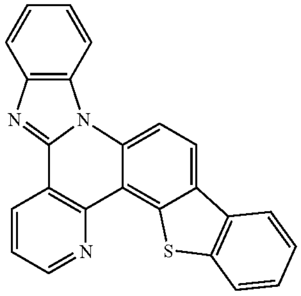

-continued
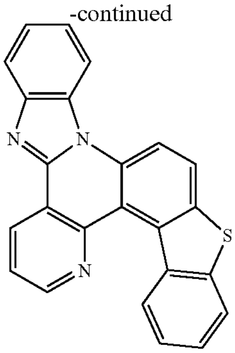
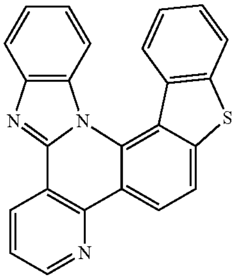
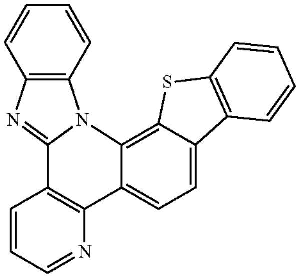
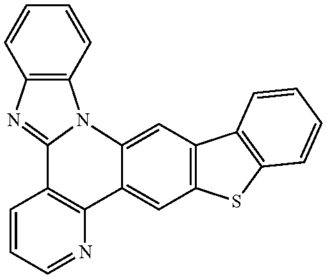
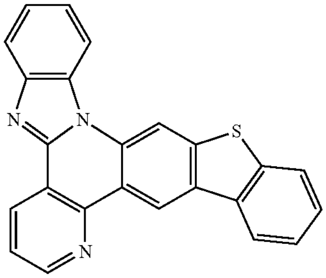
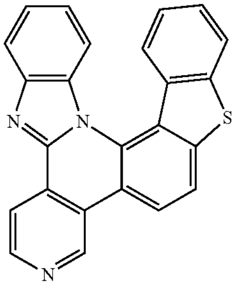
-continued
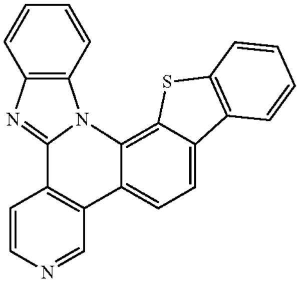
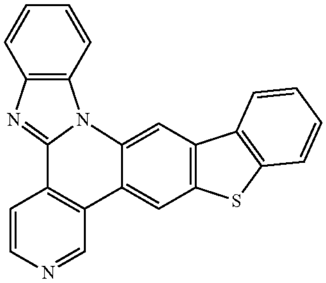
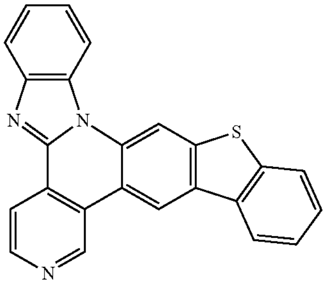
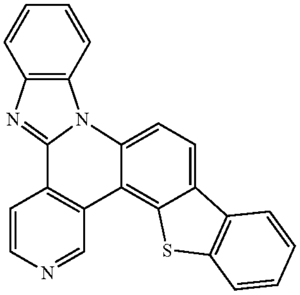
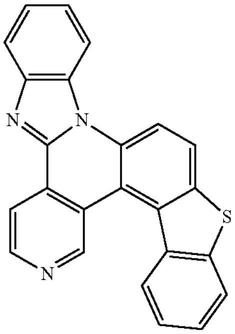

-continued
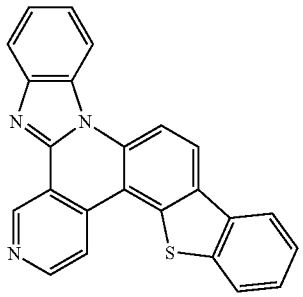
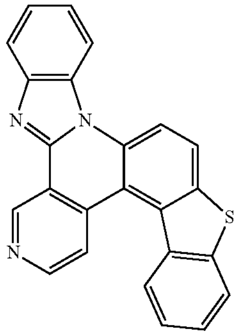
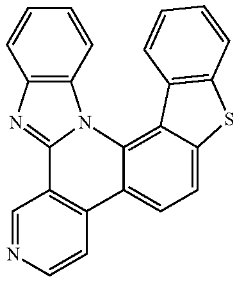
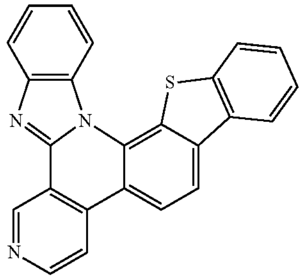
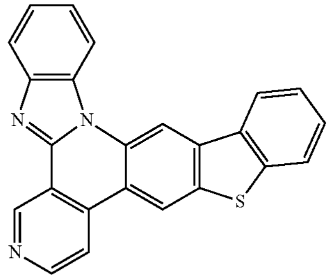
-continued
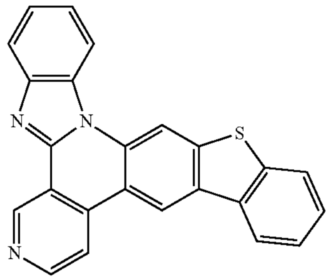
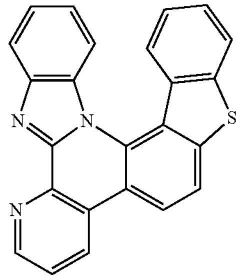
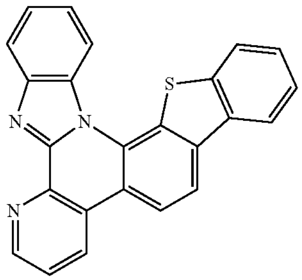
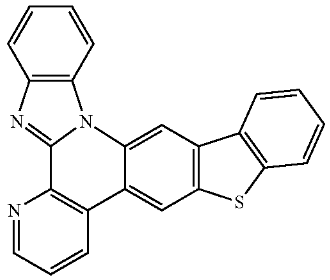
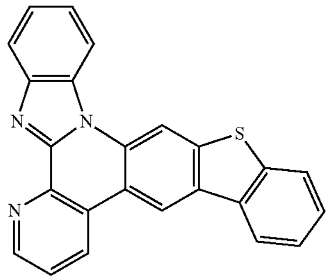
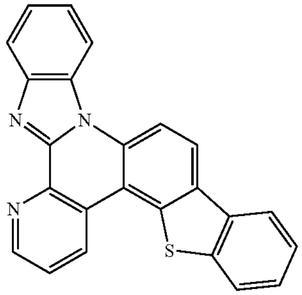

-continued
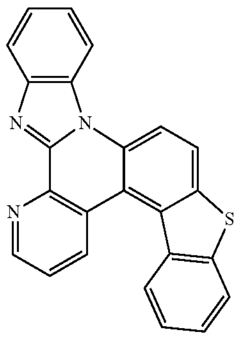
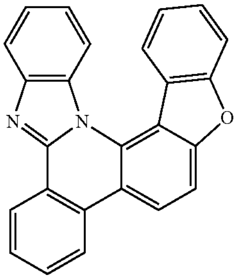
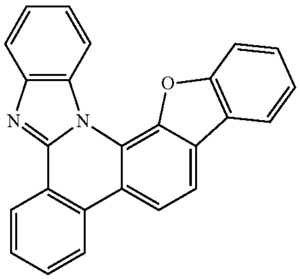
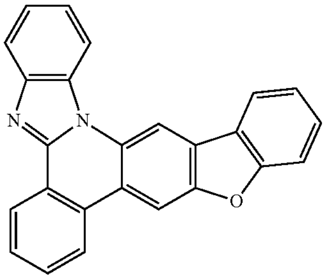
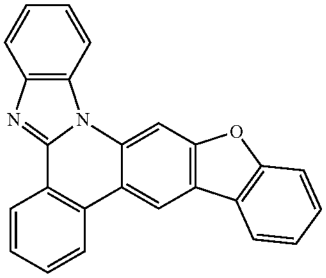
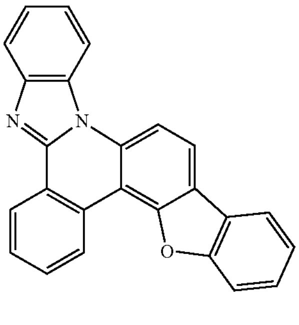
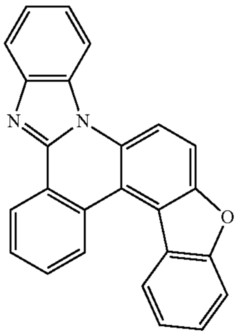
-continued
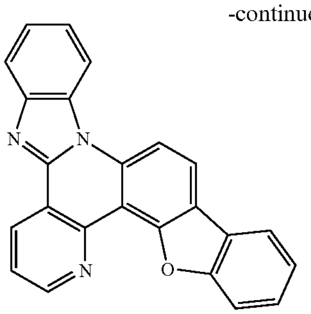
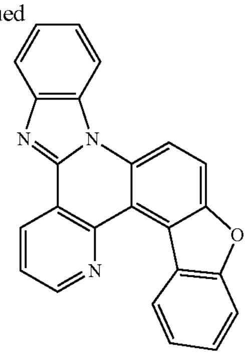
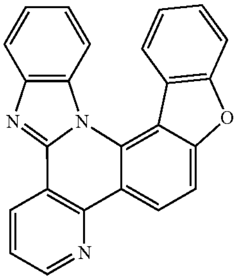
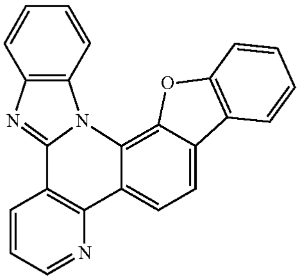
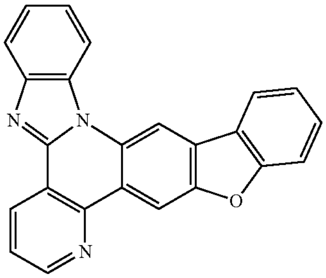
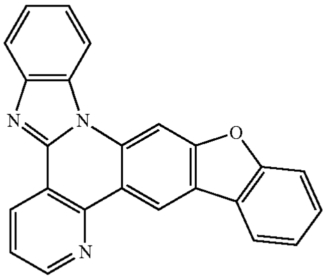
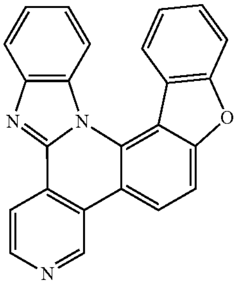
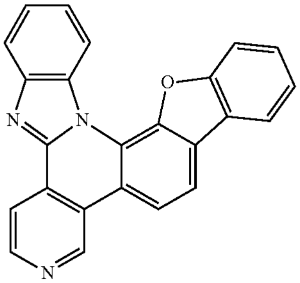
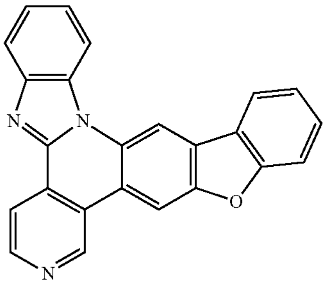

-continued
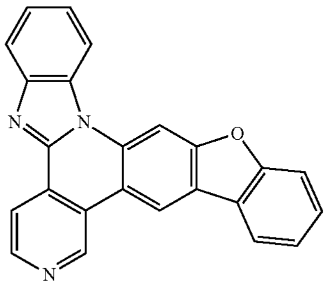
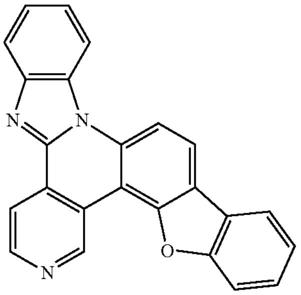
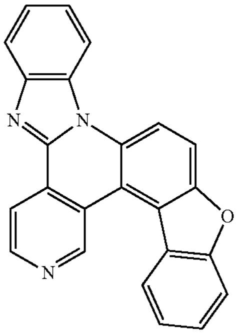
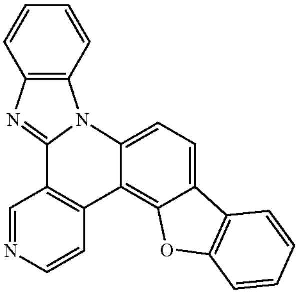
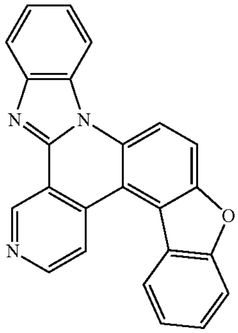
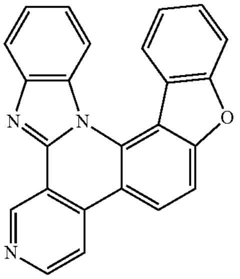
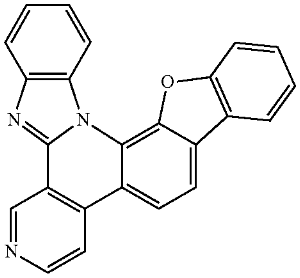
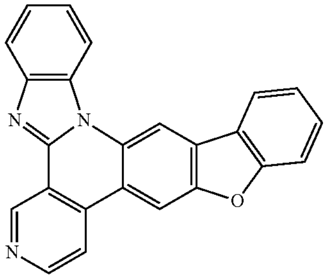
-continued
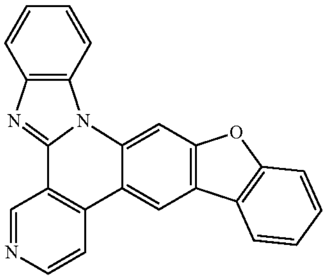
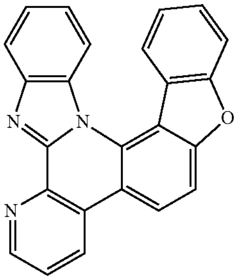
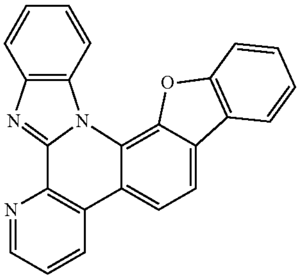
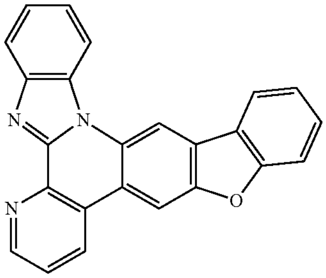
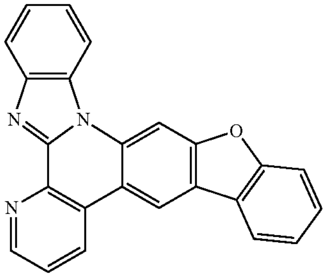
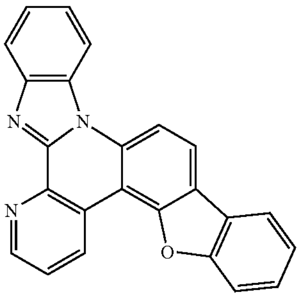
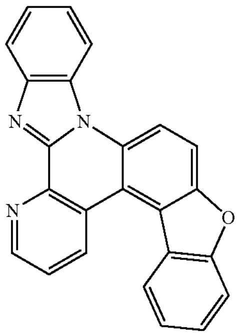

-continued
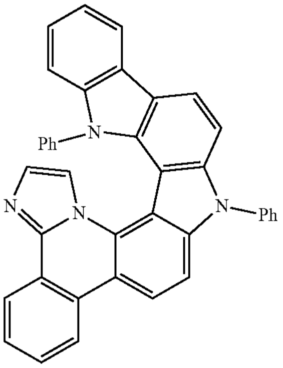
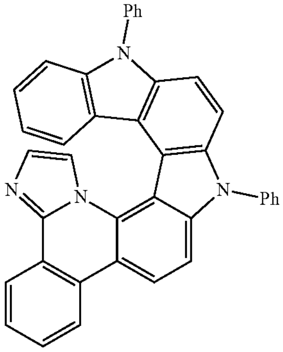
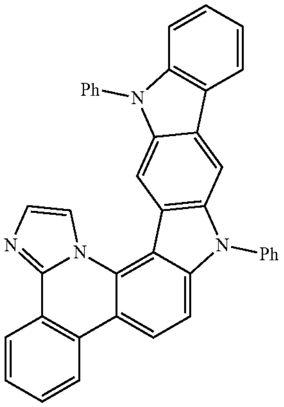
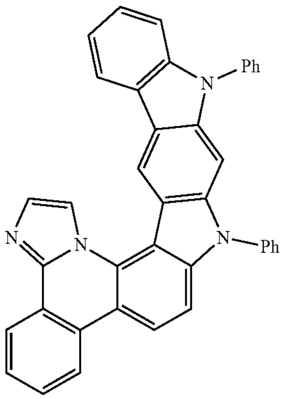
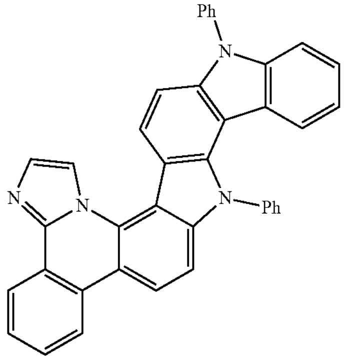
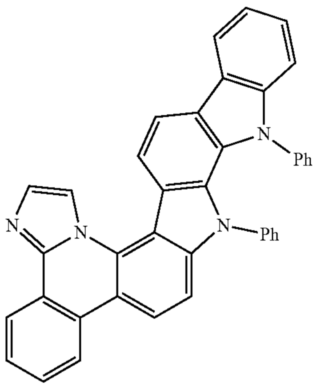
-continued
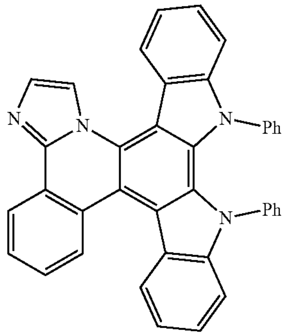
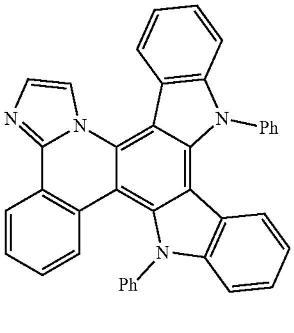
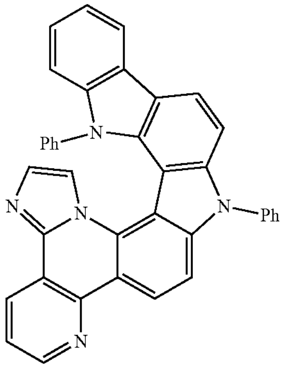
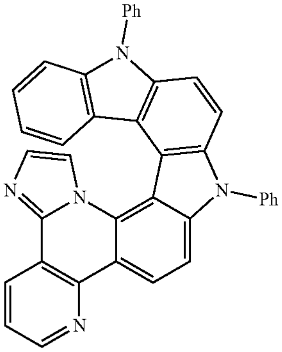
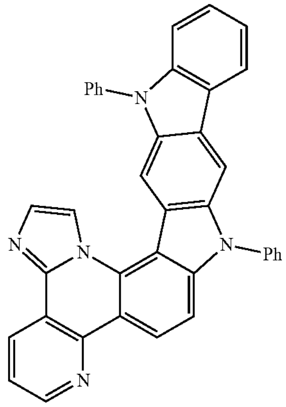
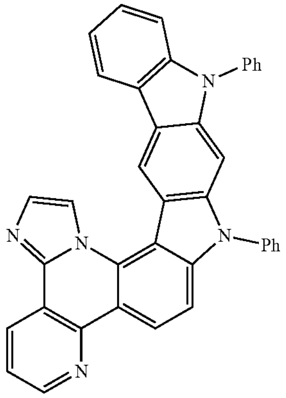
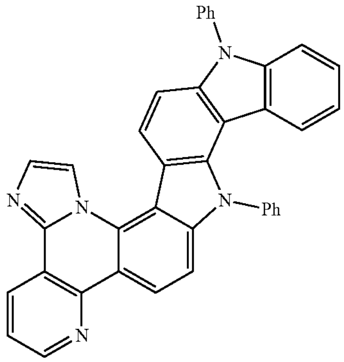

-continued
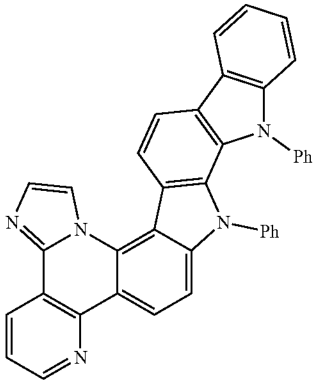
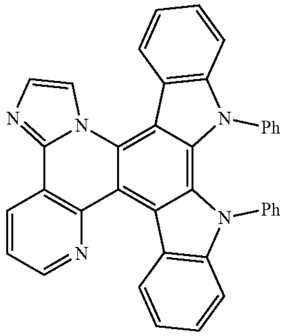
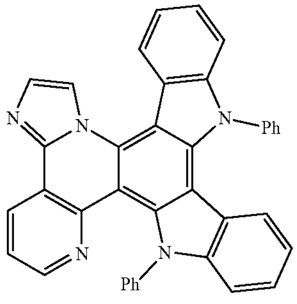
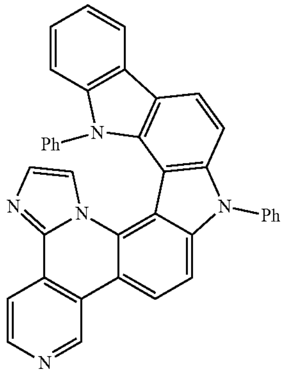
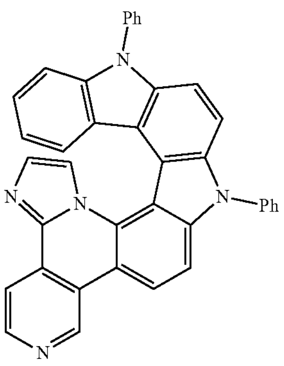
-continued
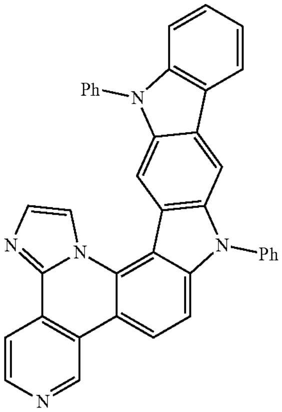
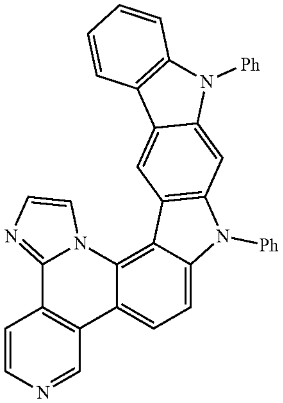
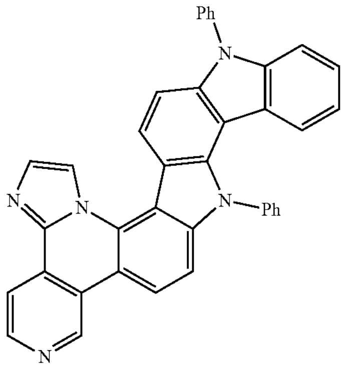
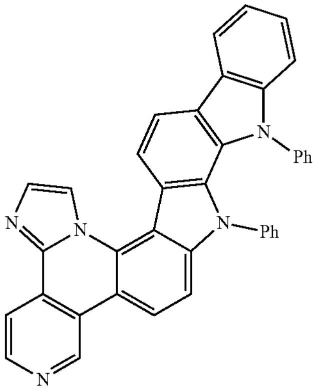
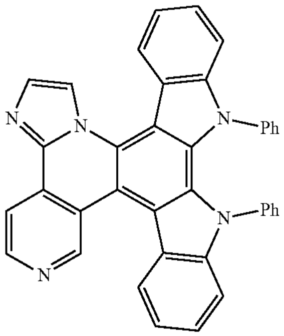
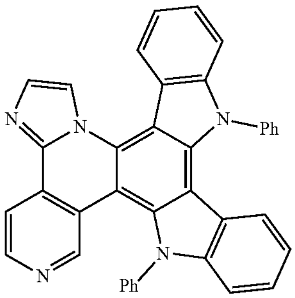

-continued
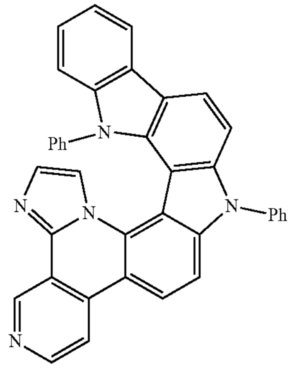
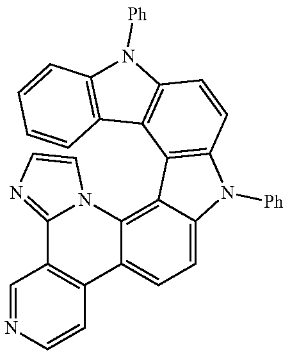
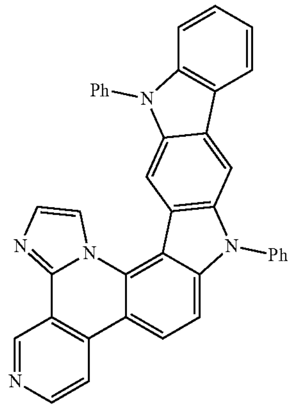
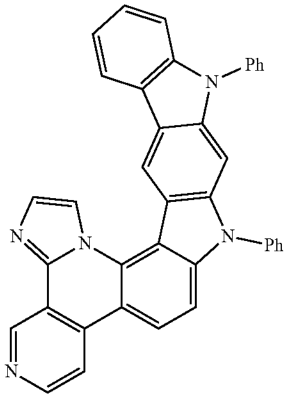
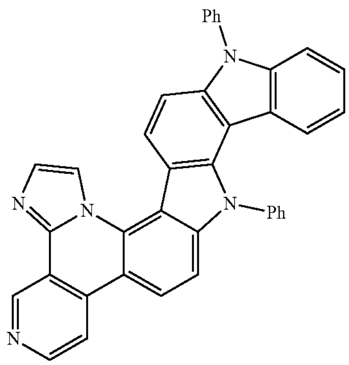
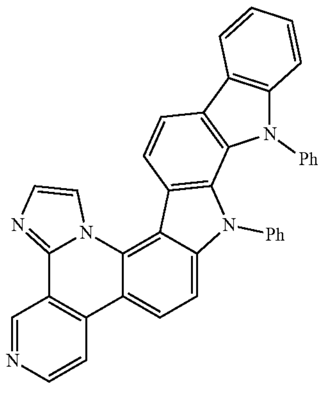
-continued
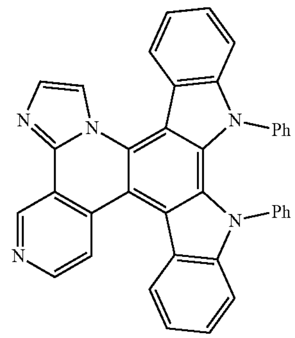
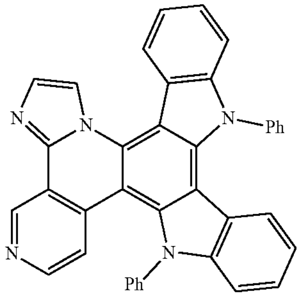
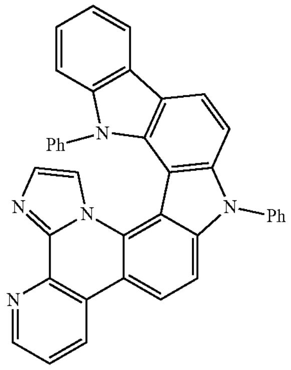
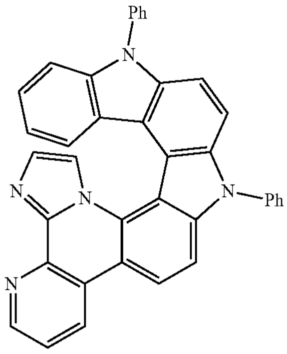
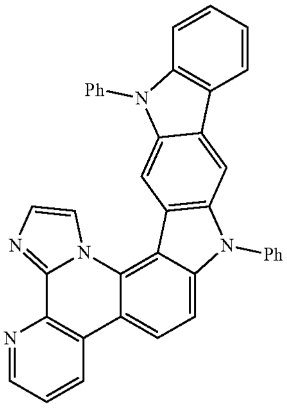

-continued
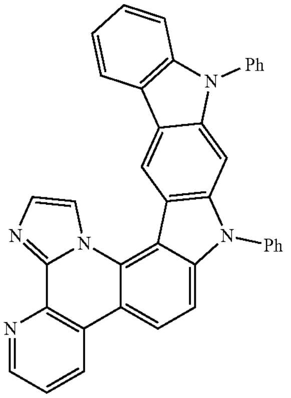
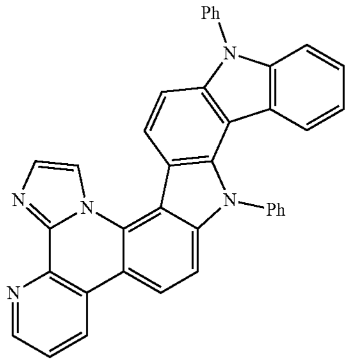
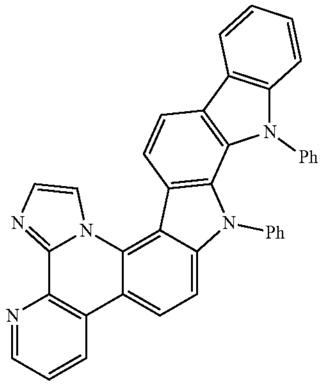
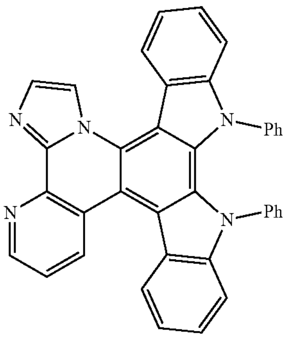
-continued
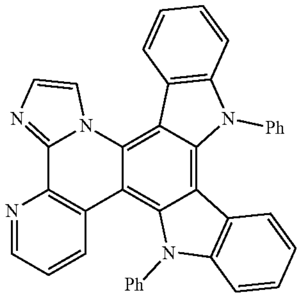
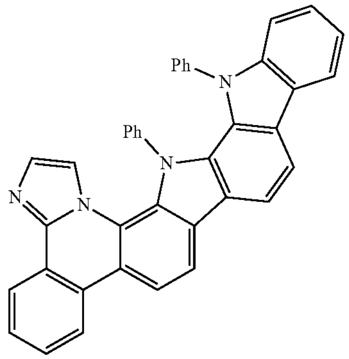
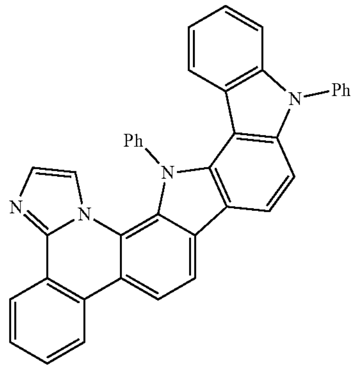
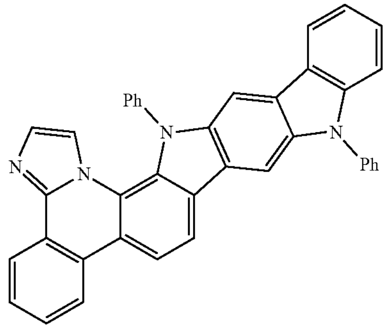
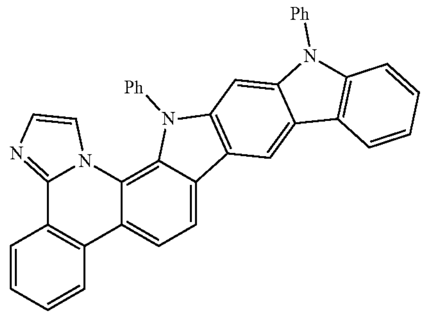

-continued
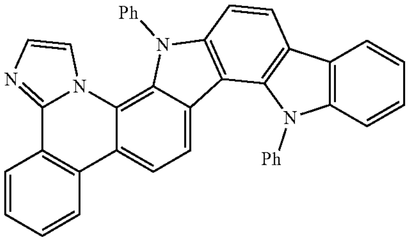
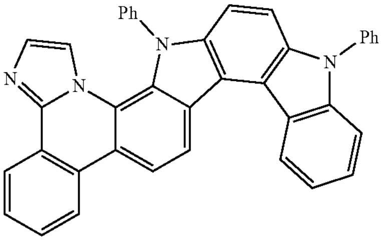
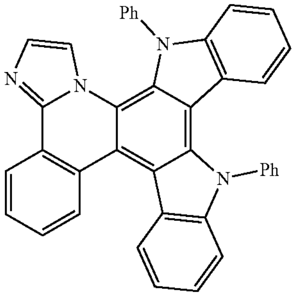
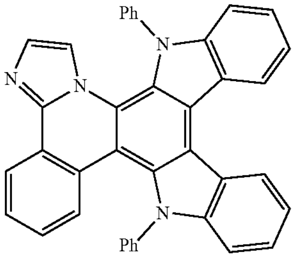
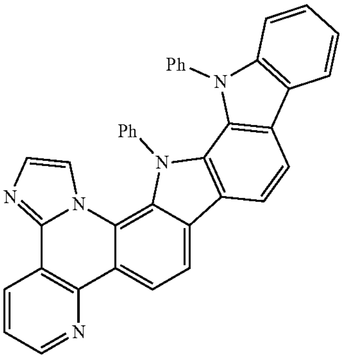
-continued
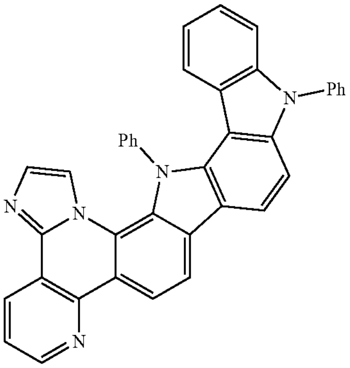
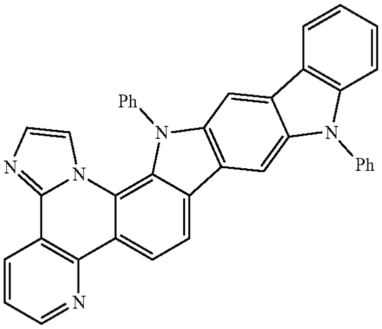
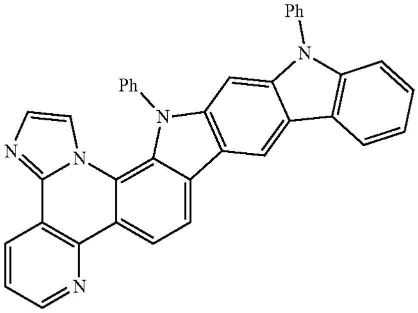
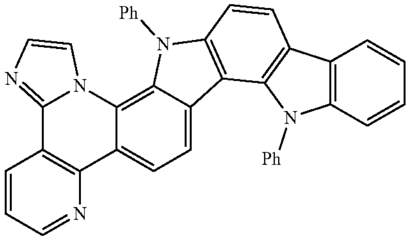
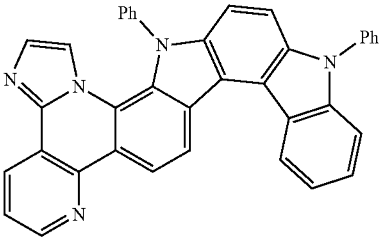

-continued
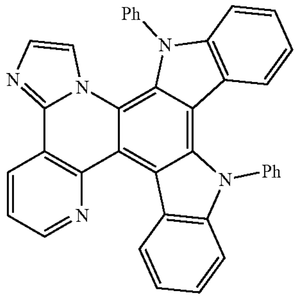
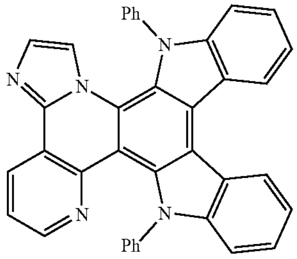
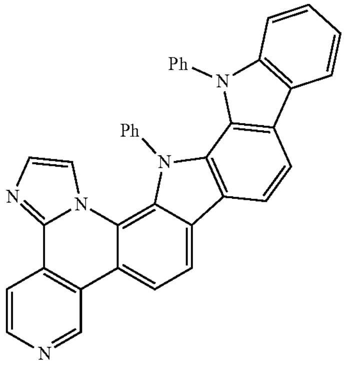
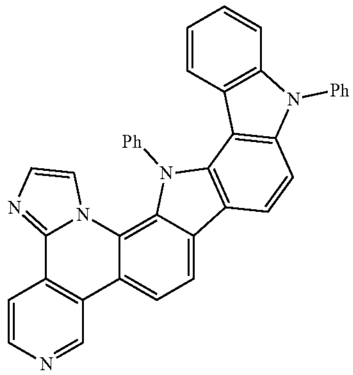
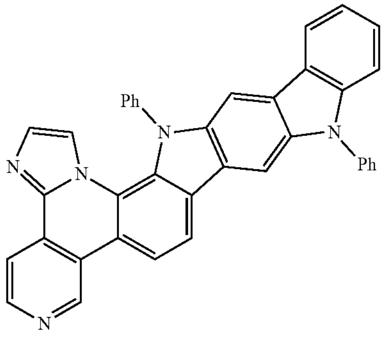
-continued
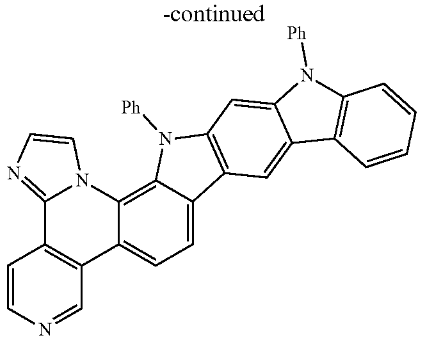
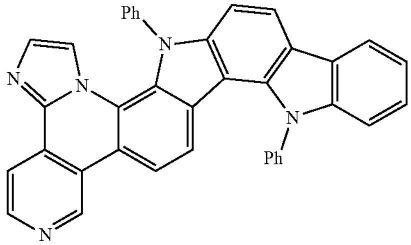
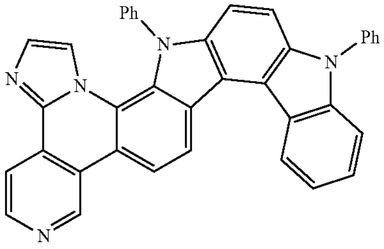
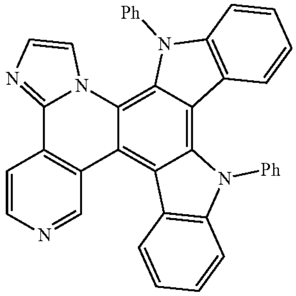
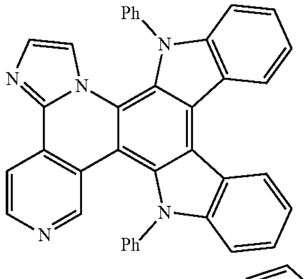
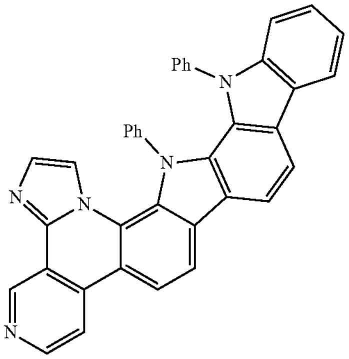

-continued
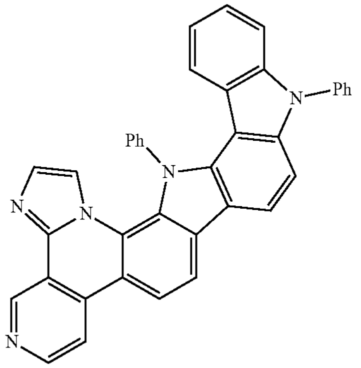
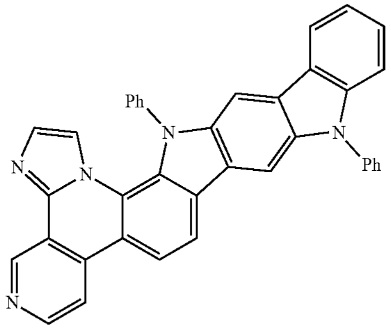
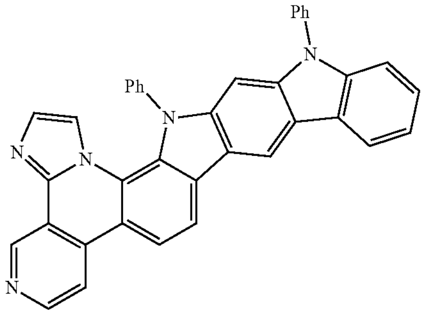
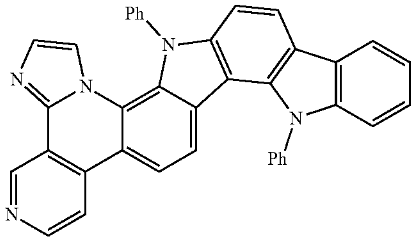
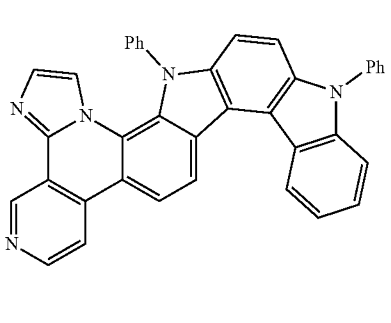
-continued
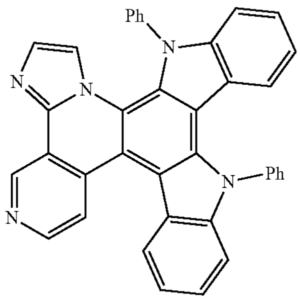
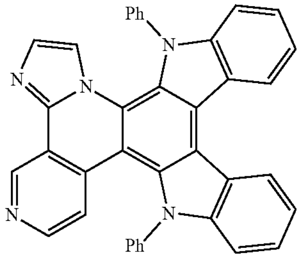
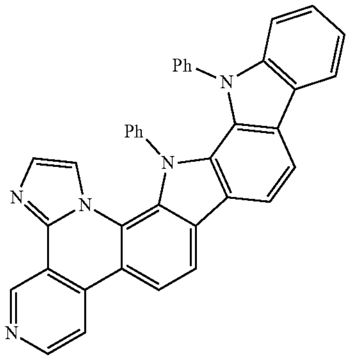
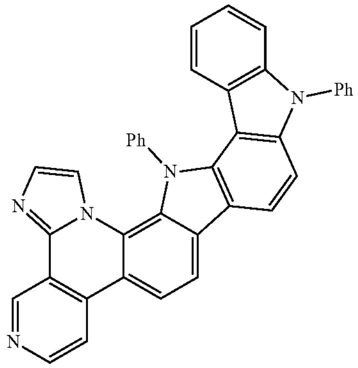
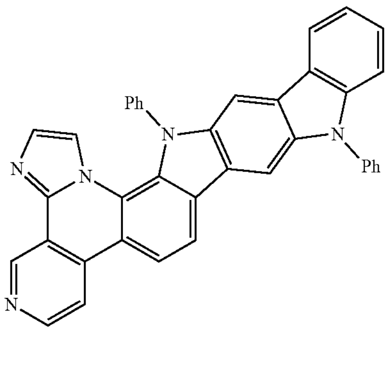

-continued
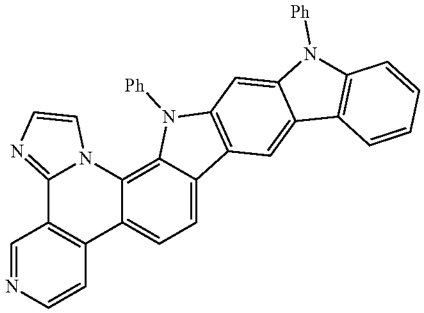
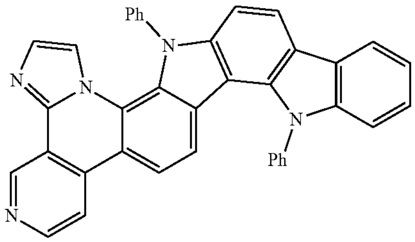
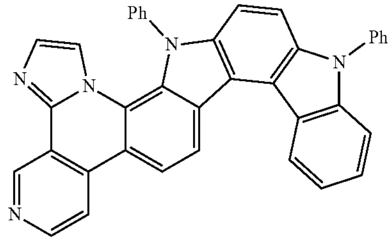
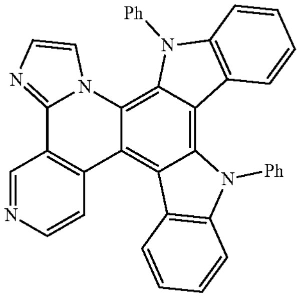
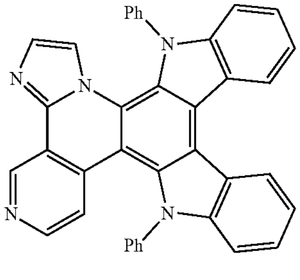
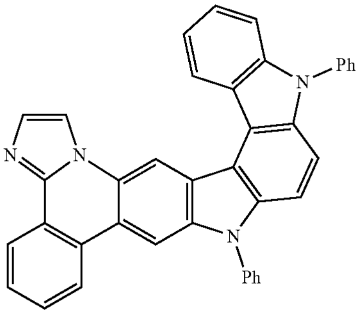
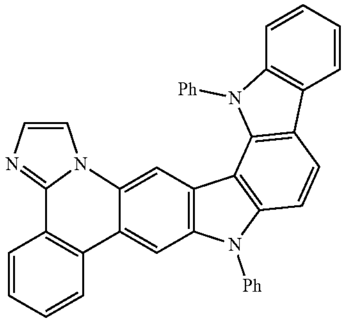
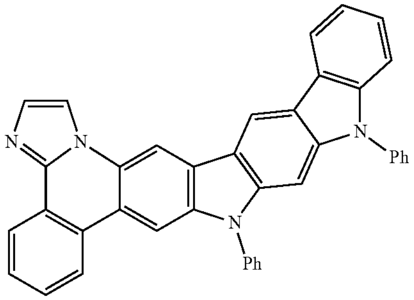
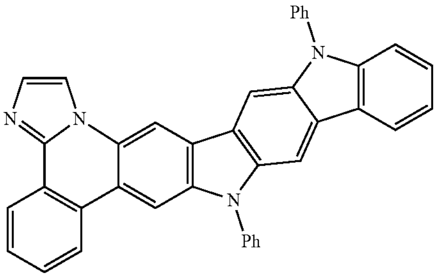
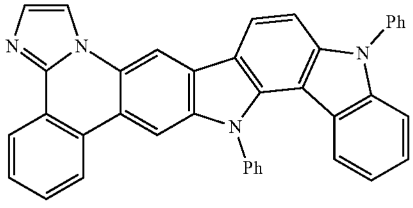
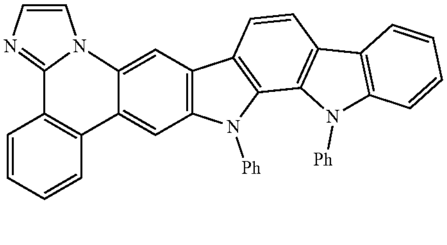

-continued
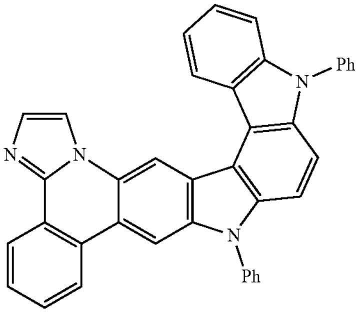
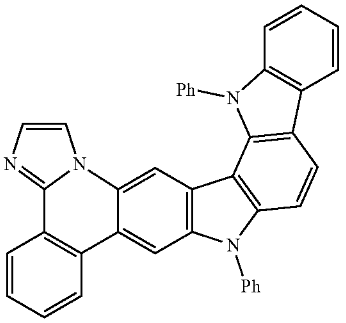
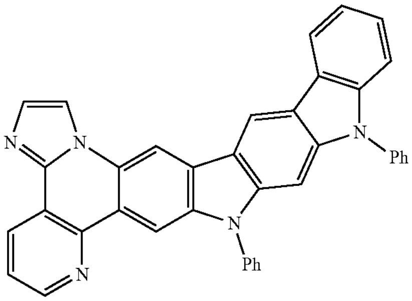
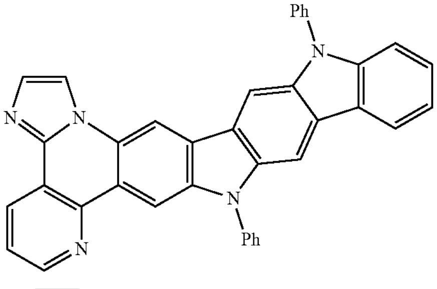
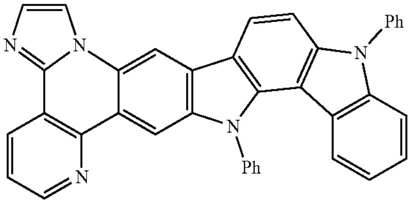
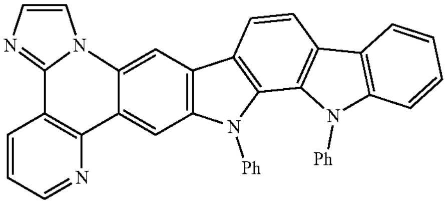
-continued
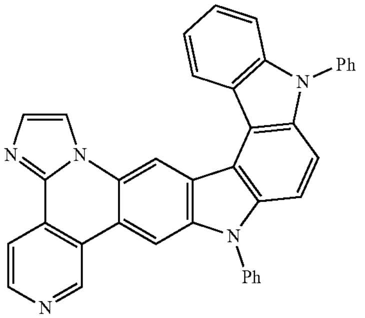
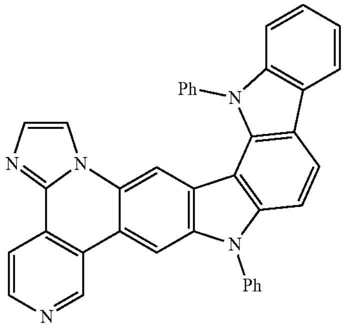
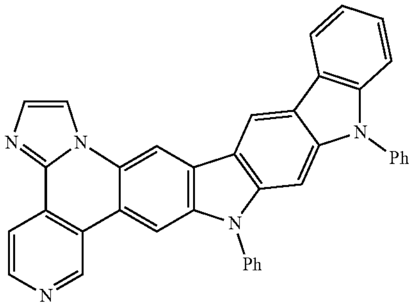
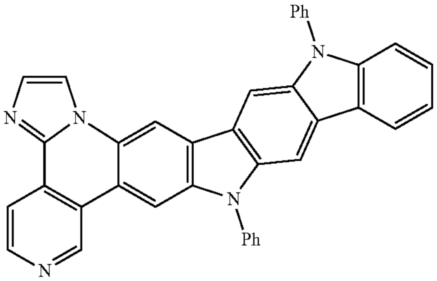
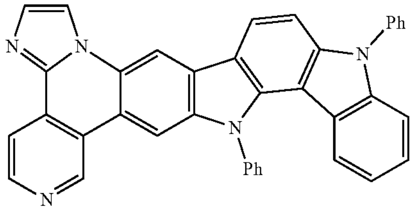
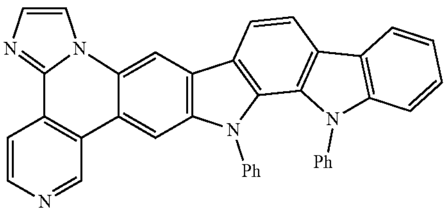

-continued
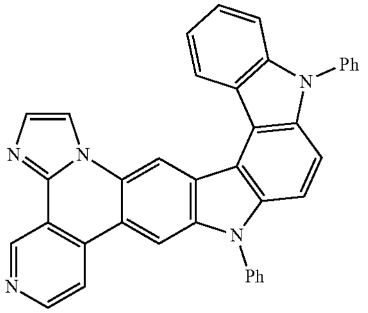
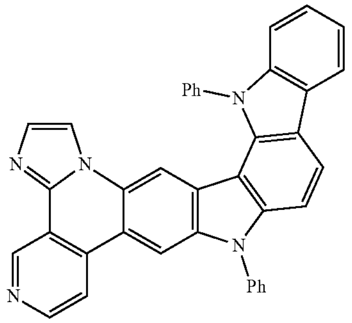
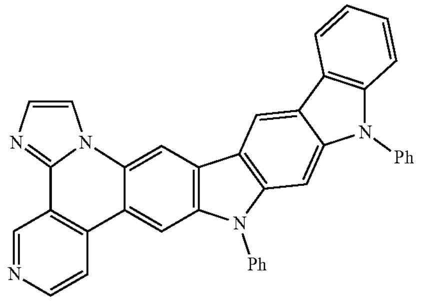
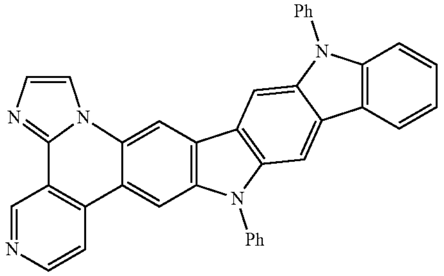
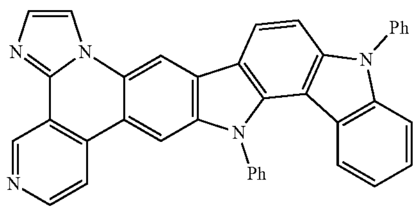
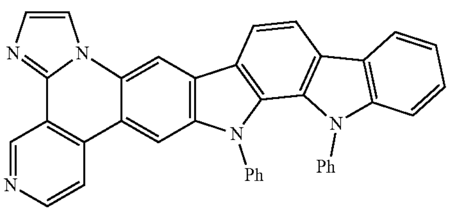
-continued
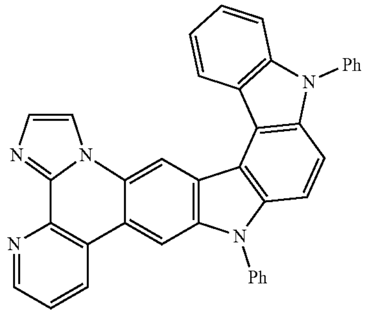
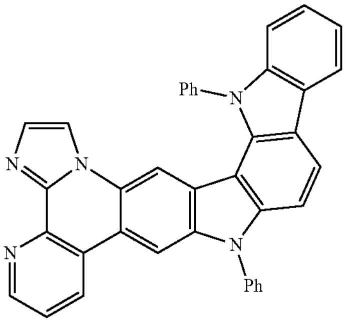
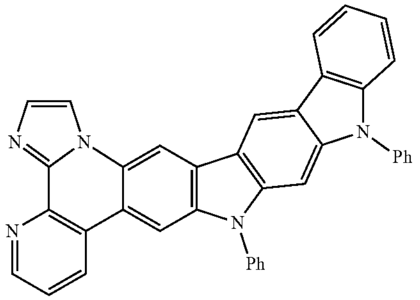
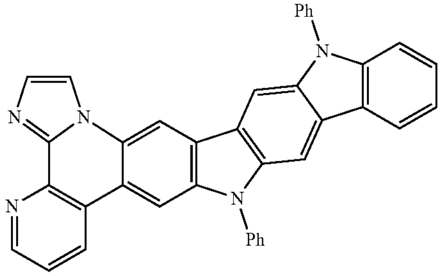
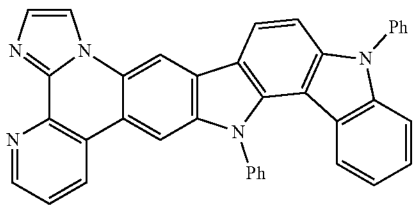
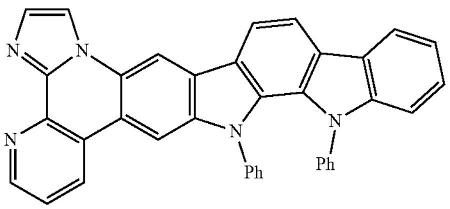

-continued
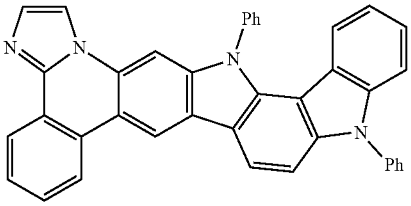
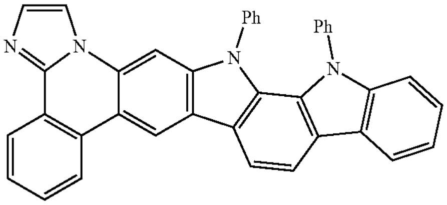
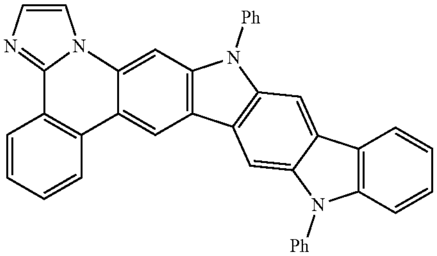
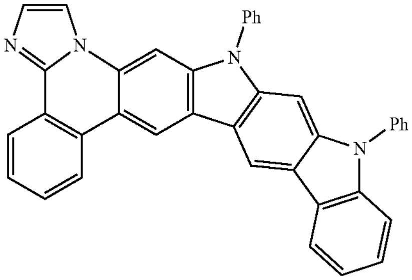
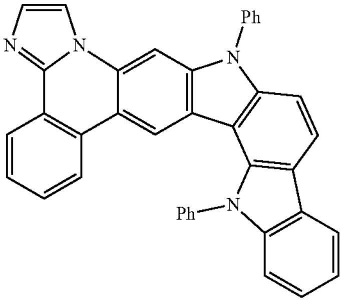
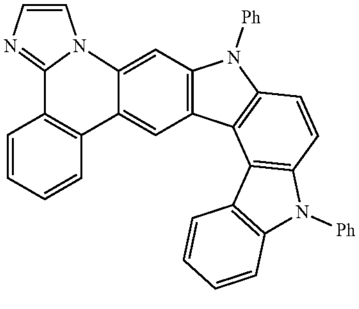
-continued
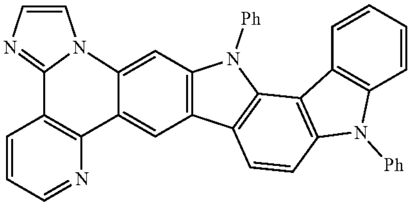
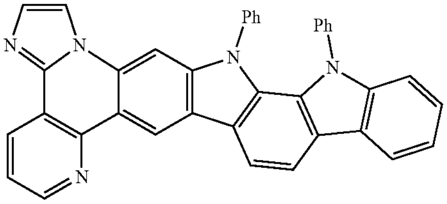
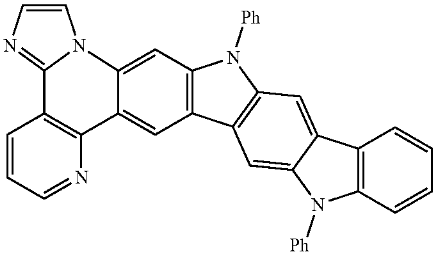
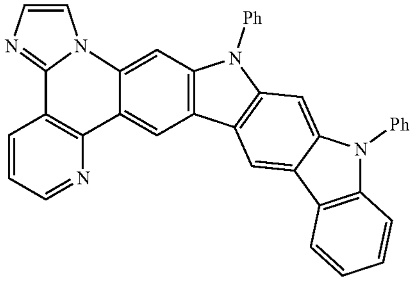
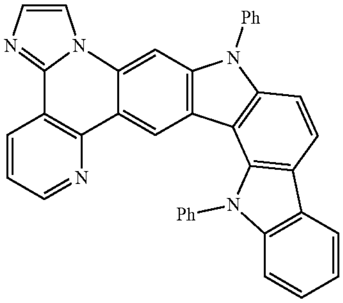
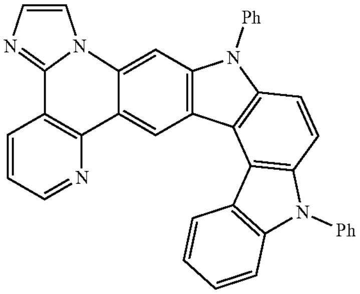

-continued
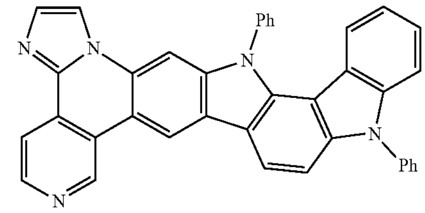
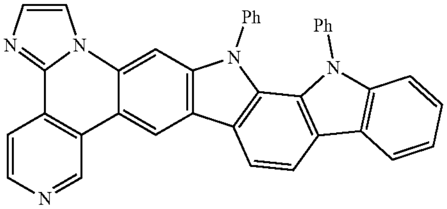
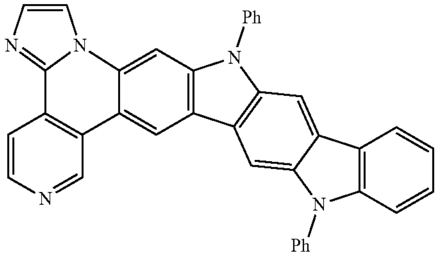
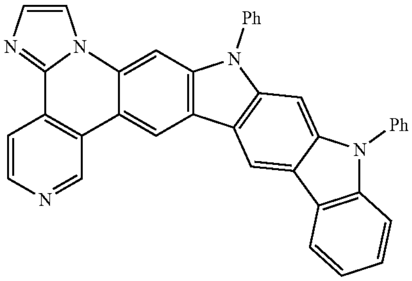
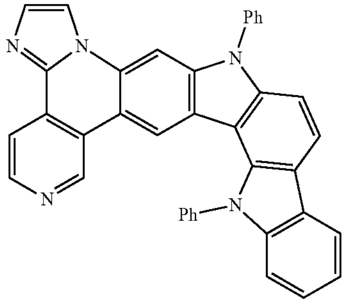
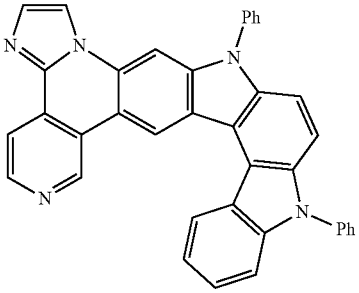
-continued
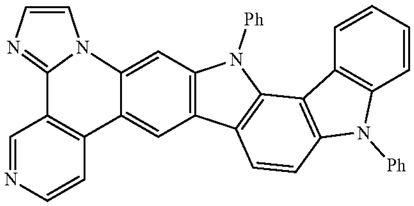
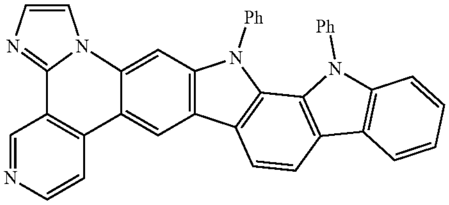
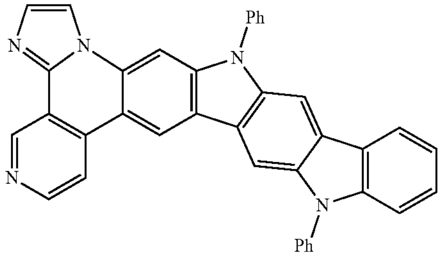
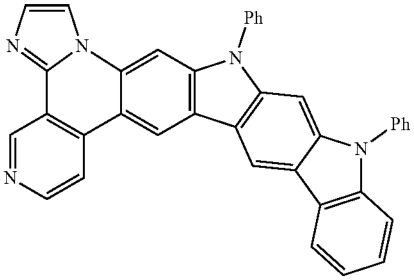
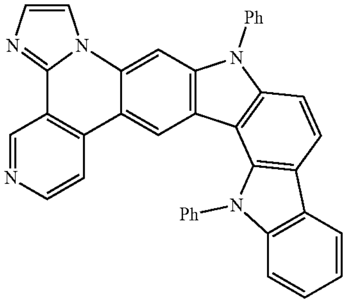
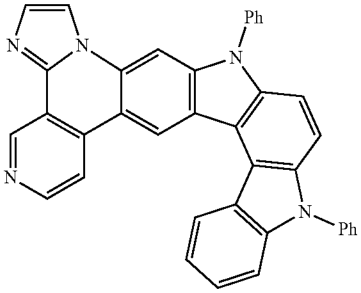

-continued
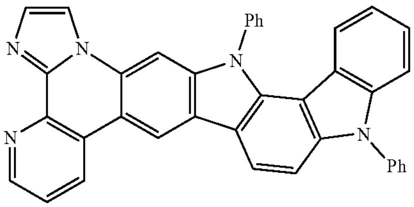
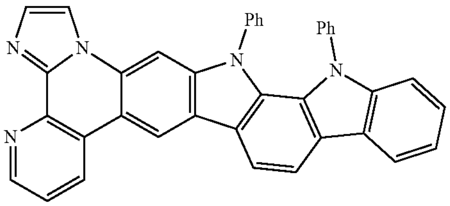
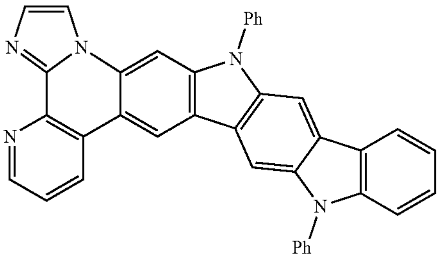
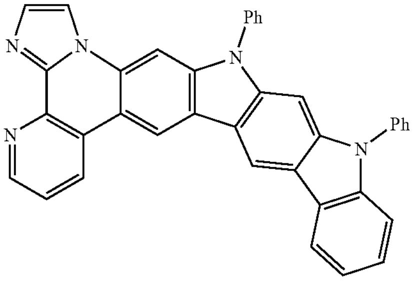
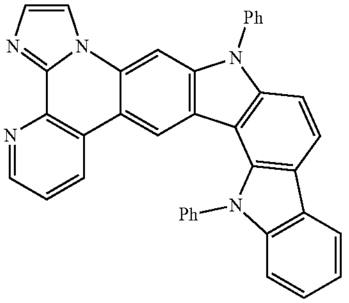
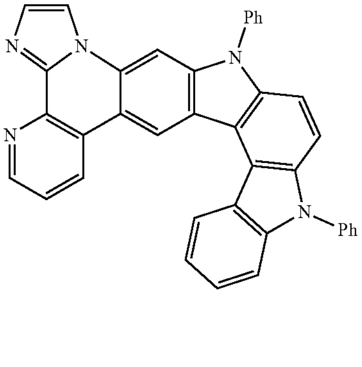
-continued
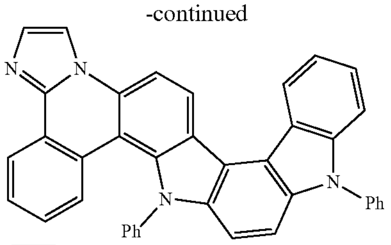
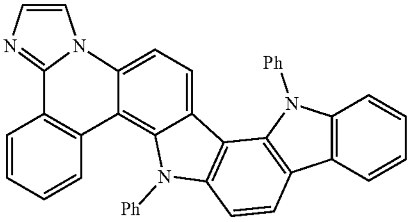
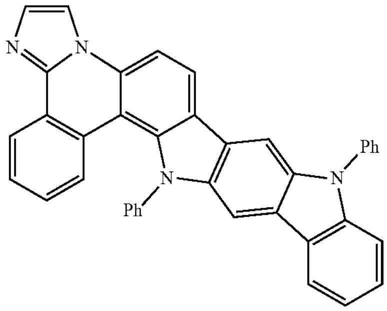
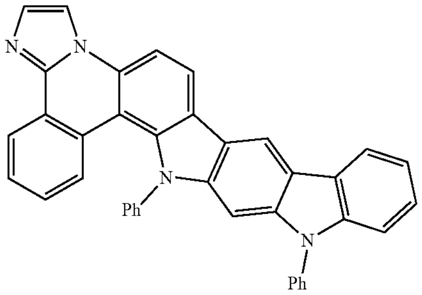
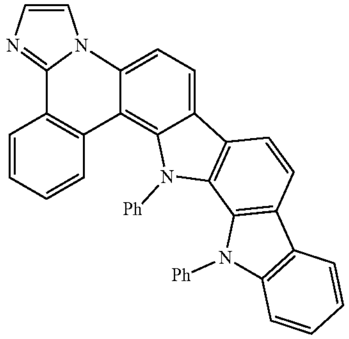
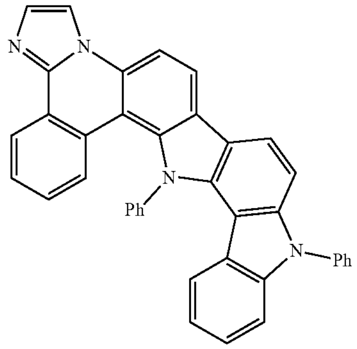

-continued
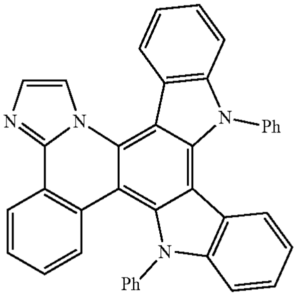
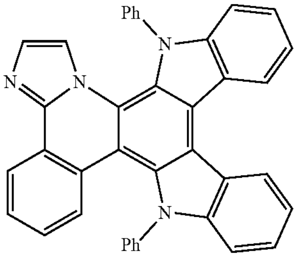
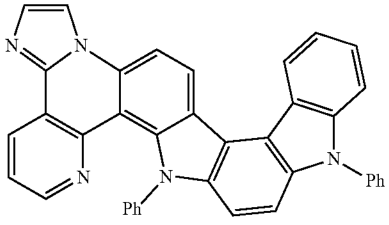
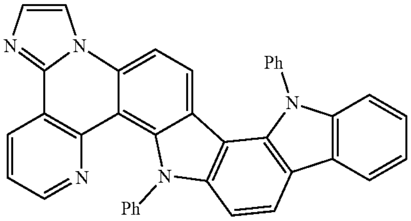
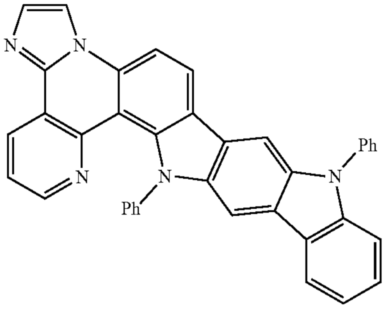
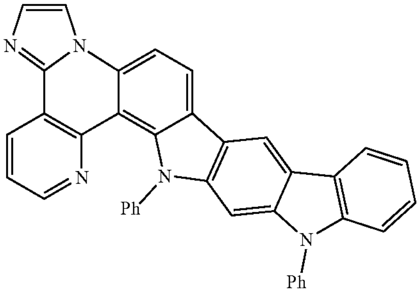
-continued
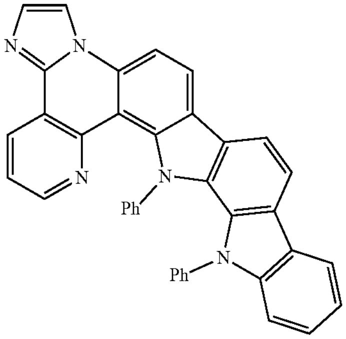
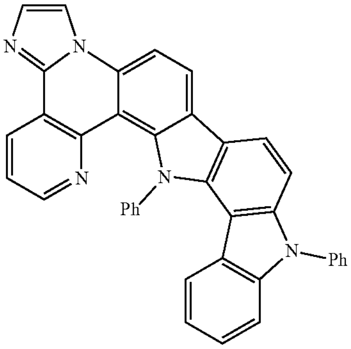
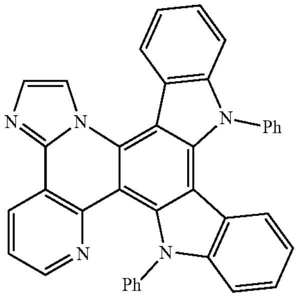
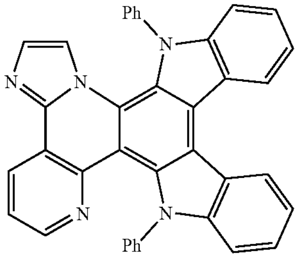
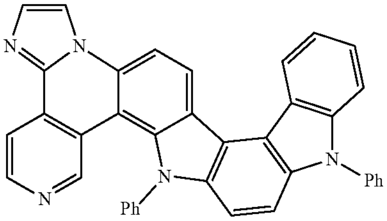
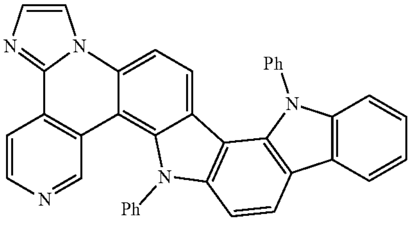

-continued
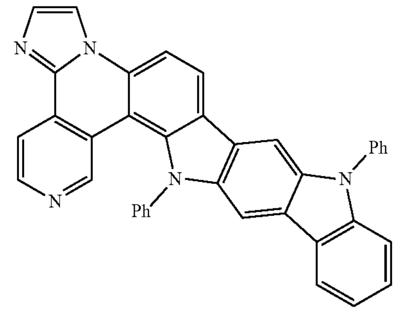
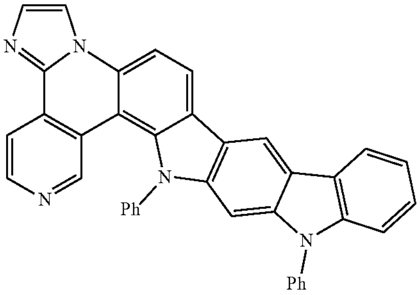
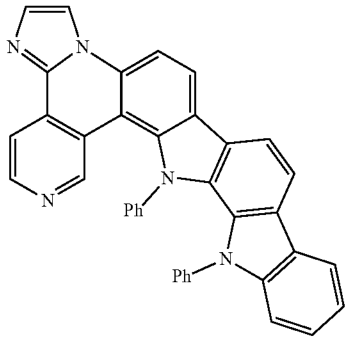
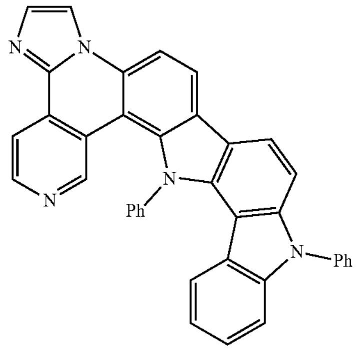
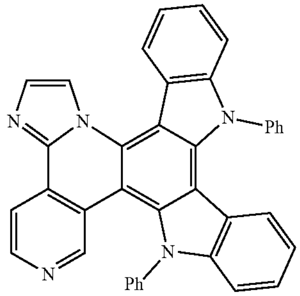
-continued
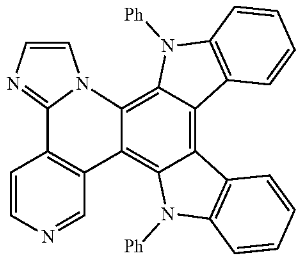
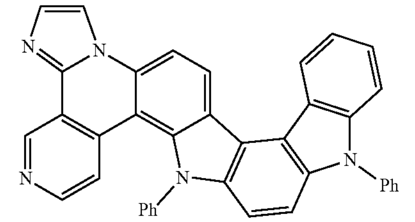
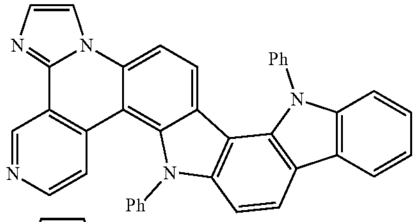
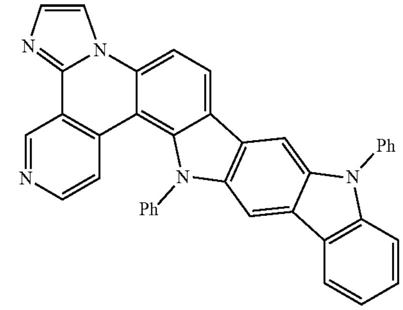
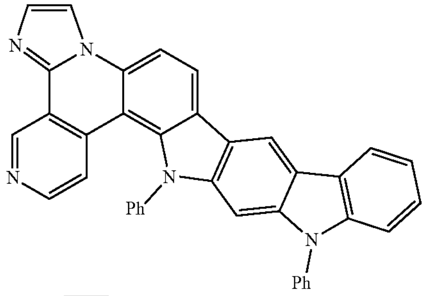
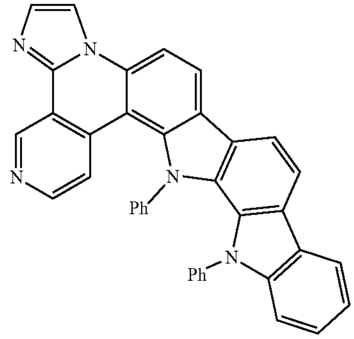

-continued
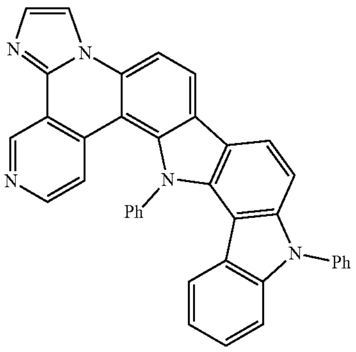
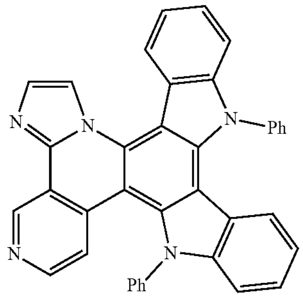
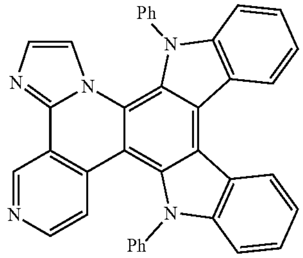
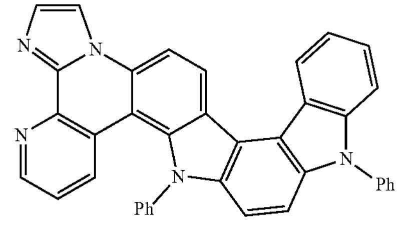
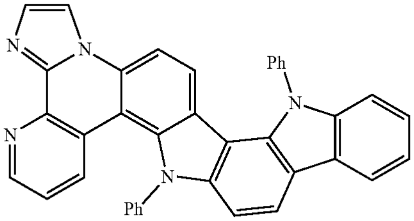
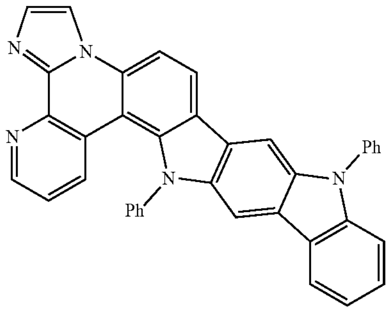
-continued
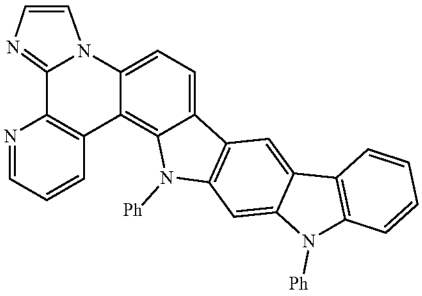
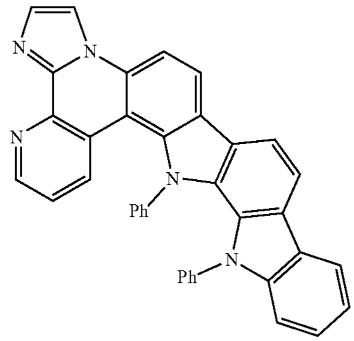
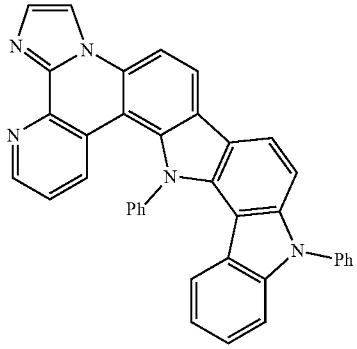
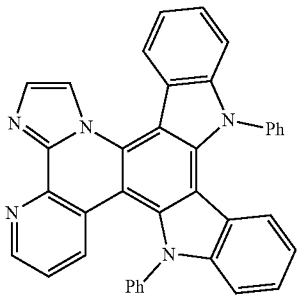
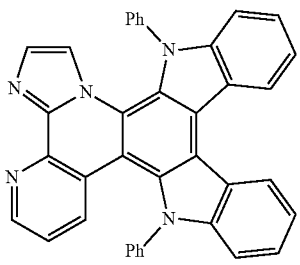

-continued
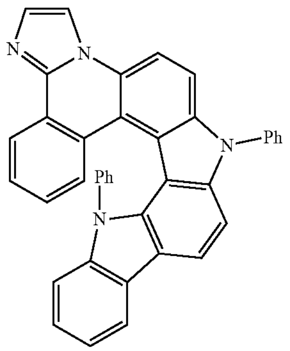
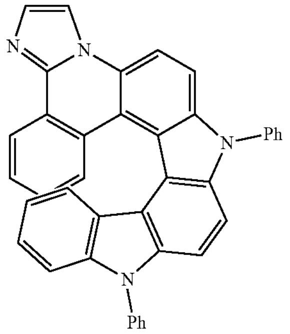
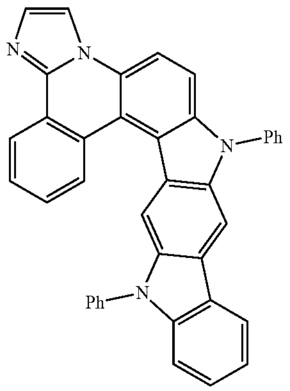
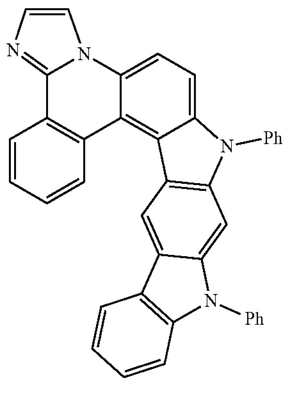
-continued
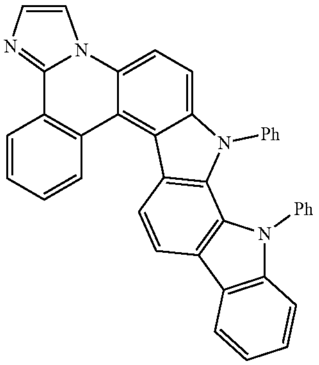
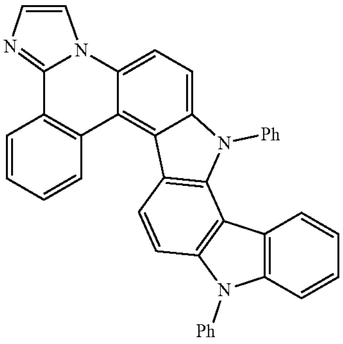
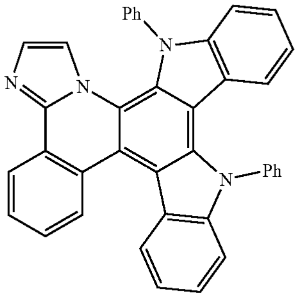
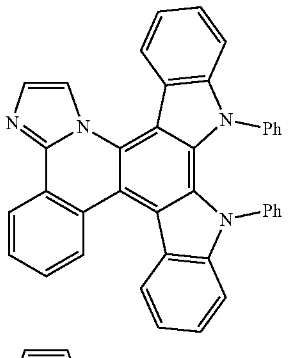
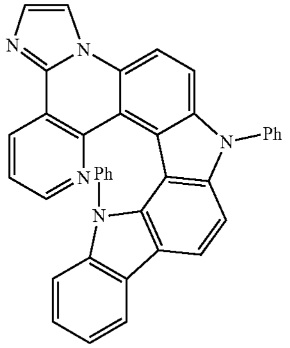

-continued
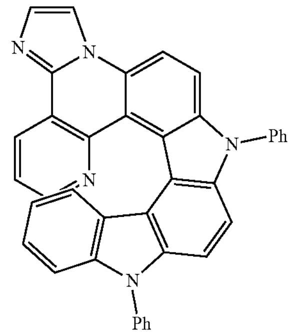
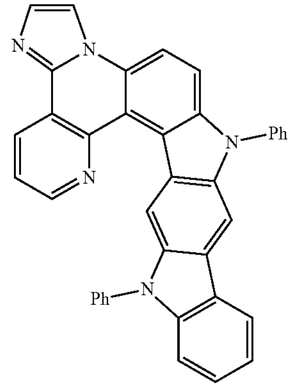
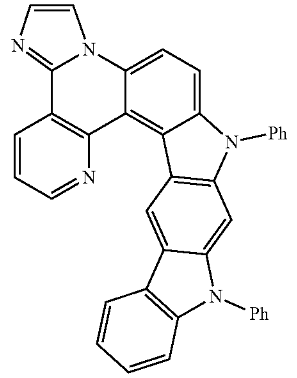
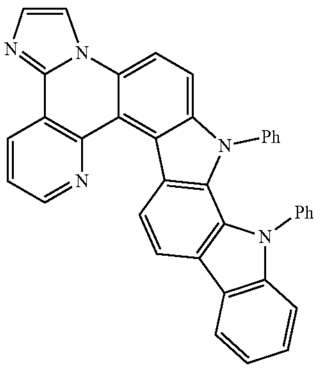
-continued
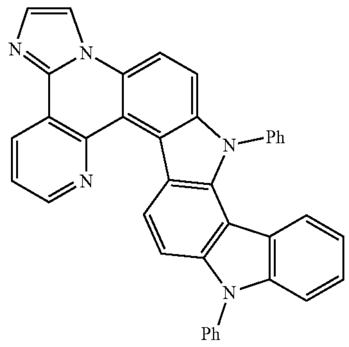
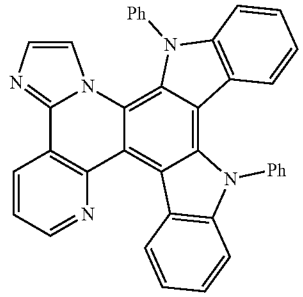
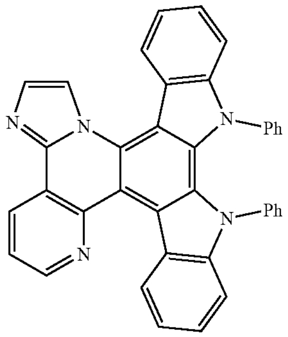
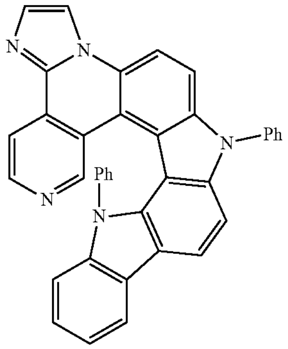
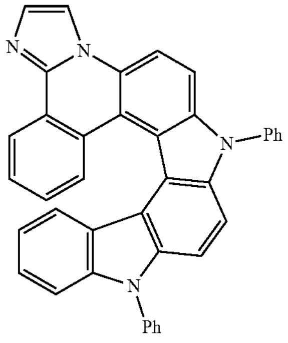

-continued
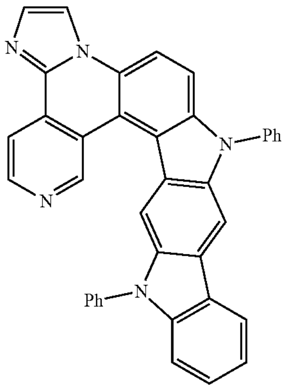
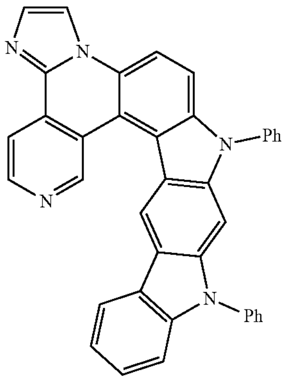
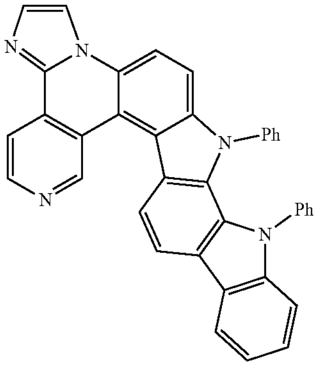
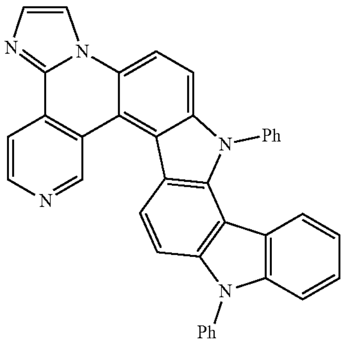
-continued
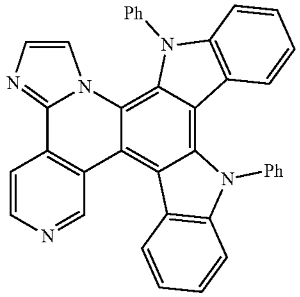
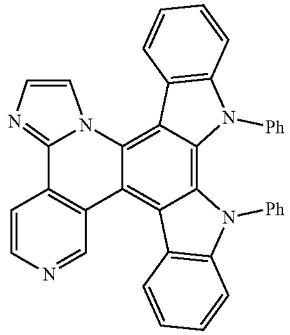
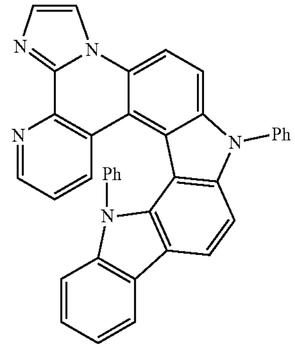
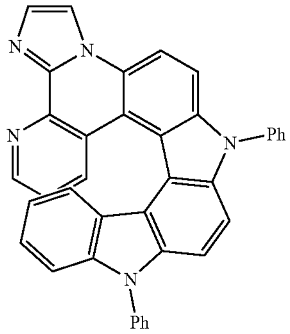
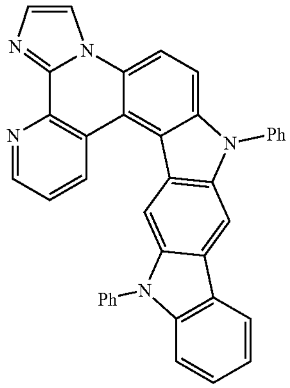

-continued
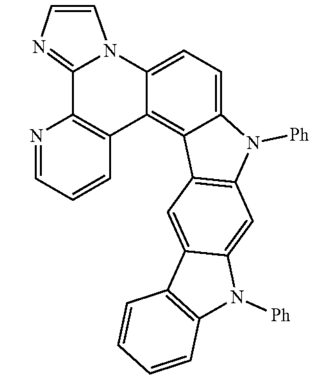
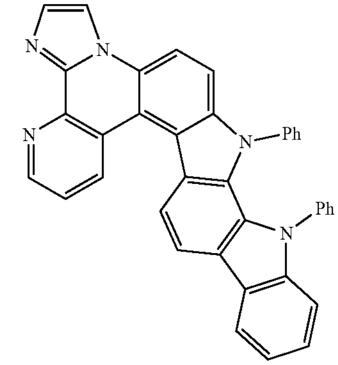
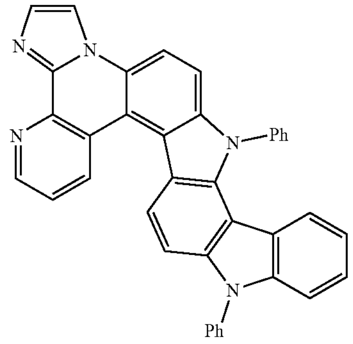
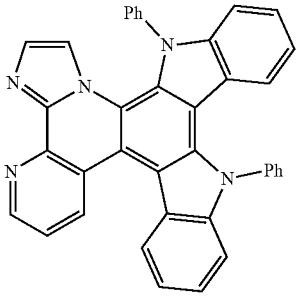
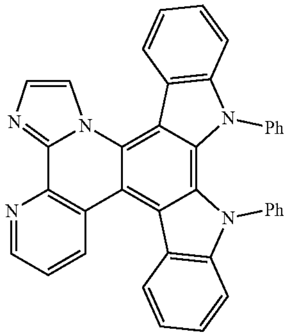
-continued
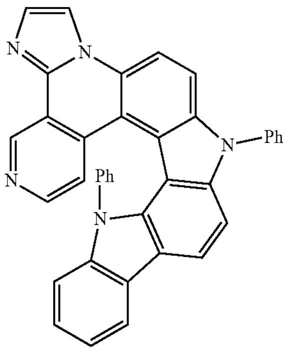
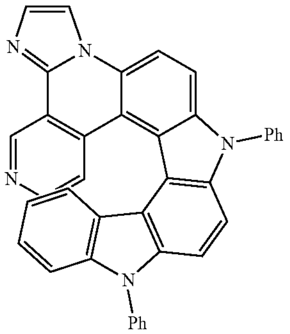
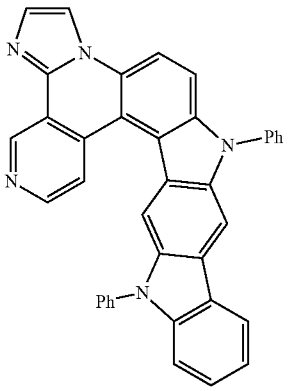
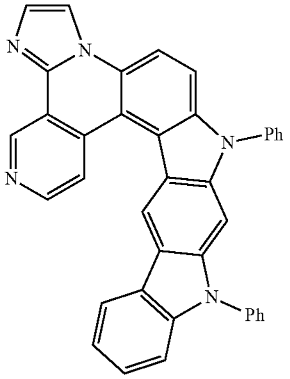

-continued
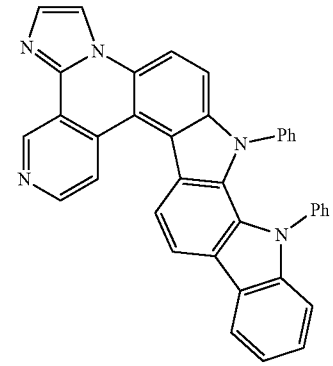
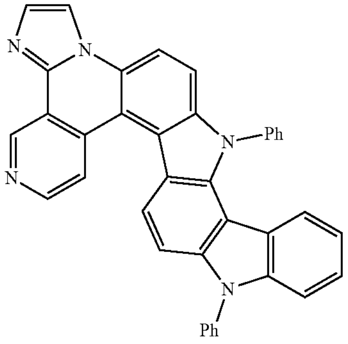
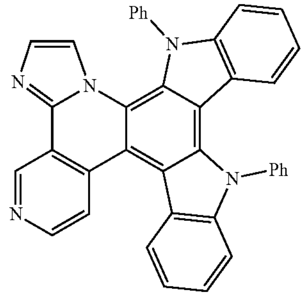
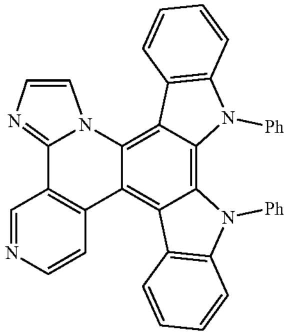
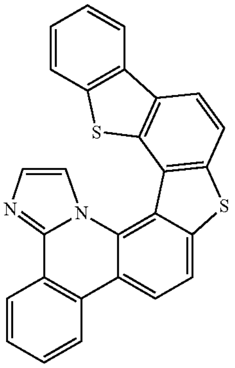
-continued
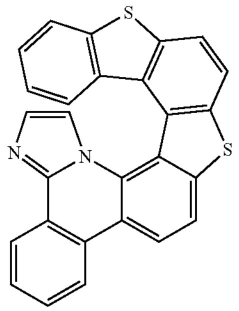
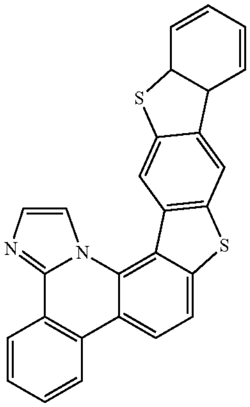
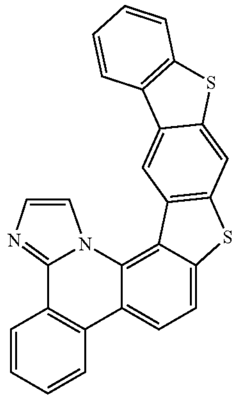
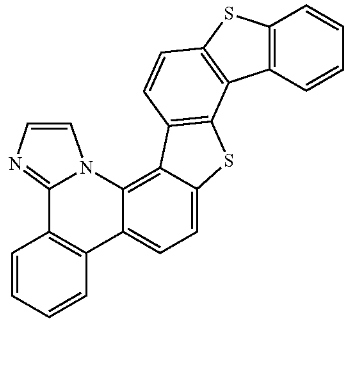

-continued
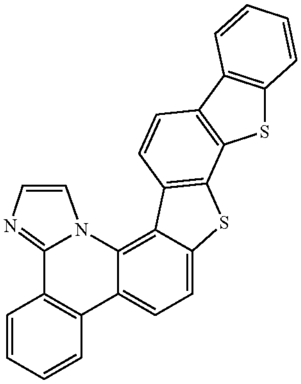
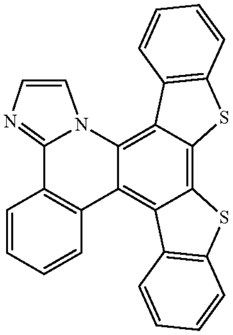
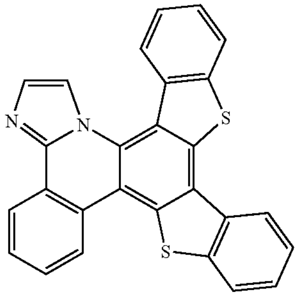
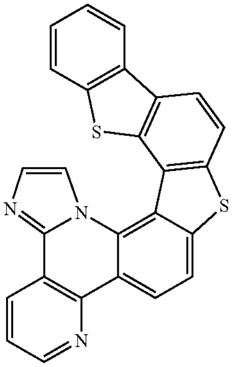
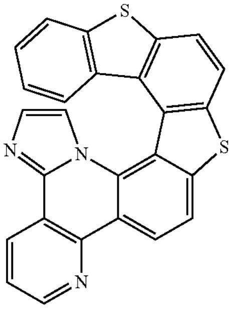
-continued
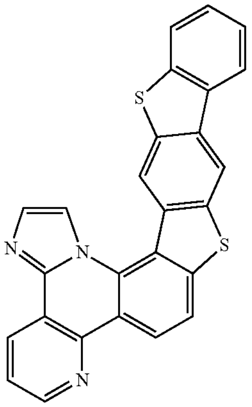
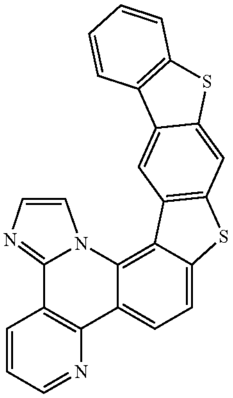
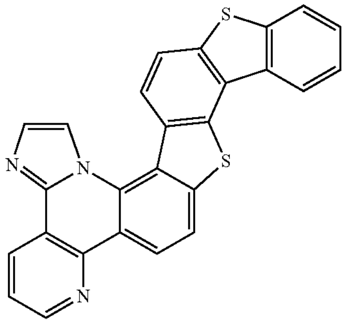
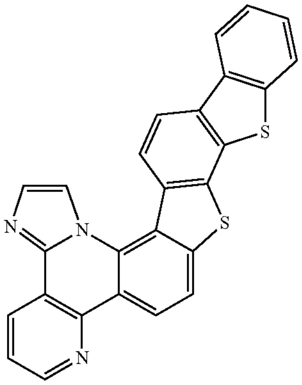

-continued
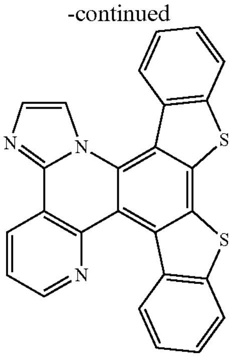
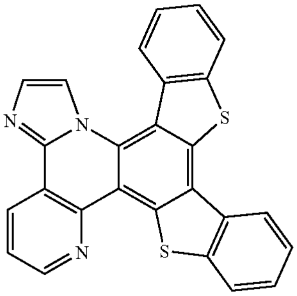
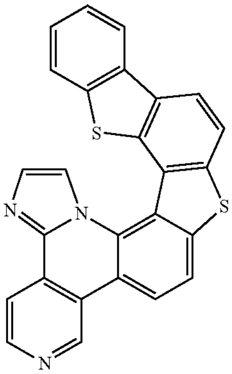
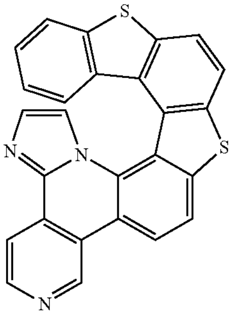
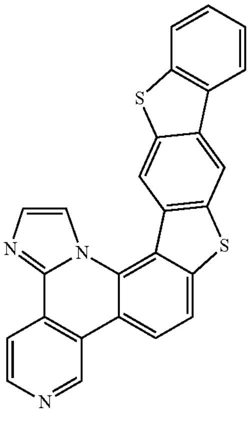
-continued
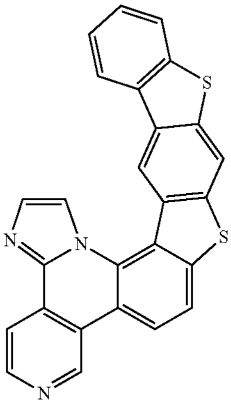
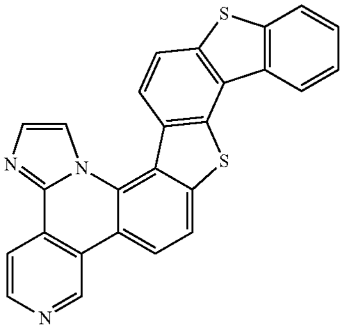
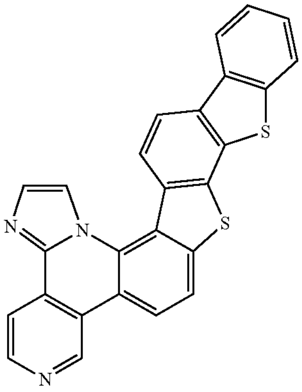
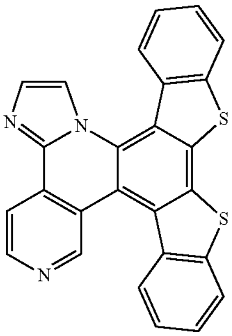

-continued
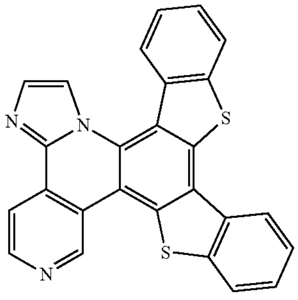
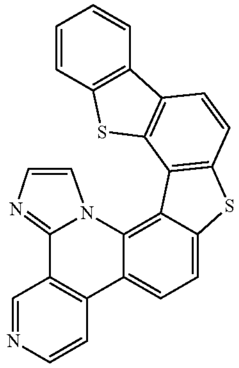
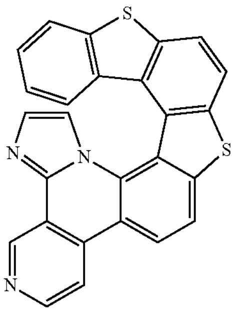
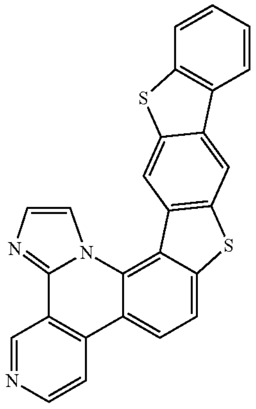
-continued
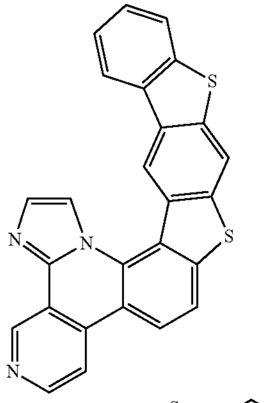
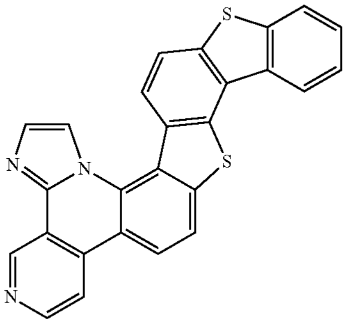
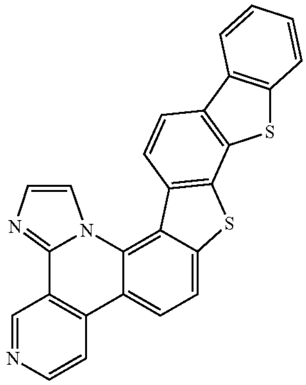
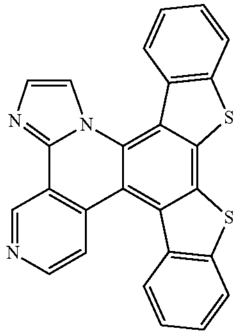
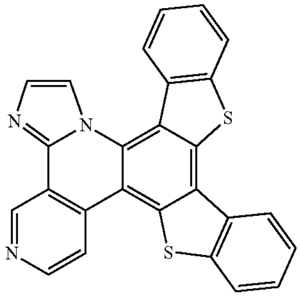

-continued
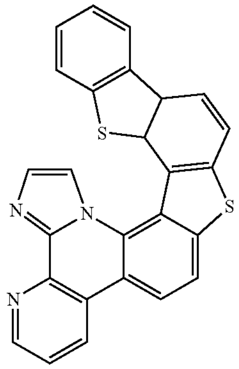
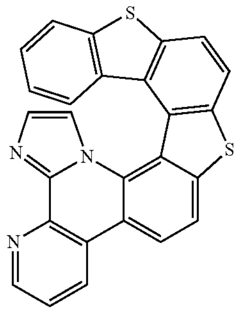
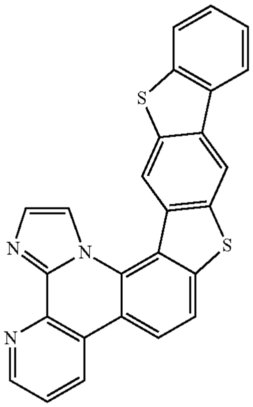
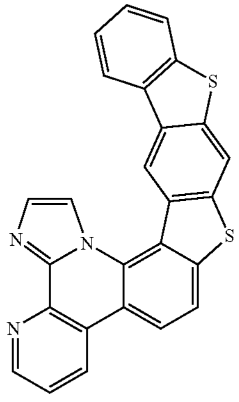
-continued
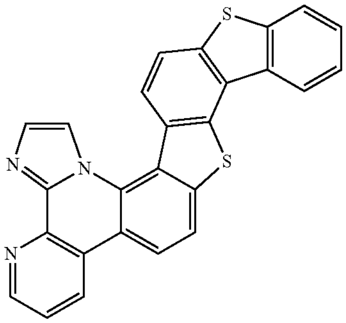
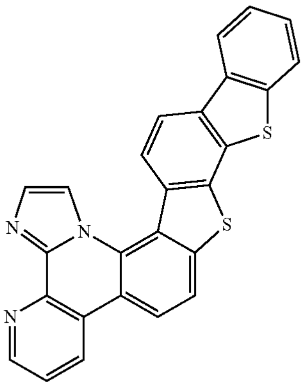
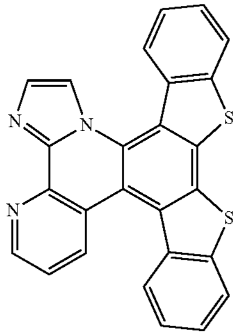
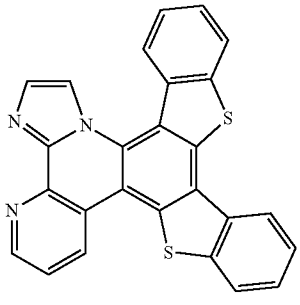

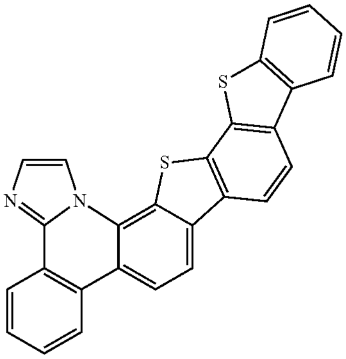
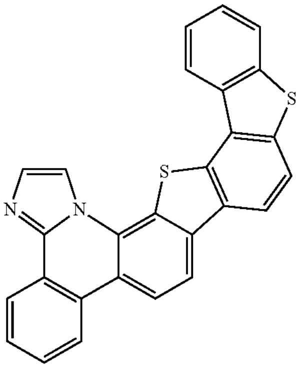
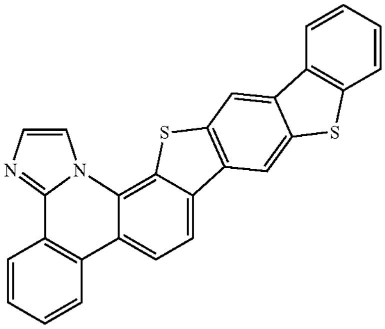
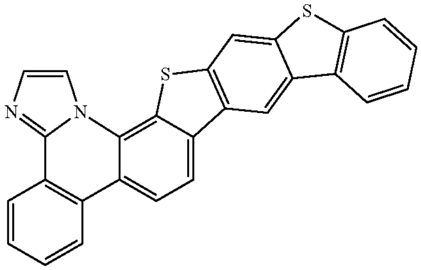
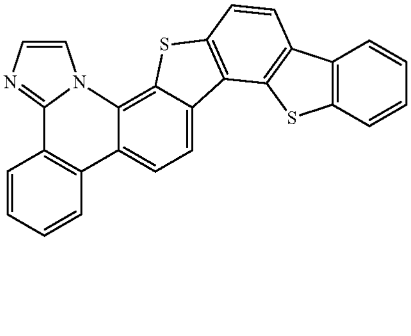
-continued
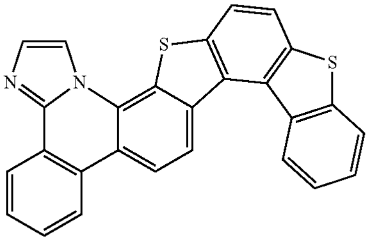
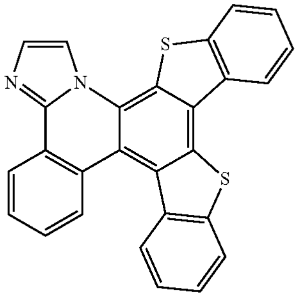
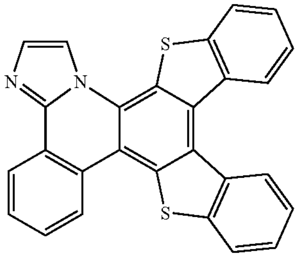
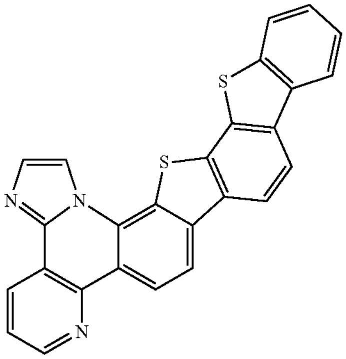
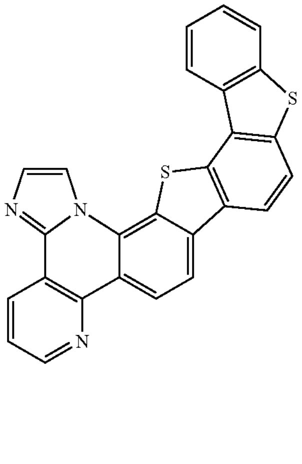

-continued
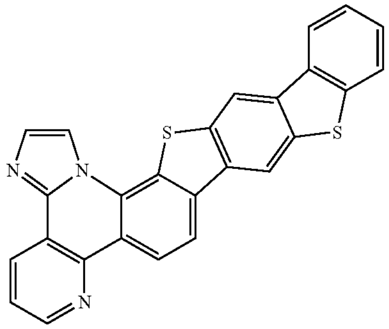
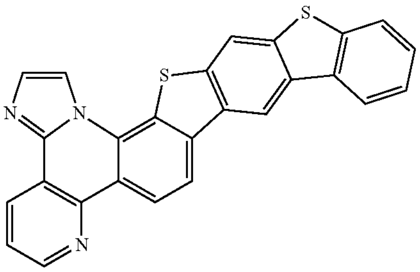
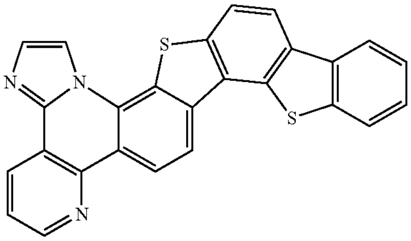
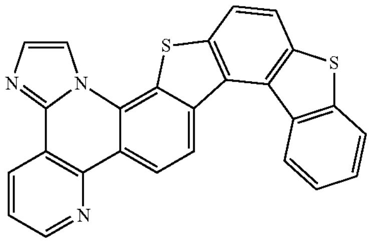
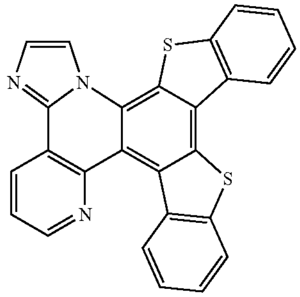
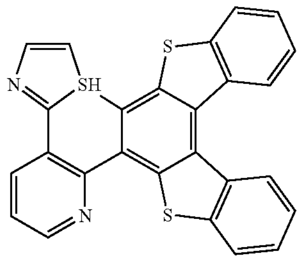
-continued
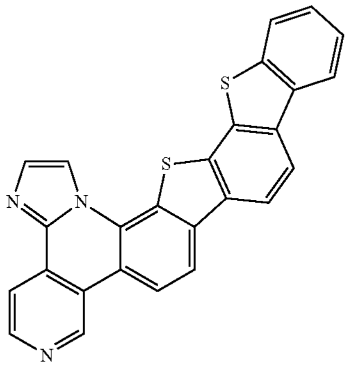
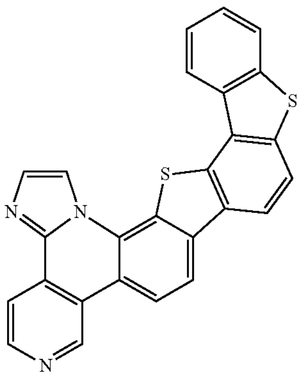
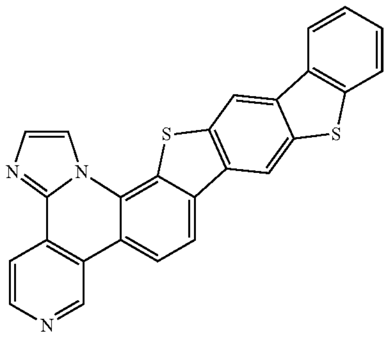
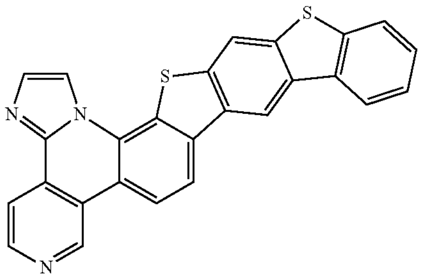
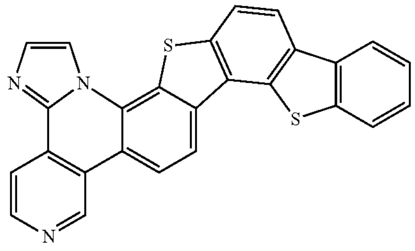

-continued
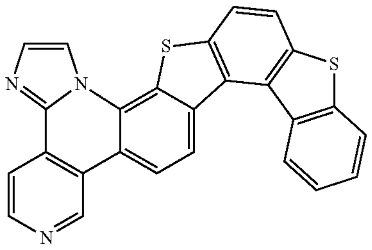
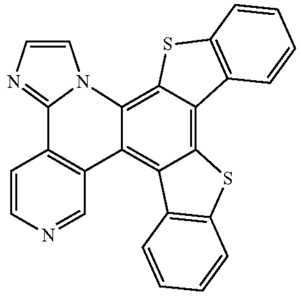
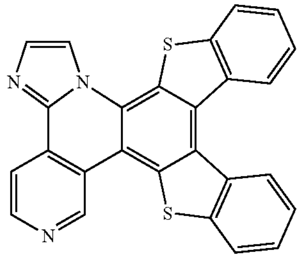
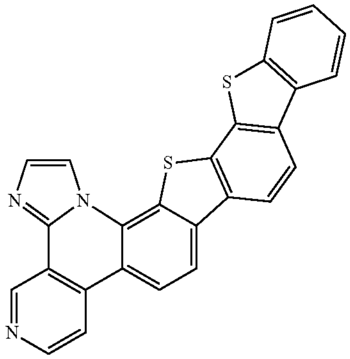
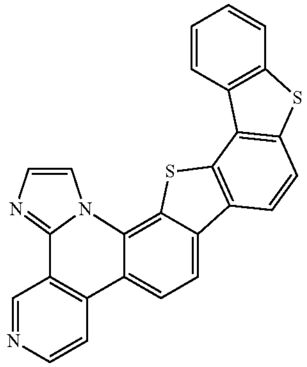
-continued
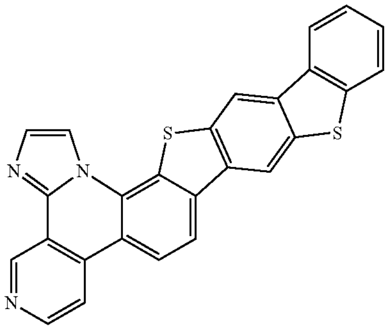
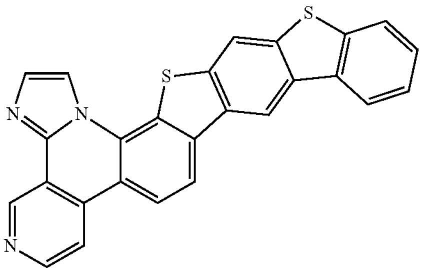
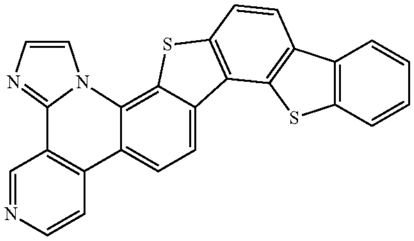
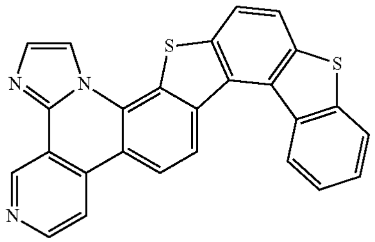
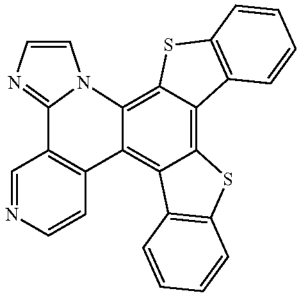
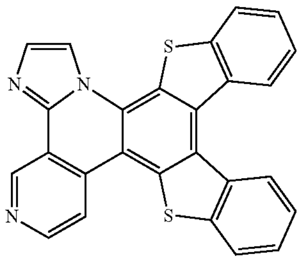

-continued
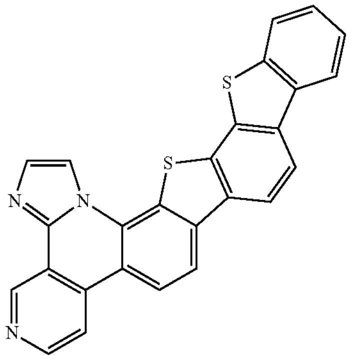
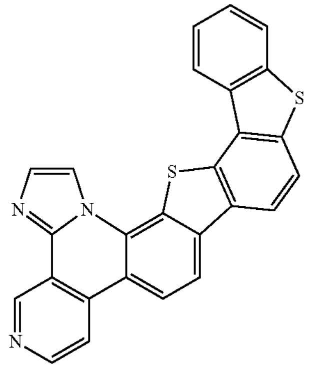
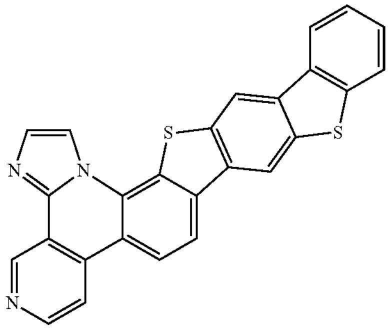
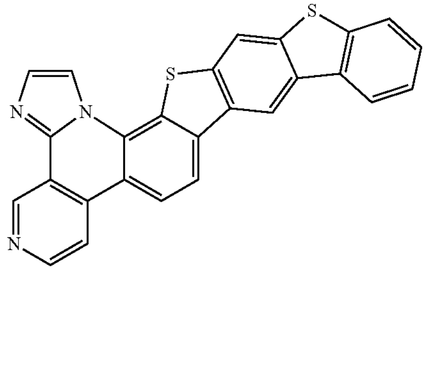
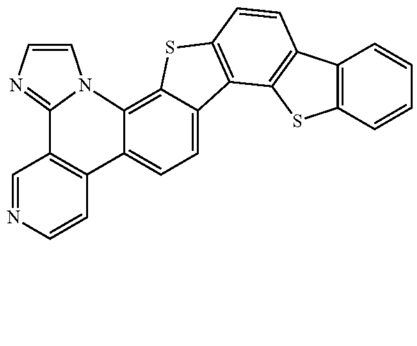
-continued
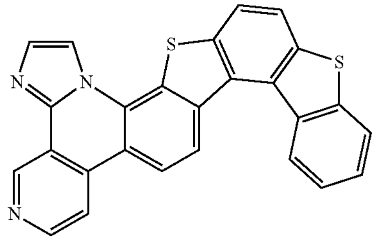
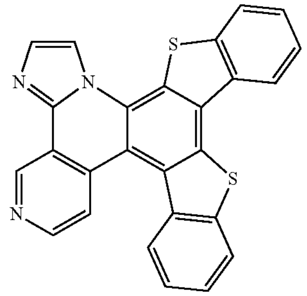
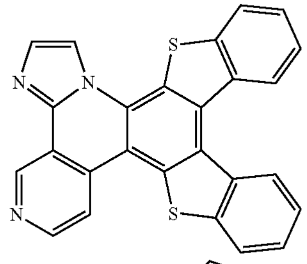
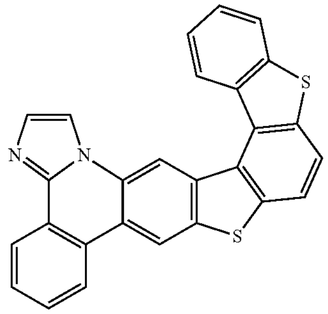
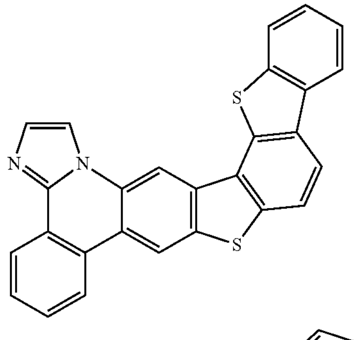
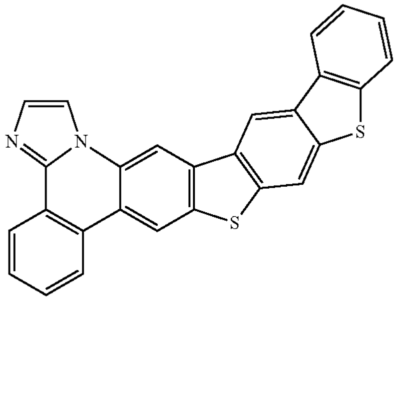

-continued
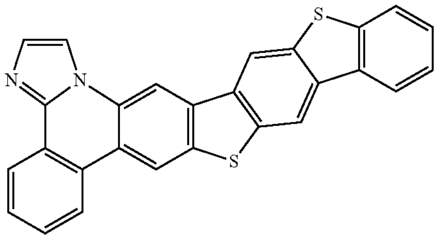
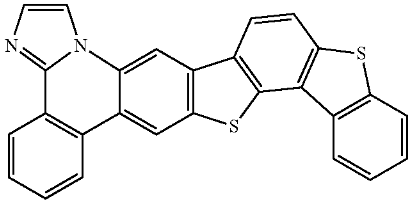
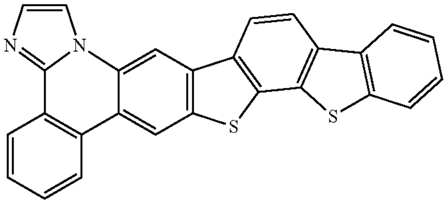
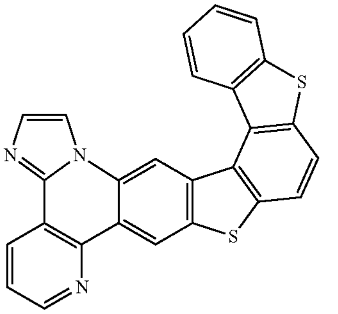
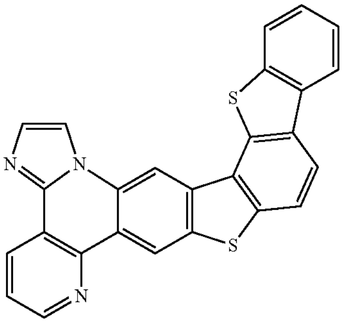
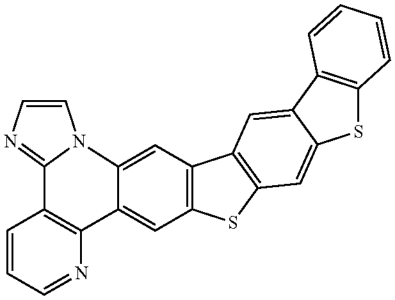
-continued
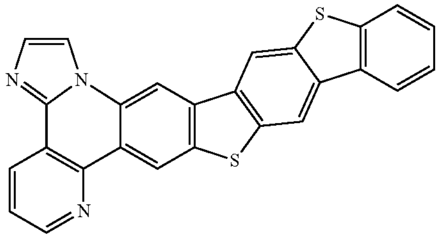
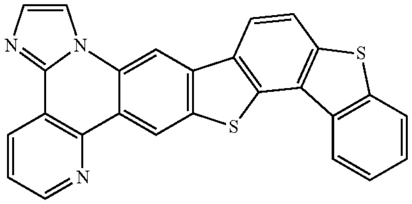
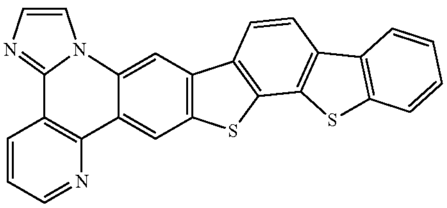
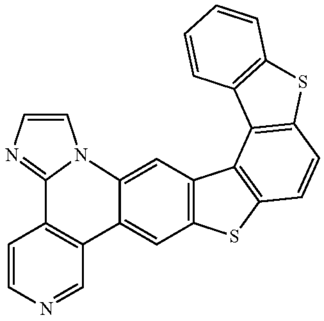
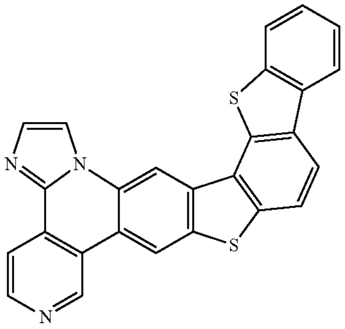
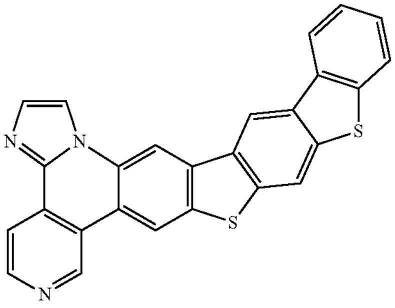

-continued
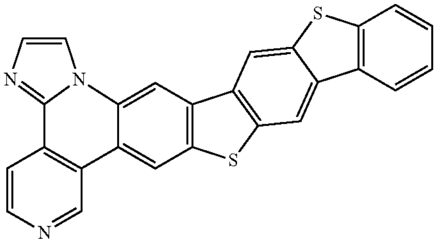
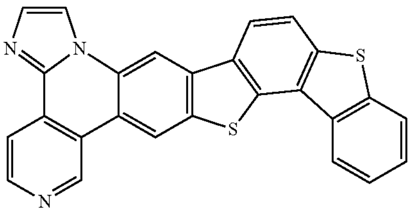
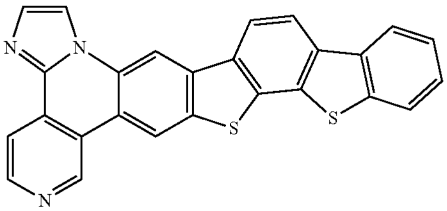
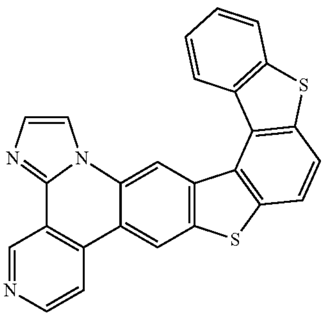
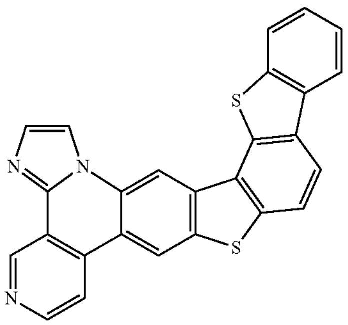
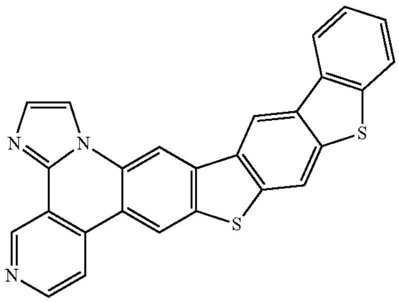
-continued
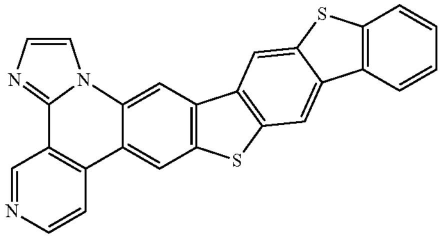
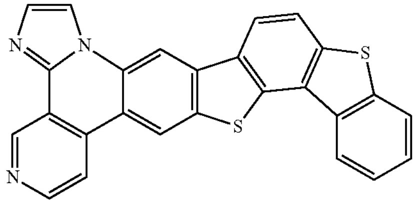
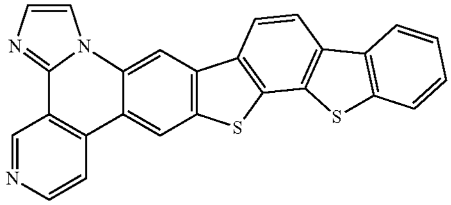
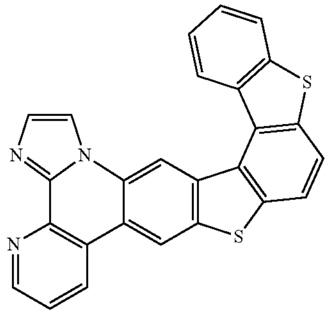
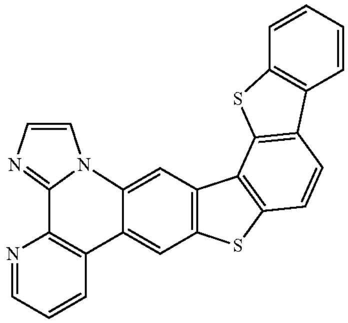
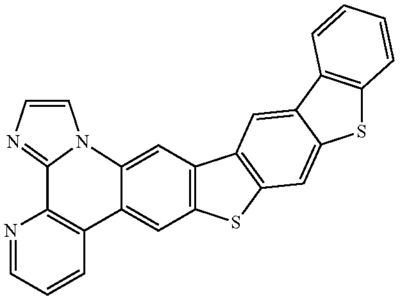

-continued
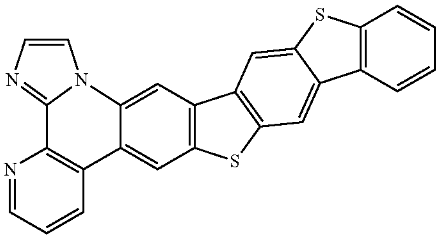
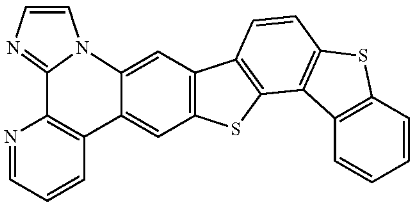
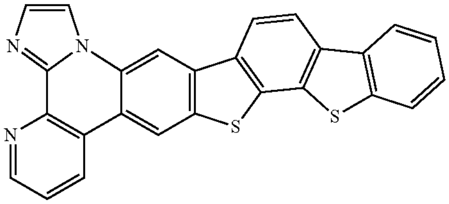
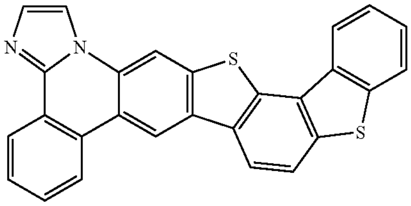
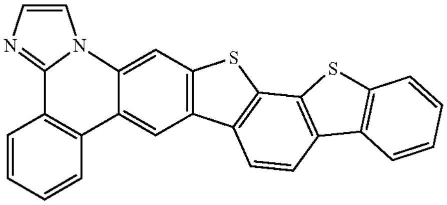
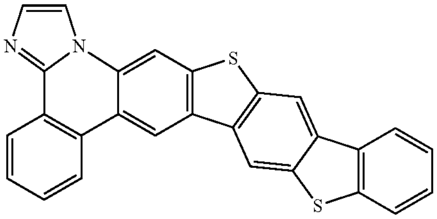
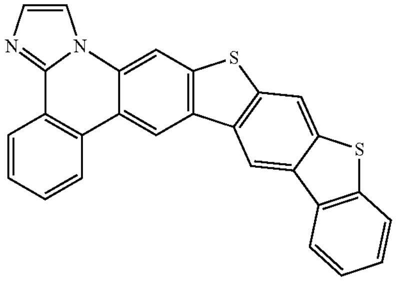
-continued
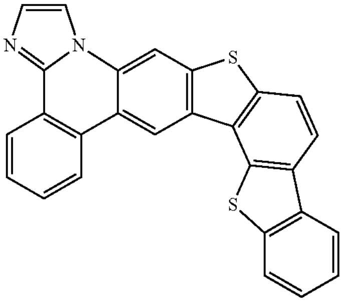
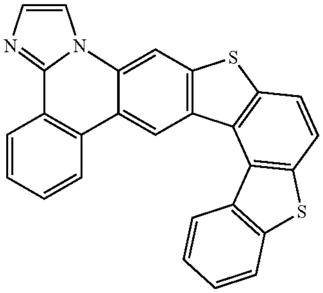
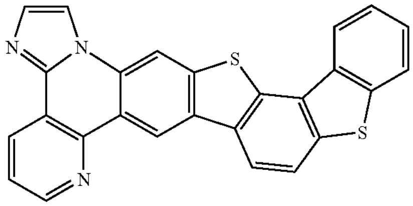
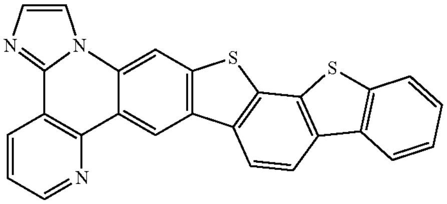
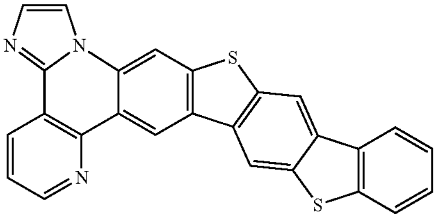
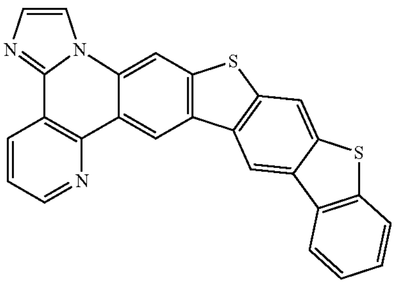

-continued
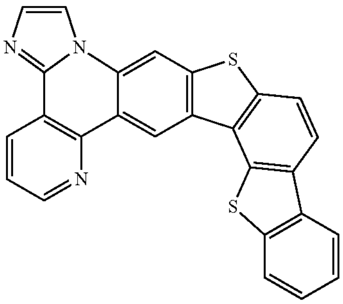
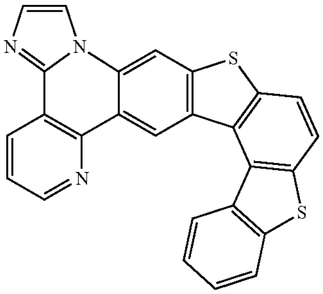
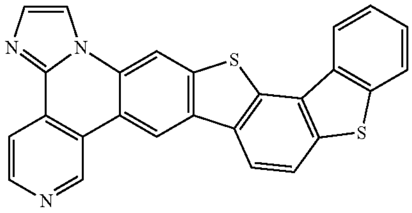
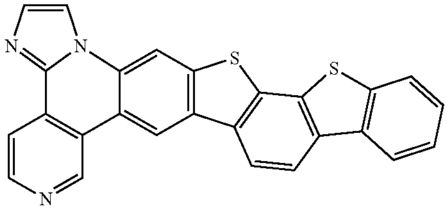
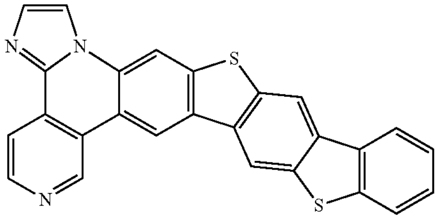
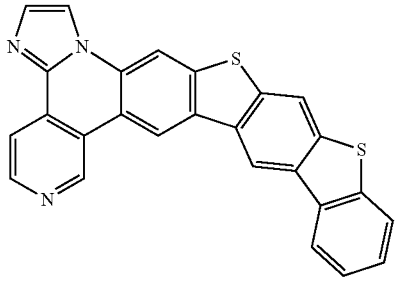
-continued
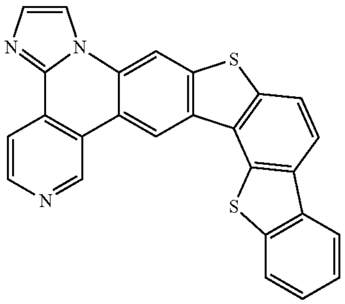
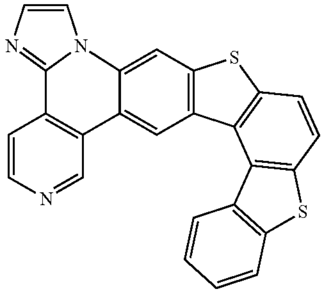
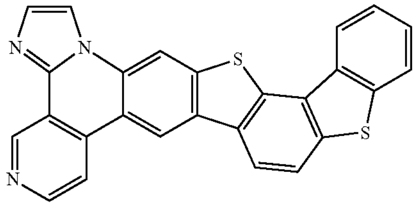
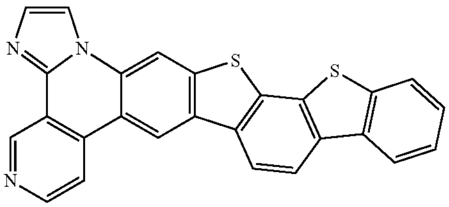
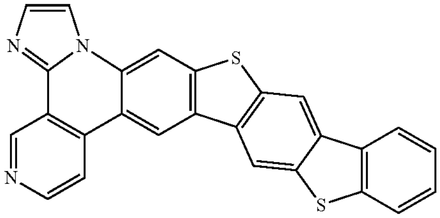
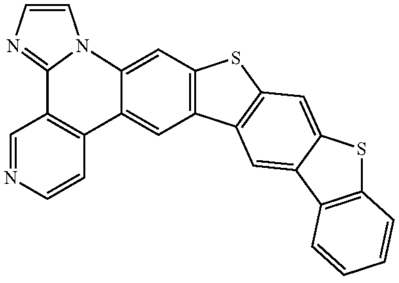

-continued
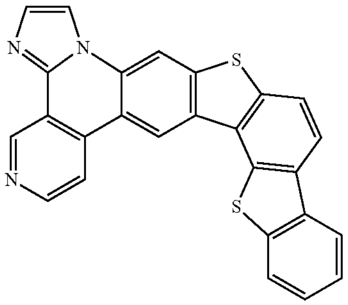
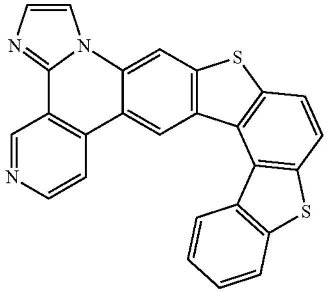
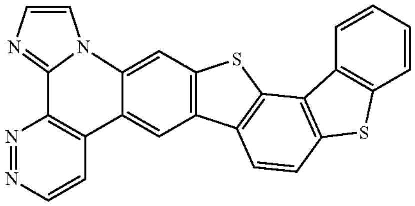
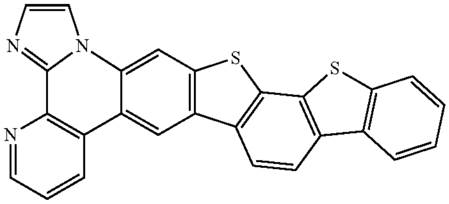
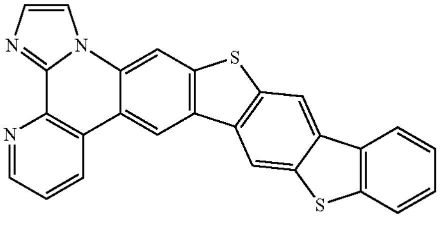
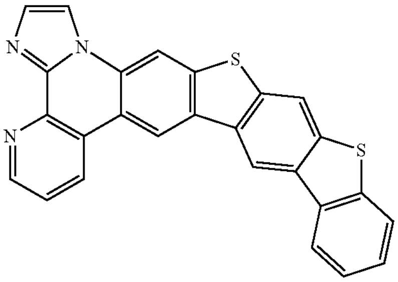
-continued
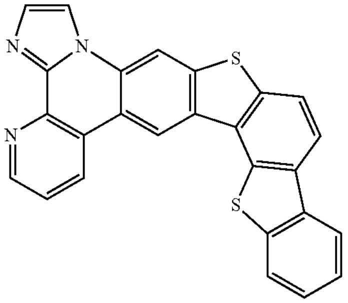
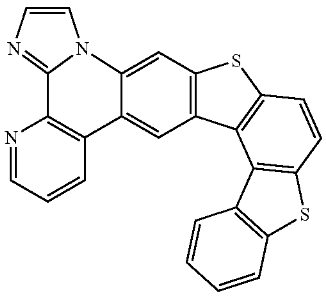
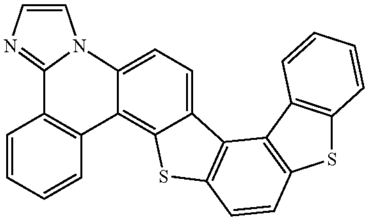
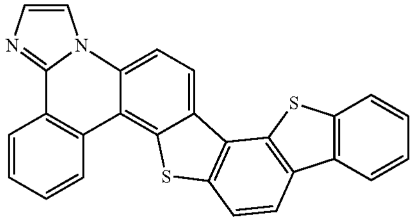
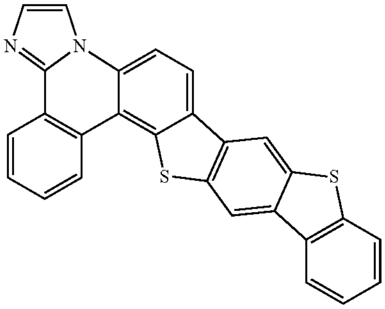
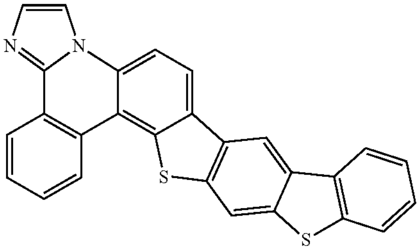

-continued
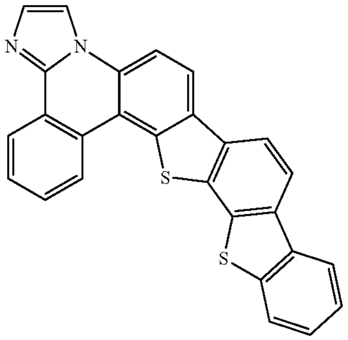
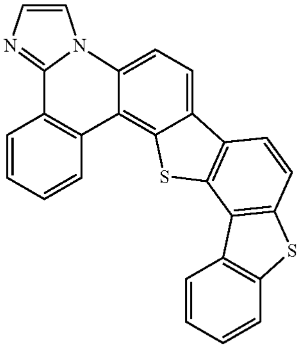
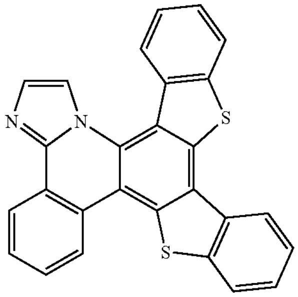
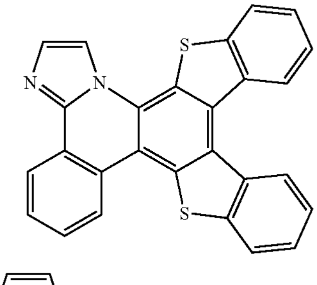
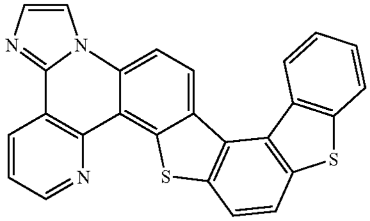
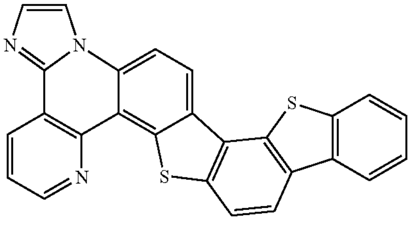
-continued
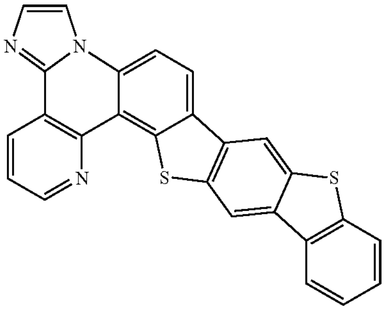
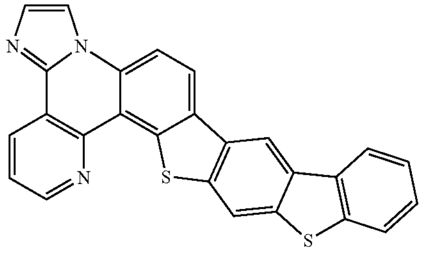
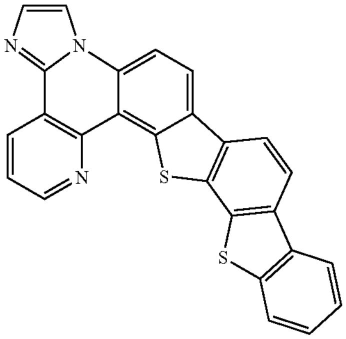
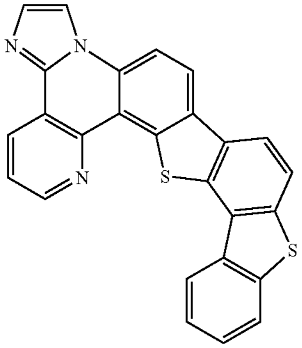
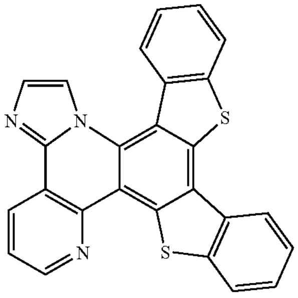

-continued
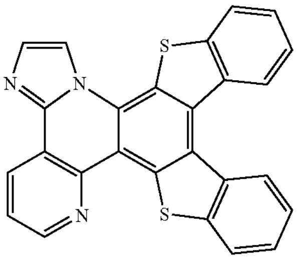
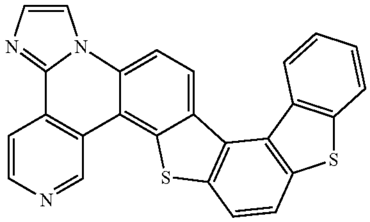
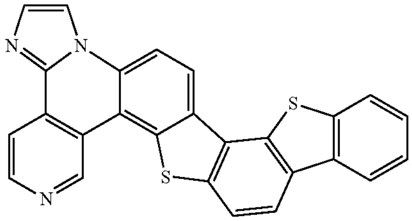
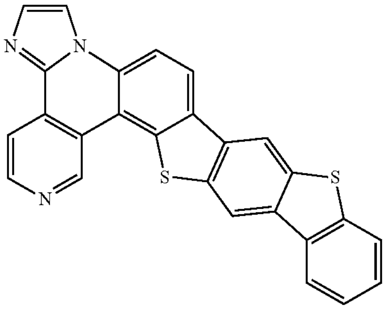
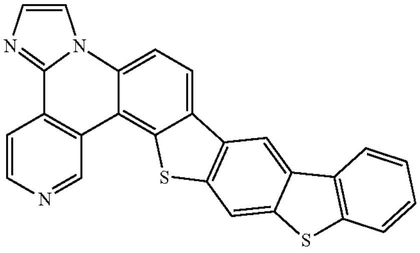
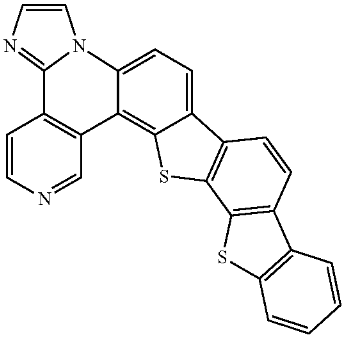
-continued
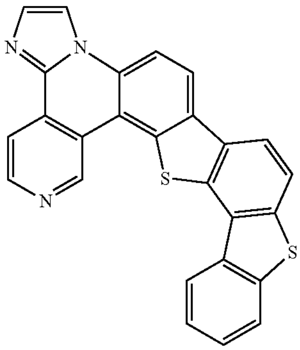
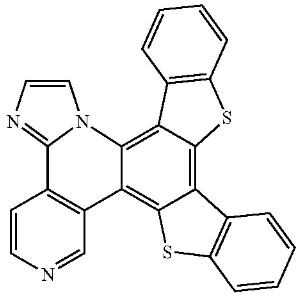
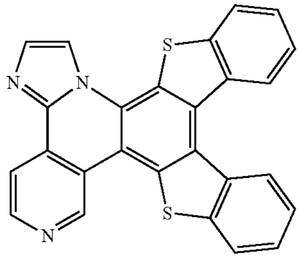
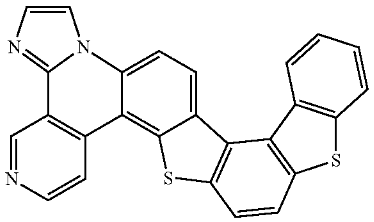
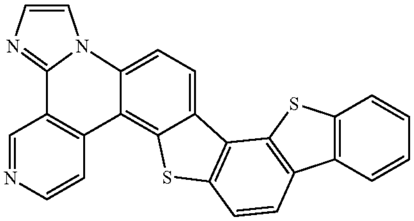
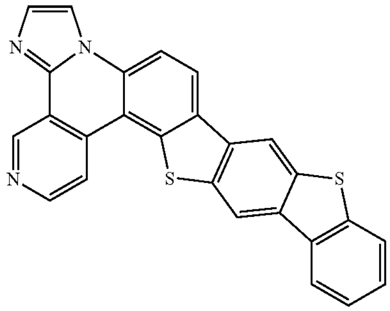

-continued
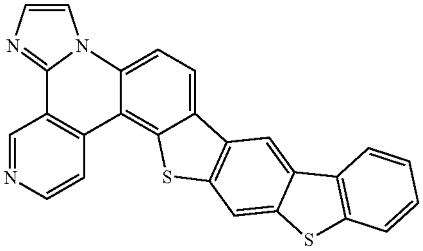
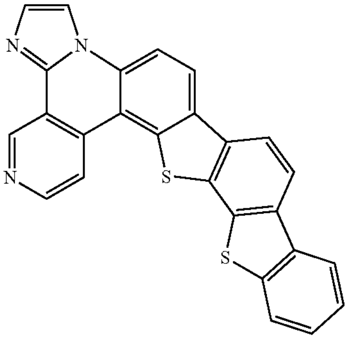
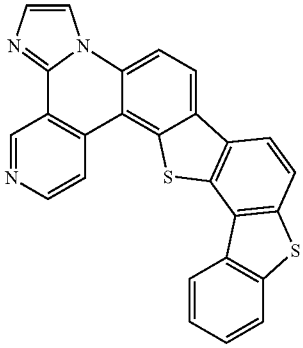
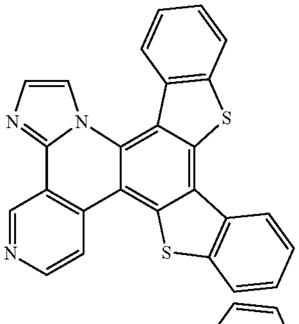
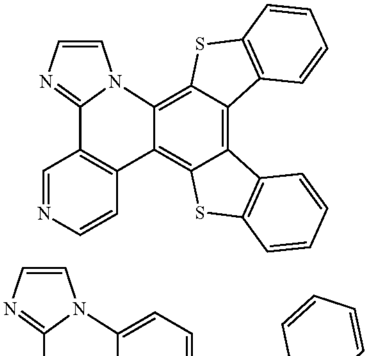
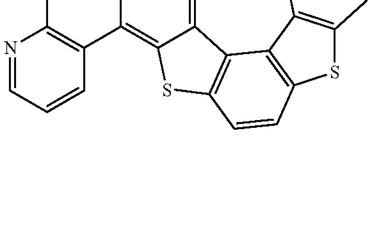
-continued
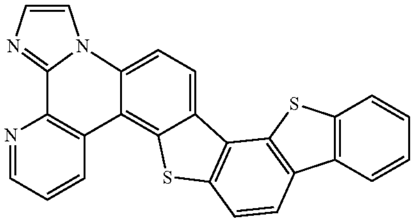
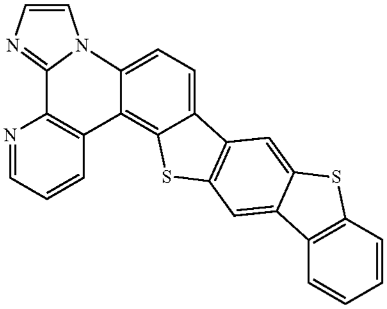
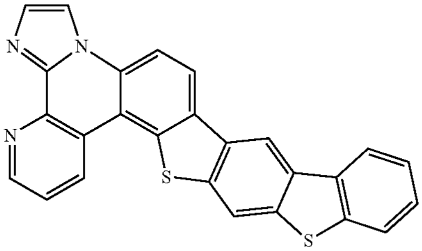
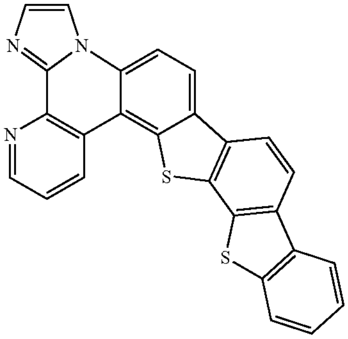
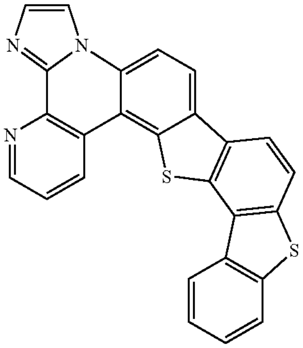

-continued
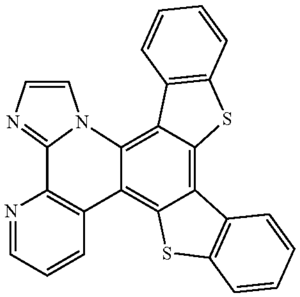
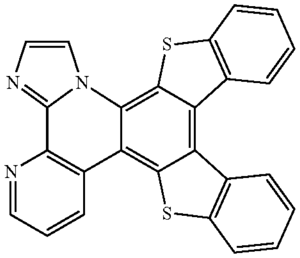
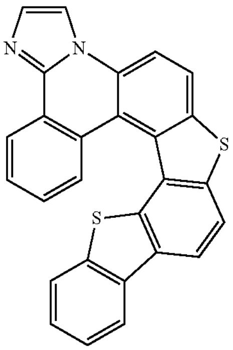
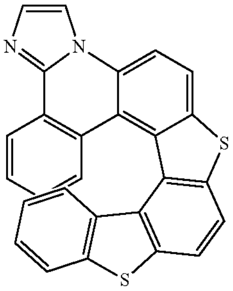
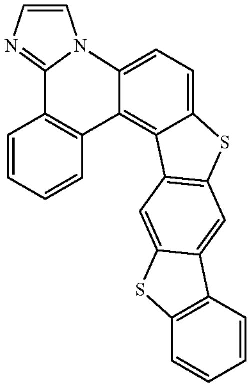
-continued
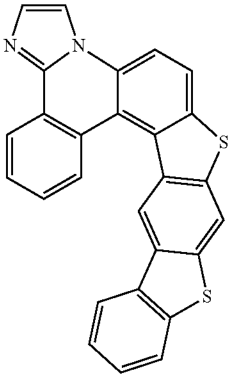
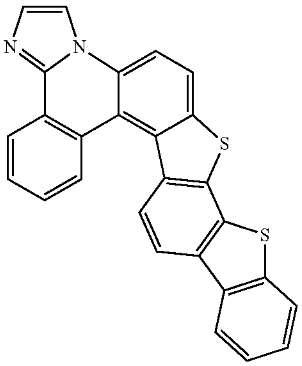
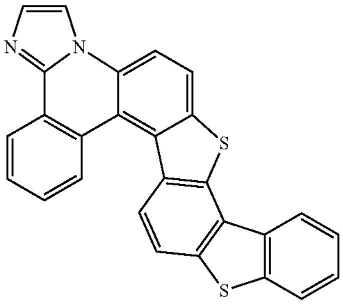
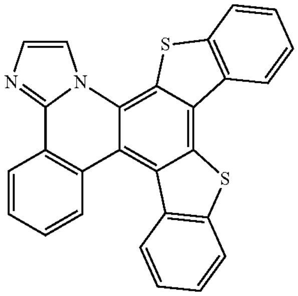
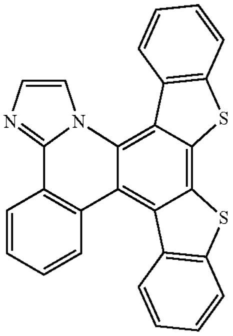

-continued
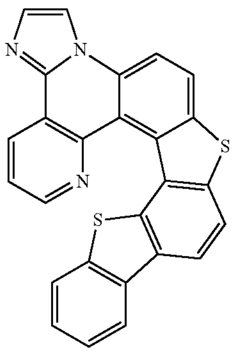
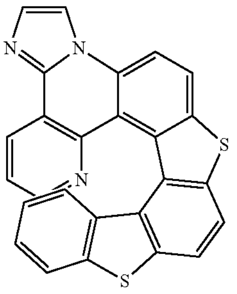
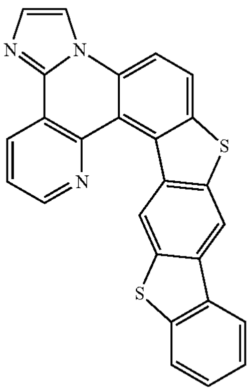
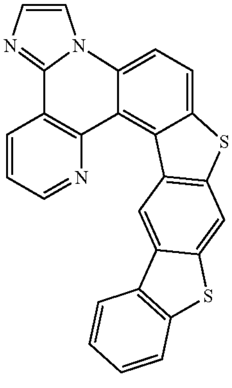
-continued
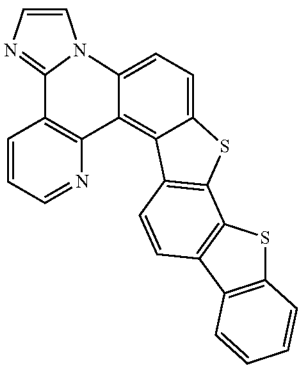
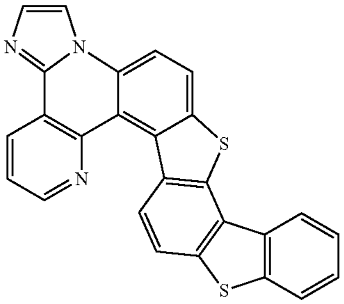
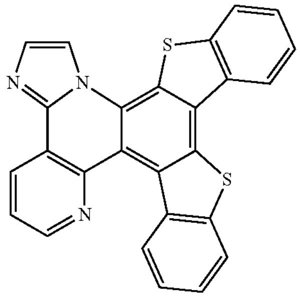
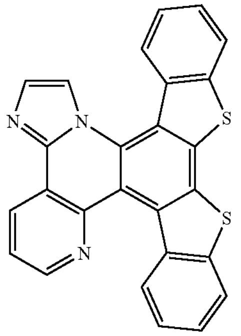
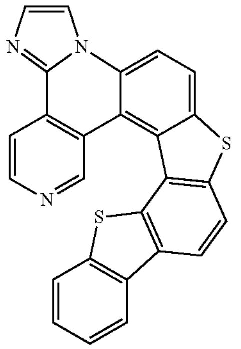

-continued
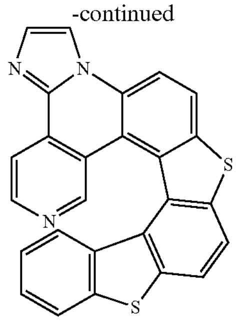
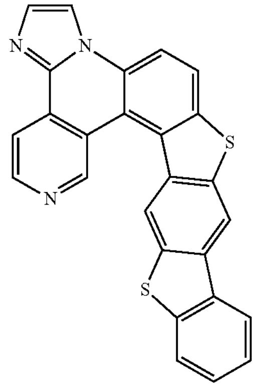
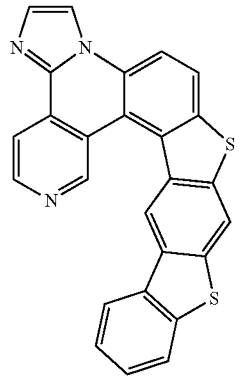
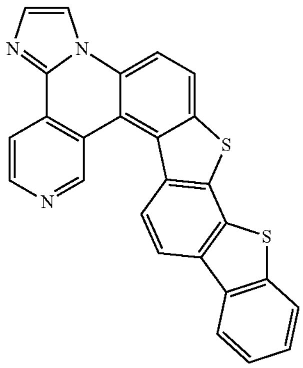
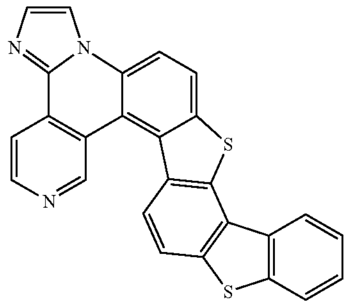
-continued
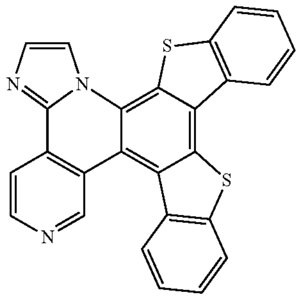
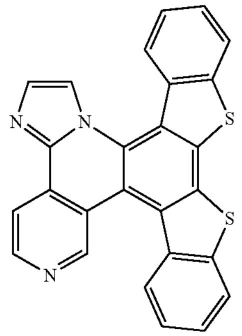
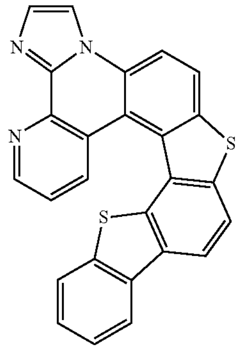
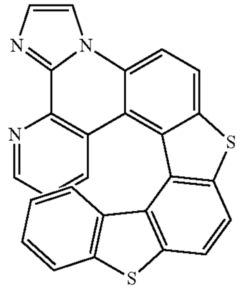
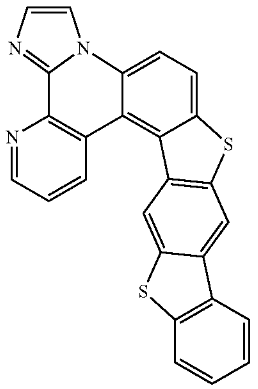

-continued
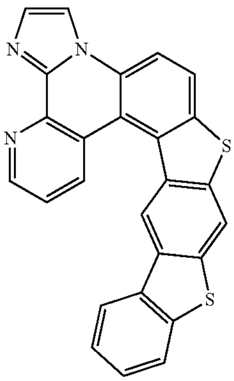
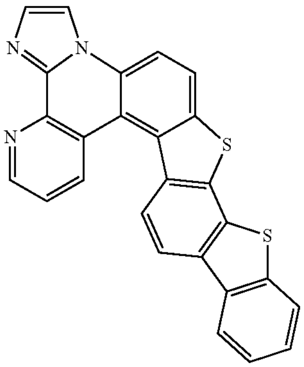
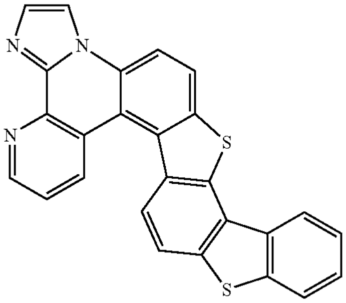
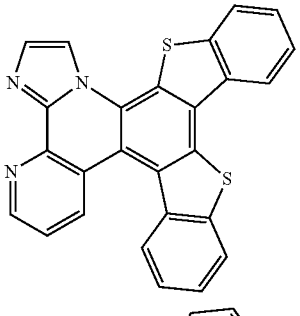
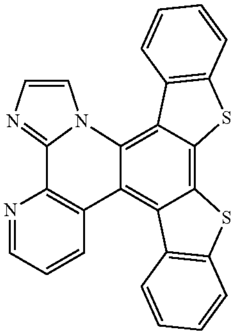
-continued
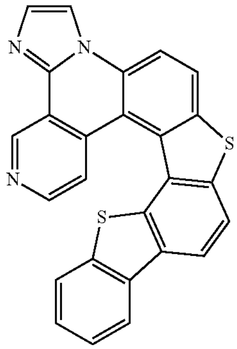
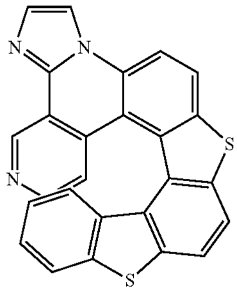
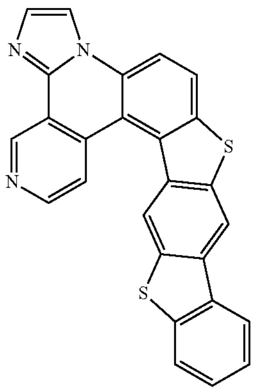
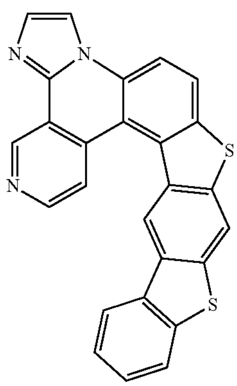

-continued
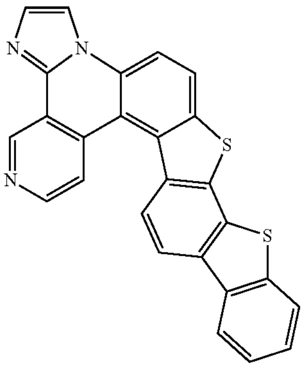
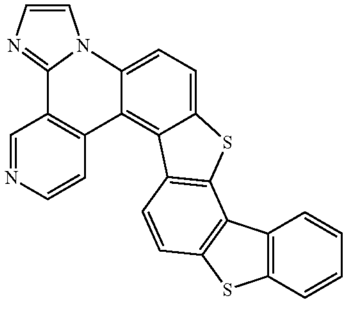
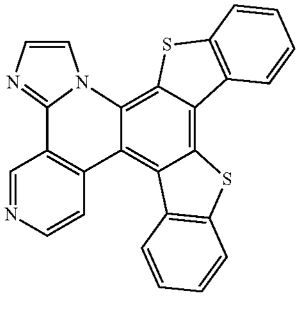
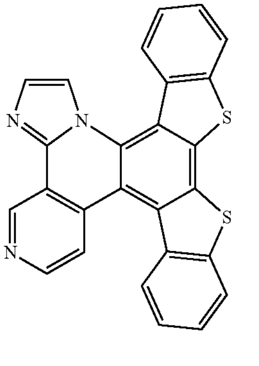
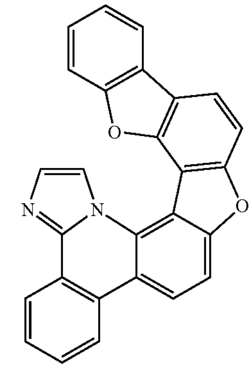
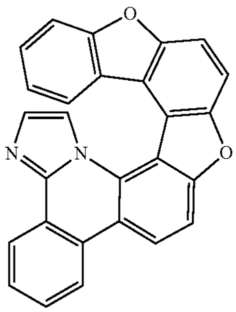
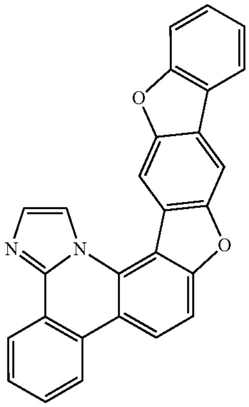
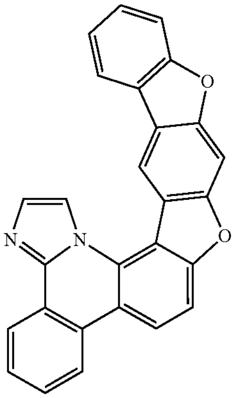
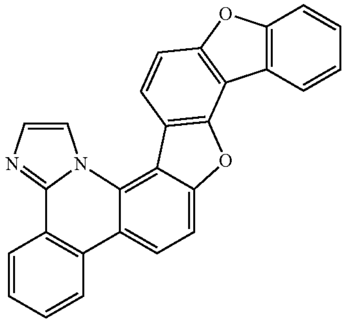
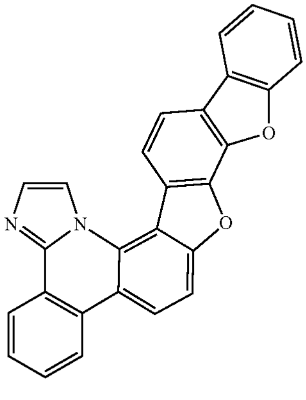
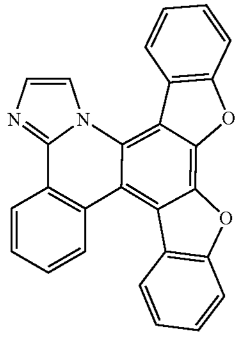

-continued
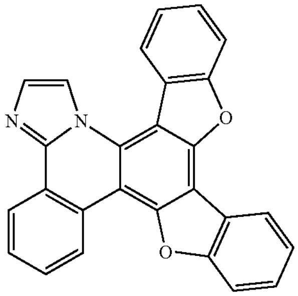
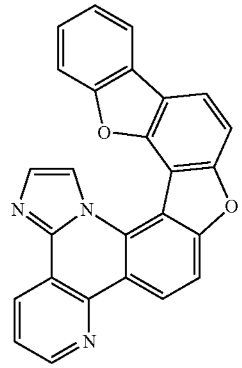
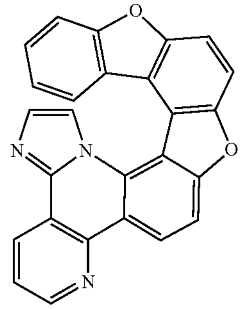
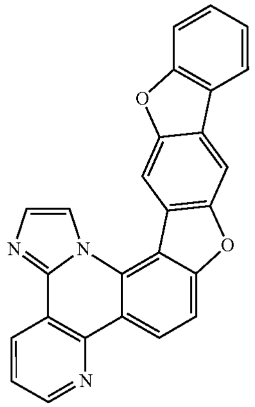
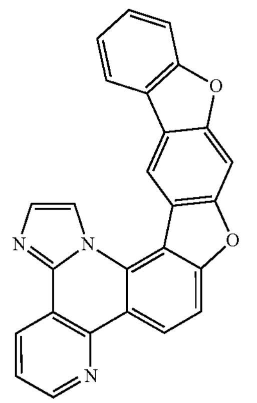
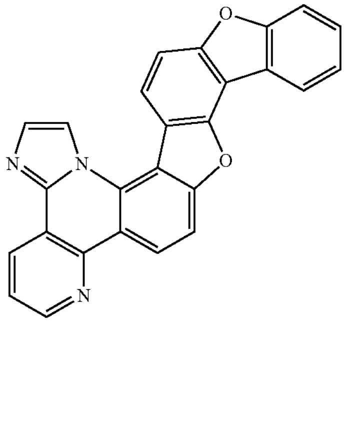
-continued
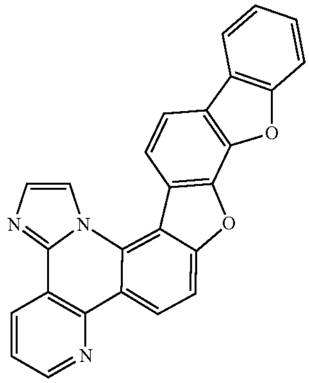
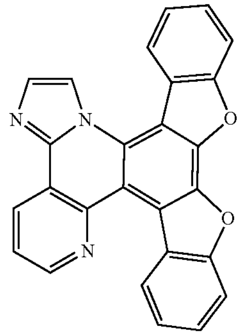
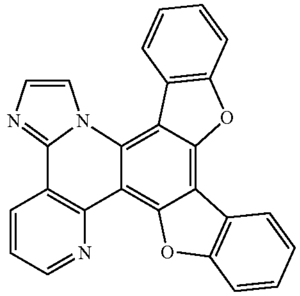
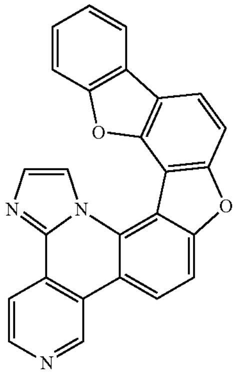
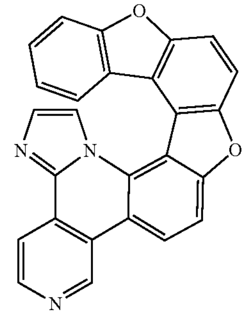
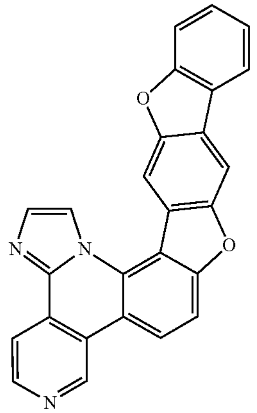
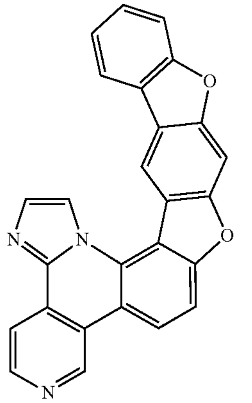

-continued
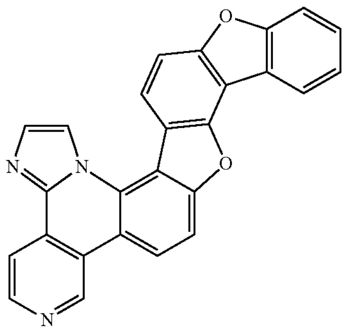
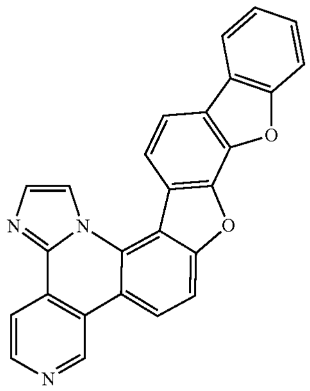
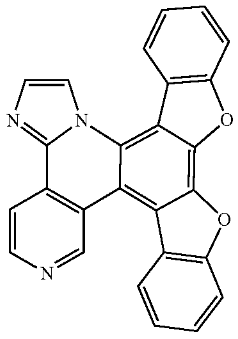
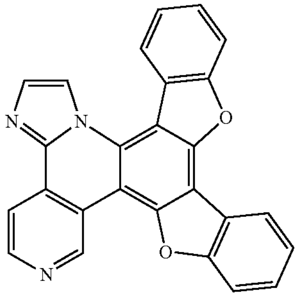
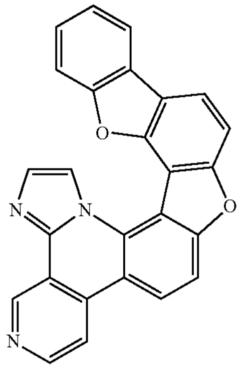
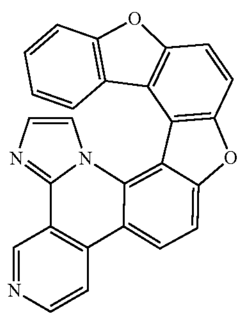
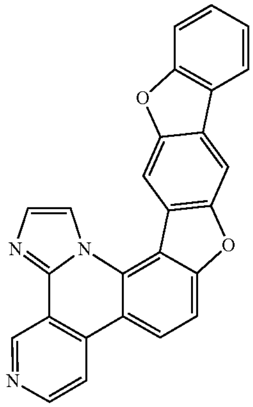
-continued
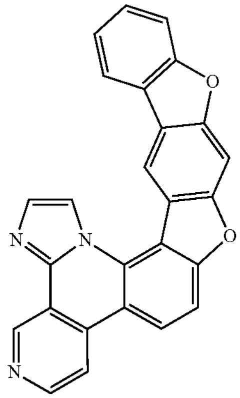
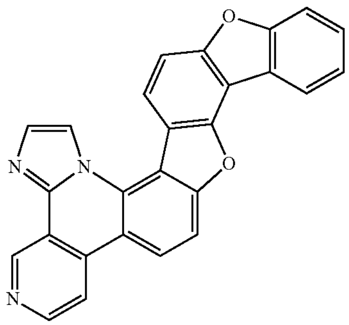
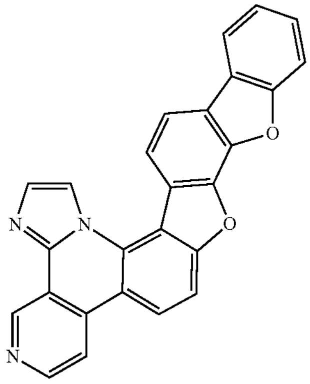
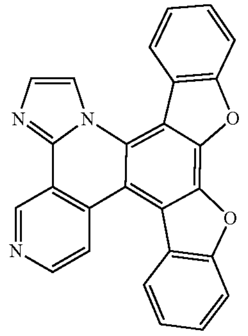
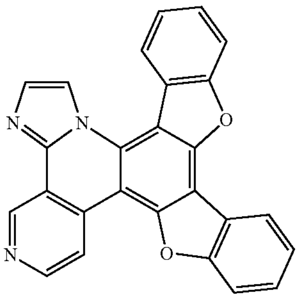
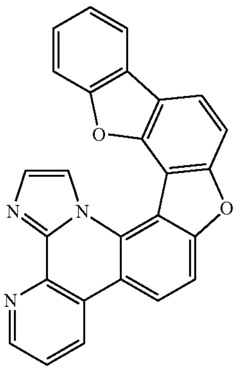

-continued
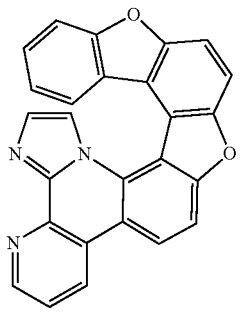
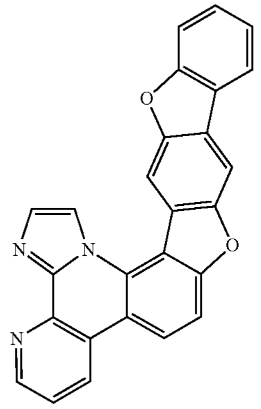
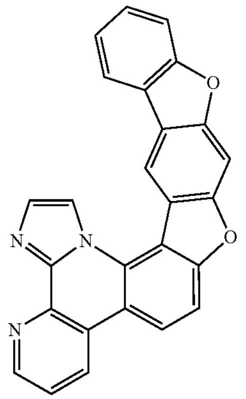
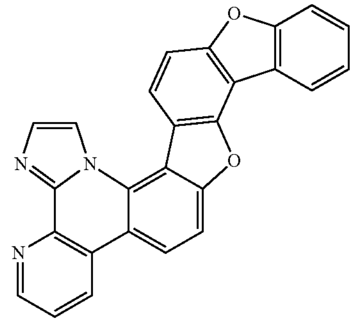
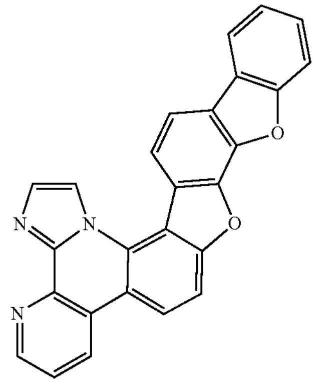
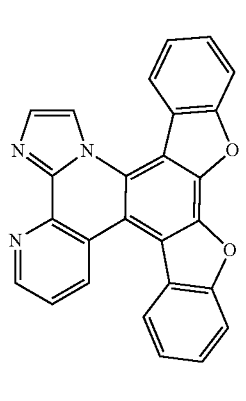
-continued
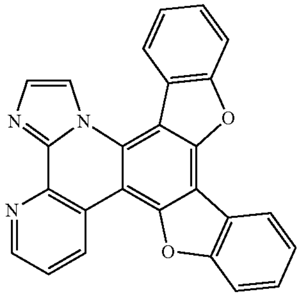
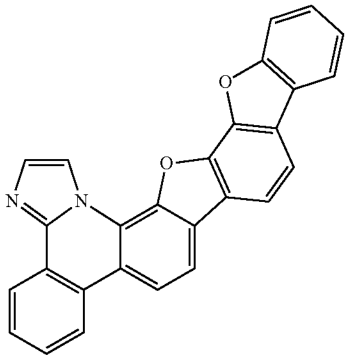
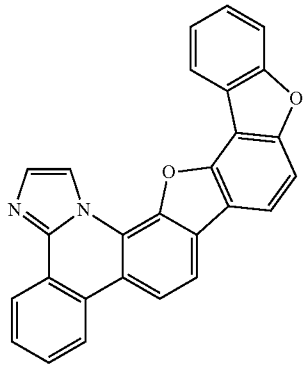
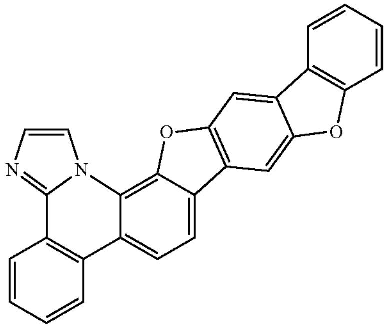
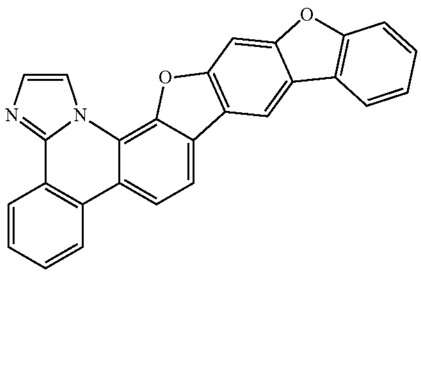

-continued
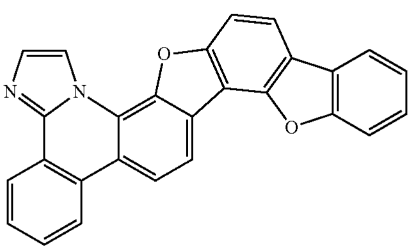
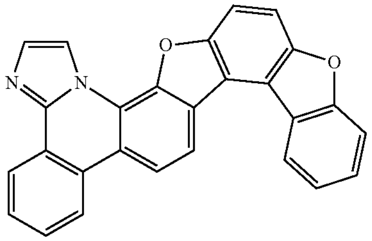
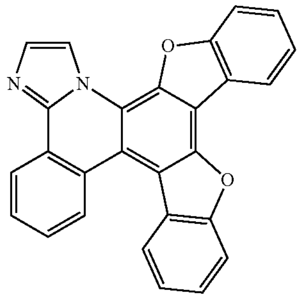
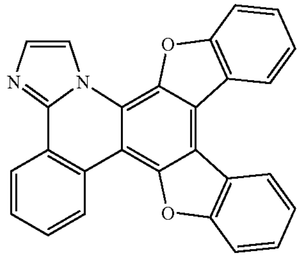
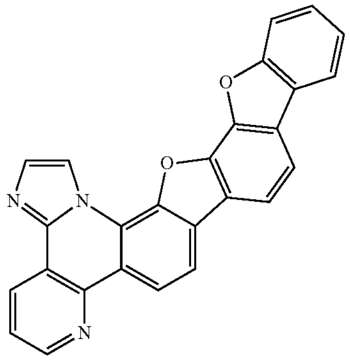
-continued
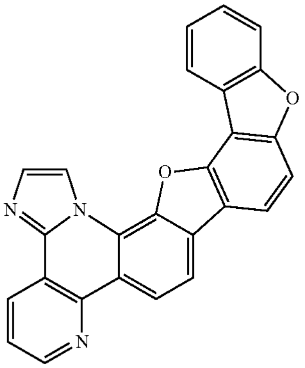
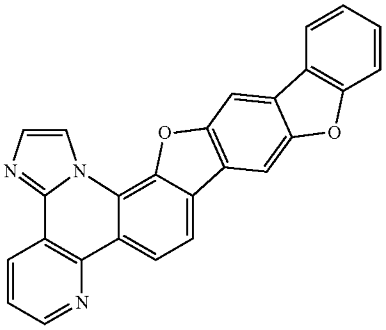
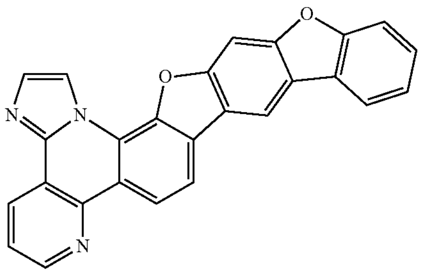
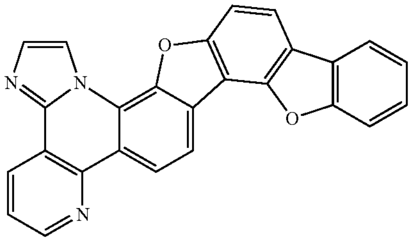
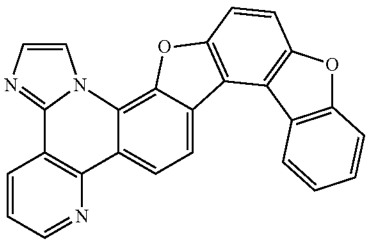

-continued
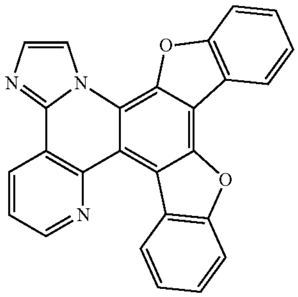
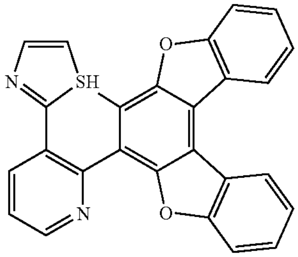
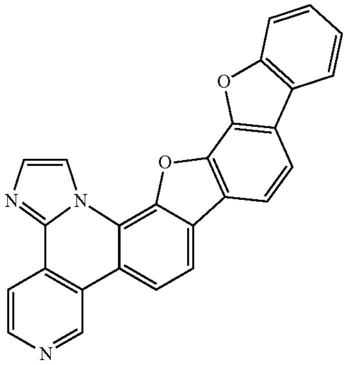
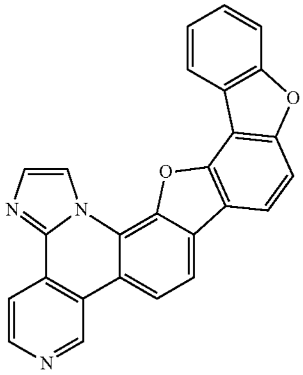
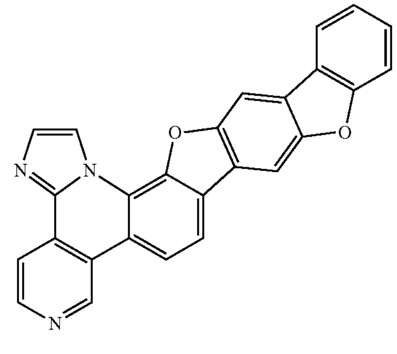
-continued
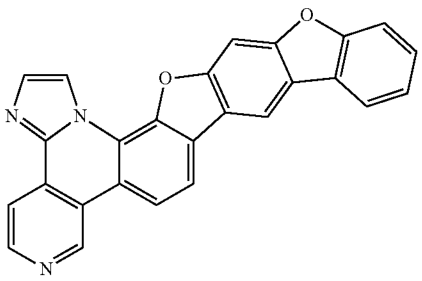
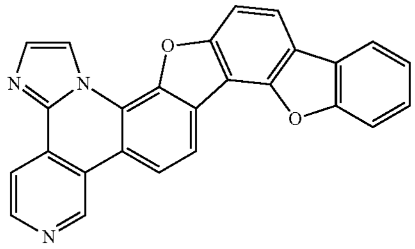
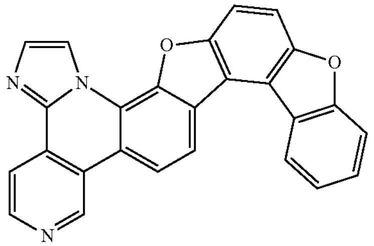
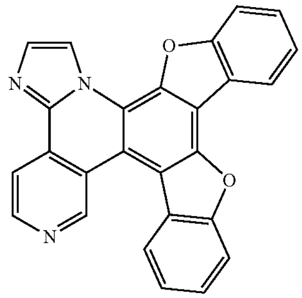
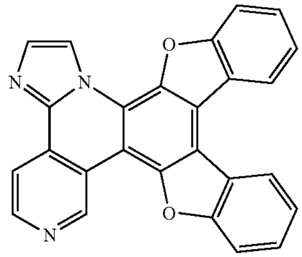
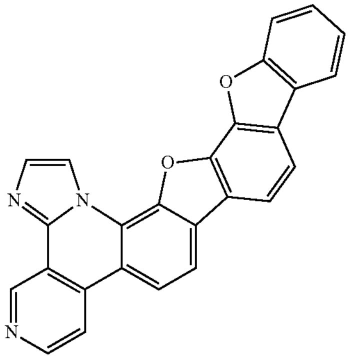

-continued
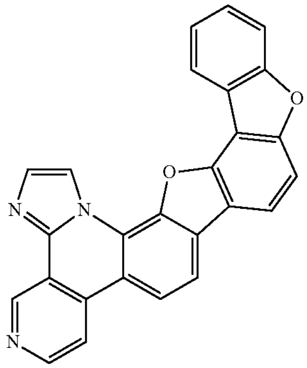
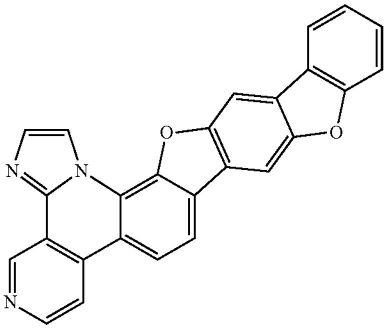
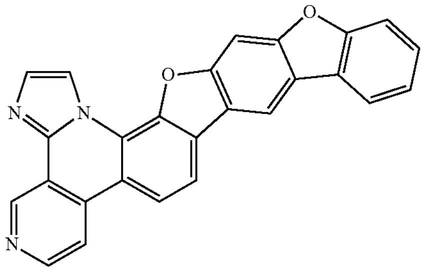
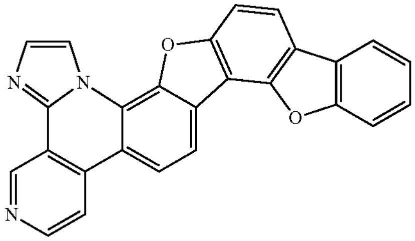
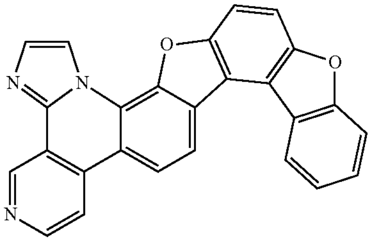
-continued
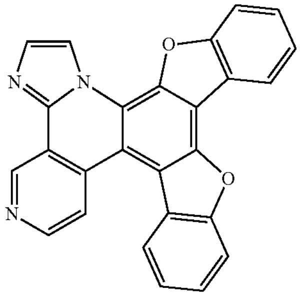
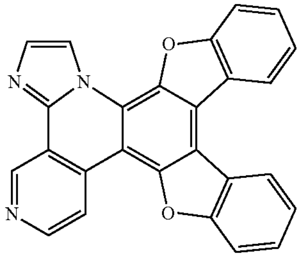
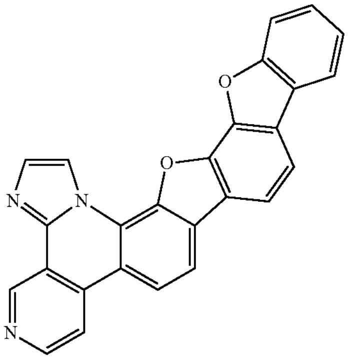
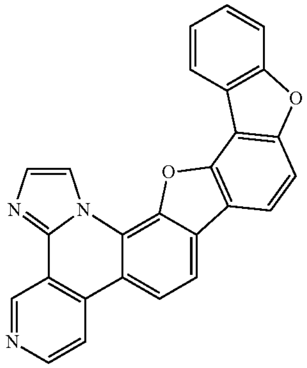
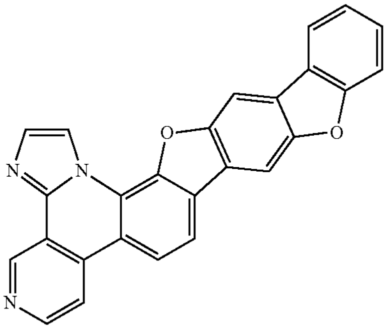

-continued
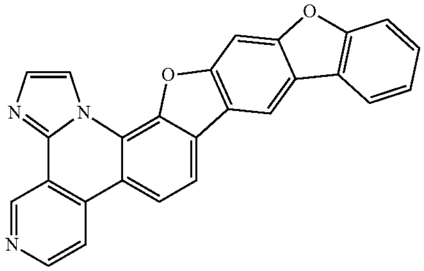
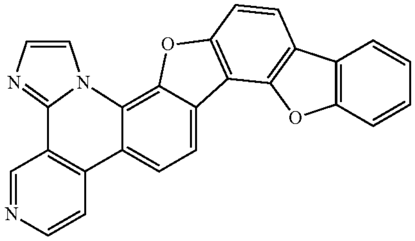
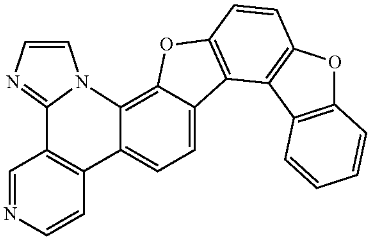
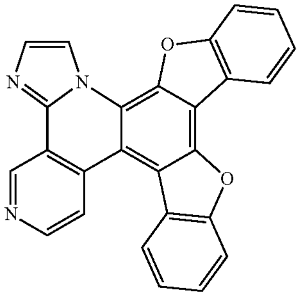
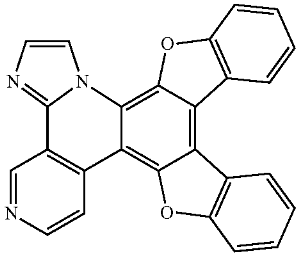
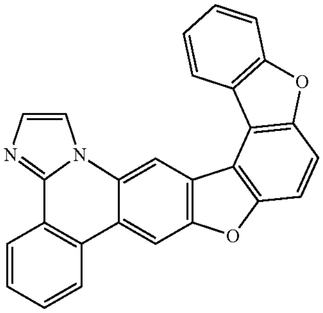
-continued
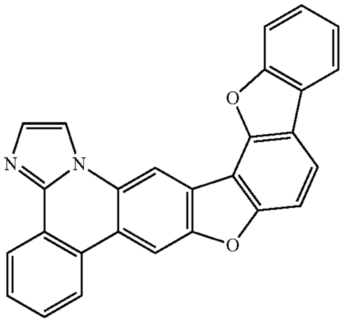
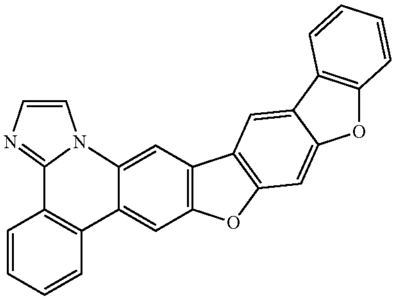
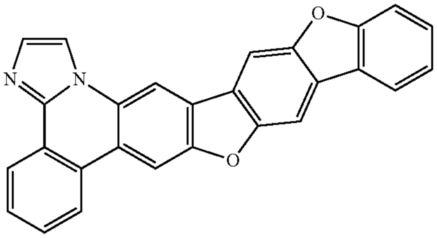
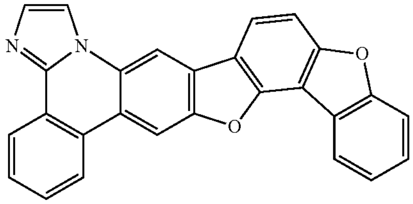
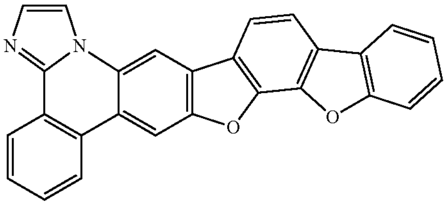
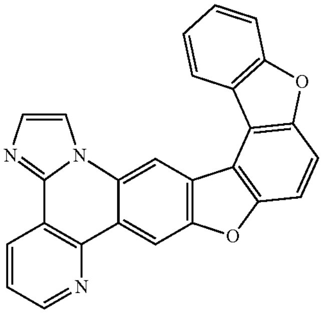

-continued
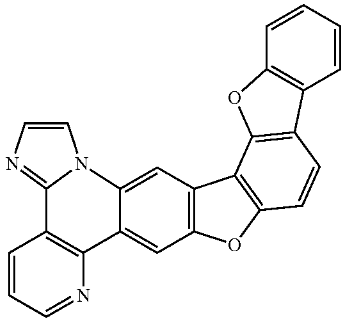
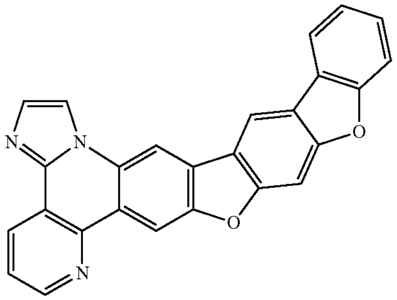
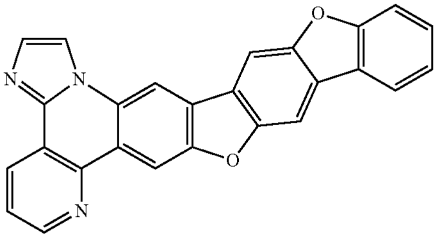
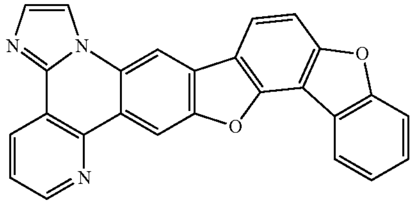
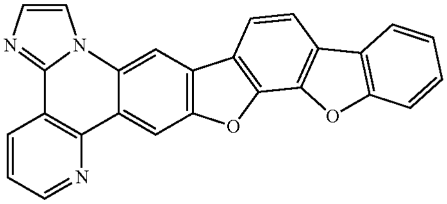
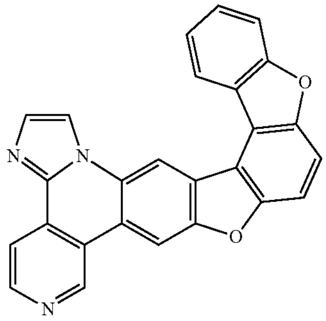
-continued
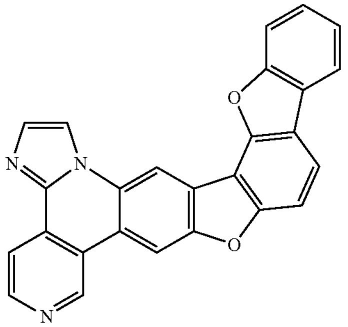
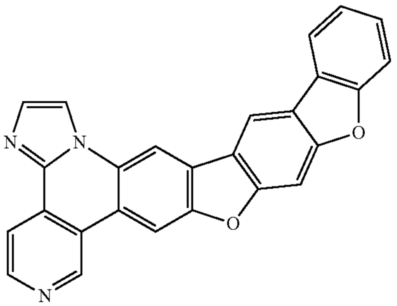
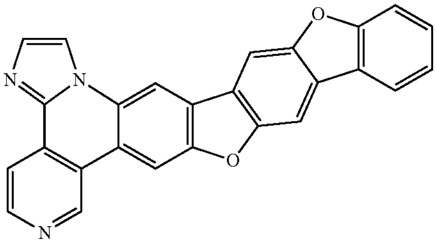
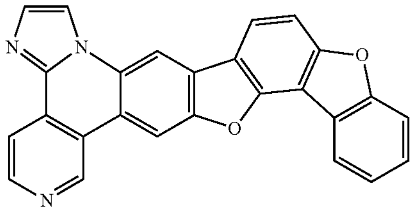
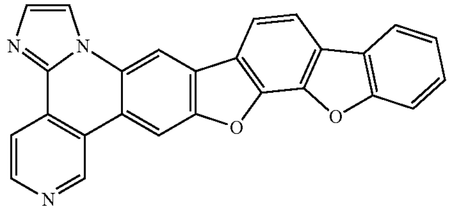
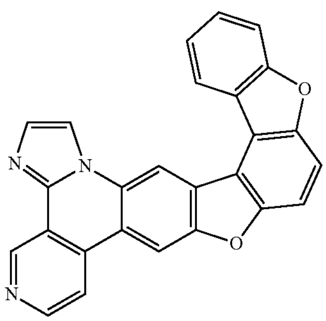

-continued
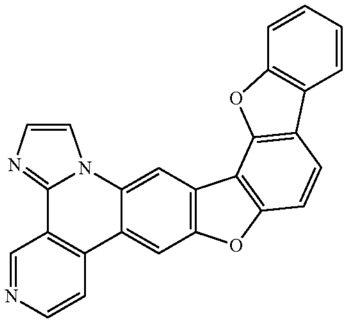
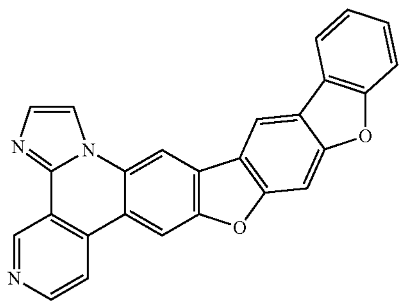
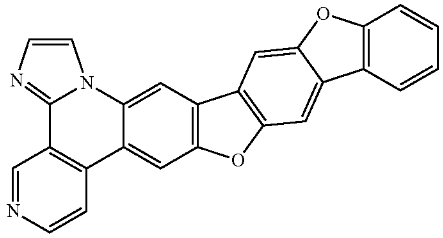
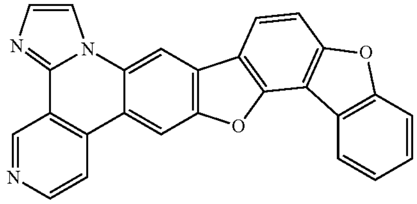
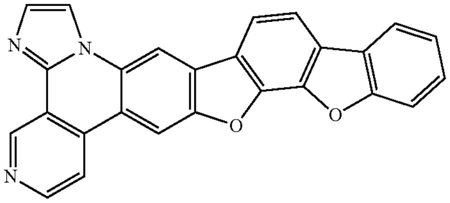
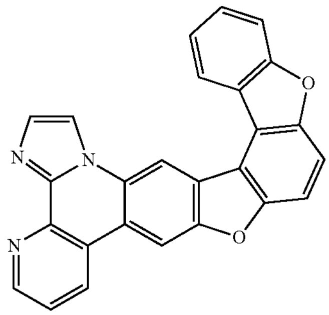
-continued
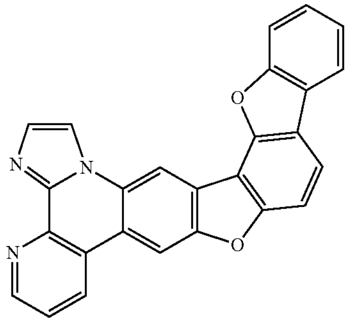
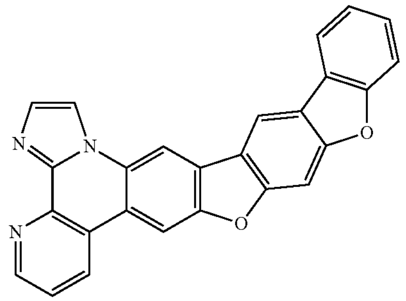
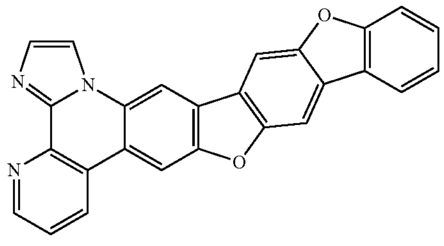
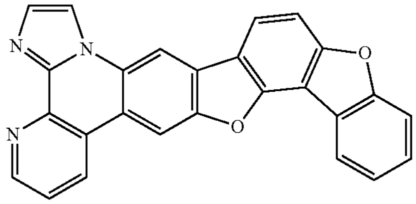
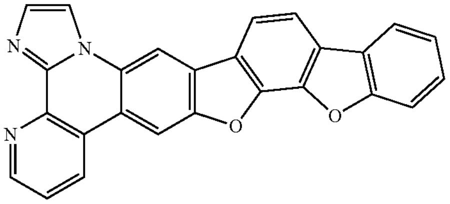
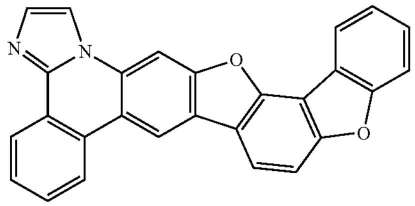
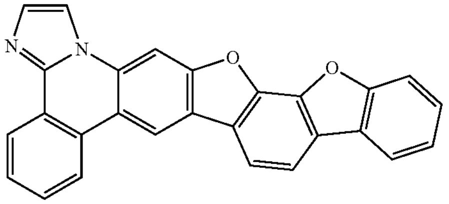

-continued
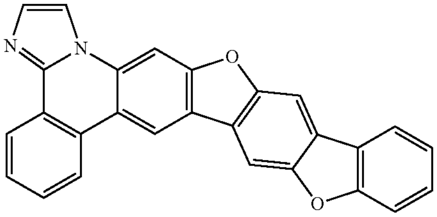
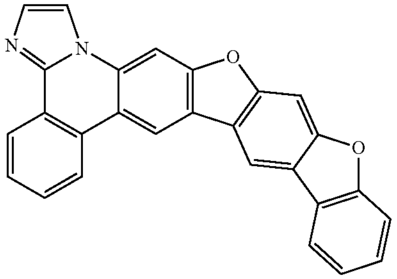
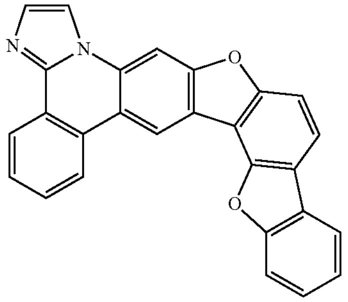
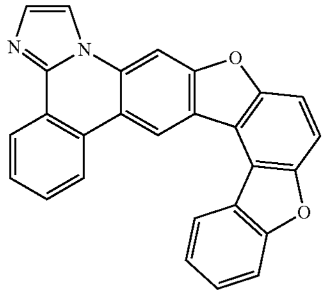
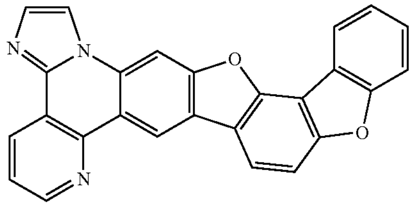
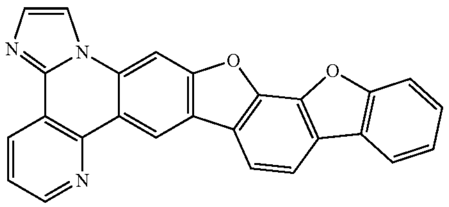
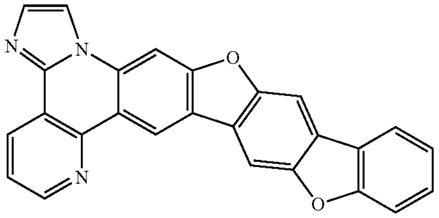
-continued
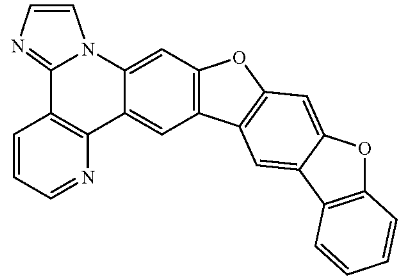
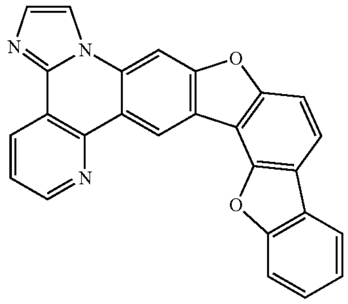
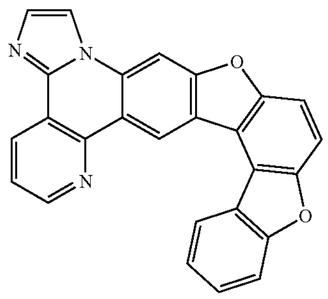
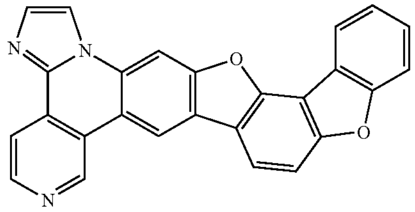
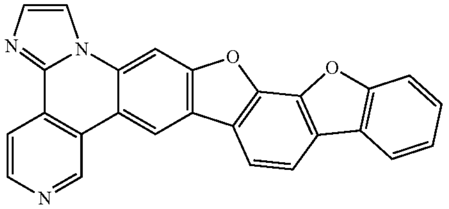
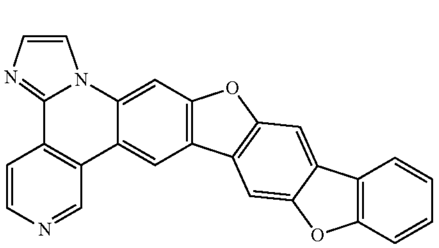

-continued
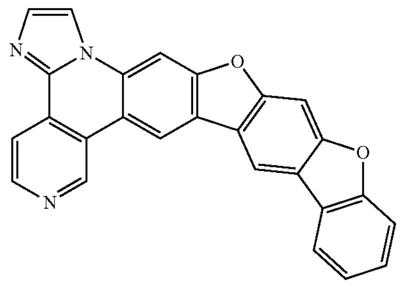
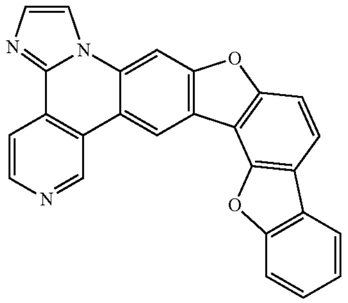
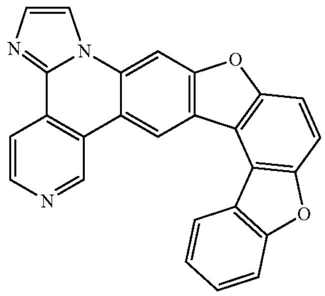
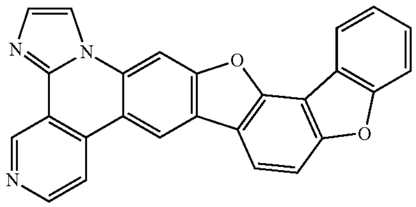
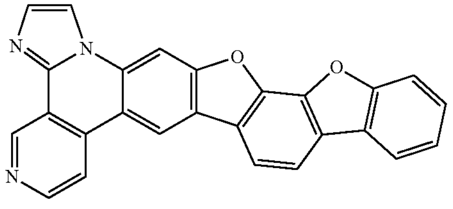
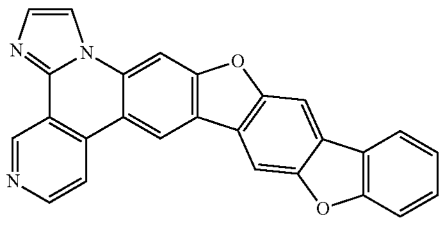
-continued
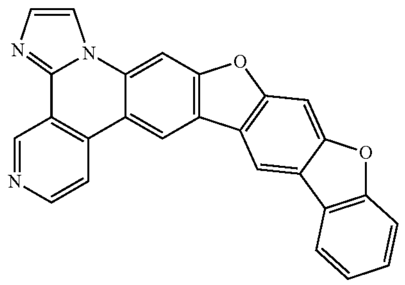
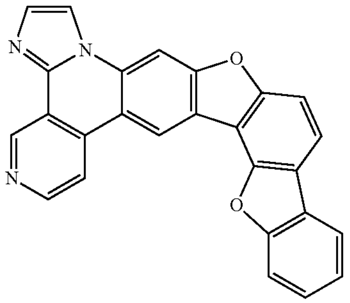
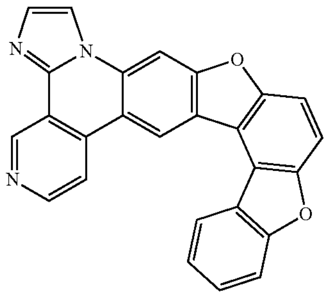
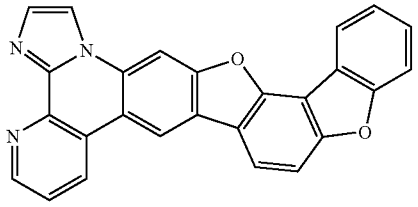
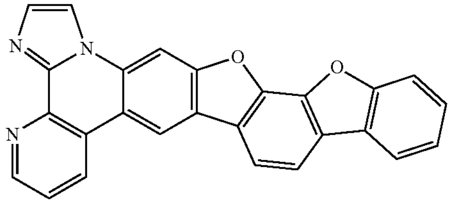
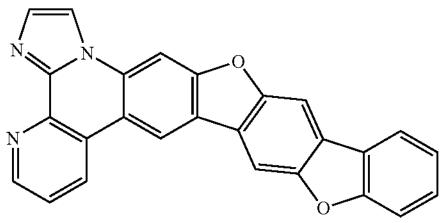

-continued
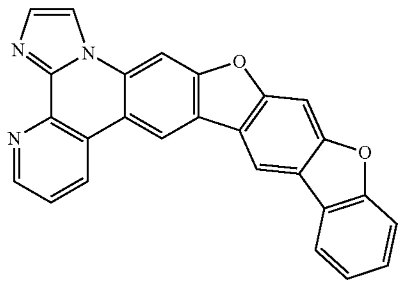
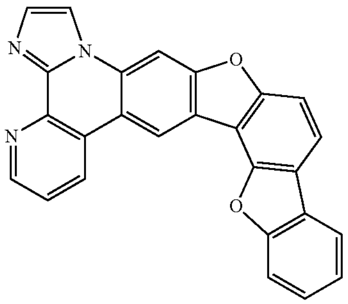
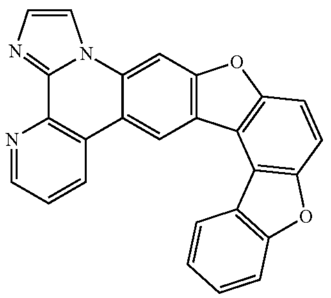
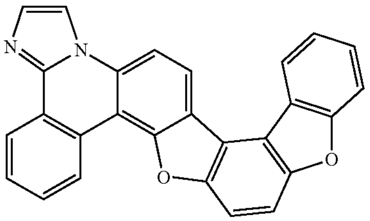
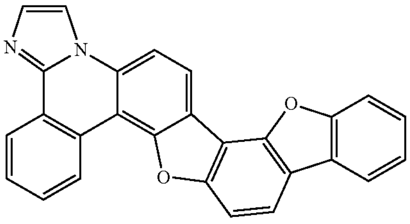
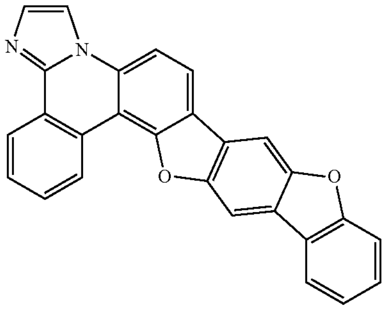
-continued
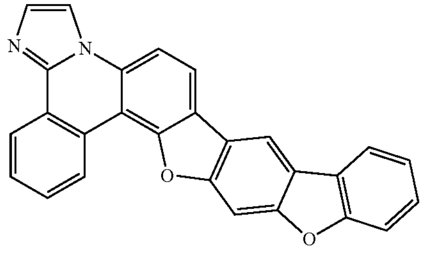
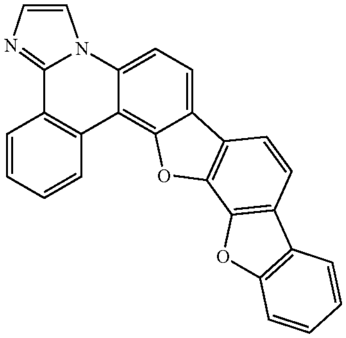
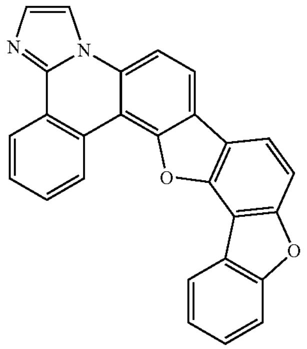
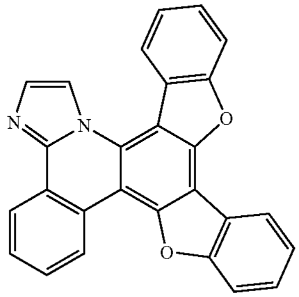
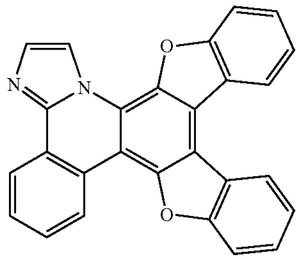
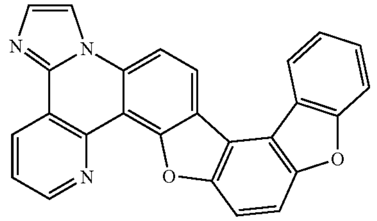

-continued
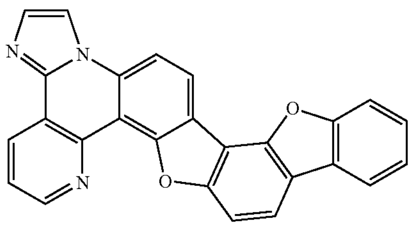
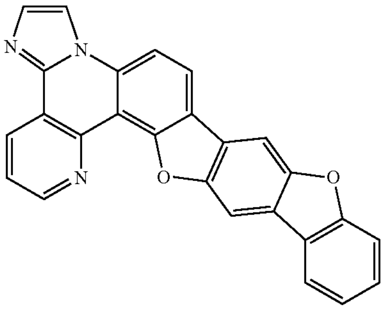
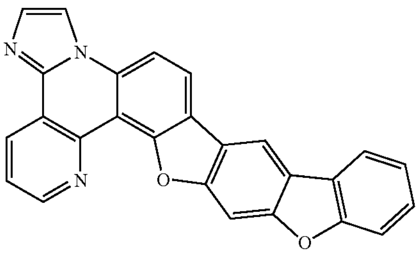
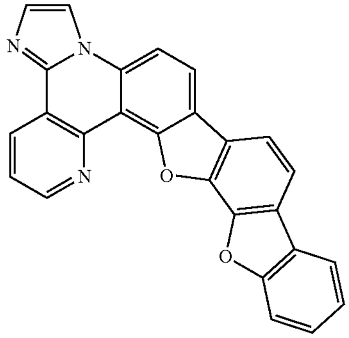
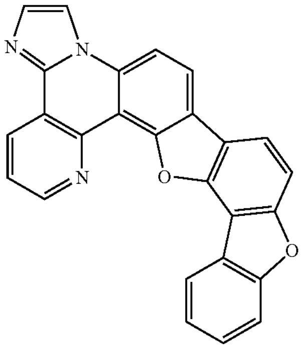
-continued
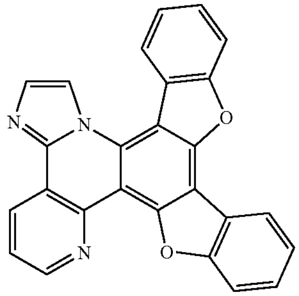
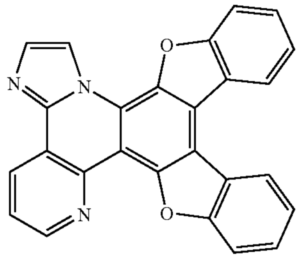
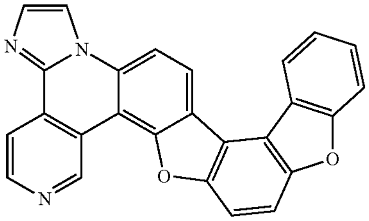
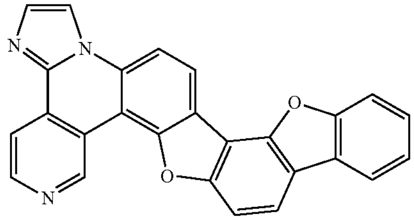
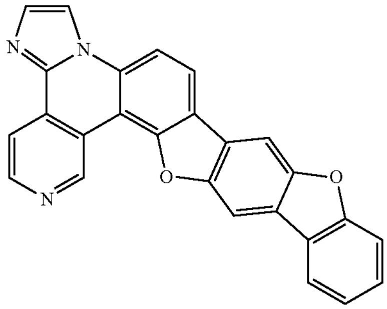
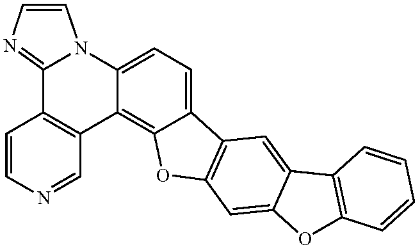

-continued
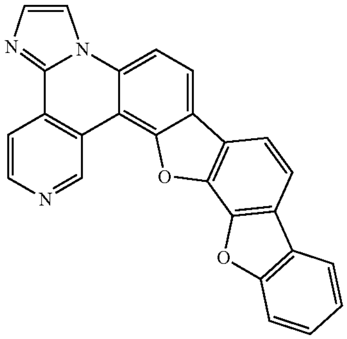
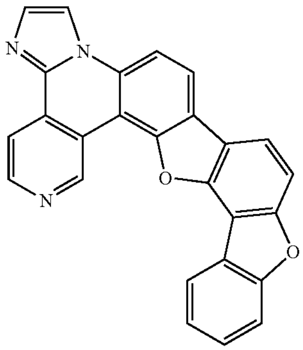
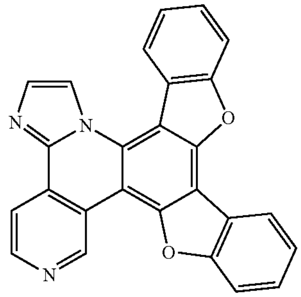
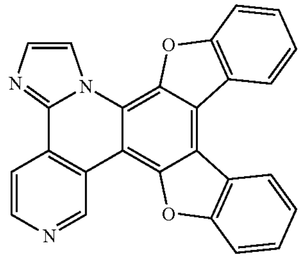
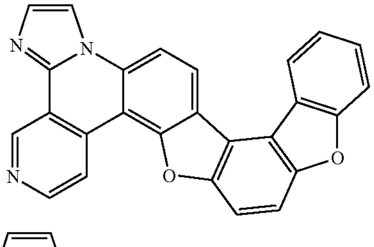
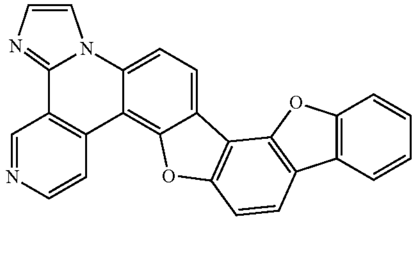
-continued
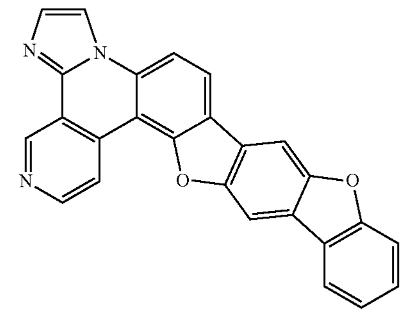
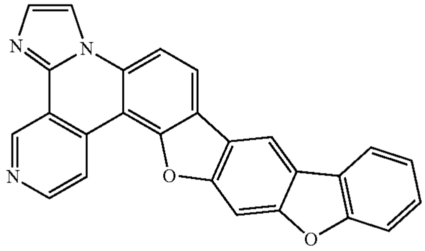
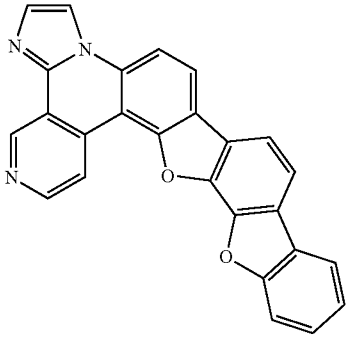
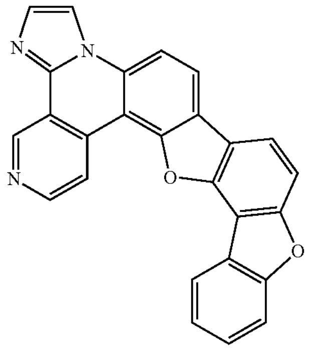
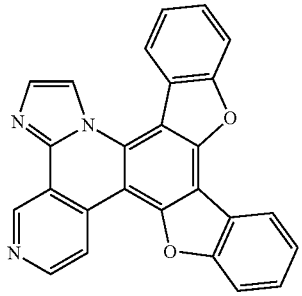

-continued
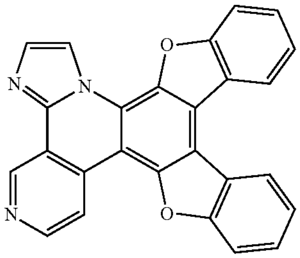
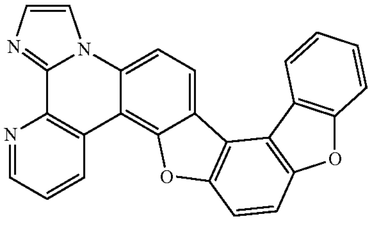
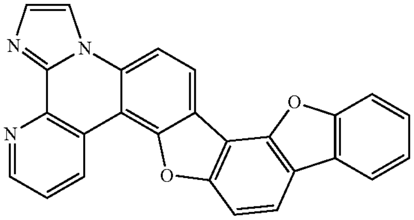
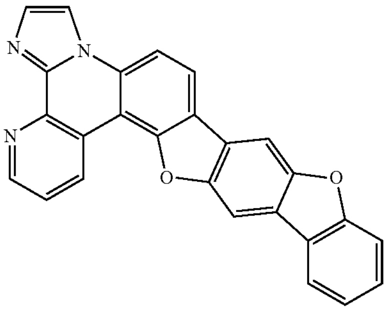
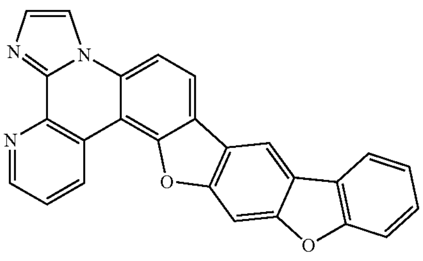
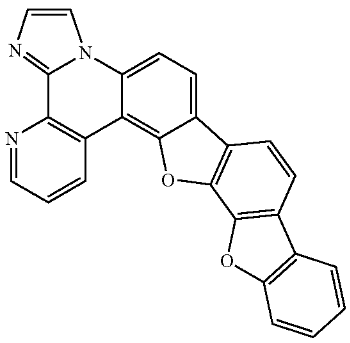
-continued
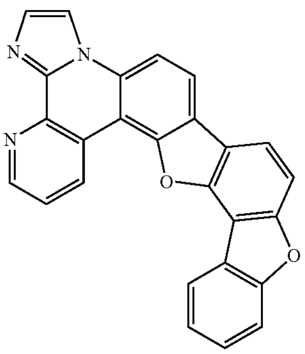
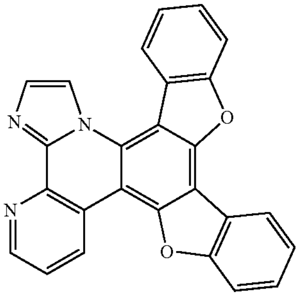
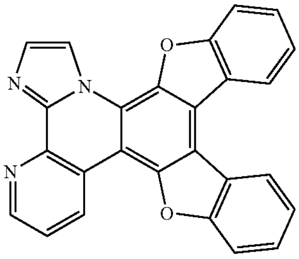
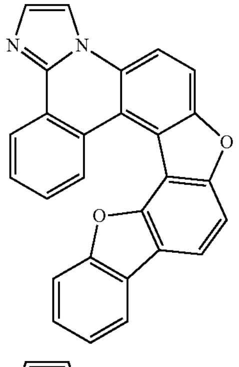
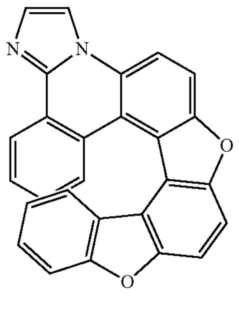

-continued
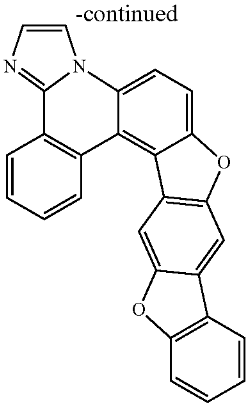
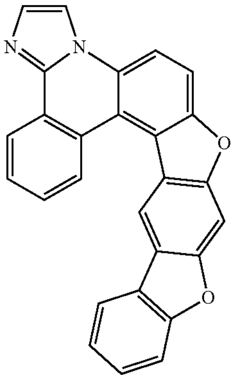
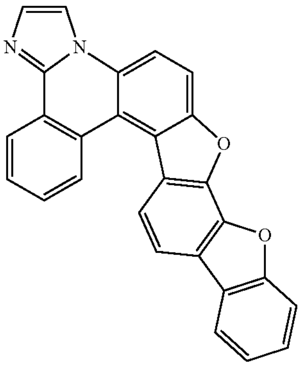
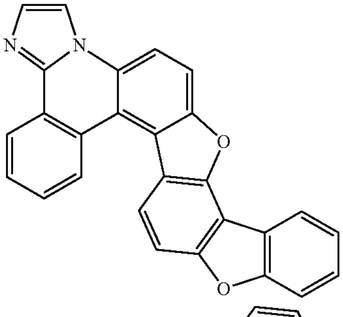
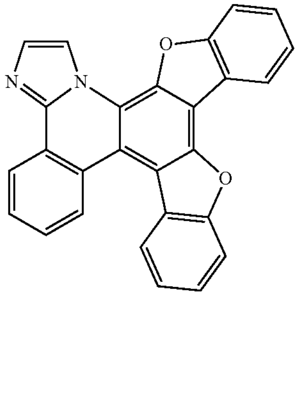
-continued
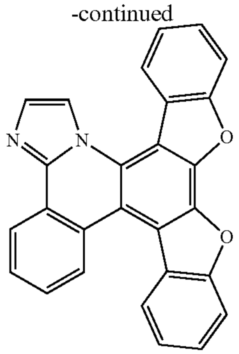
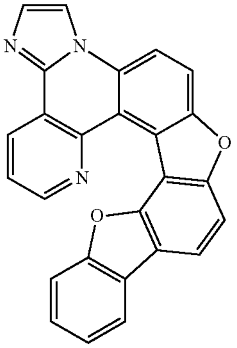
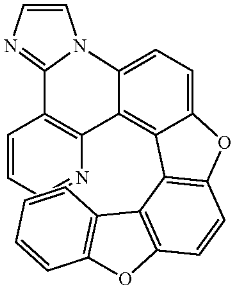
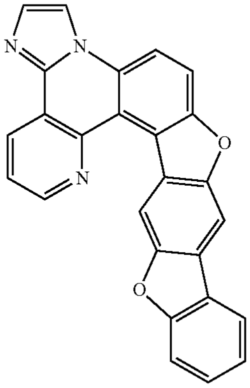
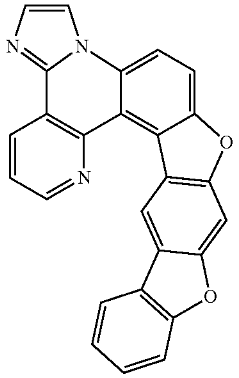

-continued
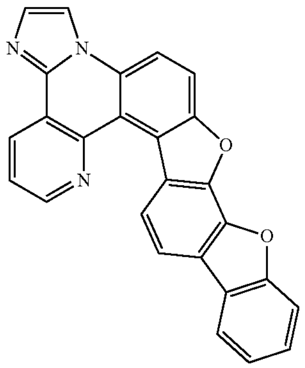
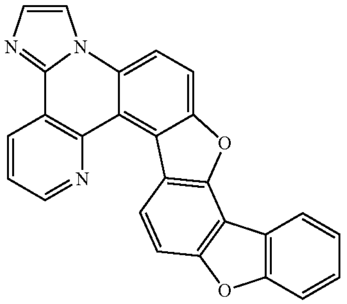
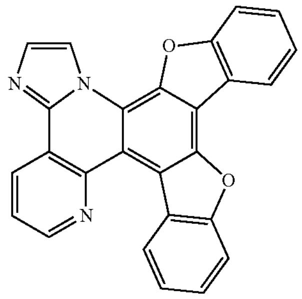
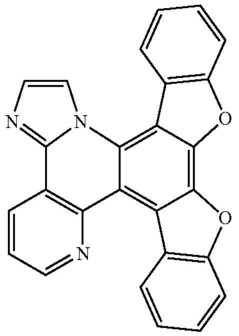
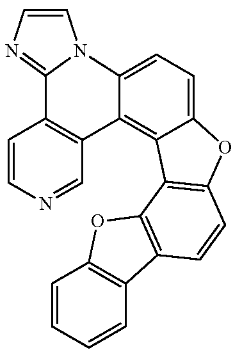
-continued
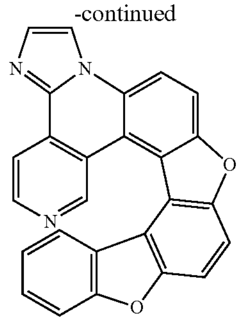
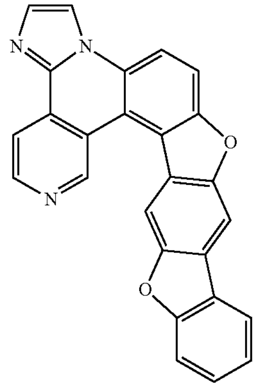
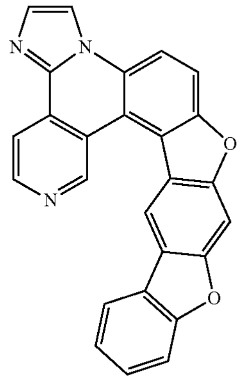
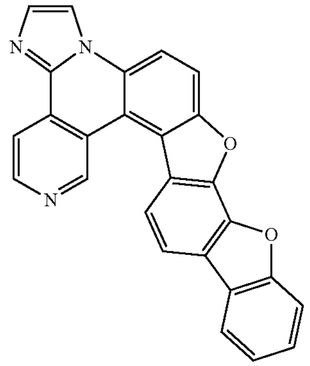
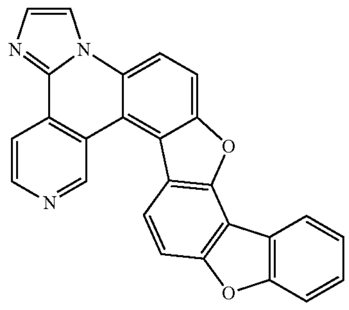

-continued
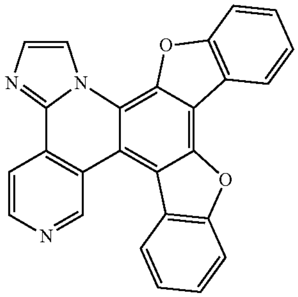
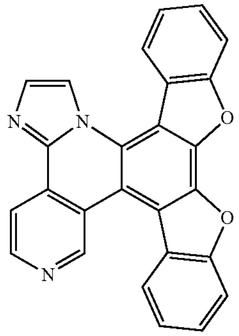
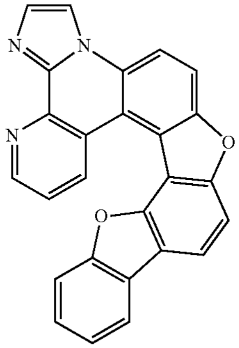
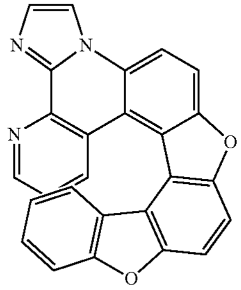
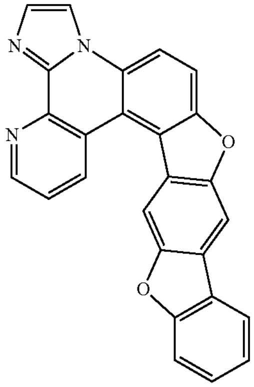
-continued
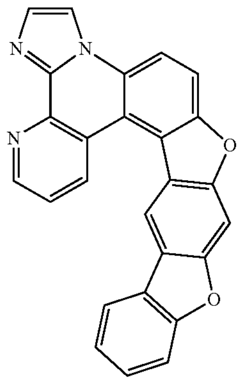
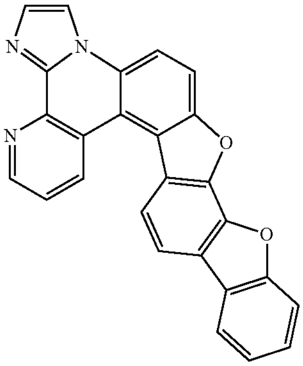
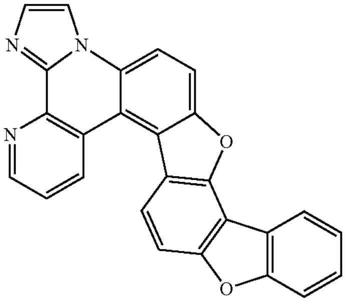
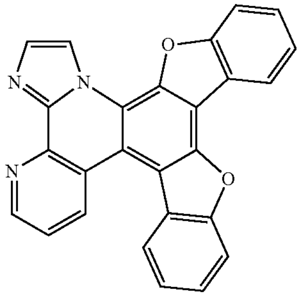
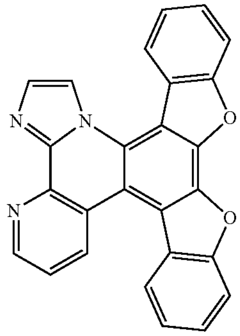

-continued
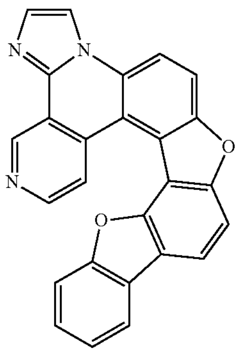
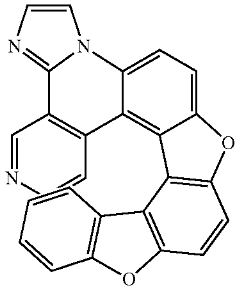
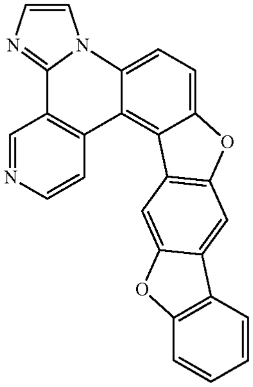
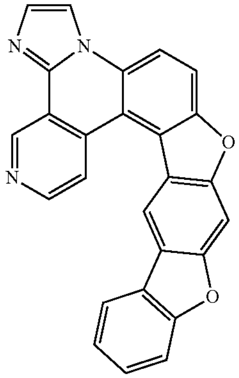
-continued
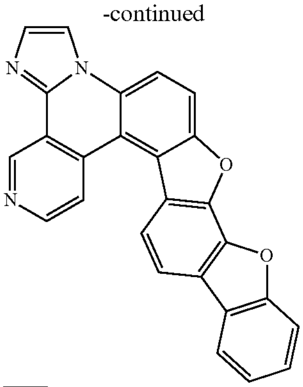
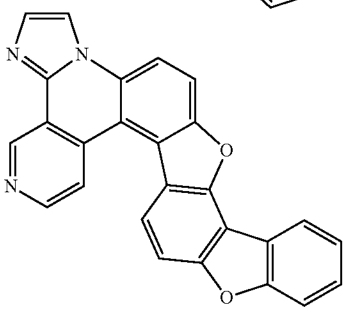
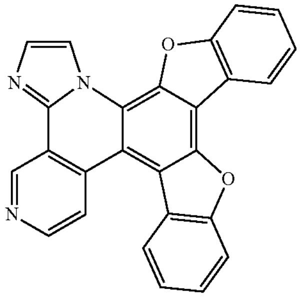
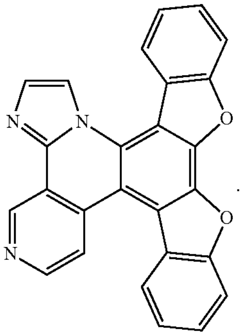
.
16. A light emitting device comprising the light emitting diode of claim 15.
17. An organic light emitting diode comprising the compound of claim 16.
* * * * *